US011189362B2

(12) United States Patent
Liu et al.

(10) Patent No.: US 11,189,362 B2
(45) Date of Patent: Nov. 30, 2021

(54) METAGENOMIC LIBRARY AND NATURAL PRODUCT DISCOVERY PLATFORM

(71) Applicant: Zymergen Inc., Emeryville, CA (US)

(72) Inventors: Oliver Liu, San Francisco, CA (US); Eyal Akiva, Foster City, CA (US); Tom Hayon Eyles, Emeryville, CA (US); Ute Galm, Danville, CA (US); Sangita Ganesh, Alameda, CA (US); Stephanie Leanne Brown Hendrix, Emeryville, CA (US); William W. Hwang, El Cerrito, CA (US); Jeffrey Hoon Kim, Berkeley, CA (US); Alexander Neckelmann, Berkeley, CA (US); Samuel Oteng-Pabi, Oakland, CA (US); Claus Pelikan, Santa Barbara, CA (US); Devin Scannell, San Francisco, CA (US); Zachariah Serber, Kenwood, CA (US); Jennifer Shock, San Francisco, CA (US); Michael Sneddon, Oakland, CA (US); Xiao Yang, Albany, CA (US)

(73) Assignee: Zymergen Inc., Emeryville, CA (US)

( * ) Notice: Subject to any disclaimer, the term of this patent is extended or adjusted under 35 U.S.C. 154(b) by 0 days.

(21) Appl. No.: 17/177,035

(22) Filed: Feb. 16, 2021

(65) Prior Publication Data
US 2021/0257056 A1 Aug. 19, 2021

Related U.S. Application Data

(60) Provisional application No. 62/976,194, filed on Feb. 13, 2020, provisional application No. 62/796,198, filed on Feb. 13, 2020, provisional application No. 62/976,201, filed on Feb. 13, 2020.

(51) Int. Cl.
*G01N 33/48* (2006.01)
*G01N 33/50* (2006.01)
*G16B 35/20* (2019.01)
*G16B 35/10* (2019.01)
*G06N 3/12* (2006.01)
*G16B 5/00* (2019.01)
*G06N 3/02* (2006.01)
*G16B 30/00* (2019.01)

(52) U.S. Cl.
CPC .......... *G16B 35/20* (2019.02); *G06N 3/02* (2013.01); *G06N 3/123* (2013.01); *G16B 5/00* (2019.02); *G16B 30/00* (2019.02); *G16B 35/10* (2019.02)

(58) Field of Classification Search
CPC .......... G16B 35/20; G16B 30/00; G16B 5/00; G16B 35/10; G06N 3/123; G06N 3/02
See application file for complete search history.

(56) References Cited

U.S. PATENT DOCUMENTS

| 5,695,934 | A | 12/1997 | Brenner |
|---|---|---|---|
| 5,714,330 | A | 2/1998 | Brenner et al. |
| 5,750,341 | A | 5/1998 | Macevicz |
| 5,858,656 | A | 1/1999 | Deugau et al. |
| 5,912,148 | A | 6/1999 | Eggerding |
| 5,935,793 | A | 8/1999 | Wong |
| 6,090,592 | A | 7/2000 | Adams et al. |
| 6,130,073 | A | 10/2000 | Eggerding |
| 6,210,891 | B1 | 4/2001 | Nyren et al. |
| 6,258,568 | B1 | 7/2001 | Nyren |
| 6,261,782 | B1 | 7/2001 | Lizardi et al. |
| 6,300,070 | B1 | 10/2001 | Boles et al. |
| 6,306,597 | B1 | 10/2001 | Macevicz |
| 6,432,360 | B1 | 8/2002 | Church |
| 6,441,148 | B1 | 8/2002 | Radomski et al. |
| 6,485,944 | B1 | 11/2002 | Church et al. |
| 6,511,803 | B1 | 1/2003 | Church et al. |
| 6,787,308 | B2 | 9/2004 | Balasubramanian et al. |
| 6,833,246 | B2 | 12/2004 | Balasubramanian |
| 6,969,488 | B2 | 11/2005 | Bridgham et al. |
| 7,115,400 | B1 | 10/2006 | Adessi et al. |
| 7,902,122 | B2 | 3/2011 | Jung et al. |
| 8,478,544 | B2 | 7/2013 | Coldwell et al. |
| 9,372,959 | B2 | 6/2016 | Mande et al. |
| 9,715,573 | B2 | 7/2017 | Putnam et al. |
| 9,988,624 | B2 | 6/2018 | Berber et al. |
| 10,227,585 | B2 | 3/2019 | Shendure et al. |
| 10,457,934 | B2 | 10/2019 | Green et al. |
| 10,526,641 | B2 | 1/2020 | Fields et al. |
| 10,557,133 | B2 | 2/2020 | Steemers et al. |

(Continued)

FOREIGN PATENT DOCUMENTS

| EP | 0972081 B1 | 6/2007 |
|---|---|---|
| EP | 2977455 B1 | 4/2020 |

(Continued)

OTHER PUBLICATIONS

Hannigan et al. A deep learning genome-mining strategy for biosynthetic gene cluster prediction. Nucleic Acids Research, vol. 476, Aug. 10, 2019, article e110, 13 pages.*

(Continued)

*Primary Examiner* — Russell S Negin
(74) *Attorney, Agent, or Firm* — Cooley LLP

(57) ABSTRACT

The present disclosure provides methods and systems for identifying natural product-encoding multi-gene clusters (MGCs). In some embodiments, the present disclosure also teaches methods for producing sequenced and assembled metagenomic libraries that are amenable to MGC search bioinformatic tools and techniques.

25 Claims, 36 Drawing Sheets

(56) References Cited

U.S. PATENT DOCUMENTS

| | | |
|---|---|---|
| 10,557,166 B2 | 2/2020 | Drmanac et al. |
| 10,577,601 B2 | 3/2020 | Shendure et al. |
| 10,577,603 B2 | 3/2020 | Steemers et al. |
| 10,590,484 B2 | 3/2020 | Korlach et al. |
| 10,726,942 B2 | 7/2020 | Drmanac et al. |
| 10,907,188 B2 | 2/2021 | Bowman et al. |
| 2003/0187587 A1 | 10/2003 | Swindells et al. |
| 2005/0130173 A1 | 6/2005 | Leamon et al. |
| 2007/0020640 A1 | 1/2007 | Mccloskey et al. |
| 2007/0185656 A1* | 8/2007 | Schadt ............... G01N 33/6803 702/19 |
| 2009/0026082 A1 | 1/2009 | Rothberg et al. |
| 2009/0068645 A1 | 3/2009 | Sibson |
| 2009/0098555 A1 | 4/2009 | Roth et al. |
| 2009/0127589 A1 | 5/2009 | Rothberg et al. |
| 2010/0137143 A1 | 6/2010 | Rothberg et al. |
| 2010/0188073 A1 | 8/2010 | Rothberg et al. |
| 2010/0197507 A1 | 8/2010 | Rothberg et al. |
| 2010/0222237 A1 | 9/2010 | Stemmer et al. |
| 2010/0227329 A1 | 9/2010 | Cuppens |
| 2010/0273219 A1 | 10/2010 | May et al. |
| 2010/0301398 A1 | 12/2010 | Rothberg et al. |
| 2010/0304982 A1 | 12/2010 | Hinz et al. |
| 2011/0015096 A1 | 1/2011 | Chiu et al. |
| 2011/0257023 A1 | 10/2011 | Serber et al. |
| 2011/0257031 A1 | 10/2011 | Bodeau et al. |
| 2012/0028814 A1 | 2/2012 | Toloue et al. |
| 2013/0124574 A1 | 5/2013 | Swindells et al. |
| 2017/0159045 A1 | 6/2017 | Serber et al. |
| 2018/0119203 A1 | 5/2018 | Rice et al. |
| 2018/0373833 A1 | 12/2018 | Merwin et al. |
| 2019/0032113 A1 | 1/2019 | Troll et al. |
| 2019/0241933 A1 | 8/2019 | Green, Jr. et al. |
| 2020/0123539 A1 | 4/2020 | Apte et al. |
| 2020/0160936 A1 | 5/2020 | Fang et al. |
| 2020/0202144 A1 | 6/2020 | Porter et al. |
| 2020/0216839 A1 | 7/2020 | Shendure et al. |

FOREIGN PATENT DOCUMENTS

| | | |
|---|---|---|
| EP | 3636757 A1 | 4/2020 |
| EP | 3207169 B1 | 7/2020 |
| EP | 3377625 B1 | 7/2020 |
| WO | WO 2000/018957 A1 | 4/2000 |
| WO | WO 2006/084132 A2 | 8/2006 |
| WO | WO 2009/130520 A1 | 10/2009 |
| WO | WO 2016/073690 A1 | 5/2016 |
| WO | WO 2017/196795 A2 | 11/2017 |
| WO | WO 2018/222507 A1 | 12/2018 |
| WO | WO 2019/055816 A1 | 3/2019 |
| WO | WO 2019/094636 A1 | 5/2019 |
| WO | WO 2019/147753 A1 | 8/2019 |
| WO | WO 2019/152543 A1 | 8/2019 |
| WO | WO 2020/157684 A1 | 8/2020 |
| WO | WO 2020/165433 A1 | 8/2020 |

OTHER PUBLICATIONS

Roy et al. Refined physical map of the spinal muscular atrophy gene (SMA) region at 5q 13 based on YAC and cosmid contiguous arrays. Genomics, vol. 26, pp. 451-460. (Year: 1995).*

Quadri et al. Identification of a *Mycobacterium tuberculosis* gene cluster encoding the biosynthetic enzymes for assembly of the virulence-conferring siderophore mycobactin. Chemistry & Biology, vol. 5, pp. 631-645. (Year: 1998).*

Baltz. Natural product drug discovery in the genomic era: realities, conjectures, misconceptions, and opportunities. Journal of Industrial Microbiology & Biotechnology, vol. 46, Nov. 27, 2018, pp. 281-299.*

U.S. Appl. No. 17/175,120, filed Feb. 12, 2021, Tymoshenko, et al.

[Author Unknown] GPU-Based Deep Learning Inference: A Performance and Power Analysis, NVidia Whitepaper, Nov. 2015, 12 pages.

Adessi, Céline, et al. "Solid phase DNA amplification: characterisation of primer attachment and amplification mechanisms." Nucleic Acids Research 28.20 (2000): e87-e87.

Ahmadi, Elahe, et al. "Rapid and economical protocols for genomic and metagenomic DNA extraction from oak (*Quercus brantii* Lindl.)." Annals of Forest Science 75.2 (2018): 1-14.

Alanjary, Mohammad, et al. "The Antibiotic Resistant Target Seeker (ARTS), an exploration engine for antibiotic cluster prioritization and novel drug target discovery." Nucleic Acids Research 45.W1 (2017): W42-W48.

Allen, J.E., et al. "Computational gene prediction using multiple sources of evidence." Genome Research 14.1 (2004): 142-148.

Allen, J.E., et al. "JIGSAW: integration of multiple sources of evidence for gene prediction." Bioinformatics 21.18 (2005): 3596-3603.

Alteio, L. V., et al. "Complementary metagenomic approaches improve reconstruction of microbial diversity in a forest soil." mSystems 5.2 (2020): e00768-19.

Altschul, S.F., et al. "Basic local alignment search tool." J Mol Biol. Oct. 5, 1990; 215(3): 403-410.

Altschul, S.F., et al. "Gapped BLAST and PSI-BLAST: a new generation of protein database search programs". Nucleic Acids Res. Sep. 1, 1997; 25(17):3389-3402.

Amann, Rudolf I., et al. "Phylogenetic identification and in situ detection of individual microbial cells without cultivation." Microbiological Reviews 59.1 (1995): 143-169.

Amarasinghe, Shanika L., et al. "Opportunities and challenges in long-read sequencing data analysis." Genome Biology 21.1 (2020): 1-16.

Anand, Swadha, et al. "SBSPKS: structure based sequence analysis of polyketide synthases." Nucleic acids research 38.suppl_2 (2010): W487-W496.

Anderson, Christopher L., and Samodha C. Fernando. "Insights into rumen microbial biosynthetic gene cluster diversity through genome-resolved metagenomics." bioRxiv May 20, 2020, https://www.biorxiv.org/content/10.1101/2020.05.19.105130v1.full.pdf, pp. 1-31.

Ardui, Simon, et al. "Detecting AGG interruptions in females with a FMR1 premutation by long-read single-molecule sequencing: a 1 year clinical experience." Frontiers in Genetics 9 (2018): 150.

Astier, Yann, et al. "Toward single molecule DNA sequencing: direct identification of ribonucleoside and deoxyribonucleoside 5'-monophosphates by using an engineered protein nanopore equipped with a molecular adapter." Journal of the American Chemical Society 128.5 (2006): 1705-1710.

Ayuso-Sacido, A., and O. Genilloud. "New PCR primers for the screening of NRPS and PKS-I systems in actinomycetes: detection and distribution of these biosynthetic gene sequences in major taxonomic groups." Microbial Ecology 49.1 (2005): 10-24.

Badger, Jonathan H., et al. "CRITICA: coding region identification tool invoking comparative analysis." Molecular Biology and Evolution 16.4 (1999): 512-524.

Bag, Satyabrata, et al. "An improved method for high quality metagenomics DNA extraction from human and environmental samples." Scientific Reports 6.1 (2016): 1-9.

Bajusz, David, et al. "Why is Tanimoto index an appropriate choice for fingerprint-based similarity calculations?." Journal of Cheminformatics 7.1 (2015): 1-13.

Bankevich, Anton, et al. "SPAdes: a new genome assembly algorithm and its applications to single-cell sequencing." Journal of Computational Biology 19.5 (2012): 455-477.

Baranašić, Damir, et al. "Predicting substrate specificity of adenylation domains of nonribosomal peptide synthetases and other protein properties by latent semantic indexing." Journal of Industrial Microbiology and Biotechnology 41.2 (2014): 461-467.

Baxevanis, Andreas D., and Alex Bateman. "The importance of biological databases in biological discovery." Current Protocols in Bioinformatics Unit 1.1, Supplement 34 (2011): 1.1.1-1.1.6, 6 pages.

Bennett, Simon T., et al. "Toward the $1000 human genome." Pharmacogenomics 6.4 (2005): 373-382.

Bentley, David R., et al. "Accurate whole human genome sequencing using reversible terminator chemistry." Nature 456.7218 (2008): 53-59.

(56) References Cited

OTHER PUBLICATIONS

Besemer, John, and Mark Borodovsky. "GeneMark: web software for gene finding in prokaryotes, eukaryotes and viruses." Nucleic Acids Research 33.suppl_2 (2005): W451-W454.
Blin, Kai, et al. "antiSMASH 2.0—a versatile platform for genome mining of secondary metabolite producers." Nucleic Acids Research 41.W1 (2013): W204-W212.
Blin, Kai, et al. "antiSMASH 4.0—improvements in chemistry prediction and gene cluster boundary identification." Nucleic Acids Research 45.W1 (2017): W36-W41.
Blin, Kai, et al. "antiSMASH 5.0: updates to the secondary metabolite genome mining pipeline." Nucleic Acids Research 47.W1 (2019): W81-W87.
Blin, Kai, et al. "Improved lanthipeptide detection and prediction for antiSMASH." PLoS One 9.2 (2014): e89420, pp. 1-7.
Blin, Kai, et al. "Recent development of antiSMASH and other computational approaches to mine secondary metabolite biosynthetic gene clusters." Briefings in Bioinformatics 20.4 (2019): 1103-1113. Advance Access Publication Date: Nov. 3, 2017.
Boisvert, Sébastien, et al. "Ray Meta: scalable de novo metagenome assembly and profiling." Genome Biology 13.12 (2012): 1-13.
Bonfield, James K., and Andrew Whitwham. "Gap5—editing the billion fragment sequence assembly." Bioinformatics 26.14 (2010): 1699-1703.
Brenner, Sydney, et al. "Gene expression analysis by massively parallel signature sequencing (MPSS) on microbead arrays." Nature Biotechnology 18.6 (2000): 630-634.
Bryant, Douglas W., et al. "QSRA—a quality-value guided de novo short read assembler." BMC Bioinformatics 10.1 (2009): 1-6.
Burge, Christopher B., et al. "Finding the genes in genomic DNA." Current Opinion in Structural Biology 8.3 (1998): 346-354.
Burton, Joshua N., et al. "Species-Level Deconvolution of Metagenome Assemblies with Hi-C-Based Contact Probability Maps". G3 Genes|Genomes|Genetics Jul. 2014; 4(7): 1339-1346.
Cane, David E., et al. "Exploration and mining of the bacterial terpenome." Accounts of Chemical Research 45.3 (2012): 463-472.
Carneiro, Mauricio O., et al. "Pacific biosciences sequencing technology for genotyping and variation discovery in human data." BMC Genomics 13.1 (2012): 1-7.
Chaisson, Mark J, and Pavel A Pevzner. "Short read fragment assembly of bacterial genomes." Genome Research 18.2 (2008): 324-330.
Chanson, Anaïs, et al. "Assessing biosynthetic gene cluster diversity in a multipartite nutritional symbiosis between herbivorous turtle ants and conserved gut symbionts." bioRxiv (2020), https://www.biorxiv.org/content/biorxiv/early/2020/05/07/2020.05.05.072835.full.pdf, pp. 1-32.
Chevreux, Bastien, et al. "Using the miraEST assembler for reliable and automated mRNA transcript assembly and SNP detection in sequenced ESTs." Genome Research 14.6 (2004): 1147-1159.
Chiara, Matteo, et al. "A-GAME: improving the assembly of pooled functional metagenomics sequence data." BMC Genomics 19.1 (2018), Article No. 44, pp. 1-10.
Cimermancic, Peter, et al. "Insights into secondary metabolism from a global analysis of prokaryotic biosynthetic gene clusters." Cell 158.2 (2014): 412-421.
Condurso, Heather L., et al. "Structure and noncanonical chemistry of nonribosomal peptide biosynthetic machinery." Natural Product Reports 29.10 (2012): 1099-1110.
Cottrell, Matthew T., et al. "Chitinases from uncultured marine microorganisms." Applied and Environmental Microbiology 65.6 (1999): 2553-2557.
Cruz-Morales, Pablo, et al. "Phylogenomic analysis of natural products biosynthetic gene clusters allows discovery of arseno-organic metabolites in model streptomycetes." Genome Biology and Evolution 8.6 (2016): 1906-1916.
Dahl, George E., et al. "Multi-task neural networks for QSAR predictions." arXiv preprint arXiv: 1406.1231 (2014).
Daniel, Rolf. "The metagenomics of soil." Nature Reviews Microbiology 3.6 (2005): 470-478.
Dayarian, Adel, et al. "SOPRA: Scaffolding algorithm for paired reads via statistical optimization." BMC Bioinformatics 11.1 (2010): 1-21.
De Jong, Anne, et al. "BAGEL2: mining for bacteriocins in genomic data." Nucleic Acids Research 38.suppl_2 (2010): W647-W651.
De la Bastide, Melissa, and W. Richard McCombie. "Assembling genomic DNA sequences with PHRAP." Current Protocols in Bioinformatics 17.1 (2007): 11.4.1-11.4.15, 15 pages.
Deamer, David, et al. "Three decades of nanopore sequencing." Nature Biotechnology 34.5 (2016): 518-524.
Delmont, Tom O., et al. "Reconstructing rare soil microbial genomes using in situ enrichments and metagenomics." Frontiers in Microbiology 6 (2015): 358, pp. 1-15.
DeLong, Edward F. "Microbial community genomics in the ocean." Nature Reviews Microbiology 3.6 (2005): 459-469.
Desai, Aarti, et al. "Identification of optimum sequencing depth especially for de novo genome assembly of small genomes using next generation sequencing data." PLoS One 8.4 (2013): e60204.
DiGuistini, Scott, et al. "De novo genome sequence assembly of a filamentous fungus using Sanger, 454 and Illumina sequence data." Genome Biology 10.9 (2009); Article No. R94, pp. 1-12.
Dohm, Juliane C., et al. "Substantial biases in ultra-short read data sets from high-throughput DNA sequencing." Nucleic Acids Research 36.16 (2008): e105, pp. 1-10.
Drmanac, Radoje, et al. "Human genome sequencing using unchained base reads on self-assembling DNA nanoarrays." Science 327.5961 (2010): 78-81.
Dunbar, Kyle L., et al. "Revealing nature's synthetic potential through the study of ribosomal natural product biosynthesis." ACS Chemical Biology 8.3 (2013): 473-487.
Džunková, Mária, et al. "Hybrid sequencing approach applied to human fecal metagenomic clone libraries revealed clones with potential biotechnological applications." PLoS One 7.10 (2012): e47654, pp. 1-7.
Edgar, Robert C. "MUSCLE: multiple sequence alignment with high accuracy and high throughput." Nucleic Acids Research 32.5 (2004): 1792-1797.
Eid, John, et al. "Real-time DNA sequencing from single polymerase molecules." Science 323.5910 (2009): 133-138.
Feldmeyer, Barbara, et al. "Short read Illumina data for the de novo assembly of a non-model snail species transcriptome (Radix balthica, Basommatophora, Pulmonata), and a comparison of assembler performance." BMC Genomics 12.1 (2011): 1-12.
Fitzpatrick, Kelly A., et al. "Practical method for extraction of PCR-quality DNA from environmental soil samples." Applied and Environmental Microbiology 76.13 (2010): 4571-4573.
Flores, Emiliano Pereira. "Improvements in natural product biosynthetic gene clusters research and functional trait-based approaches in metagenomics". Diss. Department of Life Science and Chemistry, Jacobs University Bremen, Sep. 3, 2019, https://d-nb.info/1205545018/34, 152 pages.
Gerner, Samuel M., et al. "Assessment of urban microbiome assemblies with the help of targeted in silico gold standards." Biology Direct 13.1 (2018), Article No. 22, pp. 1-21.
Gnerre, Sante, et al. "High-quality draft assemblies of mammalian genomes from massively parallel sequence data." Proceedings of the National Academy of Sciences 108.4 (2011): 1513-1518.
Gregory, Ann C., et al. "The gut virome database reveals age-dependent patterns of virome diversity in the human gut." Cell Host & Microbe 28.5 (2020): 724-740.
Gremme, Gordon, et al. "Engineering a software tool for gene structure prediction in higher organisms." Information and Software Technology 47.15 (2005): 965-978.
Grettenberger, Christen L., and Trinity L. Hamilton. "Metagenome assembled genomes of novel taxa from an acid mine drainage environment." bioRxiv (2020), https://www.biorxiv.org/content/biorxiv/early/2020/07/03/2020.07.02.185728.full.pdf, 30 pages.
Gross, S.S., et al. "Using multiple alignments to improve gene prediction". J Comput Biol. Mar. 2006;13(2):379-393.
Guthals, Adrian, et al. "The spectral networks paradigm in high throughput mass spectrometry." Molecular BioSystems 8.10 (2012): 2535-2544.

(56) References Cited

OTHER PUBLICATIONS

Haft, Daniel H., et al. "TIGRFAMs: a protein family resource for the functional identification of proteins." Nucleic Acids Research 29.1 (2001): 41-43.
Handelsman, Jo, et al. "Molecular biological access to the chemistry of unknown soil microbes: a new frontier for natural products." Chemistry & Biology 5.10 (1998): R245-R249.
Henne, Anke, et al. "Screening of environmental DNA libraries for the presence of genes conferring lipolytic activity on Escherichia coli." Applied and Environmental Microbiology 66.7 (2000): 3113-3116.
Hertweck, Christian. "The biosynthetic logic of polyketide diversity." Angewandte Chemie International Edition 48.26 (2009): 4688-4716.
Hong, Jiong, et al. "Cloning and functional expression of thermostable β-glucosidase gene from Thermoascus aurantiacus." Applied Microbiology and Biotechnology 73.6 (2007): 1331-1339.
Howe, Adina Chuang, et al. "Tackling soil diversity with the assembly of large, complex metagenomes." Proceedings of the National Academy of Sciences 111.13 (2014): 4904-4909.
Jackman, Shaun D., et al. "ABySS 2.0: resource-efficient assembly of large genomes using a Bloom filter." Genome Research 27.5 (2017): 768-777.
Jain, Miten, et al. "Nanopore sequencing and assembly of a human genome with ultra-long reads." Nature Biotechnology 36.4 (2018): 338-345.
Jaswal, Rajneesh, et al. "Metagenomics-guided survey, isolation, and characterization of uranium resistant microbiota from the Savannah River Site, USA." Genes 10.5 (2019): 325. Epub Apr. 28, 2019.
Jeck, William R., et al. "Extending assembly of short DNA sequences to handle error." Bioinformatics 23.21 (2007): 2942-2944.
Kale, Andrew J., et al. "Bacterial self-resistance to the natural proteasome inhibitor salinosporamide A." ACS Chemical Biology 6.11 (2011): 1257-1264.
Kang, Hahk-Soo, and Sean F. Brady. "Arimetamycin A: improving clinically relevant families of natural products through sequence-guided screening of soil metagenomes." Angew Chem Int Ed Engl. 52.42 (2013): 11063-11067. Epub Sep. 3, 2013.
Karlin, S., et al. "Applications and statistics for multiple high-scoring segments in molecular sequences". Proc Natl Acad Sci U S A. Jun. 15, 1993;90(12):5873-5877.
Karlin, S., et al. "Methods for assessing the statistical significance of molecular sequence features by using general scoring schemes". Proc Natl Acad Sci U S A. Mar. 1990;87(6):2264-2268.
Kashyap, Hirak, et al. "Big data analytics in bioinformatics: A machine learning perspective." Journal of Latex Class Files (2014); 13(9): 20 pages. arXiv preprint arXiv: 1506.05101 (2015).
Katz, Leonard, and Richard H. Baltz. "Natural product discovery: past, present, and future." Journal of Industrial Microbiology and Biotechnology 43.2-3 (2016): 155-176.
Kersten, Roland D., et al. "A mass spectrometry-guided genome mining approach for natural product peptidogenomics." Nature Chemical Biology 7.11 (2011): 794-802.
Kersten, Roland D., et al. "Glycogenomics as a mass spectrometry-guided genome-mining method for microbial glycosylated molecules." Proceedings of the National Academy of Sciences 110.47 (2013): E4407-E4416.
Khaldi, Nora, et al. "SMURF: genomic mapping of fungal secondary metabolite clusters." Fungal Genetics and Biology 47.9 (2010): 736-741.
Khayatt, Barzan I., et al. "Classification of the adenylation and acyl-transferase activity of NRPS and PKS systems using ensembles of substrate specific hidden Markov models." PLoS One 8.4 (2013): e62136, pp. 1-10.
Khosla, Chaitan, et al. "Tolerance and specificity of polyketide synthases." Annual Review of Biochemistry 68.1 (1999): 219-253.
Kim, Jae Bum, et al. "Polony multiplex analysis of gene expression (PMAGE) in mouse hypertrophic cardiomyopathy." Science 316. 5830 (2007): 1481-1484.

Koren, Sergey, et al. "An algorithm for automated closure during assembly." BMC Bioinformatics 11.1 (2010): 1-7.
Korf I, Flicek P, et al. Integrating genomic homology into gene structure prediction. Bioinformatics (2001);17 Suppl 1:S140-8.
Kouprina, Natalay, and Vladimir Larionov. "Selective isolation of genomic loci from complex genomes by transformation-associated recombination cloning in the yeast Saccharomyces cerevisiae." Nature Protocols 3.3 (2008): 371-377.
Krogh, Anders. "Two methods for improving performance of an HMM and their application for gene finding." Proc Int Conf Intell Syst Mol Biol. (1997); 5:179-186.
Kuhn, Ramona, et al. "Comparison of ten different DNA extraction procedures with respect to their suitability for environmental samples." Journal of Microbiological Methods 143 (2017): 78-86.
Lam, Kathy N., et al. "Evaluation of a pooled strategy for high-throughput sequencing of cosmid clones from metagenomic libraries." PLoS One 9.6 (2014): e98968.
Lazarevic, Vladimir, et al. "Analysis of the salivary microbiome using culture-independent techniques." Journal of Clinical Bioinformatics 2.1 (2012): 1-8.
Leng, Xiaoyan, and Hans-Georg Müller. "Classification using functional data analysis for temporal gene expression data." Bioinformatics 22.1 (2006): 68-76.
Li, Dinghua, et al. "MEGAHIT: an ultra-fast single-node solution for large and complex metagenomics assembly via succinct de Bruijn graph." Bioinformatics 31.10 (2015): 1674-1676.
Li, Michael H.T., et al. "Automated genome mining for natural products." BMC bioinformatics 10.1 (2009): 1-10.
Libbrecht, Maxwell W., and William Stafford Noble. "Machine learning applications in genetics and genomics." Nature Reviews Genetics 16.6 (2015): 321-332.
Linard, Benjamin, et al. "Metagenome skimming of insect specimen pools: potential for comparative genomics." Genome Biology and Evolution 7.6 (2015): 1474-1489.
Linhart, Chaim, and Ron Shamir. "The degenerate primer design problem: theory and applications." Journal of Computational Biology 12.4 (2005): 431-456.
Liu, Yongchao, et al. "Parallelized short read assembly of large genomes using de Bruijn graphs." BMC Bioinformatics 12.1 (2011): 1-10.
Locey, Kenneth J., and Jay T. Lennon. "Scaling laws predict global microbial diversity." Proceedings of the National Academy of Sciences 113.21 (2016): 5970-5975.
Luo, Ruibang, et al. "SOAPdenovo2: an empirically improved memory-efficient short-read de novo assembler." Gigascience 1.1 (2012): 2047-217X, pp. 1-6.
Luo, Yunzi, Ryan E. Cobb, and Huimin Zhao. "Recent advances in natural product discovery." Current Opinion in Biotechnology 30 (2014): 230-237.
MacLean, Daniel, et al. "Application of 'next-generation' sequencing technologies to microbial genetics." Nature Reviews Microbiology 7.4 (2009): 96-97.
Majoros, William H., et al. "Efficient decoding algorithms for generalized hidden Markov model gene finders." BMC Bioinformatics 6.1 (2005): 1-13.
Manion et al. "De novo assembly of short sequence reads with nextgene™ software & condensation tool." SoftGenetics LLC, PA, USA. Feb. 2009, pp. 1-3. https://softgenetics.com/PDF/DenovoAssembly_SSR_AppNote.pdf.
Margulies, Marcel, et al. "Genome sequencing in microfabricated high-density picolitre reactors." Nature 437.7057 (2005): 376-380.
Marotz, Clarisse, et al. "DNA extraction for streamlined metagenomics of diverse environmental samples." Biotechniques 62.6 (2017): 290-293.
McCranie, Emilianne K., et al. "Bioactive oligosaccharide natural products." Natural Product Reports 31.8 (2014): 1026-1042.
McLean, et al., "Candidate phylum TM6 genome recovered from a hospital sink biofilm provides genomic insights into this uncultivated phylum". Proc Natl Acad Sci U S A. Jun. 2, 20135; 110(26): E2390-2399. Epub Jun. 10, 2013.
Medema, Marnix H., and Michael A. Fischbach. "Computational approaches to natural product discovery." Nature Chemical Biology 11.9 (2015): 639-648.

(56) References Cited

OTHER PUBLICATIONS

Medema, Marnix H., et al. "antiSMASH: rapid identification, annotation and analysis of secondary metabolite biosynthesis gene clusters in bacterial and fungal genome sequences." Nucleic Acids Research 39.suppl_2 (2011): W339-W346.

Medema, Marnix H., et al. "Minimum information about a biosynthetic gene cluster." Nature Chemical Biology 11.9 (2015): 625-631.

Medema, Marnix H., et al. "Pep2Path: automated mass spectrometry-guided genome mining of peptidic natural products." PLoS Computational Biology 10.9 (2014): e1003822, pp. 1-7.

Menzel, P., et al. "Fast and sensitive taxonomic classification for metagenomics with Kaiju." Nature Communications 7.1 (2016): 1-9.

Mitra, Robi D., et al. "Fluorescent in situ sequencing on polymerase colonies." Analytical Biochemistry 320.1 (2003): 55-65.

Mohimani, Hosein, et al. "Automated genome mining of ribosomal peptide natural products." ACS Chemical Biology 9.7 (2014): 1545-1551.

Mohimani, Hosein, et al. "NRPquest: coupling mass spectrometry and genome mining for nonribosomal peptide discovery." Journal of Natural Products 77.8 (2014): 1902-1909.

Mullikin, James C, and Zemin Ning. "The phusion assembler." Genome Research 13.1 (2003): 81-90.

Myers, Eugene W., and Webb Miller. "Optimal alignments in linear space." Comput Appl Biosci. 4.1 (1988): 11-17.

Navarro-Muñoz, Jorge C., et al. "A computational framework for systematic exploration of biosynthetic diversity from large-scale genomic data." Biorxiv (2018); 445270, https://www.biorxiv.org/content/10.1101/445270v1.full.pdf, pp. 1-22.

Navarro-Muñoz, Jorge C., et al. "A computational framework to explore large-scale biosynthetic diversity." Nature Chemical Biology 16.1 (2020): 60-68.

Needleman, S.B. & Wunsch, C.D. "A general method applicable to the search for similarities in the amino acid sequences of two proteins." J. Mol. Biol. 48.3 (1970), pp. 443-453.

Nurk, S., et al., "Assembling single-cell genomes and mini-metagenomes from chimeric MDA products." J Comput Biol. Oct. 2013; 20(10): 714-737.

Owen, Jeremy G., et al. "Multiplexed metagenome mining using short DNA sequence tags facilitates targeted discovery of epoxyketone proteasome inhibitors." Proceedings of the National Academy of Sciences 112.14 (2015): 4221-4226.

Pace, Norman R. "A molecular view of microbial diversity and the biosphere." Science 276.5313 (1997): 734-740.

Palazzotto, Emilia, and Tilmann Weber. "Omics and multi-omics approaches to study the biosynthesis of secondary metabolites in microorganisms." Current Opinion in Microbiology 45 (2018): 109-116.

Parra, Genís, et al. "Comparative gene prediction in human and mouse." Genome Research 13.1 (2003): 108-117.

Parry, Neil J., et al. "Biochemical characterization and mechanism of action of a thermostable β-glucosidase purified from Thermoascus aurantiacus." Biochemical Journal 353.1 (2001): 117-127.

Paszkiewicz, Konrad, and David J. Studholme. "De novo assembly of short sequence reads." Briefings in Bioinformatics 11.5 (2010): 457-472.

PCT/US2021/018050, International Search Report and Written Opinion, dated Apr. 29, 2021, 27 pages.

PCT/US2021/018048, Invitation to Pay Additional Fees dated May 25, 2021, 2 pages.

Pearson, W.R., "Searching protein sequence libraries: comparison of the sensitivity and selectivity of the Smith-Waterman and FASTA algorithms". Genomics (Nov. 1991); 11(3): 635-650.

Pearson, WR., et al. "Improved tools for biological sequence comparison." Proceedings of the National Academy of Sciences 85.8 (1988): 2444-2448.

Pedersen, Jakob Skou, et al. "Gene finding with a hidden Markov model of genome structure and evolution." Bioinformatics 19.2 (2003): 219-227.

Pell, Jason, et al. "Scaling metagenome sequence assembly with probabilistic de Bruijn graphs." Proceedings of the National Academy of Sciences 109.33 (2012): 13272-13277. Epub Jul. 30, 2012.

Peng, Yu, et al. "IDBA—a practical iterative de Bruijn graph de novo assembler." In: Berger B. (eds) Research in Computational Molecular Biology. RECOMB 2010. Lecture Notes in Computer Science, vol. 6044. Springer, Berlin, Heidelberg, pp. 426-440, 15 pages.

Pennisi, Elizabeth. "Semiconductors inspire new sequencing technologies." Science (2010); 5970:1190-1190.

Pérez-Cobas, Ana Elena, et al. "Metagenomic approaches in microbial ecology: an update on whole-genome and marker gene sequencing analyses." Microbial Genomics 6.8 (2020), pp. 1-22.

Piel, Jörn. "Biosynthesis of polyketides by trans-AT polyketide synthases." Natural Product Reports 27.7 (2010): 996-1047.

Piao, Hailan, et al. "Identification of novel biomass-degrading enzymes from genomic dark matter: populating genomic sequence space with functional annotation." Biotechnology and Bioengineering 111.8 (2014): 1550-1565.

Pollard, Martin O., et al. "Long reads: their purpose and place." Human Molecular Genetics 27.R2 (2018): R234-R241.

Porteous, L. Arlene, et al. "An effective method to extract DNA from environmental samples for polymerase chain reaction amplification and DNA fingerprint analysis." Current Microbiology 29.5 (1994): 301-307.

Prompramote, et al. "Machine learning in bioinformatics." Bioinformatics Technologies. Springer Berlin Heidelberg (2005); pp. 117-153.

Quail, Michael A., et al. "A tale of three next generation sequencing platforms: comparison of Ion Torrent, Pacific Biosciences and Illumina MiSeq sequencers." BMC Genomics 13.1 (2012): 1-13.

Quince, Christopher, et al. "Shotgun metagenomics, from sampling to analysis." Nature Biotechnology 35.9 (2017): 833-844.

Ren, Hengqian, et al. "Breaking the silence: new strategies for discovering novel natural products." Current Opinion in Biotechnology 48 (2017): 21-27.

Rondon, Michelle R., et al. "Cloning the soil metagenome: a strategy for accessing the genetic and functional diversity of uncultured microorganisms." Applied and Environmental Microbiology 66.6 (2000): 2541-2547.

Röttig, Marc, et al. "NRPSpredictor2—a web server for predicting NRPS adenylation domain specificity." Nucleic Acids Research 39.suppl_2 (2011): W362-W367.

Sahli, Mohammed, and Tetsuo Shibuya. "An Algorithm for Classifying DNA Reads." 2012 International Conference on Bioscience, Biochemistry and Bioinformatics, IPCBEE vol. 31 (2012); pp. 59-63.

Sahli, Mohammed, and Tetsuo Shibuya. "Arapan-S: a fast and highly accurate whole-genome assembly software for viruses and small genomes." BMC Research Notes 5.1 (2012): 1-11.

Santos-Aberturas, Javier, et al. "Uncovering the unexplored diversity of thioamidated ribosomal peptides in Actinobacteria using the RiPPER genome mining tool." Nucleic Acids Research 47.9 (2019): 4624-4637.

Schiex, Thomas, et al. "EuGene: an eukaryotic gene finder that combines several sources of evidence." International Conference on Biology, Informatics, and Mathematics. Springer, Berlin, Heidelberg, (2000): 111-125.

Schmidt, Bertil, et al. "A fast hybrid short read fragment assembly algorithm." Bioinformatics 25.17 (2009): 2279-2280.

Sebat, Jonathan L., Frederick S. Colwell, and Ronald L. Crawford. "Metagenomic profiling: microarray analysis of an environmental genomic library." Applied and Environmental Microbiology 69.8 (2003): 4927-4934.

SenGupta, Dhruba J., et al. "Whole-genome sequencing for high-resolution investigation of methicillin-resistant Staphylococcus aureus epidemiology and genome plasticity." Journal of Clinical Microbiology 52.8 (2014): 2787-2796.

Shamim, Kashif, et al. "Rapid and efficient method to extract metagenomic DNA from estuarine sediments." 3 Biotech 7.3 (2017): 1-8.

Shendure, Jay, et al. "Accurate multiplex polony sequencing of an evolved bacterial genome." Science 309.5741 (2005): 1728-1732.

(56) References Cited

OTHER PUBLICATIONS

Shevade, Shirish Krishnaj, and S. Sathiya Keerthi. "A simple and efficient algorithm for gene selection using sparse logistic regression." Bioinformatics 19.17 (2003): 2246-2253.
Sievers, Fabian, et al. "Fast, scalable generation of high-quality protein multiple sequence alignments using Clustal Omega." Molecular Systems Biology 7.1 (2011): 539.
Simeonidis, Evangelos, and Nathan D. Price. "Genome-scale modeling for metabolic engineering." Journal of Industrial Microbiology and Biotechnology 42.3 (2015): 327-338.
Simon, H. Ye, et al. "Benchmarking metagenomics tools for taxonomic classification." Cell 178.4 (2019): 779-794.
Simpson, Jared T., and Richard Durbin. "Efficient de novo assembly of large genomes using compressed data structures." Genome Research 22.3 (2012): 549-556.
Singhal, Poonam, et al. "Prokaryotic gene finding based on physicochemical characteristics of codons calculated from molecular dynamics simulations." Biophysical Journal 94.11 (2008): 4173-4183.
Skinnider, Michael A., et al. "Comprehensive prediction of secondary metabolite structure and biological activity from microbial genome sequences." Nature Communications 11.1 (2020): 1-9.
Skinnider, Michael A., et al. "PRISM 3: expanded prediction of natural product chemical structures from microbial genomes." Nucleic Acids Research 45.W1 (2017): W49-W54.
Small, Jack, et al. "Direct detection of 16S rRNA in soil extracts by using oligonucleotide microarrays." Applied and Environmental Microbiology 67.10 (2001): 4708-4716.
Smith, Temple F., and Michael S. Waterman. "Identification of common molecular subsequences." Journal of Molecular Biology 147.1 (1981): 195-197.
Solovyev, Victor V., et al. "Predicting internal exons by oligonucleotide composition and discriminant analysis of spliceable open reading frames." Nucleic Acids Research 22.24(1994): 5156-5163.
Sonnhammer, Erik LL, et al. "Pfam: multiple sequence alignments and HMM-profiles of protein domains." Nucleic Acids Research 26.1 (1998): 320-322.
Stanke, Mario, et al. "Gene prediction with a hidden Markov model and a new intron submodel." Bioinformatics 19.Suppl_2 (2003): ii215-ii225.
Starcevic, Antonio, et al. "ClustScan: an integrated program package for the semi-automatic annotation of modular biosynthetic gene clusters and in silico prediction of novel chemical structures." Nucleic Acids Research 36.21 (2008): 6882-6892.
Stewart, Eric J. "Growing unculturable bacteria." Journal of Bacteriology 194.16 (2012): 4151-4160.
Sutton, Granger G., et al. "TIGR Assembler: A new tool for assembling large shotgun sequencing projects." Genome Science and Technology 1.1 (1995): 9-19.
Tan, Gao-Yi, et al. "Rational synthetic pathway refactoring of natural products biosynthesis in actinobacteria." Metabolic Engineering 39 (2017): 228-236.
Tenconi, Elodie, et al. "Self-resistance mechanisms to DNA-damaging antitumor antibiotics in actinobacteria." Current Opinion in Microbiology 45 (2018): 100-108.
Thareja, Gaurav, et al. "PadeNA: A Parallel De Novo Assembler." Bioinformatics (2011); Proceedings of the International Conference on Bioinformatics Models, Methods and Algorithms, Rome, Italy, Jan. 26-29, 2011, pp. 196-203.
Tietz, Jonathan I., et al. "A new genome-mining tool redefines the lasso peptide biosynthetic landscape." Nature Chemical Biology 13.5 (2017): 470-478.
Uniprot Accession No. A4WQL8, www.uniprot.org/uniprot/A4WQL8; Date May 29, 2017. Last modified Jun. 2, 2021, downloaded Jul. 6, 2021: pp. 1-5.
Van Dijk, Erwin L., et al. "The third revolution in sequencing technology." Trends in Genetics 34.9 (2018): 666-681.
Van Heel, Auke J., et al. "BAGEL3: automated identification of genes encoding bacteriocins and (non-) bactericidal posttranslationally modified peptides." Nucleic acids research 41.W1 (2013): W448-W453.
Vandova, Gergana A., et al. "Identification of polyketide biosynthetic gene clusters that harbor self-resistance target genes." bioRxiv (2020), https://www.biorxiv.org/content/biorxiv/early/2020/06/02/2020.06.01.128595.full.pdf.
Venter, J. Craig, et al. "Environmental genome shotgun sequencing of the Sargasso Sea." Science 304.5667 (2004): 66-74.
Voelkerding, Karl V., et al. "Next-generation sequencing: from basic research to diagnostics." Clinical chemistry 55.4 (2009): 641-658.
Wajid, Bilal, and Erchin Serpedin. "Review of general algorithmic features for next generation sequence assemblers." Genomics, Proteomics & Bioinformatics 10.2 (2012): 58-73.
Walsh, Christopher T., et al. "Natural products version 2.0: connecting genes to molecules." Journal of the American Chemical Society 132.8 (2010): 2469-2493.
Wang, Lingling, et al. "Metagenomic insights into the carbohydrate-active enzymes carried by the microorganisms adhering to solid digesta in the rumen of cows." PLoS one 8.11 (2013): e78507.
Warren, René L., et al. "Assembling millions of short DNA sequences using SSAKE." Bioinformatics 23.4 (2007): 500-501.
Weber, Tilmann, and Hyun Uk Kim. "The secondary metabolite bioinformatics portal: computational tools to facilitate synthetic biology of secondary metabolite production." Synthetic and Systems Biotechnology 1.2 (2016): 69-79.
Weber, Tilmann, et al. "antiSMASH 3.0—a comprehensive resource for the genome mining of biosynthetic gene clusters." Nucleic Acids Research 43.W1 (2015): W237-W243.
Weber, Tilmann. "In silico tools for the analysis of antibiotic biosynthetic pathways." International Journal of Medical Microbiology 304.3-4 (2014): 230-235.
Wilson, Micheal C., and Jörn Piel. "Metagenomic approaches for exploiting uncultivated bacteria as a resource for novel biosynthetic enzymology." Chemistry & Biology 20.5 (2013): 636-647.
Wingfield, Brenda D et al. "IMA Genome-F 6: Draft genome sequences of Armillaria fuscipes, Ceratocystiopsis minuta, Ceratocystis adiposa, Endoconidiophora laricicola, E. polonica and Penicillium freii DAOMC 242723." IMA Fungus vol. 7.1 (2016): pp. 217-227.
Wu, Liyou, et al. "Development and evaluation of functional gene arrays for detection of selected genes in the environment." Applied and Environmental Microbiology 67.12 (2001): 5780-5790.
Yada, Tetsushi, et al. "Detection of short protein coding regions within the cyanobacterium genome: application of the hidden Markov model." DNA Research 3.6 (1996): 355-361.
Yada, Tetsushi, et al. "Functional prediction of B. subtilis genes from their regulatory sequences." ISMB Proceedings. vol. 5 (1997): 354-357.
Yada, Tetsushi, et al. "Gene recognition in cyanobacterium genomic sequence data using the hidden Markov model." ISMB Proceedings. vol. 96 (1996): 252-260.
Yan, Yan, et al. "Recent developments in self-resistance gene directed natural product discovery." Natural Product Reports 37.7 (2020): 879-892.
Yang, Ying-jie, et al. "Whole transcriptome analysis and gene deletion to understand the chloramphenicol resistance mechanism and develop a screening method for homologous recombination in Myxococcus xanthus." Microbial Cell Factories 18.1 (2019): 1-15.
Ye, Chengxi, et al. "Exploiting sparseness in de novo genome assembly." BMC Bioinformatics 13.6 (2012); Suppl 6(Suppl 6):S1, pp. 1-8.
Yörük, Emre, and Özlem Sefer. "FcMgv1, FcStuA and FcVeA Based Genetic Characterization in Fusarium culmorum (WG Smith)." Journal of Natural Sciences 19.1 (2018): 63-69.
Youngblut, Nicholas D., et al. "Large-scale metagenome assembly reveals novel animal-associated microbial genomes, biosynthetic gene clusters, and other genetic diversity." mSystems 5.6 (2020): e01045-20, pp. 1-15.
Zerbino, Daniel R. "Using the velvet de novo assembler for short-read sequencing technologies." Current Protocols in Bioinformatics 31.1 (2010): 11-5, pp. 1-13.

(56) References Cited

OTHER PUBLICATIONS

Zhou, Jizhong. "Microarrays for bacterial detection and microbial community analysis." Current Opinion in Microbiology 6.3 (2003): 288-294.

Ziemert, Nadine, et al. "The natural product domain seeker NaPDoS: a phylogeny based bioinformatic tool to classify secondary metabolite gene diversity." PLoS One 7.3 (2012): e34064.

Zimin, Aleksey V., et al. "The MaSuRCA genome assembler." Bioinformatics 29.21 (2013): 2669-2677.

\* cited by examiner

Fig. 3
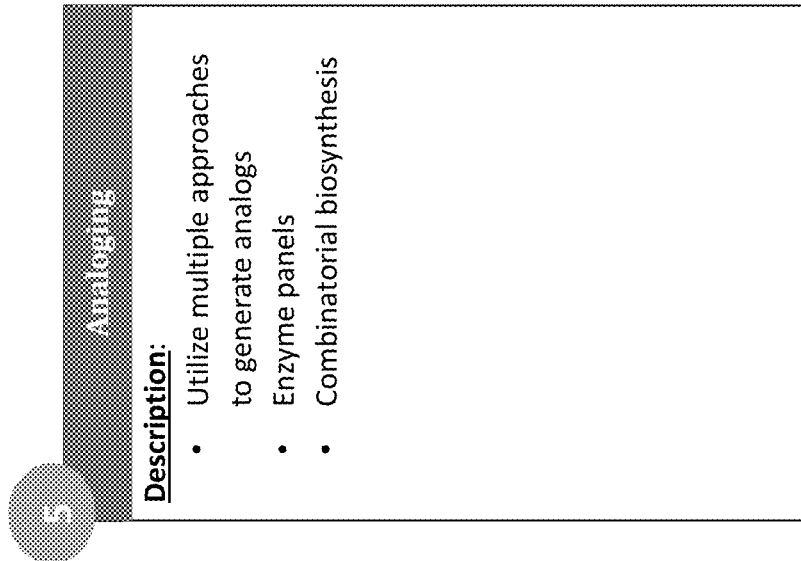
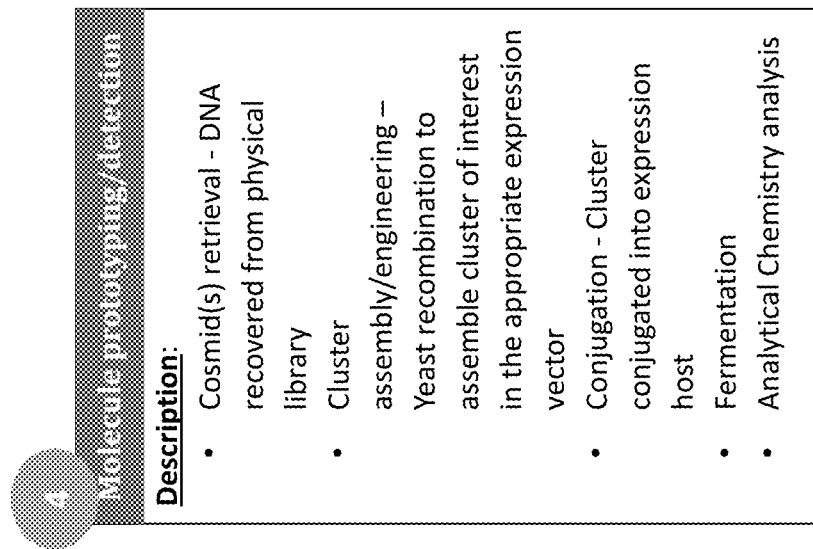

Fig. 11

| Reaction of interest | Challenges with chemical methods | Advantages of bioconversion | Example of enzyme class |
|---|---|---|---|
| Halogenation | Limited straightforward paths to selective fluorination (after assembly of molecular | Reduced # of steps and selective halogenation | • Halogenases |
| Heteroatom alkylation | Difficult to selectively alkylate heteroatoms on complex scaffolds | Access to heteroatoms not readily available in complex | • Methyltransferases (O- and N- specific) |
| Carbon coupling | Limited carbon coupling without increasing the reactivity of carbon/ less likely to involve | carbon-carbon coupling in minimal steps and without | • Lyases |
| Chirality | Selective chirality for complex scaffolds can be difficult (requiring multiple steps) without | Conversion of selective reactive groups to specific | • Transaminanes |

Fig. 27

```
┌─────────────────────────────────────────────────────────────────────────────┐
│ Computationally predict natural product multi-gene cluster feature sets      │
│ within a long-assembly digital metagenomic library.                          │
│                                                                              │
│ For example, by analyzing a long-assembly digital metagenomics library       │
│ with antiSMASH or DeepBGC.                                                   │
└─────────────────────────────────────────────────────────────────────────────┘
                                      ↓
┌─────────────────────────────────────────────────────────────────────────────┐
│ Annotate genes within the predicted natural product multi-gene cluster       │
│ feature sets (or within 1-2 ORFs of the boundaries of said clusters).        │
│                                                                              │
│ For example, by relying on annotations provided by antiSMASH, or based       │
│ on homology to enzymes annotated in MIBiG database.                          │
└─────────────────────────────────────────────────────────────────────────────┘
                                      ↓
┌──────────────────────────────────┐  Discard  ┌──────────────────────────────┐
│ Filter annotated genes from the  │ ────────→ │ • Annotated genes with        │
│ predicted natural product multi- │           │   predicted biosynthetic      │
│ gene cluster feature sets.       │           │   function                    │
└──────────────────────────────────┘           │ • Homologs of known           │
            │ Keep                             │   resistance genes            │
            ↓                                  │   (optional-to enrich for     │
                                               │   new clusters not            │
                                               │   associated with known       │
                                               │   resistance genes.)          │
                                               └──────────────────────────────┘
┌─────────────────────────────────────────────────────────────────────────────┐
│ Select one or more natural product multi-gene cluster features sets that     │
│ comprise at least one of the plurality of filtered genes of interest,        │
│ thereby creating a library of candidate MGC sequences                        │
└─────────────────────────────────────────────────────────────────────────────┘
                                      ↓
┌─────────────────────────────────────────────────────────────────────────────┐
│ Manufacture one or more host cell(s), wherein each manufactured host cell    │
│ comprises a natural product multi-gene cluster feature set from amongst      │
│ the candidate MGC sequences                                                  │
└─────────────────────────────────────────────────────────────────────────────┘
                                      ↓
              ┌──────────────────────────────────────────────┐
              │ Culture the manufactured host cell            │
              └──────────────────────────────────────────────┘
                                      ↓
┌─────────────────────────────────────────────────────────────────────────────┐
│ Analyze the cultures from above for the presence of a natural product,       │
│ wherein said natural product is not present in cultures of control host      │
│ cells lacking the natural product multi-gene cluster feature set present     │
│ in the manufactured host cell                                                │
└─────────────────────────────────────────────────────────────────────────────┘
```

METAGENOMIC LIBRARY AND NATURAL PRODUCT DISCOVERY PLATFORM

CROSS-REFERENCE TO RELATED APPLICATIONS

111 This application claims the benefit of priority to U.S. Provisional Application No. 62/976,194, filed on Feb. 13, 2020, U.S. Provisional Application No. 62/976,198, filed on Feb. 13, 2020, and U.S. Provisional Application No. 62/976,201, filed on Feb. 13, 2020, the contents of which are herein incorporated by reference in their entirety.

FIELD OF THE DISCLOSURE

The present disclosure generally relates to systems and methods for the improvement of natural product discovery. The disclosed systems and methods result in sequenced metagenomic databases that are amenable to in silico natural product discovery pipelines. Methods for identifying and validating new natural product-encoding multi-gene clusters are also provided.

BACKGROUND

Natural products from plants and microorganisms have been a historically important source for clinical drug development and research. The first antibiotic, Penicillin, was discovered in 1928 from a fungus by Alexander Fleming. Today, almost two-thirds of the clinically used antibiotics are derived from *Actinomycetales*, and in total about half of the medicines used today are natural products, or derivatives thereof.

Traditionally, the discovery of natural products in microorganisms has involved cultivating strains under different growth conditions to incite the production of secondary metabolites, and then assaying those secondary metabolites for various medical activities. These traditional approaches however have yielded diminishing returns, as fewer and fewer new natural products are discovered.

The difficulties in natural product discovery have resulted in a deprioritization of natural product research by most pharmaceutical companies in favor of high-throughput screening of synthetic libraries. Yet, natural products have advantages over synthetic molecule libraries, in that they have evolved to interact with proteins and induce biological effects.

There is an ongoing and unmet need for methods, systems, and tools to identify new natural products.

SUMMARY OF THE DISCLOSURE

In some embodiments, the present disclosure teaches novel methods for metagenomic library preparation, sequencing and assembly. In particular, in some embodiments, the present disclosure teaches methods that result in long-assembly metagenomic libraries that provide higher quality assembled sequences, which enable, for the first time, effective in silico multi-gene cluster analyses of metagenomic samples.

Thus, in some embodiments, the present disclosure teaches a method for assembling a deeply sequenced long DNA contig metagenomic library, said method comprising: a) providing an unsequenced and unassembled metagenomic DNA sample comprising unique whole genomes; b) reducing the genomic complexity of the metagenomic DNA sample by: i) cloning DNA fragments from the metagenomic library into a plurality of vectors to create a metagenomic vector fragment library that comprises the DNA from the unsequenced and unassembled metagenomic DNA sample; ii) pooling the vectors from the metagenomic vector fragment library into a plurality of discrete mini-metagenome subunits that comprise from about 1,000 to about 20,000 pooled vectors each, to create a mini-metagenome library that comprises within the plurality of mini-metagenome subunits the DNA from the unsequenced and unassembled metagenomic DNA sample; c) performing intra-pool sequencing and assembly of the metagenomic DNA contained in the pooled vectors present in the plurality of discrete mini-metagenome subunits of the mini-metagenome library to create sequenced and assembled DNA contigs; wherein the average sequenced and assembled DNA contig length is at least about 10 kb, thereby creating a sequenced and assembled intermediary DNA contig length mini-metagenome library; and d) optionally performing inter-pool DNA contig assembly, by further assembling a plurality of sequenced and assembled DNA contigs from the intermediary DNA contig length mini-metagenome library to create a long DNA contig length metagenomic library.

The present disclosure also provides platforms for the in silico identification of natural product-encoding multi-gene clusters. Thus, in some embodiments, the present disclosure teaches an in silico method for searching a multi-gene cluster feature set digital metagenomics library and identifying a natural product of interest, comprising: a) querying a digital metagenomics library for a signal indicative of a natural product multi-gene cluster feature set; b) supplying the output of said query as a plurality of signal-associated multi-gene cluster digital feature sets; c) determining and assigning biologic relevancy to the signal-associated multi-gene cluster digital feature sets, by: determining a computationally predicted biosynthetic functionality of a plurality of genes from a signal-associated multi-gene cluster digital feature set and digitally assembling a computationally determined natural product multi-gene cluster feature set comprising one or more biosynthetic operons; and/or determining a computationally predicted biological resistance gene functionality of at least one gene from a signal-associated multi-gene cluster digital feature set to thereby identify a computationally determined biological resistance gene; and d) identifying a natural product of interest based upon a computationally determined biological resistance gene being located within a threshold parameter of a computationally determined natural product multi-gene cluster feature set comprising a digitally assembled biosynthetic operon.

In some embodiments, the in silico multi-gene discovery methods of the present disclosure are conducted on long-assembly digital metagenomics libraries. Thus, in some embodiments, the present disclosure teaches in silico methods wherein the multi-gene cluster feature set digital metagenomics library comprises: sequenced and digitally assembled contig sequences having an average length of at least about 10 kb, 15 kb, 20 kb, 25 kb, 30 kb, 35 kb, or 40 kb, or any range or subrange therebetween.

In some embodiments, the systems and methods of the present disclosure are especially adept at identifying multi-gene clusters in large assembled libraries, where traditional discovery techniques are unable to fully parse the diversity of the library. Thus, in some embodiments, the present disclosure teaches in silico methods, wherein the digital metagenomics library is at least about 50 MB, 75 MB, 100 MB, 200 MB, 300 MB, 400 MB, or 500 Mega bases in size.

In some embodiments, the present disclosure teaches in silico methods, wherein the querying in step a) comprises: utilizing a HMM model to search the digital metagenomics library for a known resistance gene, or variant, or homolog thereof. Thus, in some embodiments, the present disclosure teaches in silico methods, wherein the querying in step a) comprises: utilizing a HMM model to search the digital metagenomics library for a computationally predicted or hypothesized resistance gene, or variant, or homolog thereof.

In some embodiments, the present disclosure teaches in silico methods, wherein the querying in step a) comprises: identifying all sequences that are computationally predicted to contain multi-gene clusters, comprising one or more biosynthetic operons.

In some embodiments, the present disclosure also teaches systems and methods for biosynthetically modifying natural products. For example, in some embodiments, the present disclosure teaches using enzyme panels to analog target natural products. Thus, in some embodiments, the present disclosure teaches a method for biosynthetic analoging of a target natural product, said method comprising the steps of: a) providing a plurality of enzymes known or predicted to catalyze a type of reaction for analoging of the target natural product, thereby creating an analoging enzyme panel library; b) incubating individual enzymes from the analoging enzyme panel with the target natural product, or a precursor to the target natural product, thereby producing reaction mixtures; c) analyzing at least one of the reaction mixtures of step (b), for the presence of the target natural product and/or analogs of said target natural product; and d) selecting an enzyme from the analoging enzyme panel, wherein the selected enzyme produces a desired analog of the target natural product, as determined by the analysis of step (c), thereby analoging the target natural product.

In other embodiments, the present disclosure teaches using recombinant cells for analoging natural products. For example, in some embodiments, the present disclosure teaches a method for biosynthetic analoging of a target natural product, said method comprising the steps of: a) providing a plurality of microbial strains, each expressing an enzyme known or predicted to catalyze a type of reaction for analoging of the target natural product, thereby creating an analoging enzyme panel library of microbial strains; b) contacting individual microbial strains from the analoging enzyme panel library of microbial strains with the target natural product, or a precursor to the target natural product, thereby generating a mixture; c) analyzing the mixture of step (b) for the presence of the target natural product and/or analogs of said target natural product; and d) selecting a microbial strain from the analoging enzyme panel library of microbial strains, wherein the selected microbial strain produces a desired analog of the target natural product, as determined by the analysis of step (c), thereby analoging the target natural product; wherein the enzyme expressed by the selected microbial strain is a selected enzyme.

In some embodiments, the method of using recombinant cells is applied to cells that could already produce the target natural product. Thus, in some embodiments, the present disclosure teaches a method for biosynthetic analoging of a target natural product, said method comprising the steps of: a) providing a plurality of genetic sequences, each encoding an enzyme known or predicted to catalyze a type of reaction for a first analoging of the target natural product; b) perturbing the genome of one or more cells of a first base microbial strain to each express an enzyme encoded by one or more of the plurality of genetic sequences of step (a), wherein the first base microbial strain is capable of synthesizing the target natural product, thereby creating an analoging enzyme panel library of microbial strains; c) culturing individual microbial strains from the analoging enzyme panel library of microbial strains; d) analyzing spent media from the cultures of step (c), for the presence of the target natural product and/or analogs of said target natural product; and e) selecting a microbial strain from the analoging enzyme panel of microbial strains, wherein the selected microbial strain produces a desired analog of the target natural product, as determined by the analysis of step (d), thereby analoging the target natural product.

In some embodiments, the present disclosure provides systems and methods for identifying enzymes for analoging natural products. That is, in some embodiments, the present disclosure teaches a method for biosynthetic analoging of a target natural product, said method comprising the steps of: a) accessing a training data set comprising a genetic sequence input variable and a phenotypic performance output variable; i) wherein the genetic sequence input variable comprises one or more amino acid sequences of enzymes that are known or predicted to catalyze a type of reaction for analoging of the target natural product, and ii) wherein the phenotypic performance output variable comprises one or more phenotypic performance features that are associated with the one or more amino acid sequences; b) developing a first predictive machine learning model that is populated with the training data set; c) applying, using a computer processor, the first predictive machine learning model to a metagenomic library containing amino acid sequences from one or more organisms to identify a pool of candidate sequences within the metagenomic library, wherein said candidate sequences are predicted with respective first confidence scores to catalyze the type of reaction for analoging of the target natural product, by the first predictive machine learning model; d) removing from the pool of candidate sequences, any sequence that is predicted to perform a different function by a second predictive machine learning model with a second confidence score if the ratio of the first confidence score to the second confidence score falls beyond a preselected threshold, thereby producing a filtered pool of candidate sequences; e) manufacturing one or more microbial cells to each express a sequence from the filtered pool of candidate sequences from step (d), f) culturing the manufactured host cells of step (e), and lysing the cultured cells, thereby creating an analoging enzyme panel library; g) incubating individual enzymes from the analoging enzyme panel library with the target natural product, or a precursor to the target natural product, thereby producing reaction mixtures; h) analyzing at least one of the reaction mixtures of step (g), for the presence of the target natural product and/or analogs of said target natural product; and i) selecting an enzyme from the analoging enzyme panel, wherein the selected enzyme produces a desired analog of the target natural product, as determined by the analysis of step (h), thereby analoging the target natural product.

In some embodiments, the present disclosure also teaches a method for producing an analog of a target natural product, said method comprising the steps of: a) providing a first multi-gene cluster known to produce the target natural product; b) developing a predictive model based on said first multi-gene cluster; c) querying, in silico, a digital metagenomics library for new multi-gene clusters, wherein said new multi-gene clusters are predicted, by the predictive model, to produce the target natural product or a variant of the target natural product, thereby producing a pool of candidate multi-gene clusters; d) identifying, in silico with an annotation engine, individual genes encoding biosynthetic enzymes within one or more of the new multi-gene clusters of the pool of candidate multi-gene clusters of step (c), thereby producing an analoging enzyme panel library comprising biosynthetic genes from the new multi-gene clusters; e) perturbing the genome of a base microbial host cell to express a gene from the analoging enzyme panel library, wherein the base microbial host cell comprises the first multi-gene cluster; f) culturing at least one of the microbial host cells manufactured in step (e); g) analyzing spent media from the cultures of step (f), for the target natural product and/or analogs of said target natural product; and h) selecting a microbial host cell from the microbial host cells cultured in step (f), wherein the selected microbial host cell produces an analog of the target natural product as determined by the analysis of step (g), thereby producing an analog of the target natural product.

BRIEF DESCRIPTION OF THE SEVERAL VIEWS OF THE DRAWINGS

FIG. 3—depicts steps 4-5 of the natural product discovery platform of the present disclosure.

FIG. 11—is a table comparing the biosynthetic analoging methods of the present disclosure to chemistry-based counterparts.

FIG. 21A depicts the N50 of assemblies of various pool sizes. 10× sequencing coverage of a pool of 30,000 cosmids can still produce a metagenomic assembly with N50's of sufficient length to enable MGC discovery. FIG. 21B presents the results from part A in log scale. FIG. 21C depicts the number of 15 kb+contigs generated per 500 MB of raw sequence varying with the how that raw sequence is pooled. Pool sizes of 6,000-15,000 provide the highest efficiency for MGC discovery.

FIG. 27—depicts the untargeted ("de novo") resistance signal multi-gene cluster feature set discovery workflow of the present disclosure.

DETAILED DESCRIPTION

Figure 1:
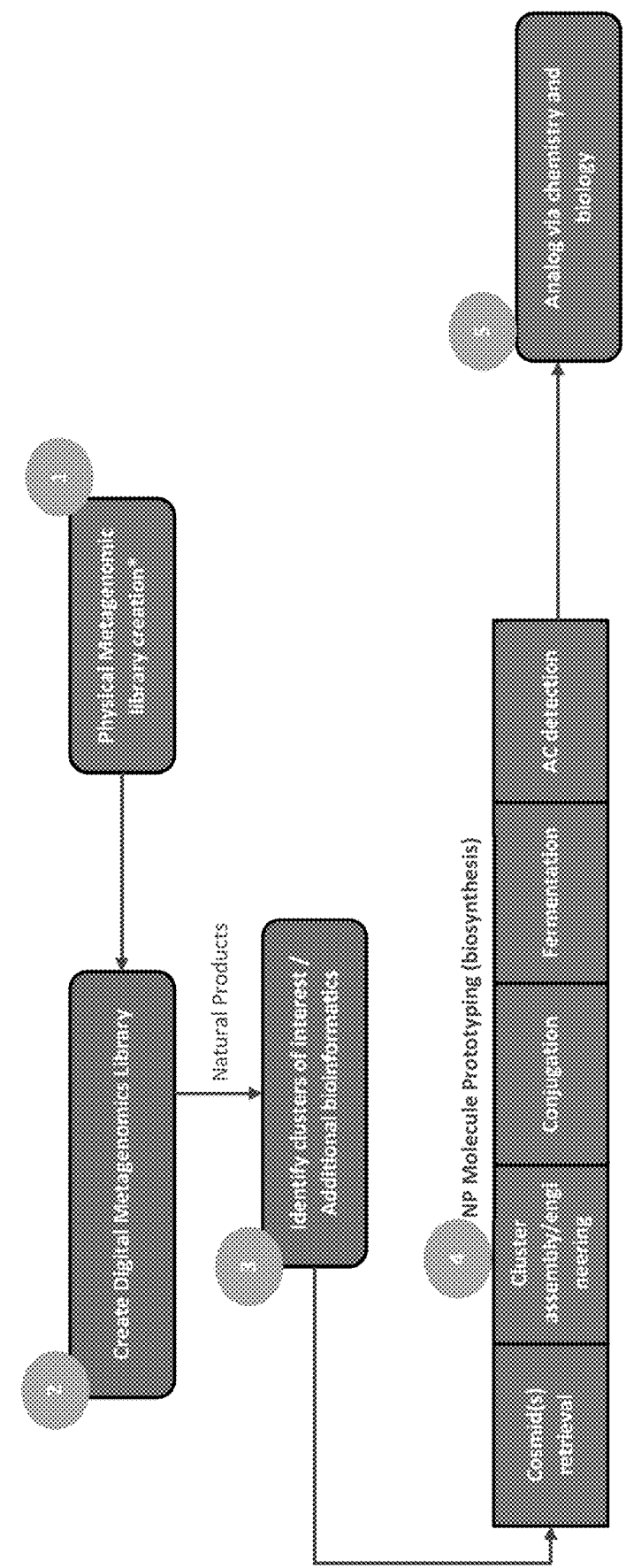
FIG. 1—depicts a workflow of the natural product discovery platform of the present disclosure. In some embodiments, the workflow comprises (1) generating physical metagenomic libraries with reduced complexity using, for example the silo pooling methods of the present disclosure; (2) creating a digital metagenomics library with long-assembly sequences; (3) applying the in silico MGC platform discovery tools to long-assembly metagenomic libraries, as disclosed herein; (4) prototyping the natural product produced by the identified MGC by reconstructing the MGC from, for example physical libraries, or long DNA synthesis; and optionally (5) analoging said natural product. Steps 1-3 represent the in-silico MGC discovery workflows of the present disclosure.

The present disclosure provides novel methods for the identification of multi-gene clusters from diverse metagenomic samples that encode natural products capable of binding a protein target of interest.

Definitions

This disclosure refers to a part, such as a protein, as being "engineered" into a host cell when the genome of the host cell is modified (e.g., via insertion, deletion, replacement of genes, including insertion of a plasmid encoding for a multi-gene cluster) so that the host cell produces at least one new gene/protein (e.g., an enzyme capable of synthesizing a natural product).

As used herein, the "confidence score" is a measure of the confidence assigned to a classification or classifier. For example, a confidence score may be assigned to the identification of an amino acid sequence as encoding a resistance gene. Confidence scores include bitscores and e-values, among other. A "bitscore" provides the confidence in the accuracy of a prediction. "Bits" refers to information content, and a bitscore generally indicates the amount of information in the hit. A higher bitscore indicates a better prediction, while a low score indicates lower information content, e.g., a lower complexity match or worse prediction. An "e-value" as used herein refers to a measure of significance assigned to a result, e.g., the identification of a sequence in a database predicted to encode a protein having the same function as the search protein (e.g., a resistance protein for a natural product). An e-value generally estimates the likelihood of observing a similar result within the same database. The lower the e-value, the more significant the result is.

A "Hidden Markov Model" or "HMM" as used herein refers to a statistical model in which the system being modeled is assumed to be a Markov process with unobservable (i.e. hidden) states. As applied to amino acid sequences, an HMM provides a way to mathematically represent a family of sequences. It captures the properties that sequences are ordered and that amino acids are more conserved at some positions than others. Once an HMM is constructed for a family of sequences, new sequences can be scored against it to evaluate how well they match and how likely they are to be a member of the family.

As used herein the term "sequence identity" refers to the extent to which two optimally aligned polynucleotides or polypeptide sequences are invariant throughout a window of alignment of residues, e.g. nucleotides or amino acids. An "identity fraction" for aligned segments of a test sequence and a reference sequence is the number of identical residues which are shared by the two aligned sequences divided by the total number of residues in the reference sequence segment, i.e. the entire reference sequence or a smaller defined part of the reference sequence. "Percent identity" is the identity fraction times 100. Comparison of sequences to determine percent identity can be accomplished by a number of well-known methods, including for example by using mathematical algorithms, such as, for example, those in the BLAST suite of sequence analysis programs. Unless noted otherwise, the term "sequence identity" in the claims refers to sequence identity as calculated by Clustal Omega® using default parameters.

As used herein, a residue (such as a nucleic acid residue or an amino acid residue) in sequence "X" is referred to as corresponding to a position or residue (such as a nucleic acid residue or an amino acid residue) "a" in a different sequence "Y" when the residue in sequence "X" is at the counterpart position of "a" in sequence "Y" when sequences X and Y are aligned using amino acid sequence alignment tools known in the art, such as, for example, Clustal Omega or BLAST®.

When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Sequences which differ by such conservative substitutions are said to have "sequence similarity" or "similarity." Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4:11-17 (1988). Similarity is more sensitive measure of relatedness between sequences than identity; it takes into account not only identical (i.e. 100% conserved) residues but also non-identical yet similar (in size, charge, etc.) residues. % similarity is a little tricky since its exact numerical value depends on parameters such as substitution matrix one uses (e.g. permissive BLOSUM45 vs. stringent BLOSUM90) to estimate it.

The methods and systems of the present disclosure can be used to identify sequences that are homologous/orthologous to one or more target genes/proteins or to one or more selected protein domains, such as resistance proteins, or shared domains within a class of resistance proteins. In some embodiments, homologous sequences are sequences that share sequence identity with the target gene/protein (e.g., at least 5%, at least 10%, at least 15%, at least 20%, at least 25%, at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% percent identity, including all values in between). In some embodiments homologous sequences are those identified by the HMM models of the present disclosure. In some embodiments, homologous sequences also carry out the same or similar biological function as the target gene/proteins.

In some embodiments, the present disclosure teaches methods and systems for identifying homolog or ortholog of a target protein or gene. As used herein in the terms "target protein" or "target gene" refers to a starting gene or protein (e.g., nucleic acid or amino acid sequence) for which homologs or orthologs are sought. In some embodiments, searches are conducted with more than one target gene/protein.

As used herein, the term "ortholog" refers to a nucleic acid or protein that is homologous to a target sequence, and from different species. In some embodiments, orthologs are hypothesized to be descended from the same ancestral sequence, separated by a speciation event.

The present disclosure teaches methods and systems for identifying homologs and orthologs of target genes/proteins, wherein said homologs and orthologs perform the same function as the target gene/protein. As used herein, the term "same function" refers to interchangeable genes or proteins, such that the newly identified homolog or ortholog can replace the original target gene/protein while maintaining at least some level of functionality. In some embodiments, an enzyme capable of catalyzing the same reaction as the target enzyme will be considered to perform the same function. In some embodiments, a transcription factor capable of regulating the same gene as the target transcription factor will be considered to perform the same function. In some embodiments, a small RNA capable of complexing with the same (or equivalent) nucleic acid as the target small RNA will be considered to perform the same function.

Performing the "same function" however, does not necessarily require the newly identified homolog or ortholog to perform all of the functions of the target gene/protein, nor does it preclude the newly identified homolog from being able to perform additional functions beyond those of the target gene/protein. Thus, in some embodiments, a newly identified homolog or ortholog may have, for example, a smaller pool of usable reactants, or may produce additional products, when compared to the target enzyme.

Persons having skill in the art will also understand that the term "the same function" may, in some embodiments, also encompass congruent, but not identical functions. For example, in some embodiments, a homolog or ortholog identified though the methods and systems of the present disclosure may perform the same function in one organism, but not be capable of performing the same function in another organism. One illustrative example of this scenario is an ortholog subunit of a multi-subunit enzyme, which is capable of performing the same function when expressed with other compatible subunits of one organism, but not be directly combinable with subunits from different organisms. Such a subunit would still be considered to perform the "same function." Techniques for determining whether an identified gene/protein performs the same function as the target gene/product are discussed in detail in the present disclosure.

The term "polypeptide" or "protein" or "peptide" is specifically intended to cover naturally occurring proteins, as well as those which are recombinantly or synthetically produced. It should be noted that the term "polypeptide" or "protein" may include naturally occurring modified forms of the proteins, such as glycosylated forms. The terms "polypeptide" or "protein" or "peptide" as used herein are intended to encompass any amino acid sequence and include modified sequences such as glycoproteins.

The term "prediction" is used herein to refer to the likelihood, probability or score that a protein will perform a given function, or to which a series of genes form a natural product-encoding multi-gene cluster.

In the description, the term "open reading frame" or an ORF refers to a DNA sequence encoding a protein gene, said open reading frame ranging from a translation start codon (e.g., ATG, GTG and TTG) to a stop codon (e.g., TGA, TAA, TAG). For the purposes of this application, DNA sequences which are either computationally predicted (or empirically determined) not to produce a protein are not considered ORFs. For example, an ORF without an associated transcription start site (i.e., a DNA sequence that would not be transcribed to mRNA) would not be considered an ORF. Additionally, ORFs encoding for less than 10, 20, 30, 40, 50, 60, 70, 80, 90, or 100 amino acids, are not considered ORFs for the purposes of the proximity calculations between elements of a computationally determined natural product multi-gene cluster feature set.

The terms "training data", "training set" or "training data set" refers to a data set for which a classification may be known. In some embodiments, training sets comprise input and output variables and can be used to train the model. The values of the features for a set can form an input vector, e.g., a training vector for a training set. Each element of a training vector (or other input vector) can correspond to a feature that includes one or more variables. For example, an element of a training vector can correspond to a matrix. The value of the label of a set can form a vector that contains strings, numbers, bytecode, or any collection of the aforementioned datatypes in any size, dimension, or combination. In some embodiments, the "training data" is used to develop a machine learning predictive model capable of identifying other sequences likely to exhibit the same function as a target gene/protein. In some embodiments, the training data set includes a genetic sequence input variable with one or more genetic sequences (e.g., nucleotides or amino acids) encoding proteins capable of performing the same function as the target protein. In some embodiments, the training data set can also contain sequences that are labeled as not performing the same function.

In some embodiments, the training data set also includes a "phenotypic performance output variable". In some embodiments, the "phenotypic output variable" can be binary (e.g., indicating whether an associated sequence exhibits the same function or not). In some embodiments, the phenotypic output variable can indicate a level of certainty about a stated function, such as indicating whether same function has been experimentally validated as positive or negative, or is predicted based on one or more other factors. In some embodiments, the phenotypic output variable is not stored as data but is merely the fact of performing a given function. For example, a training data set may comprises sequences known or predicted to perform a target function. In such embodiments, the genetic input variables are the sequences and the phenotypic performance output variables are the fact of performing the function or being predicted to perform the function. Thus, in some embodiments, inclusion in the list implies a phenotypic performance variable indicating that the sequences perform the same function.

As used herein the terms "host cell" "cellular organism", "microorganism", or "microbe" should be taken broadly. These terms are used interchangeably and include, but are not limited to, the two prokaryotic domains, Bacteria and Archaea, as well as certain eukaryotic fungi and protists. In some embodiments, the disclosure refers to the "microorganisms" or "cellular organisms" or "microbes" of lists/tables and figures present in the disclosure. This characterization can refer to not only the identified taxonomic genera of the tables and figures, but also the identified taxonomic species, as well as the various novel and newly identified or designed strains of any organism in said tables or figures. The same characterization holds true for the recitation of these terms in other parts of the Specification, such as in the Examples.

In some embodiments, the present disclosure discloses a metagenomic database comprising the genetic sequence of at least one uncultured microbe or microorganism. As used herein, the term "uncultured microbe" "uncultured cell" or "uncultured organism" refers to a cell that was not grown in laboratory media. In some embodiments the uncultured microbes/cells/organisms have not been adapted to grow in the laboratory. In some embodiments, uncultured microbes/cells/organisms are derived directly from an environmental sample. In some embodiments the uncultured microbes/cells/organisms has not been previously sequenced, or the genomic sequence is not publicly available.

The term "prokaryotes" is art recognized and refers to cells which contain no nucleus or other cell organelles. The prokaryotes are generally classified in one of two domains, the Bacteria and the Archaea. The definitive difference between organisms of the Archaea and Bacteria domains is based on fundamental differences in the nucleotide base sequence in the 16S ribosomal RNA.

The term "Archaea" refers to a categorization of organisms of the division Mendosicutes, typically found in unusual environments and distinguished from the rest of the prokaryotes by several criteria, including the number of ribosomal proteins and the lack of muramic acid in cell walls. On the basis of ssrRNA analysis, the Archaea consist of two phylogenetically-distinct groups: Crenarchaeota and Euryarchaeota. On the basis of their physiology, the Archaea can be organized into three types: methanogens (prokaryotes that produce methane); extreme halophiles (prokaryotes that live at very high concentrations of salt (NaCl); and extreme (hyper) thermophilus (prokaryotes that live at very high temperatures). Besides the unifying archaeal features that distinguish them from Bacteria (i.e., no murein in cell wall, ester-linked membrane lipids, etc.), these prokaryotes exhibit unique structural or biochemical attributes which adapt them to their particular habitats. The Crenarchaeota consists mainly of hyperthermophilic sulfur-dependent prokaryotes and the Euryarchaeota contains the methanogens and extreme halophiles.

"Bacteria" or "eubacteria" refers to a domain of prokaryotic organisms. Bacteria include at least 11 distinct groups as follows: (1) Gram-positive (gram+) bacteria, of which there are two major subdivisions: (1) high G+C group (Actinomycetes, Mycobacteria, *Micrococcus*, others) (2) low G+C group (*Bacillus, Clostridia, Lactobacillus, Staphylococci, Streptococci, Mycoplasmas*); (2) Proteobacteria, e.g., Purple photosynthetic and non-photosynthetic Gram-negative bacteria (includes most "common" Gram-negative bacteria); (3) Cyanobacteria, e.g., oxygenic phototrophs; (4) Spirochetes and related species; (5) Planctomyces; (6) *Bacteroides, Flavobacteria*; (7) *Chlamydia*; (8) Green sulfur bacteria; (9) Green non-sulfur bacteria (also anaerobic phototrophs); (10) Radioresistant micrococci and relatives; (11) *Thermotoga* and *Thermosipho thermophiles*.

A "eukaryote" is any organism whose cells contain a nucleus and other organelles enclosed within membranes.

Eukaryotes belong to the taxon Eukarya or Eukaryota. The defining feature that sets eukaryotic cells apart from prokaryotic cells (the aforementioned Bacteria and Archaea) is that they have membrane-bound organelles, especially the nucleus, which contains the genetic material, and is enclosed by the nuclear envelope.

The terms "genetically modified host cell," "recombinant host cell," and "recombinant strain" are used interchangeably herein and refer to host cells that have been genetically modified by the cloning and transformation methods of the present disclosure. Thus, the terms include a host cell (e.g., bacteria, yeast cell, fungal cell, CHO, human cell, etc.) that has been genetically altered, modified, or engineered, such that it exhibits an altered, modified, or different genotype and/or phenotype (e.g., when the genetic modification affects coding nucleic acid sequences of the microorganism), as compared to the naturally-occurring organism from which it was derived. It is understood that in some embodiments, the terms refer not only to the particular recombinant host cell in question, but also to the progeny or potential progeny of such a host cell.

The term "wild-type microorganism" or "wild-type host cell" describes a cell that occurs in nature, i.e. a cell that has not been genetically modified.

The term "genetically engineered" may refer to any manipulation of a host cell's genome (e.g. by insertion, deletion, mutation, or replacement of nucleic acids). Genetically engineered includes organisms harboring artificially added extra chromosomal DNA, such as plasmids.

The term "control" or "control host cell" refers to an appropriate comparator host cell for determining the effect of a genetic modification or experimental treatment. In some embodiments, the control host cell is a wild type cell. In other embodiments, a control host cell is genetically identical to the genetically modified host cell, save for the genetic modification(s) differentiating the treatment host cell.

The term "multi-gene cluster" or "MGC" refers to organized groups of genes involved in the production of specialized metabolites, such as microbial-encoded natural products. Genes within MGCs are typically grouped tightly together to facilitate co-inheritance. MGCs are often regulated together, sometimes forming biosynthetic operons. Methods for identifying MGCs are discussed in this application, in the sections below.

A "barcode" or "molecular barcode" is a material for labeling. The barcode can label a molecule such as a nucleic acid or a polypeptide. In some embodiments, a barcode within a nucleic acid can be used to track a nucleic acid through processing/sequencing steps. In some embodiments barcodes can be used to sort sequences after sequencing. In some embodiments, barcodes are used to de-multiplex sequence mixtures. The material for labeling is associated with information. In some embodiments, a barcode is a sequence identifier (i.e. a sequence-based barcode or sequence index). In some embodiments, a barcode is a particular nucleotide sequence. In some embodiments, a barcode is a different size molecule or different ending points of the same molecule. Barcodes can include a specific sequence within the molecule and a different ending sequence. For example, a molecule that is amplified from the same primer and has 25 nucleotide positions is different than a molecule that is amplified and has 27 nucleotide positions. The addition positions in the 27mer sequence is considered a barcode. In some embodiments, a barcode is incorporated into a polynucleotide. Some non-limiting methods for incorporating a barcode can include molecular biology methods. Some non-limiting examples of molecular biology methods to incorporate a barcode are through primers (e.g., tailed primer elongation), probes (i.e., elongation with ligation to a probe), or ligation (i.e., ligation of known sequence to a molecule).

As used herein, reference to the N50 of an assembled library refers to the length for which the collection of all contigs of that length or longer covers at least half of the assembly. In some embodiments, the N50 is calculated by first ordering every contig in the assembly by length, from longest to shortest. Starting from the longest contig, the lengths of each contig are summed, until this running sum equals half the total length of all contigs in the assembly (total assembly length). The length of the shortest contig in this list is the N50 value.

Traditional Approaches in Natural Product Discovery
Product-Based Screenings

Prior to the advent of DNA sequencing and analyses, the identification of natural products from microorganisms was conducted primarily using culture-dependent techniques in the laboratory (Katz L., Baltz R. H. Natural product discovery: Past, present and future. J. Ind. Microbiol. Biotechnol. 2016; 43:155-176). The discovery of natural products traditionally involved sampling from the environment, culturing these samples in the lab, and finally screening extracted products for biological activity. Thus, this traditional approach to natural product discovery has been restricted to culturable organisms, severely restricting both the rate of MGC discovery and the diversity discovered MGCs.

Traditional approaches to natural product identification were also limited in their ability to exploit existing diversities, because they required the natural product to be expressed and accumulate at sufficient quantities for subsequent biological assays. Most natural-product producing clusters however do not express under all conditions, if at all (Ren H., Wang B., Zhao H. Breaking the silence: New strategies for discovering novel natural products. Curr. Opin. Biotechnol. 2017; 48:21-27). Of those that are expressed, only a portion are secreted and accumulate at sufficiently high levels to allow for biological testing (Luo Y., Cobb R. E., Zhao H. Recent advances in natural product discovery. Curr. Opin. Biotechnol. 2014; 30:230-237).

Attempts to overcome the lack of expression of natural product clustering have had mix success. For example, groups have attempted to increase the expression of natural product-coding gene clusters by manipulating genetic elements embedded within the clusters (Palazzotto E., Weber T. Omics and multi-omics approaches to study the biosynthesis of secondary metabolites in microorganisms. Curr. Opin. Microbiol. 2018; 45:109-116). Other groups have attempted to trigger cluster expression in a native host by artificially knocking-in a strong promoter that is located upstream of the target cluster Ren H., Wang B., Zhao H. Breaking the silence: New strategies for discovering novel natural products. Curr. Opin. Biotechnol. 2017; 48:21-27. For example, a CRISPR-Cas9 system-based promoter knock-in strategy was used to activate multiple silent MGCs in five different *Streptomyces* species, which led to the discovery of a novel pentangular polyketide from *Streptomyces viridochromogenes*.

Other approaches have focused on attempts to serially and/or randomly screening putative natural product encoding gene clusters by expressing these (often silent) gene clusters in heterologous hosts (Kouprina N., Larionov V. Selective isolation of genomic loci from complex genomes by transformation-associated recombination cloning in the yeast *Saccharomyces cerevisiae*. Nat. Protoc. 2008; 3:371).

Heterologous hosts can provide a significant growth advantage over native hosts and can bypass the regulatory system in the latter. Although these approaches assist in expressing a target multi-gene cluster, these approaches tend to be low-throughput and are not a practical solution for large-scale screening and identification of new natural products in all known (and uncultured) microrganisms.

Natural Products from Metagenomic Libraries

One of the largest sources of untapped potential for new natural products are uncultured microorganisms. The number of bacterial species that can be grown in the laboratory comprise only a very small fraction of the total diversity that exists in nature (Stewart E. J. Growing Unculturable Bacteria. J. Bacteriol. 2012; 194:4151-4160). Multiple lines of evidence show that fewer than 0.1% of the microorganisms in soil are readily cultured using standard lab techniques (Handelsman et al. Moleculare biological access to the chemistry of unknown soil microbes: a new frontier for natural products. Chemistry & Biology. 1998, 5:R245-249). Indeed, new estimates suggest that 99.999% of microbial diversity on earth has yet to be explored (Kenneth J. Loceya, and Jay T. Lennona. Scaling laws predict global microbial diversity. *PNAS*, 2016).

As described above, uncultured organisms have not been a useful source for traditional fermentation-based natural product discovery approaches. More recently, however, tools developed in the genomics age, including high-throughput sequencing, DNA cloning and editing, and bioinformatics tools, now make it theoretically possible to explore the genomes of these uncultured organisms by looking directly at the DNA sequences of their genomes (rather than culturing an organism). This has led to the development of field of metagenomics, which is the study of genetic material recovered directly from environmental samples. Theoretically, if one had the genome of an uncultured organism, one could bioinformatically identify the MGCs encoded in that genome. However, there are a number of technical challenges that make this approach difficult to implement at anything close to the scale that the field of metagenomics aspires to. For example, it is estimated that each gram of surface soil on earth contains $10^9$ bacterial cells, and comprises at least 300,000,000 distinct genomes (Delmont et al. Reconstructing rare soil microbial genomes using in situ enrichments and metagenomics. Front Microbiol 2015; 6; 358). This tremendous complexity make it extremely difficult to bioinformatically assemble DNA sequence to any significant length. Studies of metagenomic libraries suggest that most of the distinct microbes within soils represent minorities within the ecosystem, further exacerbating the problem of discovery by reducing sensitivity. Previous approaches to mining metagenomic diversity are discussed in further detail below.

Metagenome Screening for MGCs Using Degenerate Primers

A popular approach for investigating multi-gene clusters in metagenomic libraries is the use of degenerate primers. Degenerate primers are oligonucleotide sequences, with some positions containing more than one possible nucleotide base. The flexible hybridization properties of degenerate primers can be used to target and amplify areas in the genome that are very similar but have slight variations (Linhart C., Shamir R. The degenerate primer design problem: Theory and applications. J. Comput. Biol. A J. Comput. Mol. Cell Biol. 2005; 12:431-456). Degenerate primers have been used to selectively amplify non-ribosomal peptide synthases NRPS genes associated with adenylation and thiolation domains that have been found to be well-conserved amongst sequenced cultured genomes (Khosla C., Gokhale R. S., Jacobsen J. R., Cane D. E. Tolerance and Specificity of Polyketide Synthases. Annu. Rev. Biochem. 1999; 68:219-253). Genomic sequences that are identified through degenerate primers can then be sequenced and used to identify surrounding DNA sequences through traditional "primer walking" techniques.

Degenerate primers have been used across a large number of natural product identification efforts. Customized primer sets were used to screen for NRPS and type I PKS (PKS-I) systems in Actinomycetes (Ayuso-Sacido A., Genilloud O. New PCR primers for the screening of NRPS and PKS-I systems in actinomycetes: Detection and distribution of these biosynthetic gene sequences in major taxonomic groups. Microb. Ecol. 2005; 49:10-24). In this study, primer sets were tested on 210 reference strains that covered the major families and 33 different genera in actinomycetes. PCR amplification of primers targeting NRPS was observed in 79.5% of strains while PCR amplification of primers targeting PKS-I was seen in 56.7% of strains.

In another study, degenerate primers derived from conserved biosynthetic motifs were used to survey the ketosynthase domains from 185 soil microbiome samples (Owen J. G., Charlop-Powers Z., Smith A. G., Ternei M. A., Calle P. Y., Reddy B. V. B., Montiel D., Brady S. F. Multiplexed metagenome mining using short DNA sequence tags facilitates targeted discovery of epoxyketone proteasome inhibitors. Proc. Natl. Acad. Sci. USA. 2015; 112:4221-4226). Biosynthetic multi-gene clusters encoding epoxyketone proteasome inhibitors were detected and a further analysis led to the isolation and characterization of seven epoxyketone natural products, including compounds with a unique warhead structure.

The use of degenerate primers as a first-pass discovery tool, however, suffer from several drawbacks. First, they rely on the identification of only a select number of genes that are hypothesized to be conserved across cultured and uncultured organisms. The level of degeneracy within the primers however, is limited, and even minor unexpected variations in the target sequence can result in loss of hybridization. This limits the types of genes that can be targeted by this technique, and further raises questions as to whether the focus on genes with such specific shared motifs is preventing the user from exploring the full diversity of new and never sequenced microorganisms.

Reliance on degenerate primers in exponential PCR amplifications is also somewhat problematic in view of the large variation in genome copy numbers. PCR amplification of such libraries can exacerbate the issue of library representation by producing amplification products that are highly enriched for one type of cluster, while potentially failing to detect others.

The second limitation of degenerate primers is the amount of downstream processing required before a full natural product cluster is available for review. Sequences from PCR amplifications with degenerate primers are often run on a gel to separate the products by size, before extracting and sequencing each band. This limitation is relevant, not only because of the time and expense to reach a fully sequenced multi-gene cluster, but also because of the pressure it places to avoid false positives. Degenerate primers with too much hybridization range, while potentially capable of uncovering additional multi-gene clusters, may also end up amplifying non-specific genes, which will have to be processed for several more steps before they can be excluded from the working set. Thus, degenerate primers remain a relatively clumsy tool for the task of identifying MGCs in metagenomic libraries.

Other Prior Attempts to Generate Metagenome Libraries

Many other approaches for generating high quality metagenomes have been attempted, with little success. For example, several groups have attempted to reduce the complexity of metagenomic library assemblies by breaking metagenomic samples using cell sorters. These attempts have shown some success at extremely small scales (e.g. 100 cells per pool), and have reported recovering only a handful of low-coverage genomes. These papers have generally concluded that the "assemblies are often highly fragmented and incomplete, and the overall process is prone to biases and contamination." (e.g., Alteio L V, Schulz F, Seshadri R, et al. *mSystems*. 2020; 5(2):e00768-19. Published 2020 Mar. 10. doi:10.1128/mSystems.00768-19).

Another avenue being explored, is the creation of "synthetic long read sequence data." This approach generally utilizes standard short-read Illumina® sequencing, but process DNA samples to incorporate contiguity data information. For example, the art has attempted to use transposome complexes added at various stages of the library assembly, to provide contiguity data (e.g., EP 3636757, US 2020/0202144, U.S. Pat. No. 10,577,603, and EP 3377625B1). Similar attempts utilize unique molecular identifier bar codes to similarly provide sequence contiguity information (see e.g., US 2020/0123539, EP 2977455, U.S. Pat. Nos. 10,557,166, 10,557,133, and 10,726,942). While these approaches work at small scales, attempts to apply synthetic long read techniques to metagenomic databases have all concluded in failure (see WO 2020/165433 "1024 barcodes did not represent sufficient diversity for unique tagging of a mix of molecules from a genomic or metagenomic DNA from biological samples.").

Researchers have also attempted to use in silico approaches for reducing the complexity of metagenomic samples. These include, binning (i.e., assigning sequences to assembly groups) based on methylation patterns (US 2020/0160936), predicted species (Christopher Quince, Alan W. Walker, Jared T. Simpson, Nicholas J. Loman, Nicola Segata "Shotgun metagenomics, from sampling to analysis."). These approaches, through promising, are highly error prone, and unable at this time to fully bin sequences across the full taxonomic spectrum present in metagenomic samples, most of which has yet to be explored. (see Simon H Ye, Katherine J Siddle, Daniel J Park, Pardis C Sabeti Cell. 2019 Aug. 8; 178(4): 779-794. doi:10.1016/j.cell.2019.07.010. explaining how the attempts to bin sequences based on taxonomy failed, which "further underlines the influence of evolutionary distance and poorly described taxa on classification performance.").

These approaches, through admirable in their attempts to advance the cause, have all failed to provide viable digital metagenomic databases for natural product discovery. Most writers in this space have been open about the limitations in the art. (see Ana Elena Pérez-Cobas, Laura Gomez-Valero, Carmen Buchrieser, Metagenomic approaches in microbial ecology: an update on whole-genome and marker gene sequencing analyses "Based on this, genome assembly has to be done and analyzed with caution when performing WGS, and most of the reads obtained from these samples will remain non-assembled"; see also WO 2019/147753 "The complexity of soil microbiomes has limited the utility of shotgun sequencing as a tool for identifying biosynthetic gene clusters in soil metagenomes."). The present disclosure addresses these limitations in the art, and provides a method for creating digital metagenomics libraries amenable to in silico MGC discovery.

Detection and Analyses via Bioinformatic Pipelines

Recent efforts at multi-gene cluster analyses rely on sequenced genomes and bioinfomatic tools. Many bioinformatics tools have now been developed to detect known MGCs in regular genome sequences and genome-resolved metagenomes (Weber T., Kim H. U. The secondary metabolite bioinformatics portal: Computational tools to facilitate synthetic biology of secondary metabolite production. Synth. Syst. Biotechnol. 2016; 1:69-79). These tools, originally developed for use in sequenced public databases, are also being applied to environmental genome-resolved metagenomes (Cimermancic P., Medema M. H., Claesen J., Kurita K., Brown L. C., Mavrommatis K., Pati A., Godfrey P. A., Koehrsen M., Clardy J., et al. Insights into Secondary Metabolism from a Global Analysis of Prokaryotic Biosynthetic Gene Clusters. Cell. 2014; 158:412-421).

AntiSMASH, NAPDOS and ClustScan are examples of bioinformatics software that provide low novelty but high confidence in its analysis and thus, are suitable for users looking for gene clusters of a known biosynthetic class or for surveying all detectable MGCs in single or multiple genomes for annotation purposes. (Blin K., Wolf T., Chevrette M. G., Lu X., Schwalen C. J., Kautsar S. A., Suarez Duran H. G., de los Santos E. L. C., Kim H. U., Nave M., et al. antiSMASH 4.0—Improvements in chemistry prediction and gene cluster boundary identification. Nucleic Acids Res. 2017; 45:W36-W41; and Starcevic A., Zucko J., Simunkovic J., Long P. F., Cullum J., Hranueli D. ClustScan: An integrated program package for the semi-automatic annotation of modular biosynthetic gene clusters and in silico prediction of novel chemical structures. Nucleic Acids Res. 2008; 36:6882-6892). Newer versions of antiSMASH now also incorporate algorithms for additional types of MGCs, including novel ones (Kai Blin et al., antiSMASH 5.0: updates to the secondary metabolite genome mining pipeline, *Nucleic Acids Research*, Volume 47, Issue W1, 2 Jul. 2019, Pages W81-W87.

Other available tools are designed with more greedy algorithms. ClusterFinder, for example, is a recently developed software providing low confidence but high novelty analysis (Cimermancic P., Medema M. H., Claesen J., Kurita K., Brown L. C., Mavrommatis K., Pati A., Godfrey P. A., Koehrsen M., Clardy J., et al. Insights into Secondary Metabolism from a Global Analysis of Prokaryotic Biosynthetic Gene Clusters. Cell. 2014; 158:412-421). The ClusterFinder algorithm has recently been integrated into antiSMASH tool. Predicting gene clusters from novel classes is valuable as they have the possibility of encoding molecules with new chemical scaffolds. ClusterFinder uses a hidden Markov model that switches between MGC and non-MGC analysis to look for patterns of broad gene functions encoded in a genomic region rather than searching for the presence of specific individual signature genes. This method enabled ClusterFinder to identify a large, previously unrecognized family of gene clusters that encode the biosynthesis of aryl polyenes in a wide range of bacteria from various phyla (Id.).

A non-limiting list of currently-available bioinformatics tools for MGC discovery is provided below, in Table 1. Each of the references describing these tools is incorporated by reference to this application.

TABLE 1

Bioinformatic Software for MGC Discovery and Analysis
(Tools Capable of Applying MGC prediction Algorithms)

| Category | Software | Year/version | Features | User interface | Computation platform | Target organism(s) |
|---|---|---|---|---|---|---|
| MGC prediction | BAGEL | 2006/v1, 2010/v2, 2013/v3 | Identify bacteriocins and RiPPs using HMM search with bacteriocin database | Web | Server | Bacteria |
| | References: de Jong A, van Heel A J, Kok J, Kuipers O P (2010) BAGEL2: mining for bacteriocins in genomic data. Nucleic Acids Res 38(Web Server issue): W647-W651. van Heel A J, de Jong A, Montalban-Lopez M, Kok J, Kuipers O P (2013) BAGEL3: automated identification of genes encoding bacteriocins and (non-)bactericidal posttranslationally modified peptides. Nucleic Acids Res 41(Web Server issue): W448-W453 | | | | | |
| | ClustScan | 2008 | Identify MGCs using HMM search and predict product structure | GUI | Local PC | Bacteria |
| | References: Starcevic A, Zucko J, Simunkovic J, Long P F, Cullum J, Hranueli D. ClustScan: an integrated program package for the semi-automatic annotation of modular biosynthetic gene clusters and in silico prediction of novel chemical structures. Nucleic Acids Res. 2008; 36(21): 6882-6892. | | | | | |
| | NP.searcher | 2009 | Identify MGCs using BLAST and construct the structure of natural products | Web/command line | Server/local PC | Bacteria |
| | References: Li M H, Ung P M, Zajkowski J, Garneau-Tsodikova S, Sherman D H. Automated genome mining for natural products. BMC Bioinformatics. 2009; 10: 185. | | | | | |
| | SMURF | 2010 | Predict secondary metabolite biosynthesis gene clusters based on their genomic context and domain content using HMM search | Web | Server | Fungi |
| | References: Khaldi N, Seifuddin F T, Turner G, Haft D, Nierman W C, Wolfe K H, Fedorova N D. SMURF: genomic mapping of fungal secondary metabolite clusters. Fungal Genet Biol. 2010; 47(9): 736-741. | | | | | |
| | anti SMASH | 2011/v1, 2013/v2, 2015/v3, 2017/v4 2019/v5 | Identify MGCs using HMMer3 to search experimentally characterized signature proteins | Web/command line | Server/local PC | Bacteria, fungi, plants |
| | References: Blin K, Wolf T, Chevrette M G, Lu X, Schwalen C J, Kautsar S A, Suarez Duran H G, de Los Santos E L C, Kim H U, Nave M, Dickschat J S, Mitchell D A, Shelest E, Breitling R, Takano E, Lee S Y, Weber T, Medema M H (2017) antiSMASH 4.0-improvements in chemistry prediction and gene cluster boundary identification. Nucleic Acids Res 45(W1): W36-W41. Weber T, Blin K, Duddela S, Krug D, Kim H U, Bruccoleri R, Lee S Y, Fischbach M A, Muller R, Wohlleben W, Breitling R, Takano E, Medema M H (2015) antiSMASH 3.0-a comprehensive resource for the genome mining of biosynthetic gene clusters. Nucleic Acids Res 43(W1): W237-W243. | | | | | |

TABLE 1-continued

Bioinformatic Software for MGC Discovery and Analysis
(Tools Capable of Applying MGC prediction Algorithms)

| Category | Software | Year/version | Features | User interface | Computation platform | Target organism(s) |
|---|---|---|---|---|---|---|
| | ClusterFinder | 2014 | Identify MGCs using a hidden Markov model-based probabilistic algorithm | Command line | Local PC | Bacteria |
| | References: Cimermancic P, Medema M H, Claesen J, Kurita K, Brown L C W, Mavrommatis K, Pati A, Godfrey P A, Koehrsen M, Clardy J (2014) Insights into secondary metabolism from a global analysis of prokaryotic biosynthetic gene clusters. Cell 158(2): 412-421. | | | | | |
| | PRISM | 2015/PRISM, 2016/RiPP-PRISM, 2017/PRISM3 | Identify MGCs using BLAST and HMMER and structure prediction using HMM | Web | Server | Bacteria |
| | References: Skinnider M A, Merwin N J, Johnston C W, Magarvey N A (2017) PRISM 3: expanded prediction of natural product chemical structures from microbial genomes. Nucleic Acids Res 45(W1): W49-W54. | | | | | |
| | EvoMining | 2016 | Identify MGCs using phylogenomic analysis | Command line | Local PC | Actinobacteria |
| | References: Cruz-Morales P, Kopp J F, Martinez-Guerrero C, Yanez-Guerra L A, Selem-Mojica N, Ramos-Aboites H, Feldmann J, Barona-Gomez F (2016) Phylogenomic analysis of natural products biosynthetic gene clusters allows discovery of arseno-organic metabolites in model streptomycetes. Genome Biol Evol 8(6): 1906-1916. | | | | | |
| | RODEO | 2017 | Identify MGC and RiPP precursor peptide using HMM and machine learning | Web | Server | Bacteria |
| | References: Tietz J I, Schwalen C J, Patel P S, Maxson T, Blair P M, Tai H C, Zakai U I, Mitchell D A (2017) A new genome-mining tool redefines the lasso peptide biosynthetic landscape. Nat Chem Biol 13(5): 470-478. | | | | | |
| | ARTS | 2017 | Uses three additional selection criteria, including MGC proximity, gene duplication and horizontal gene transfer, to prioritize antiSMASH-detected MGCs | Web | Server | Bacteria |
| | References: Alanjary M, Kronmiller B, Adamek M, Blin K, Weber T, Huson D, Philmus B, Ziemert N (2017) The Antibiotic Resistant Target Seeker (ARTS), an exploration engine for antibiotic cluster prioritization and novel drug target discovery. Nucleic Acids Res 45: W42-W48. | | | | | |
| Biosynthetic gene analysis | SBSPKS | 2010 | Analyze the 3D structure of PKS protein using BLAST and SCWRL; predict the | Web | Server | Bacteria, fungi, plants |

TABLE 1-continued

Bioinformatic Software for MGC Discovery and Analysis
(Tools Capable of Applying MGC prediction Algorithms)

| Category | Software | Year/version | Features | User interface | Computation platform | Target organism(s) |
|---|---|---|---|---|---|---|
| | | | order of substrate channeling between multiple ORFs in a modular PKS cluster based on docking domain interaction | | | |
| | References: Anand S, Prasad M V, Yadav G, Kumar N, Shehara J, Ansari M Z, Mohanty D (2010) SBSPKS: structure based sequence analysis of polyketide synthases. Nucleic Acids Res 38(Web Server issue): W487-W496. | | | | | |
| | NaPDoS | 2012 | Predict natural products of secondary metabolite genes using BLAST and domain phylogeny | Web | Server | Bacteria |
| | References: Ziemert N, Podell S, Penn K, Badger J H, Allen E, Jensen P R (2012) The natural product domain seeker NaPDoS: a phylogeny based bioinformatic tool to classify secondary metabolite gene diversity. PLoS One 7(3): e34064. | | | | | |
| | DeepBGC | 2019 | Predict MGCs with reduced false positive rates. Incorporates random forest classifiers that predict MGC product classes and potential chemical activity. | Web | | Bacteria |
| | References: Geoffrey D Hannigan et al., A deep learning genome-mining strategy for biosynthetic gene cluster prediction, Nucleic Acids Research, Volume 47, Issue 18, 10 Oct. 2019, Page e110 | | | | | |
| | Ripper | 2019 | Tool for the family-independent identification of RiPP precursor peptide | Web | | Bacteria and some Fungi |
| | Santos-Aberturas, et al. Uncovering the unexplored diversity of thioamidated ribosomal peptides in Actinobacteria using the RiPPER genome mining tool. Nucleic Acids Res. 2019; 47(9): 4624-4637. doi: 10.1093/nar/gkz192 | | | | | |

Bioinformatic tools, such as the ones described above however, rely heavily on high quality genome-resolved metagenomes for effective and reliable outputs (Blin K., Kim H. U., Medema M. H., Weber T. Recent development of anti SMASH and other computational approaches to mine secondary metabolite biosynthetic gene clusters. Brief. Bioinform. 2017). Indeed, the quality of the sequencing data or resolved genomes from metagenomes can influence the reliability of results. Further complications regarding the analysis of metagenomic sequencing data for MGCs have been previously reviewed in more detail (Medema M. H., Fischbach M. A. Computational approaches to natural product discovery. Nat. Chem. Biol. 2015; 11:639-648; and Wilson M. C., Piel J. Metagenomic Approaches for Exploiting Uncultivated Bacteria as a Resource for Novel Biosynthetic Enzymology. Chem. Biol. 2013; 20:636-647). These limitations are discussed in more detail below Challenges of MGC Discovery in Metagenome Sequences Compared to regular (e.g., publicly available complete) genome sequences, the analysis of metagenomic sequence data for MGCs presents several key challenges. There are two main approaches to identifying biosynthetic gene clusters in metagenomes: the PCR-based sequence tag approach and the shotgun assembly approach. The PCR-based approach has been discussed supra in detail, and is therefore not addressed again this section.

In the shotgun assembly approach, metagenomic DNA from uncultured organisms is sequenced in bulk and then assembled en masse. This approach however is met by several technical challenges, which limit its application to relatively low-complexity ecosystems or taxonomically enriched samples from more complex ecosystems. At issue, is the ability to generate sufficiently long portions of the genome to permit for meaningful sequence analysis and subsequent MGC recovery.

In post-sequencing genomic assembly, there is an expectation that a sample contains a single species (apart from any contamination, which can be screened for prior to assembly). This expectation allows assembly tools to make certain assumptions that facilitate assembly. The expected coverage of the target genome can be predicted from the total size of the data set divided by the estimated size of the genome. DNA inputs into sequencers are assumed to be relatively stable for sequences across the genome. Therefore, it can be assumed that nodes or edges in a graph occurring with very low coverage compared to the expected coverage are likely the result of sequencing errors or low level contamination, and the graph is simplified considerably by removing such nodes or paths. Similarly, nodes with much higher than average coverage can be assumed to be part of repeat structures within the genome. The typical optimal sequence coverage for a single genome assembler is in the 20-200× range, with a common 'sweet spot' of ~50× (Desai A, Marwah V S, Yadav A, et al. Identification of optimum sequencing depth especially for de novo genome assembly of small genomes using next generation sequencing data. PLOS One 2013; 8(4):e60204).

However, in metagenomic data sets this assumption and simplifications cannot be made. Lower coverage nodes may originate from genomes with a lower abundance, not from errors, and so should not be discarded out of hand. Compounding this problem, the number of species within a sample, and the distribution of abundances of species is unknown. Abundance in heterogeneous samples often follows a power law, which means that many species will occur with similarly low abundances making the problem of distinguishing one from another problematic (Li D, Liu C M, Luo R, et al. MEGAHIT: an ultra-fast single-node solution for large and complex metagenomics assembly via succinct de Bruijn graph. Bioinformatics 2015; 31(10): 1674-6). The low coverage of most species means de novo assembly is unlikely unless the genome in question is relatively small.

Indeed, assemblies from most complex metagenomic libraries are highly limited in length, and thus prevent meaningful MGC analysis. Short assemblies often do not include complete MGCs, which makes it difficult for bioinformatic algorithms to identify and analyze clusters. When genes are identified, it is often time difficult, if not impossible, to reconstruct the original MGC in order to express and test the resulting natural product. Because of these limitations, there have not been any in silico bioinformatics MGC analysis of highly complex metagenomic libraries. Instead, most bioinformatics work reported to date has either relied on publicly available pre-assembled libraries, or limited small metagenome assemblies of less than 10 k genomes.

The presently disclosed inventions solve these technical issues, and provide methods, systems, and tools for generating long read fragment assembled metagenomic libraries capable of being searched by the MGC bioinformatics tools of the present disclosure. The instant disclosure also provides several novel in silico workflows for identifying new natural-product encoding MGCs, once the metagenomic libraries are created.

Methods, Systems, and Tools of the Present Natural Product Discovery Platform

The present disclosure provides several advanced metagenomic library preparation and bioinformatics analysis pipelines that enable large quantities of MGCs to be mined from microorganisms without having to culture the MGC-containing microorganism. The tools provided in this disclosure thus provide an incredible opportunity to elucidate the secondary metabolism properties of microbial dark matter, which is the uncultured majority of microbial diversity.

Figure 2:
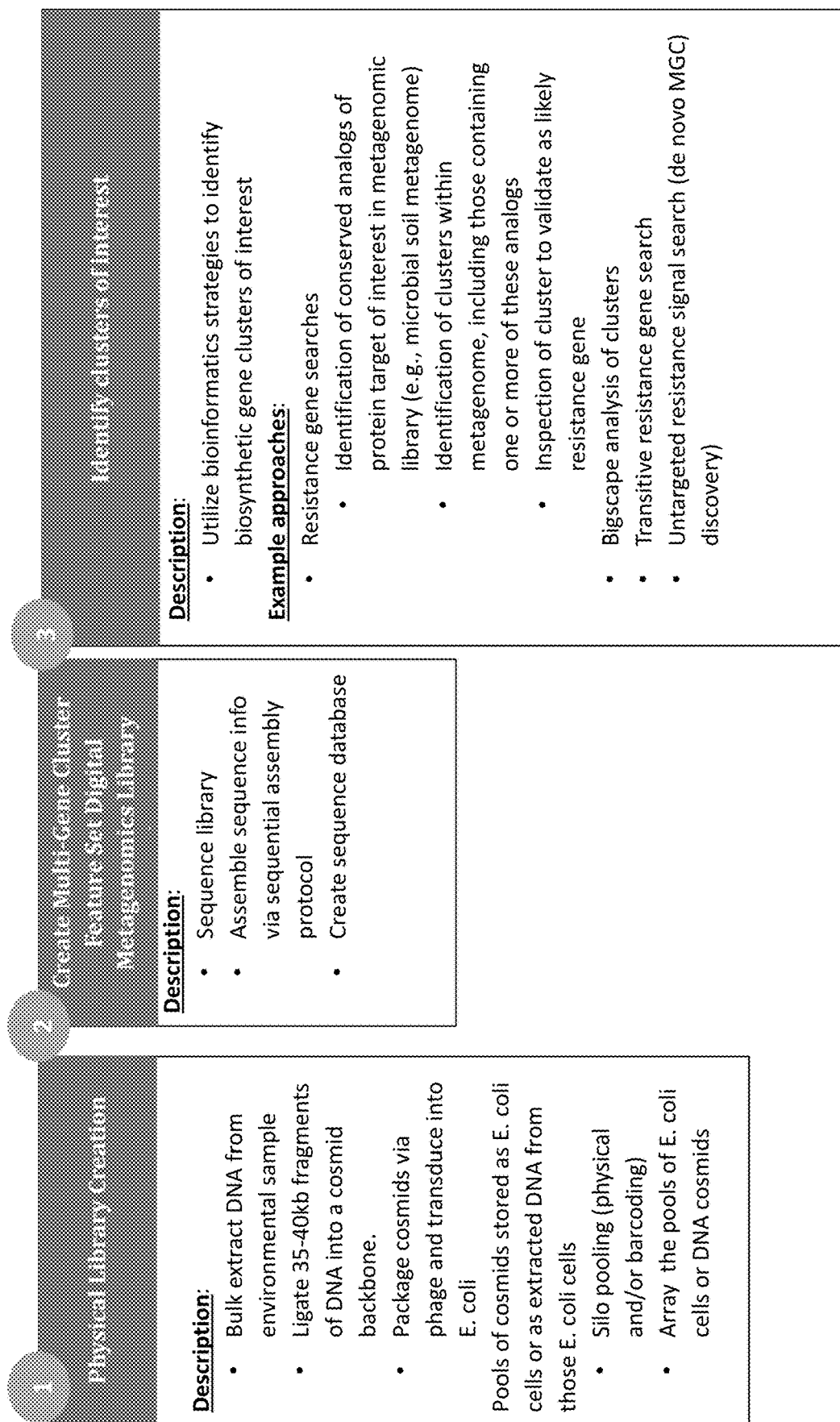
FIG. 2—depicts steps 1-3 of the natural product discovery platform of the present disclosure.

In some embodiments, the present disclosure teaches a natural product discovery workflow comprising: 1) physical metagenomic library creation, 2) sequencing and creation of digital metagenomics libraries ("DML"), 3) Querying DML and identifying clusters of interest based on novel bioinformatics discovery approaches, 4) natural product molecule prototyping, 5) in silico and/or wet lab natural product structure elucidation, and optionally 6) analoging via chemical or biosynthetic approaches. (See e.g., FIGS. 1-3). Each of the elements of the natural product discovery platform are discussed in more detail below.

Digital Metagenomics Library—Introduction

In some embodiments the present disclosure teaches methods and systems for identifying MGCs from metagenomic libraries. The present disclosure also teaches methods and systems for generating metagenomic libraries amenable to MGC bioinformatic searching.

In some embodiments, the MGC discovery systems and methods of the present disclosure are applied to metagenomic libraries, or more specifically to digital metagenomics libraries (DMLs). For the purposes of this disclosure, a metagenomic library is defined in the following ways:

1) A physical or digital sequence library that comprises the genomes of uncultured species (e.g., a library derived from environmental samples without an intervening culturing step). In some embodiments, the uncultured species are from yeast, fungus, bacterium, archae, protist, virus, parasite or algae species. The uncultured species may be obtained from any source, e.g., soil, gut, aquatic habitat. In some embodiments, a library is considered a metagenomics library if a majority of the sequence within the assembled library is from uncultured organisms, and if the library meets other size limitations. In some embodiments, the physical and/or digital sequence library of the present disclosure is representative of the environmental sample from which it was extracted, and is not an agglomeration of existing small (e.g., less than 100 organism) assemblies. Any exogenously added/spiked sequence beyond that sourced from the environmental sample may be considered outside of the library of the present disclosure.

2) A physical or digital sequence library that meets the definition of point 1 above, and further wherein a majority of the sequence within the library is from uncultured organisms. In some embodiments, a digital metagenomics library is considered to contain a majority of sequence from uncultured organisms if it is produced by sequencing physical libraries where a majority of the organisms in the library are uncultured. In some embodiments, a digital metagenomics library is considered to contain a majority of sequence from uncultured organisms if it is produced by sequencing physical libraries where none of the organisms were cultured prior to sequencing. In some embodiments, a library is considered a metagenomics library if substantially all of the sequence within the assembled library is from uncultured organisms, and if the library meets other size limitations. As used in this context, the term "substantially all" refers to a library wherein at least 90% of the assembled sequence is from uncultured organisms. In some embodiments, a digital metagenomics library is considered to contain substantially all of its sequence from uncultured organisms if it is produced by sequencing physical libraries where substantially all of the organisms in the library are uncultured. In some embodiments, a digital metagenomics library is considered to contain substantially all of the sequence from uncultured organisms if it is produced by sequencing physical libraries where none of the organisms were cultured prior to sequencing.

3) A physical or digital sequence library that meets the definition of points 1 and/or 2 above, and further comprises more than one uncultured species' genome. In some embodiments the metagenomic library comprises the genomes of at least 100, 500, 1000, $10^4$, $10^5$, $10^6$, $10^7$ or more uncultured species. In some embodiments, the number of assembled genomes in a digital metagenomics library is calculated by dividing the total assembled sequence in the DML and dividing it by the average size of genomes of the kind of organisms expected to be present in the genome. In some embodiments, the number of assembled genomes in a digital metagenomics library is assessed by counting the number of unique 16s rRNA sequences in the DML. In some embodiments, the number of assembled genomes in a digital metagenomics library is assessed by counting the number of unique Internal transcribed spacers (ITS) in the DML.

4) A digital sequence library that meets the definition of one or more of points 1-3 above, and wherein the digital metagenomics library is at least about 50 Mb, 60 Mb, 70 Mb, 80 Mb, 90 Mb, 100 Mb, 110 Mb, 120 Mb, 130 Mb, 140 Mb, 150 Mb, 160 Mb, 170 Mb, 180 Mb, 190 Mb, 200 Mb, 210 Mb, 220 Mb, 230 Mb, 240 Mb, 250 Mb, 260 Mb, 270 Mb, 280 Mb, 290 Mb, 300 Mb, 310 Mb, 320 Mb, 330 Mb, 340 Mb, 350 Mb, 360 Mb, 370 Mb, 380 Mb, 390 Mb, 400 Mb, 410 Mb, 420 Mb, 430 Mb, 440 Mb, 450 Mb, 460 Mb, 470 Mb, 480 Mb, 490 Mb, 500 Mb, 550 Mb, 600 Mb, 650 Mb, 700 Mb, 750 Mb, 800 Mb, 850 Mb, 900 Mb, 950 Mb, 1000 Mb, 1050 Mb, 1100 Mb, 1150 Mb, 1200 Mb, 1250 Mb, 1300 Mb, 1350 Mb, or 1400 Mb in size. Assembled sequence is the additive lengths of all contigs in the DML.

5) A digital sequence library that meets the definition of one or more of points 1-4 above, and further comprises an N50 of at least about 10 kb, 11 kb, 12 kb, 13 kb, 14 kb, 15 kb, 16 kb, 17 kb, 18 kb, 19 kb, 20 kb, 21 kb, 22 kb, 23 kb, 24 kb, 25 kb, 26 kb, 27 kb, 28 kb, 29 kb, 30 kb, 31 kb, 32 kb, 33 kb, 34 kb, 35 kb (i.e., long-assembly digital metagenomic library).

In some embodiments, metagenomics involves the direct extraction of DNA from environmental samples. Another advantage of metagenomic databases is that they can be enriched for organisms that are more likely to comprise genes likely to encode the desired natural product. For example, MGCs for natural products with anti-fungal properties may be enriched in metagenomic databases produced from microbial samples that have been regularly challenged by fungal infection. MGCs for natural products associated with human digestive health may be enriched in metagenomic databases produced from microbial samples gathered from human or animal intestines. Thus, the methods and systems of the present disclosure benefit from the wide diversity of sequences available through metagenomic databases, and from the potential for enriching such databases for the desired end use.

Microorganisms play an essential role in the function of ecosystems and are well represented quantitatively. Environmental samples, such as soil samples, food samples, or biological tissue samples can contain extremely large numbers of organisms and, consequently, generate a large set of genomic data. For example, it is estimated that the human body, which relies upon bacteria for modulation of digestive, endocrine, and immune functions, can contain up to 100 trillion organisms. In addition, it is estimated that one gram of soil can contain between 1,000 and 10,000 different species of bacteria with between $10^7$ and $10^9$ cells, including cultivatable and non-cultivatable bacteria. Reproducing this whole diversity in metagenomic DNA libraries requires the ability to generate and manage a large number of clones. In some embodiments, the metagenomic database may comprise at least one, several dozen, hundreds of thousands, or even several million recombinant clones which differ from one another by the DNA which they have incorporated. In some embodiments, the metagenomic library may be constructed from metagenomic fragments and/or assembled into contigs, as described in U.S. Pat. Nos. 8,478,544, 10,227,585, and 9,372,959, each incorporated by reference in its entirety herein. In some embodiments, the metagenomic sequences may be assembled into whole genomes. In some embodiments, the metagenomic library may be optimized to comprise an average size (or N50) of the cloned metagenomic inserts to facilitate the search for microbial biosynthesis pathways, because these pathways are often organized in clusters in the microorganism's genome. The larger the cloned fragments of DNA (larger than 30 Kb), the more the number of clones to be analyzed is limited and the greater the possibility of reproducing complete metabolic pathways. Given a large number of recombinant clones to be studied, high density hybridization systems (high density membranes or DNA chips) may be employed, such as for the characterization of bacterial communities (for a review, see Zhou et al., Curr. Opin. Microbial. 2003; 6:288-294, incorporated herein by reference).

Persons having skill in the art will be aware of the relationship between DNA, RNA, and protein sequences, and will thus be able to readily convert DNA sequence data to create metagenomic libraries with RNA or protein information. In some embodiments, the metagenomic libraries of the present disclosure comprise DNA sequences obtained from cellular populations. Thus, in some embodiments, metagenomic libraries comprise information obtained from direct DNA sequencing. In some embodiments, the metagenomic libraries comprise transcribed RNAs that are either directly measured, or predicted based on DNA sequence. Thus, in some embodiments metagenomic libraries can be searched for siRNAs, miRNAs, rRNAs, and aptamers. In some embodiments, metagenomic libraries comprise amino acid protein sequence data, either measured, or predicted based on measured DNA sequences. For example, metagenomic libraries may comprise a list of predicted or validated protein sequences that are accessible to the machine learning models described in the present disclosure.

In some embodiments, the MGC discovery systems and methods of the present disclosure are applied to assembled sequence libraries from environmental samples. ("environmental libraries" or "ELs"). In some embodiments Els are deeply (i.e. at least 10× coverage) sequenced assemblies of environmental DNA samples, which have either been directly sequenced (and may thus be metagenomic samples), or which have undergone at least one culturing step (e.g., to enrich for one or more kinds of organisms). In some embodiments, the ELs of the present disclosure will comprise the following properties, which improve their functioning with the MGC discovery methods and systems of the present disclosure:

1) ELs comprise a digitally assembled sequence library that is at least about 50 Mb, 60 Mb, 70 Mb, 80 Mb, 90 Mb, 100 Mb, 110 Mb, 120 Mb, 130 Mb, 140 Mb, 150 Mb, 160 Mb, 170 Mb, 180 Mb, 190 Mb, 200 Mb, 210 Mb, 220 Mb, 230 Mb, 240 Mb, 250 Mb, 260 Mb, 270 Mb, 280 Mb, 290 Mb, 300 Mb, 310 Mb, 320 Mb, 330 Mb, 340 Mb, 350 Mb, 360 Mb, 370 Mb, 380 Mb, 390 Mb, 400 Mb, 410 Mb, 420 Mb, 430 Mb, 440 Mb, 450 Mb, 460 Mb, 470 Mb, 480 Mb, 490 Mb, 500 Mb in size. Assembled sequence is the additive lengths of all contigs in the El.

2) ELs meet the definition of points EL point 1 above, and further comprise an N50 of at least about 10 kb, 11 kb, 12 kb, 13 kb, 14 kb, 15 kb, 16 kb, 17 kb, 18 kb, 19 kb, 20 kb, 21 kb, 22 kb, 23 kb, 24 kb, 25 kb, 26 kb, 27 kb, 28 kb, 29 kb, 30 kb, 31 kb, 32 kb, 33 kb, 34 kb, 35 kb. (i.e., a long-assembly digital environmental library)

Subsequent sections of this document teach methods of preparing the environmental libraries and metagenomic libraries used in the methods of the present disclosures. Methods discussed below for preparing metagenomic libraries also apply to environmental libraries. For example, in some embodiments, the environmental libraries of the present disclosure are still extracted from environmental samples, are siloed into pools prior to sequencing, and can optionally be assembled in two stages, as discussed below. Moreover, all of the digital searching workflows discussed in this document can also be applied to Els. That is, all references to use of the DML in methods discussed in this specification below, can be replaced with the term EL. This paragraph merely notes the applicability of the presently disclosed methods to libraries that may contain cultured organisms, but does not contradict the benefits of true metagenomic libraries, as defined above.

Metagenomic Library Creation—DNA Extraction

The first step in producing a metagenomic library is extracting DNA from the metagenomic sample of interest (e.g., soil, river water, gut feces). Persons having skill in the art will be familiar with methods of DNA extraction. There are many commercial DNA extraction kits that are optimized for sequencing applications from metagenomic samples. MP Biomedicals® for example, sells an FastDNA™ Spin kit for DNA extraction from soil samples. Other known techniques are disclosed in the art (Shamim K, Sharma J, Dubey S K. Rapid and efficient method to extract metagenomic DNA from estuarine sediments. 3 Biotech. 2017; 7(3):182; see also Bag, S., Saha, B., Mehta, O. et al. An Improved Method for High Quality Metagenomics DNA Extraction from Human and Environmental Samples. Sci Rep 6, 26775 (2016); and Ahmadi, E., Kowsari, M., Azadfar, D. et al. Annals of Forest Science (2018) 75: 43).

In some embodiments, the present disclosure teaches a protocol for soil metagenomic DNA extraction comprising: a) removing non-soil debris from a soil sample with a wire mesh; b) extracting DNA from the resulting soil by adding 300 mL of a CTAB-based lysis buffer (100 mM Tris-HCl, 100 mM EDTA, 1.5M NaCl, 1% (w/v) CTAB, 2% (w/v) SDS, pH 8.0), followed by incubation at 70° C. for 2 h with consistent inversion to mix; c) centrifuging the sample at 4,000 g for 20 minutes at 4° C. and transferring the supernatant to a clean bottle before centrifuging a second time at 4,000 g for 20 min. at 4° C.; d) transferring the lysate to a new bottle and adding 0.7 volumes of isopropanol and gently mixing for 30 min; e) pelting the precipitated DNA with two rounds of centrifugation at 4,000 g for 30 min. at 4° C., washing with 70% ethanol between the first and second centrifugation; f) removing the supernatant and allowing the pellet to dry; and g) resuspending the pellet in 10 mL of TE buffer. The extracted DNA can optionally be quantified by a spectrophotometer, and saved for further processing. Persons having skill in the art will be familiar with the many other methods for extracting DNA from environmental samples (see e.g., Bag, S., Saha, B., Mehta, O. et al. An Improved Method for High Quality Metagenomics DNA Extraction from Human and Environmental Samples. Sci Rep 6, 26775 (2016); Porteous, L. A. et al. An effective method to extract DNA from environmental samples for polymerase chain reaction amplification and DNA fingerprint analysis. Current Microbiology 29, 301-307 (1994); C. Marotz et al., DNA extraction for streamlined metagenomics of diverse environmental samples. Biotechniques Vol. 62 NO. 6; R. Kuhn et al. Comparison of ten different DNA extraction procedures with respect to their suitability for environmental samples. Journal of Microbiological Methods, Volume 143, 2017, Pages 78-86; K. Fitzpatrick et al. Practical Method for Extraction of PCR-Quality DNA from Environmental Soil Samples. Applied and Environmental Microbiology June 2010, 76 (13) 4571-4573).

Metagenomic Library Creation—Size Selection and Cosmid Packaging

The next step in producing a metagenomic library is cloning large fragments of the extracted DNA into a recombinant DNA vector and transducing the resulting recombinant plasmid into a microbial host for storage and propagation. In addition, the cloned DNA can be used to prepare the extracted DNA for sequencing. Persons having skill in the art will be familiar with the many methods for processing DNA for various next generation sequencing platforms. In some embodiments, however, the present disclosure teaches specific methods of pooling DNA samples to reduce the complexity of downstream genome assemblies.

In some embodiments, DNA samples are cloned into cosmid vector backbones, packaged by phage, and transduced into E. coli cells to amplify and create physical copies of extracted DNA. In some embodiments, DNA extracted from metagenomic samples is loaded and run through agarose gels for an initial size fractionation step. In some embodiments, DNA that is around 35-45 kb is excised and electroluted from the agarose gel for further processing. In some embodiments no size fraction is necessary, particularly if the phage packaging technique selectively packages inserts of the desired size (e.g., by using Gigapack III XL™ by Agilent®).

In some embodiments, the DNA is then packaged into cosmids in phages for amplification. In some embodiments, packaging DNA into cosmids comprises the following general steps: (1) ligation of the foreign DNA between two cos sites; (2) making a concatemeric DNA; (3) in vitro packaging to introduce the DNA into the phage head to form the matured phage particle; and (4) introduction of the cloned DNA into E. coli by transduction. Persons having skill in the art will be familiar with various cosmid production and amplification techniques. A non-limiting list of commercial kits for phage packaging include: MaxPlax™ Lambda Packaging Extracts Kit, Gigapack III Gold™, Gigapack III Plus™, Gigapack III XL™, Packagene®.

In some embodiments, the present disclosure teaches a protocol for lambda phage packaging, said protocol comprising the steps of: a) processing the extracted DNA with an End-It DNA End-Repair kit (Lucigen, ER0720) to produce blunt ended DNA, b) ligating 250 ng of the resulting blunt-ended DNA into 500 ng of a blunt-ended cosmid vector using T4 ligase, and c) packaging the resulting cosmids into phages using a MaxPlax™ packaging kit following manufacturer's instructions.

Metagenomic Library Creation—Silo Pooling

As discussed above, the primary challenge in applying bioinformatic MGC discovery tools to sequenced metagenomic libraries is the inability to assemble long sequences from complex environmental DNA samples. The present disclosure teaches complexity-reducing methods in the library preparation and assembly steps that solve the issues of the prior art, and produce digital metagenomics libraries amenable to in silico multi-gene cluster discovery.

It is not uncommon for next generation sequencing protocols to include a sample pooling step. The pooling of samples before sequencing is typically done to reduce costs, and to make efficient use of sequencers, which are often capable of sequencing much more than a single sample. The average size of a bacterial genome, for example, is about 3.65 Mb (see diCenzo G C, Finan T M. 2017. The divided bacterial genome: structure, function, and evolution. Microbiol Mol Biol Rev 81:e00019-17). Illumina's NovaSeq 6000™ sequencing machine, on the other hand, is capable of sequencing between 32 and 40 billion bases per run (i.e., roughly equivalent to about 10,000× the average bacterial genome). This type of intentional sample pooling typically relies on the use of barcoding technology, which allows the computer to sort the resulting sequences into files corresponding to each individual (pre-mixed) sample before genomic assembly begins.

Metagenomic DNA samples represent massive, involuntary, and unmarked, DNA pools comprising the genomes of hundreds to millions of microbes present in the original material sample (e.g., soil). Because the genomes were premixed, the resulting sequences from a metagenomic NGS must be assembled without the ability to pre-sort the reads according to which organism they belong to.

In some embodiments, the present disclosure teaches methods of silo-pooling of metagenomic samples to decrease complexity, and improve assemblies. In some embodiments, DNA cosmids from a metagenomic DNA sample are processed and stored within an *E. coli* library. Each colony within the *E. coli* library comprises one cosmid of about 35-40 kb in length. In some embodiments, breaking up the genomes of the metagenomic library into individual cosmids reduces the assembly difficulty of such fragments. This is contrasted with some traditional approaches of sequencing a whole genome at once, without first separating the library into individual cosmids.

Many traditional sequencing protocols teach extracting metagenomic environmental DNA composed of whole genomes into a single sample for shotgun sequencing (e.g., combining all clones within a metagenomic library into a single pool). The presently disclosed approach differs from these traditional approaches in that it produces a plurality of small pools of sizes that maximize use of the sequencer while still producing assemblies of sufficient quality for MGC discovery.

Figure 14:
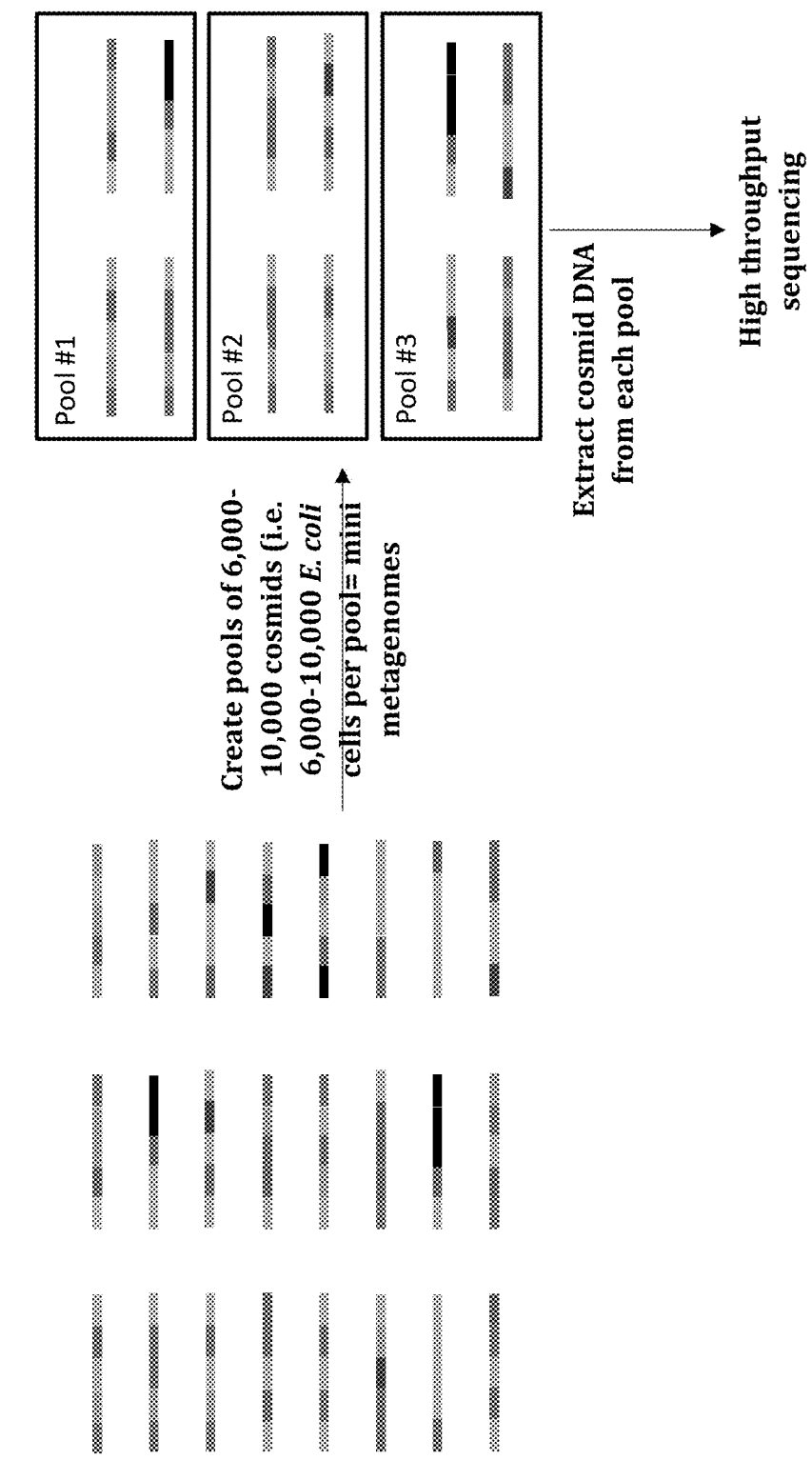
FIG. 14—depicts of steps of the library preparation methods of the present disclosure. E. coli containing cosmids (predominantly one per cell) from the metagenomic DNA library are silo pooled into mini-meta genomes prior to sequencing. Pool sizes are based on results of simulations discussed in this disclosure.

Specifically, in some embodiments, the presently disclosed methods teach the 1) cloning of fragments of genomes into cosmids with 2) selective pooling of limited numbers of *E. coli* colonies containing cosmids into a plurality of sequencing silos. (See step 1 of FIG. 2, and FIG. 14) The resulting sequencing silos comprise a limited number of full length cosmids, thus reducing the complexity of subsequent assemblies. As will be discussed in more detail below, the silo pooling methods reduce the problem from one of assembling, in parallel, whole genomes or 20 million cosmids corresponding to hundreds/thousands of genomes, to one in which the assembly focuses on only a few thousand cosmids.

Some publications have previously disclosed pooling of small numbers of clones, as alternatives to barcoding or whole genome sequencing (Dž᠎unkova᾿M, D'Auria G, Pe᾿rez-Villarroya D, Moya A (2012) Hybrid Sequencing Approach Applied to Human Fecal Metagenomic Clone Libraries Revealed Clones with Potential Biotechnological Applications. PLoS One 7: e47654.; Wang L, Hatem A, Catalyurek U V, Morrison M, Yu Z (2013) Metagenomic Insights into the Carbohydrate-Active Enzymes Carried by the Microorganisms Adhering to Solid Digesta in the Rumen of Cows. PloS One 8: e78507)). Lam et al. 2013, for example, disclosed the pooling of 92 distinct clones derived from environmental samples. (Lam K N, Hall M W, Engel K, Vey G, Cheng J, et al. (2014) Evaluation of a Pooled Strategy for High-Throughput Sequencing of Cosmid Clones from Metagenomic Libraries. PloS ONE 9(6): e98968. Doi:10.1371/journal.pone.0098968). The experiments in Lam et al. however were limited to a small number of pre-screened clones, which were sequenced to approximately 900-fold read depth and >100 fold coverage. Despite this extraordinarily high level of sequencing, Lam reported only recovering reference contigs for 77 out of the 92 original clones. The results of Lam et al. thus did not provide any expectation of success of producing digital metagenomic libraries from silo pooling of 3,000 to 14,000 cosmids, as presently disclosed.

Figure 21A:
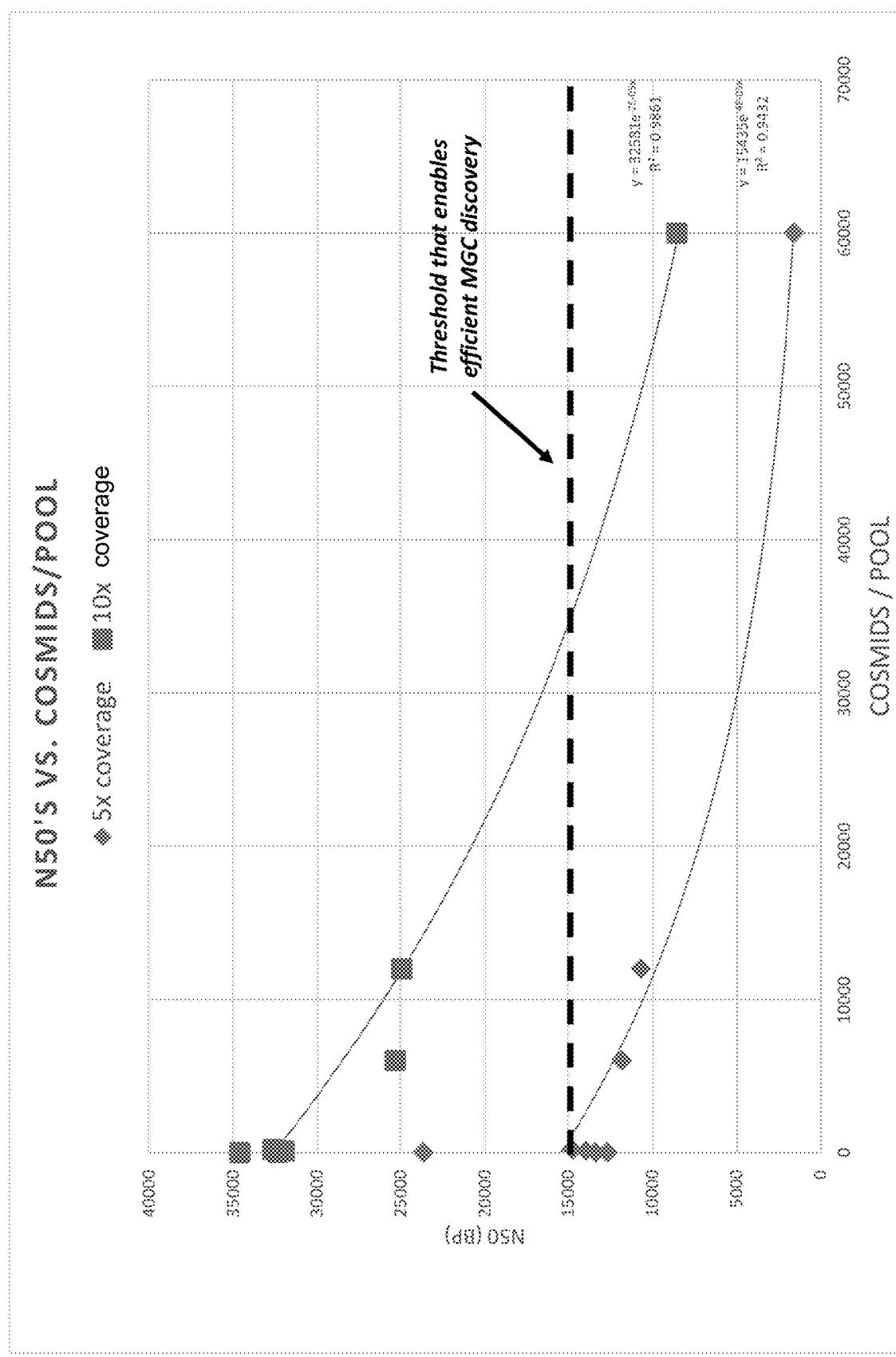
FIG. 21A-C—depicts the results of various assemblies created to test the effect of increasing silo pool size on overall assembly quality.

The instant invention is based in part, on Applicant's unexpected discovery that large physical libraries, such as those from Environmental Libraries or Metagenomic Libraries could be created, sequenced, and successfully assembled for MGC discovery, by creating pools of silos between 5-20 k cosmids, 10-15 k cosmids, or 12-12 k cosmids. Studies described in this application demonstrate the number of cosmids that can be pooled, while still producing digital environmental or metagenomic libraries amenable to MGC discovery, according to the methods of the present disclosure. FIG. 21A for example, demonstrates that, at 10× coverage sequencing, it is possible to pool about 30,000 cosmids, while still generating libraries with N50 of at least 15 kb (determined to allow for optimum discovery of MGC). FIG. 21C provides further insight into optimum pooling of silos. Pooling of too many cosmids causes difficulties at the assembly stage, reducing the number of 15 kb assembled contigs at the library and the overall efficiency of assembly. Pooling of too few cosmids results in inefficient use of the sequencer, resulting in less total sequence, and thus fewer assembled 15+ kb assembled contigs).

In some embodiments, each of the resulting sequencing silos comprises between 3,000-35,000 cosmids. In some embodiments, each sequencing silo comprises 3,000, 3,100, 3,200, 3,300, 3,400, 3,500, 3,600, 3,700, 3,800, 3,900, 4,000, 4,100, 4,200, 4,300, 4,400, 4,500, 4,600, 4,700, 4,800, 4,900, 5,000, 5,100, 5,200, 5,300, 5,400, 5,500, 5,600, 5,700, 5,800, 5,900, 6,000, 6,100, 6,200, 6,300, 6,400, 6,500, 6,600, 6,700, 6,800, 6,900, 7,000, 7,100, 7,200, 7,300, 7,400, 7,500, 7,600, 7,700, 7,800, 7,900, 8,000, 8,100, 8,200, 8,300, 8,400, 8,500, 8,600, 8,700, 8,800, 8,900, 9,000, 9,100, 9,200, 9,300, 9,400, 9,500, 9,600, 9,700, 9,800, 9,900, 10,000, 10,100, 10,200, 10,300, 10,400, 10,500, 10,600, 10,700, 10,800, 10,900, 11,000, 11,100, 11,200, 11,300, 11,400, 11,500, 11,600, 11,700, 11,800, 11,900, 12,000, 12,100, 12,200, 12,300, 12,400, 12,500, 12,600, 12,700, 12,800, 12,900, 13,000, 13,100, 13,200, 13,300, 13,400, 13,500, 13,600, 13,700, 13,800, 13,900, 14,000, 15,000, 16,000, 17,000, 18,000, 19,000, 20,000, 21,000, 22,000, 23,000, 24,000, 25,000, 26,000, 27,000, 28,000, 29,000, 30,000, 31,000, 32,000, 33,000, 34,000, or 35,000 cosmids, including all ranges and subranges therebetween. In some embodiments, each of the resulting sequencing silos comprises between 6,000-10,000 cosmids. In some embodiments, the silo pool varies with sequencing coverage. In some embodiments the size of silo pools are defined according to the curves defined in FIG. 21A-C.

In some embodiments, each sequencing silo comprises DNA totaling a length between 105 and 1,400 million bases (Mb). In some embodiments, each sequencing silo comprises DNA totaling a length of 100 Mb, 101 Mb, 102 Mb, 103 Mb, 104 Mb, 105 Mb, 106 Mb, 107 Mb, 108 Mb, 109 Mb, 110 Mb, 111 Mb, 112 Mb, 113 Mb, 114 Mb, 115 Mb, 116 Mb, 117 Mb, 118 Mb, 119 Mb, 120 Mb, 121 Mb, 122 Mb, 123 Mb, 124 Mb, 125 Mb, 126 Mb, 127 Mb, 128 Mb, 129 Mb, 130 Mb, 131 Mb, 132 Mb, 133 Mb, 134 Mb, 135 Mb, 136 Mb, 137 Mb, 138 Mb, 139 Mb, 140 Mb, 141 Mb, 142 Mb, 143 Mb, 144 Mb, 145 Mb, 146 Mb, 147 Mb, 148 Mb, 149 Mb, 150 Mb, 151 Mb, 152 Mb, 153 Mb, 154 Mb, 155 Mb, 156 Mb, 157 Mb, 158 Mb, 159 Mb, 160 Mb, 161 Mb, 162 Mb, 163 Mb, 164 Mb, 165 Mb, 166 Mb, 167 Mb, 168 Mb, 169 Mb, 170 Mb, 171 Mb, 172 Mb, 173 Mb, 174 Mb, 175 Mb, 176 Mb, 177 Mb, 178 Mb, 179 Mb, 180 Mb, 181 Mb, 182 Mb, 183 Mb, 184 Mb, 185 Mb, 186 Mb, 187 Mb, 188 Mb, 189 Mb, 190 Mb, 191 Mb, 192 Mb, 193 Mb, 194 Mb, 195 Mb, 196 Mb, 197 Mb, 198 Mb, 199 Mb, 200 Mb, 201 Mb, 202 Mb, 203 Mb, 204 Mb, 205 Mb, 206 Mb, 207 Mb, 208 Mb, 209 Mb, 210 Mb, 211 Mb, 212 Mb, 213 Mb, 214 Mb, 215 Mb, 216 Mb, 217 Mb, 218 Mb, 219 Mb, 220 Mb, 221 Mb, 222 Mb, 223 Mb, 224 Mb, 225 Mb, 226 Mb, 227 Mb, 228 Mb, 229 Mb, 230 Mb, 231 Mb, 232 Mb, 233 Mb, 234 Mb, 235 Mb, 236 Mb, 237 Mb, 238 Mb, 239 Mb, 240 Mb, 241 Mb, 242 Mb, 243 Mb, 244 Mb, 245 Mb, 246 Mb, 247 Mb, 248 Mb, 249 Mb, 250 Mb, 251 Mb, 252 Mb, 253 Mb, 254 Mb, 255 Mb, 256 Mb, 257 Mb, 258 Mb, 259 Mb, 260 Mb, 261 Mb, 262 Mb, 263 Mb, 264 Mb, 265 Mb, 266 Mb, 267 Mb, 268 Mb, 269 Mb, 270 Mb, 271 Mb, 272 Mb, 273 Mb, 274 Mb, 275 Mb, 276 Mb, 277 Mb, 278 Mb, 279 Mb, 280 Mb, 281 Mb, 282 Mb, 283 Mb, 284 Mb, 285 Mb, 286 Mb, 287 Mb, 288 Mb, 289 Mb, 290 Mb, 291 Mb, 292 Mb, 293 Mb, 294 Mb, 295 Mb, 296 Mb, 297 Mb, 298 Mb, 299 Mb, 300 Mb, 301 Mb, 302 Mb, 303 Mb, 304 Mb, 305 Mb, 306 Mb, 307 Mb, 308 Mb, 309 Mb, 310 Mb, 311 Mb, 312 Mb, 313 Mb, 314 Mb, 315 Mb, 316 Mb, 317 Mb, 318 Mb, 319 Mb, 320 Mb, 321 Mb, 322 Mb, 323 Mb, 324 Mb, 325 Mb, 326 Mb, 327 Mb, 328 Mb, 329 Mb, 330 Mb, 331 Mb, 332 Mb, 333 Mb, 334 Mb, 335 Mb, 336 Mb, 337 Mb, 338 Mb, 339 Mb, 340 Mb, 341 Mb, 342 Mb, 343 Mb, 344 Mb, 345 Mb, 346 Mb, 347 Mb, 348 Mb, 349 Mb, 350 Mb, 351 Mb, 352 Mb, 353 Mb, 354 Mb, 355 Mb, 356 Mb, 357 Mb, 358 Mb, 359 Mb, 360 Mb, 361 Mb, 362 Mb, 363 Mb, 364 Mb, 365 Mb, 366 Mb, 367 Mb, 368 Mb, 369 Mb, 370 Mb, 371 Mb, 372 Mb, 373 Mb, 374 Mb, 375 Mb, 376 Mb, 377 Mb, 378 Mb, 379 Mb, 380 Mb, 381 Mb, 382 Mb, 383 Mb, 384 Mb, 385 Mb, 386 Mb, 387 Mb, 388 Mb, 389 Mb, 390 Mb, 391 Mb, 392 Mb, 393 Mb, 394 Mb, 395 Mb, 396 Mb, 397 Mb, 398 Mb, 399 Mb, 400 Mb, 401 Mb, 402 Mb, 403 Mb, 404 Mb, 405 Mb, 406 Mb, 407 Mb, 408 Mb, 409 Mb, 410 Mb, 411 Mb, 412 Mb, 413 Mb, 414 Mb, 415 Mb, 416 Mb, 417 Mb, 418 Mb, 419 Mb, 420 Mb, 421 Mb, 422 Mb, 423 Mb, 424 Mb, 425 Mb, 426 Mb, 427 Mb, 428 Mb, 429 Mb, 430 Mb, 431 Mb, 432 Mb, 433 Mb, 434 Mb, 435 Mb, 436 Mb, 437 Mb, 438 Mb, 439 Mb, 440 Mb, 441 Mb, 442 Mb, 443 Mb, 444 Mb, 445 Mb, 446 Mb, 447 Mb, 448 Mb, 449 Mb, 450 Mb, 451 Mb, 452 Mb, 453 Mb, 454 Mb, 455 Mb, 456 Mb, 457 Mb, 458 Mb, 459 Mb, 460 Mb, 461 Mb, 462 Mb, 463 Mb, 464 Mb, 465 Mb, 466 Mb, 467 Mb, 468 Mb, 469 Mb, 470 Mb, 471 Mb, 472 Mb, 473 Mb, 474 Mb, 475 Mb, 476 Mb, 477 Mb, 478 Mb, 479 Mb, 480 Mb, 481 Mb, 482 Mb, 483 Mb, 484 Mb, 485 Mb, 486 Mb, 487 Mb, 488 Mb, 489 Mb, 490 Mb, 491 Mb, 492 Mb, 493 Mb, 494 Mb, 495 Mb, 496 Mb, 497 Mb, 498 Mb, 499 Mb, 500 Mb, 505 Mb, 510 Mb, 515 Mb, 520 Mb, 525 Mb, 530 Mb, 535 Mb, 540 Mb, 545 Mb, 550 Mb, 555 Mb, 560 Mb, 565 Mb, 570 Mb, 575 Mb, 580 Mb, 585 Mb, 590 Mb, 595 Mb, 600 Mb, 605 Mb, 610 Mb, 615 Mb, 620 Mb, 625 Mb, 630 Mb, 635 Mb, 640 Mb, 645 Mb, 650 Mb, 655 Mb, 660 Mb, 665 Mb, 670 Mb, 675 Mb, 680 Mb, 685 Mb, 690 Mb, 695 Mb, 700 Mb, 705 Mb, 710 Mb, 715 Mb, 720 Mb, 725 Mb, 730 Mb, 735 Mb, 740 Mb, 745 Mb, 750 Mb, 755 Mb, 760 Mb, 765 Mb, 770 Mb, 775 Mb, 780 Mb, 785 Mb, 790 Mb, 795 Mb, 800 Mb, 805 Mb, 810 Mb, 815 Mb, 820 Mb, 825 Mb, 830 Mb, 835 Mb, 840 Mb, 845 Mb, 850 Mb, 855 Mb, 860 Mb, 865 Mb, 870 Mb, 875 Mb, 880 Mb, 885 Mb, 890 Mb, 895 Mb, 900 Mb, 905 Mb, 910 Mb, 915 Mb, 920 Mb, 925 Mb, 930 Mb, 935 Mb, 940 Mb, 945 Mb, 950 Mb, 955 Mb, 960 Mb, 965 Mb, 970 Mb, 975 Mb, 980 Mb, 985 Mb, 990 Mb, 995 Mb, 1000 Mb, 1005 Mb, 1010 Mb, 1015 Mb, 1020 Mb, 1025 Mb, 1030 Mb, 1035 Mb, 1040 Mb, 1045 Mb, 1050 Mb, 1055 Mb, 1060 Mb, 1065 Mb, 1070 Mb, 1075 Mb, 1080 Mb, 1085 Mb, 1090 Mb, 1095 Mb, 1100 Mb, 1105 Mb, 1110 Mb, 1115 Mb, 1120 Mb, 1125 Mb, 1130 Mb, 1135 Mb, 1140 Mb, 1145 Mb, 1150 Mb, 1155 Mb, 1160 Mb, 1165 Mb, 1170 Mb, 1175 Mb, 1180 Mb, 1185 Mb, 1190 Mb, 1195 Mb, 1200 Mb, 1205 Mb, 1210 Mb, 1215 Mb, 1220 Mb, 1225 Mb, 1230 Mb, 1235 Mb, 1240 Mb, 1245 Mb, 1250 Mb, 1255 Mb, 1260 Mb, 1265 Mb, 1270 Mb, 1275 Mb, 1280 Mb, 1285 Mb, 1290 Mb, 1295 Mb, 1300 Mb, 1305 Mb, 1310 Mb, 1315 Mb, 1320 Mb, 1325 Mb, 1330 Mb, 1335 Mb, 1340 Mb, 1345 Mb, 1350 Mb, 1355 Mb, 1360 Mb, 1365 Mb, 1370 Mb, 1375 Mb, 1380 Mb, 1385 Mb, 1390 Mb, 1395 Mb, or 1400 Mb, including all ranges and subranges therebetween.

Metagenomic Library Creation-Silo Pooling Through Barcoding

Persons having skill in the art will recognize that the physical silo pooling described above can be replicated, supplemented and/or extended, in various degrees, through the use of barcoding technology. DNA Barcodes, also commonly referred to as tags, indexing sequences, or identifier codes, include specific sequences that are incorporated into a nucleic acid molecule for identification purposes. Barcodes can be used to identify individual nucleic acid molecules or groups of nucleic acid molecules.

In some embodiments, the present disclosure teaches using barcodes to silo pool DNA from metagenomic libraries. For example, the present disclosure contemplates barcoding cosmids from *E. coli* colonies, either individually, or in groups, prior to sequencing. Thus, in some embodiments, the methods of the present disclosure comprise processing and barcoding individual cosmids for NGS.

In some embodiments, the present disclosure teaches traditional use of barcodes to further reduce the complexity of existing sequencing silos. Thus, in some embodiments, the present disclosure teaches the barcoding of individual cosmids.

Certain barcoding embodiments of the present disclosure differ from traditional barcode use, in that the barcodes are not applied to every cosmid, but are instead added to processed sequences in sequencing silos (as described above), or in processed sequences in mini-silo pools, which can then be further pooled into sequencing silos.

In some embodiments, the present disclosure teaches creating mini-silo pools in which a plurality of cosmids are pooled and processed for NGS. In some embodiments each mini silo comprises 100, 200, 300, 400, 500, 600, 700, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, 4,100, 4,200, 4,300, 4,400, 4,500, 4,600, 4,700, 4,800, 4,900, 5,000, 5,100, 5,200, 5,300, 5,400, 5,500, 5,600, 5,700, 5,800, 5,900, 6,000, 6,500, 7,000, 7,500, 8,000, 8,500, 9,000, 9,500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 20,500, 21,000, 21,500, 22,000, 22,500, 23,000, 23,500, 24,000, 24,500, 25,000, 25,500, 26,000, 26,500, 27,000, 27,500, 28,000, 28,500, 29,000, 29,500, 30,000, 30,500, 31,000, 31,500, 32,000, 32,500, 33,000, 33,500, 34,000, 34,500, 35,000, cosmids, including any ranges and subranges therebetween.

In some embodiments, the barcodes are added to mini-silo pools after the pooling has occurred, and after the sequences within each silo have been fragmented into fragment sizes for next generation sequencing. Barcoded mini silo pools could then be further combined into broader sequencing pools before running through the sequencer.

Figure 4:
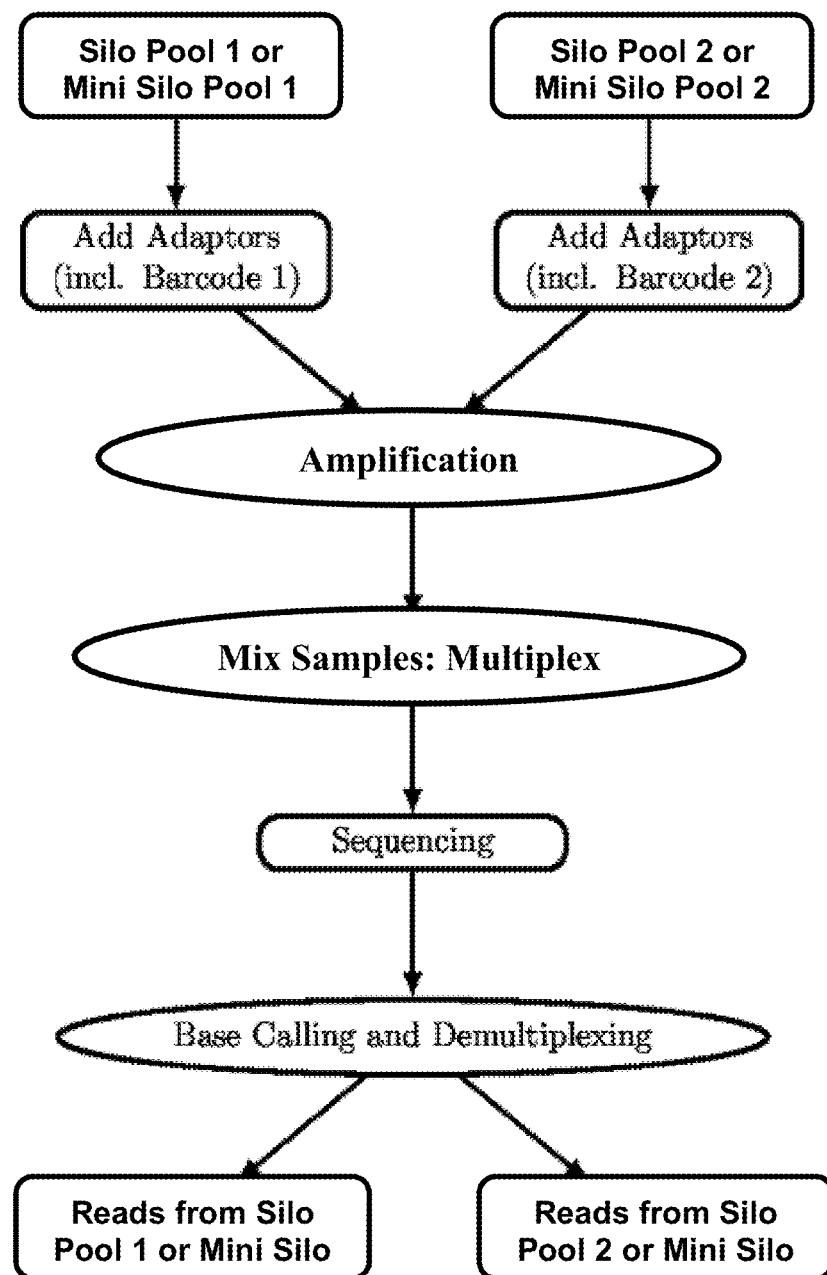
FIG. 4—depicts a diagram of DNA sequencing multiplexing strategies using barcodes. Distinguishable sequences can be added to DNA prior to sequencing (e.g., through the addition of adaptor sequences). DNA fragments with different barcodes can then be pooled (i.e., multiplexed) into a single sequence run. The barcodes are identified in post-sequencing processing, and are used to separate reads belonging to the different DNA samples (i.e., demultiplexing).

In some embodiments, the individually barcoded sequences are sequenced together with other barcoded samples. The barcoded reads can then be sorted (e.g., de-multiplexed) via known techniques, and assigned to their corresponding groups. (See e.g., FIG. 4).

Barcodes can be generated based on selecting a particular nucleic acid sequence. For example, the Illumina™ sequencing can utilize 6 bases to effectively generate 48 different barcodes. The Ion Torrent sequencer (e.g., the Ion Proton™ Sequencer or the Ion PGM™ sequencer) can utilize 6 bases to generate 16 barcodes. In some embodiments, rules may be applied to the generation of bar codes that allow for separate barcodes to be correctly identified even if two errors occur during sequencing. Barcoding is described, e.g., in U.S. Pat. No. 7,902,122 and U.S. Pat. Publn. 2009/0098555. Barcode incorporation by primer extension, for example via PCR may be performed using methods described in U.S. Pat. No. 5,935,793 or US 2010/0227329. In some embodiments, a barcode may be incorporated into a nucleic acid via using ligation, which can then be followed by amplification; for example, methods described in U.S. Pat. Nos. 5,858,656, 6,261,782, U.S. Pat. Publn. 2011/0319290, or U.S. Pat. Publn. 2012/0028814 may be used with the present invention. In some embodiments, one or more bar code may be used, e.g., as described in U.S. Pat. Publn. 2007/0020640, U.S. Pat. Publn. 2009/0068645, U.S. Pat. Publn. 2010/0273219, U.S. Pat. Publn. 2011/0015096, or U.S. Pat. Publn. 2011/0257031.

Persons having skill in the art will recognize that the nucleic acid sequencing of silo pools, as described above can be replicated and/or potentially improved through the use of synthetic long read technology. In some embodiments, the methods of the present disclosure can be combined with "chromatin capture" technology such as that disclosed in US 2018/0119203, US 2019/0241933, U.S. Pat. Nos. 9,715,573, 10,457,934, and 10,526,641, which are hereby incorporated by reference for all purposes. In some embodiments, barcoding and/or chromatic capture of samples can be automated via commercially-available robotics (e.g., liquid handlers, such as a Tecan) known to persons having skill in the art, or otherwise described in this document.

Regardless of the exact implementation of barcodes, the resulting digital assembled libraries should still meet the limitations of digital libraries discussed above. In some embodiments, digital environmental or metagenomic libraries created with barcodes should exhibit N50s of at least 10 kb, 11 kb, 12 kb, 13 kb, 14 kb, or 15 kb.

Metagenomic Library Creation—Arraying Library

In some embodiments, the present disclosure teaches methods of creating physical (DNA stock) copies of the multi-gene cluster features set digital metagenomics library. In some embodiments, the physical library copy provides a biological backup copy of digitally stored assembled sequences. In some embodiments, the physical library can be used to conduct further sequencing of one or more silo pool or barcode groups to enhance the sequenced library (e.g., by increasing sequence coverage for one or more portions of the database).

In some embodiments, the physical library provides a mechanism for cloning and studying MGCs that are identified through the systems and methods of the present disclosure. That is, in some embodiments, each sequence within the multi-gene cluster features set digital metagenomics library is associated with a location within the physical library, where the relevant DNA can be accessed.

Figure 16:
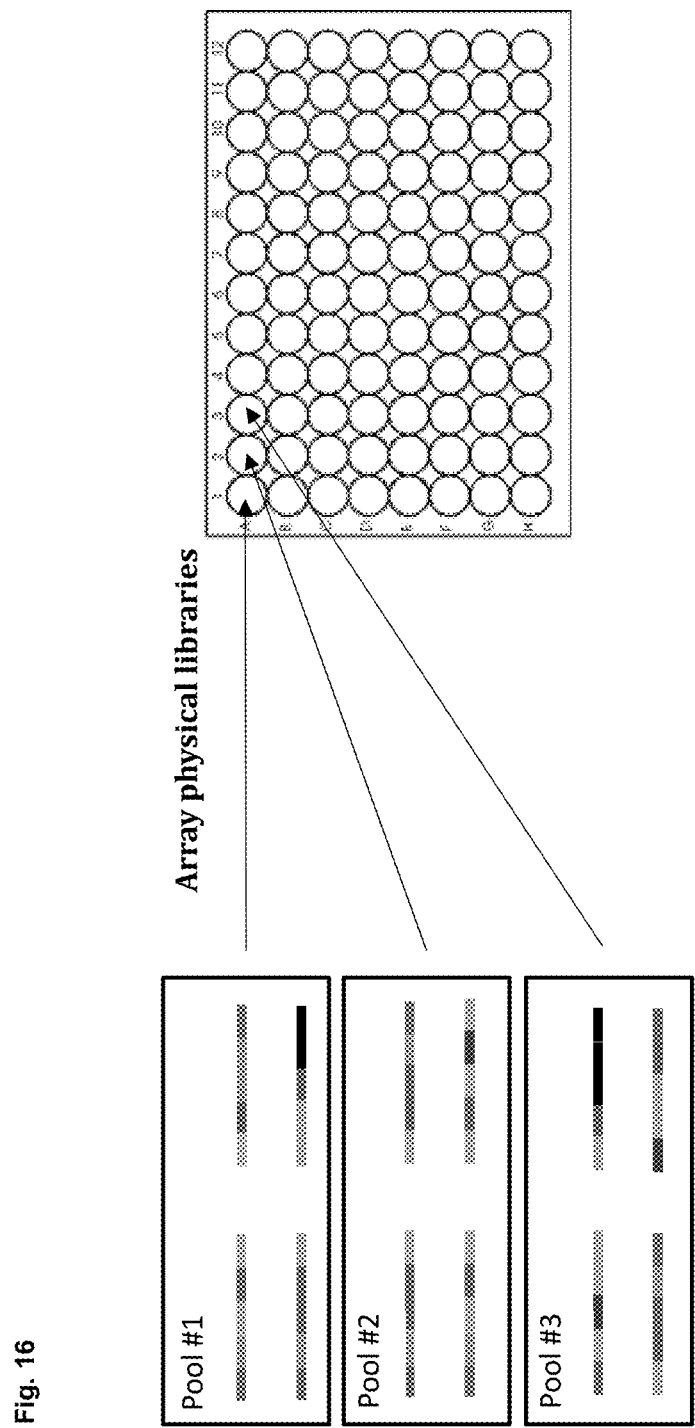
FIG. 16—depicts arraying of mini-metagenomes pools as either E. coli or DNA stocks to create physical metagenomic libraries. These arrayed libraries are later used to recover sequences of interest for further analysis.

Thus, in some embodiments, cosmid silo pools generated by the methods above are stored in glycerol stocks of *E. coli* comprising the cosmids. In some embodiments, cosmid silo pools generated by the methods above are stored as isolated DNA stocks. In some embodiments, cosmid silo pools generated by the methods above are stored as glycerol stocks of microorganisms comprising the pooled cosmids. In some embodiments, the physical libraries are stored in 96-well format for easier storage and access. (See step 1 of FIG. 2, and FIG. 16). These physical libraries are herein referred to as "metagenomic physical libraries" Or "environmental physical libraries," depending on the source of their sequences.

Methods of Producing Digital Metagenomics Libraries—Library Prep and Sequencing

In some embodiments, the resulting silo pools (or cosmids or mini-silo pools) generated above are individually prepared for sequencing. Numerous kits for making sequencing libraries from DNA are available commercially from a variety of vendors. Kits are available for making libraries from microgram down to picogram quantities of starting material. Higher quantities of starting material however require less amplification and can thus better library complexity.

With the exception of Illumina's Nextera prep, library preparation generally entails: (i) fragmentation, (ii) end-repair, (iii) phosphorylation of the 5' prime ends, (iv) A-tailing of the 3' ends to facilitate ligation to sequencing adapters, (v) ligation of adapters, and (vi) optionally, some number of PCR cycles to enrich for product that has adapters ligated to both ends. The primary differences in an Ion Torrent workflow are the use of blunt-end ligation to different adapter sequences.

To facilitate multiplexing, different barcoded adapters can be used with each sample. Alternatively, barcodes can be introduced at the PCR amplification step by using different barcoded PCR primers to amplify different samples. High quality reagents with barcoded adapters and PCR primers are readily available in kits from many vendors. However, all the components of DNA library construction are now well documented, from adapters to enzymes, and can readily be assembled into "home-brew" library preparation kits.

An alternative method is the Nextera DNA Sample Prep Kit (Illumina), which prepares genomic DNA libraries by using a transposase enzyme to simultaneously fragment and tag DNA in a single-tube reaction termed "tagmentation." The engineered enzyme has dual activity; it fragments the DNA and simultaneously adds specific adapters to both ends of the fragments. These adapter sequences are used to amplify the insert DNA by PCR. The PCR reaction also adds index (barcode) sequences. The preparation procedure improves on traditional protocols by combining DNA fragmentation, end-repair, and adaptor-ligation into a single step. This protocol is very sensitive to the amount of DNA input compared with mechanical fragmentation methods. In order to obtain transposition events separated by the appropriate distances, the ratio of transposase complexes to sample DNA can be important. Because the fragment size is also dependent on the reaction efficiency, all reaction parameters, such as temperatures and reaction time, should be tightly controlled for optimal results.

A number of DNA sequencing techniques are known in the art, including fluorescence-based sequencing methodologies (See, e.g., Birren et al., Genome Analysis Analyzing DNA, 1, Cold Spring Harbor, N.Y.). In some embodiments, automated sequencing techniques understood in that art are utilized. In some embodiments, parallel sequencing of partitioned amplicons can be utilized (PCT Publication No WO2006084132). In some embodiments, DNA sequencing is achieved by parallel oligonucleotide extension (See, e.g., U.S. Pat. Nos. 5,750,341; 6,306,597). Additional examples of sequencing techniques include the Church polony technology (Mitra et al., 2003, Analytical Biochemistry 320, 55-65; Shendure et al., 2005 Science 309, 1728-1732; U.S. Pat. Nos. 6,432,360, 6,485,944, 6,511,803), the 454 picotiter pyrosequencing technology (Margulies et al., 2005 Nature 437, 376-380; US 20050130173), the Solexa single base addition technology (Bennett et al., 2005, Pharmacogenomics, 6, 373-382; U.S. Pat. Nos. 6,787,308; 6,833,246), the Lynx massively parallel signature sequencing technology (Brenner et al. (2000). Nat. Biotechnol. 18:630-634; U.S. Pat. Nos. 5,695,934; 5,714,330), and the Adessi PCR colony technology (Adessi et al. (2000). Nucleic Acid Res. 28, E87; WO 00018957).

Next-generation sequencing (NGS) methods share the common feature of massively parallel, high-throughput strategies, with the goal of lower costs in comparison to older sequencing methods (see, e.g., Voelkerding et al., Clinical Chem., 55: 641-658, 2009; MacLean et al, Nature Rev. Microbiol, 7-287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the Heli Scope platform commercialized by Helicos Biosciences, and emerging platforms commercialized by VisiGen, Oxford Nanopore Technologies Ltd., Life Technologies/Ion Torrent, and Pacific Biosciences, respectively.

In pyrosequencing (U.S. Pat. Nos. 6,210,891; 6,258,568), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and 106 sequence reads can be achieved, resulting in up to 500 million base pairs (Mb) of sequence.

In the Solexa/Illumina platform (Voelkerding et al, Clinical Chem., 55-641-658, 2009; MacLean et al, Nature Rev. Microbiol, 7-' 287-296; U.S. Pat. Nos. 6,833,246; 7,115,400; 6,969,488), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluorophore and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLiD technology (Voelkerding et al, Clinical Chem., 55-641-658, 2009; U.S. Pat. Nos. 5,912,148; 6,130,073) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, nanopore sequencing is employed (see, e.g., Astier et al., J. Am. Chem. Soc. 2006 Feb. 8; 128(5):1705-10). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

The Ion Torrent technology is a method of DNA sequencing based on the detection of hydrogen ions that are released during the polymerization of DNA (see, e.g., Science 327 (5970): 1190 (2010); U.S. Pat. Appl. Pub. Nos. 20090026082, 20090127589, 20100301398, 20100197507, 20100188073, and 20100137143). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per base accuracy of the Ion Torrent sequencer is ~99.6% for 50 base reads, with ~100 Mb generated per run. The read-length is 100 base pairs. The accuracy for homopolymer repeats of 5 repeats in length is ~98%. The benefits of ion semiconductor sequencing are rapid sequencing speed and low upfront and operating costs.

In some embodiments, the present disclosure teaches use of long-assembly sequencing technology. For example, in some embodiments, the present disclosure teaches PacBio sequencing and/or Nanopore sequencing.

PacBio SMRT technology is based on special flow cells harboring individual picolitre-sized wells with transparent bottoms. Each of the wells, referred to as zero mode waveguides (ZMW), contain a single fixed polymerase at the bottom (Ardui, S., Race, V., de Ravel, T., Van Esch, H., Devriendt, K., Matthijs, G., et al. (2018b). Detecting AGG interruptions in females with a FMR1 premutation by long-read single-molecule sequencing: a 1 year clinical experience. Front. Genet. 9:150). This allows a single DNA molecule, which is circularized in the library preparation (i.e., the SMRTbell), to progress through the well as the polymerase incorporates labeled bases onto the template DNA. Incorporation of bases induces fluorescence that can be recorded in real-time through the transparent bottoms of the ZMW (Pollard, M. O., Gurdasani, D., Mentzer, A. J., Porter, T., and Sandhu, M. S. (2018). Long reads: their purpose and place. Hum. Mol. Genet. 27, R234-R241. The average read length for SMRT was initially only ~1.5 Kb, and with reported high error rate of ~13% characterized by false insertions (arneiro, M. O., Russ, C., Ross, M. G., Gabriel, S. B., Nusbaum, C., and DePristo, M. A. (2012). Pacific biosciences sequencing technology for genotyping and variation discovery in human data. BMC Genomics 13:375; Quail, M. A., Smith, M., Coupland, P., Otto, T. D., Harris, S. R., Connor, T. R., et al. (2012). A tale of three next generation sequencing platforms: comparison of Ion Torrent, Pacific Biosciences and Illumina MiSeq sequencers. BMC Genomics 13:341). Since its introduction, the read length and throughput of SMRT technology have substantially increased. Throughput can reach >10 Gb per SMRT cell for the Sequel machine, while the average read length for both RSII and Sequel is >10 kb with some reads spanning >100 kb (van Dijk, E. L., Jaszczyszyn, Y., Naquin, D., and Thermes, C. (2018). The third revolution in sequencing technology. Trends Genet. 34, 666-681).

Nanopore sequencing by ONT was introduced in 2015 with a portable MinION sequencer, which was followed by more high-throughput desktop sequencers GridION and PromethION. The basic principle of nanopore sequencing is to pass a single strand of DNA molecule through a nanopore which is inserted into a membrane, with an attached enzyme, serving as a biosensor (Deamer, D., Akeson, M., and Branton, D. (2016). Three decades of nanopore sequencing. Nat. Biotechnol. 34, 518-524). Changes in electrical signal across the membrane are measured and amplified in order to determine the bases passing through the pore in real-time. The nanopore-linked enzyme, which can be either a polymerase or helicase, is bound tightly to the polynucleotide controlling its motion through the pore (Pollard, M. O., Gurdasani, D., Mentzer, A. J., Porter, T., and Sandhu, M. S. (2018). Long reads: their purpose and place. Hum. Mol. Genet. 27, R234-R241). For nanopore sequencing, there is no clear-cut limitation for read length, except the size of the analyzed DNA fragments. On average, ONT single molecule reads are >10 kb in length but can reach ultra-long for some individual reads lengths of >1 Mb surpassing SMRT (Jain, M., Koren, S., Miga, K. H., Quick, J., Rand, A. C., Sasani, T. A., et al. (2018). Nanopore sequencing and assembly of a human genome with ultra-long reads. Nat. Biotechnol. 36, 338-345). Also, the throughput per run of ONT GridION and PromethION sequencers are higher than for PacBio (up to 100 Gb and 6 Tb per run, respectively) (van Dijk, E. L., Jaszczyszyn, Y., Naquin, D., and Thermes, C. (2018). The third revolution in sequencing technology. Trends Genet. 34, 666-681).

The present disclosure also teaches use of a technique selected from the group consisting of Hi-C, 3C, 4C, 5C, TLA, TCC, and in situ Hi-C. For example, DNA sequence reads incubating DNA a fixation agent for a period of time to allow crosslinking of the genomic DNA in situ and thereby forming crosslinked genomic DNA; fragmenting the crosslinked genomic DNA; ligating the crosslinked and fragmented genomic DNA to form a proximally ligated complex; shearing the proximally ligated complex to form proximally-ligated DNA fragments; and obtaining a plurality of the proximally-ligated DNA fragments to form a library thereby obtaining the plurality of genomic DNA fragments. For more information on synthetic long reads, see Amarasinghe, S. L., Su, S., Dong, X. et al. Opportunities and challenges in long-read sequencing data analysis. *Genome Biol* 21, 30 (2020).

In some embodiments, the present disclosure teaches hybrid approaches to sequencing the metagenomic library. That is, in some embodiments, the present disclosure teaches sequencing with two or more sequencing technologies (e.g., one short read and one long read). In some embodiments, access to long read sequencing can improve subsequent assembly of the library by providing a reference sequence for DNA regions where the assembly would not otherwise proceed with just the short reads.

Methods of Producing Digital Metagenomics Libraries—Post-Sequencing Processing and Sequential Assembly In some embodiments, the present disclosure teaches a sequential sequence assembly method to produce long-assembly sequenced metagenomic libraries. Sequence assembly describes the process of piecing together the various sequence reads obtained from the sequencing machine into longer reads representing the original DNA molecule. Assembly is particularly relevant for short-read NGS platforms, where sequences range in the 50-500 base range.

In some embodiments, sequences obtained from the sequencing step can be directly assembled. In some embodiments, the sequences from the sequencing step undergo some processing according to the sequencing manufacturer's instructions, or according to methods known in the art. For example, in some embodiments, the reads from pooled samples are trimmed to remove any adaptor/barcode sequences and quality filtered. In some embodiments, sequences from some sequencers (e.g., Illumina®) are processed to merge paired end reads. In some embodiments, contaminating sequences (e.g. cloning vector, host genome) are also removed. In some embodiments, the methods of the present disclosure are compatible with any applicable post-NGS sequence processing tool. In some embodiments, the sequences of the present disclosure are processed via BBTools (BBMap—Bushnell B.—sourceforge.net/projects/bbmap/).

Sequence assembly techniques can be widely divided into two categories: comparative assembly and de novo assembly. Persons having skill in the art will be familiar with the fundamentals of genome assemblers, which include the overlap-layout-consensus, alignment-layout-consensus, the greedy approach, graph-based schemes and the Eulerian path (Bilal Wajid, Erchin Serpedin, Review of General Algorithmic Features for Genome Assemblers for Next Generation Sequencers, Genomics, Proteomics & Bioinformatics, Volume 10, Issue 2, 2012, Pages 58-73).

According to some embodiments, the assembly of metagenomic library sequences may be a de novo assembly that is assembled using any suitable sequence assembler known in the art including, but not limited to, ABySS, ALLPATHS-LG, AMOS, Arapan-M, Arapan-S, Celera WGA Assembler/CABOG, CLC Genomics Workbench & CLC Assembly Cell, Cortex, DNA Baser, DNA Dragon, DNAnexus, Edena, Euler, Euler-sr, Forge, Geneious, Graph Constructor, IDBA, IDBA-UD, LIGR Assembler, MaSuRCA, MIRA, Next-GENe, Newbler, PADENA, PASHA, Phrap, TIGR Assembler, Ray, Sequencher, SeqMan NGen, SGA, SGARCGS, SOPRA, SparseAssembler, SSAKE, SOAPdenovo, SPAdes, Staden gap4 package, Taipan, VCAKE, Phusion assembler, QSRA, and Velvet.

A non-limiting list of sequence assemblers available to date is provided in Table 2.

TABLE 2

| | | | |
|---|---|---|---|
| Non-limiting List of de novo Sequence Assemblers | | | |
| Name | Type | Technologies and algorithm | Reference/Link |
| ABySS | (large) genomes | Solexa, SOLiD De Bruijn graph(DBG) | ABySS 2.0: resource-efficient assembly of large genomes using a Bloom filter. Jackman S D, Vandervalk B P, Mohamadi H, Chu J, Yeo S, Hammond S A, Jahesh G, Khan H, Coombe L, Warren R L, Birol I. Genome Research, 2017 27: 768-777 |
| ALLPATHS-LG | (large) genomes | Solexa, SOLiD (DBG) | Gnerre S et al. 2010. High-quality draft assemblies of mammalian genomes from massively parallel sequence data. Proceedings of the National Academy of Sciences December 2010, 201017351 |
| AMOS | genomes | Sanger, 454 | //sourceforge.net/projects/amos/ |
| Arapan-M | Medium Genomes (e.g. E.coli) | All | Sahli and Shibuya. An algorithm for classifying DNA reads. 2012 International conference on Bioscience, Biochemistry and Bioinformatics. IPCBEE vol. 31(2012) |
| Arapan-S | Small Genomes (Viruses and Bacteria) | All | Sahli M, Shibuya T. Arapan-S: a fast and highly accurate whole-genome assembly software for viruses and small genomes. *BMC Res Notes*. 2012; 5: 243. Published 2012 May 16. |
| Celera WGA Assembler/ CABOG | (large) genomes | Sanger, 454, Solexa overlap-layout-consensus(OLC) | Koren S, Miller J R, Walenz B P, Sutton G. An algorithm for automated closure during assembly. *BMC Bioinformatics*. 2010; 11: 457. Published 2010 Sep. 10. |
| CLC Genomics Workbench & CLC Assembly Cell | genomes | Sanger, 454, Solexa, SOLiD OLC | Wingfield B D, Ambler J M, Coetzee M P, et al. IMA Genome-F 6: Draft genome sequences of Armillaria fuscipes, Ceratocystiopsis minuta, Ceratocystis adiposa, Endoconidiophora laricicola, E. polonica and Penicillium freii DAOMC 242723. *IMA Fungus*. 2016; 7(1): 217-227. //digitalinsights.qiagen.com |
| Cortex | genomes | Solexa, SOLiD | Whole Genome Sequencing for High-Resolution Investigation of Methicillin Resistant *Staphylococcus aureus* Epidemiology and Genome Plasticity SenGupta D J, Cummings L, Hoogestraat D R, Butler-Wu S M, Shendure J, Cookson B T, Salipante S J JCM doi: 10.1128/JCM.00759-14 |
| DNA Baser | genomes | Sanger, 454 | www.DnaBaser.com |
| DNA Dragon | genomes | Illumina, SOLiD, Complete Genomics, 454, Sanger | Yörük, E, Sefer, Ö. (2018). FcMgv1, FcStuA AND FcVeA based genetic characterization in Fusarium culmorum (W. G. Smith). Trakya University Journal of Natural Sciences, 19 (1), 63-69. www.dna-dragon.com/ |

TABLE 2-continued

Non-limiting List of de novo Sequence Assemblers

| Name | Type | Technologies and algorithm | Reference/Link |
| --- | --- | --- | --- |
| Edena | genomes | Illumina OLC | Analysis of the salivary microbiome using culture-independent techniques. Lazarevic V, Whiteson K, Gaia N, Gizard Y, Hernandez D, Farinelli L, Osteras M, Francois P, Schrenzel J. *J Clin Bioinforma.* 2012 Feb. 2; 2: 4. |
| Euler-sr | genomes | 454, Solexa | Chaisson and Pevzner. Short read fragment assembly of bacterial genomes. Genome Res. 2008. 18: 324-330 |
| Forge | (large) genomes, EST, metagenomes | 454, Solexa, SOLID, Sanger | DiGuistini, S., Liao, N. Y., Platt, D. et al. De novo genome sequence assembly of a filamentous fungus using Sanger, 454 and Illumina sequence data. *Genome Biol* 10, R94 (2009). https://doi.org/10.1186/gb-2009-10-9-r94 |
| Geneious | genomes | Sanger, 454, Solexa, Ion Torrent, Complete Genomics, PacBio, Oxford Nanopore, Illumina | www.geneious.com/features/assembly-mapping/ |
| IDBA (Iterative De Bruijn graph short read Assembler) | (large) genomes | Sanger, 454, Solexa | Peng, Y., et al. (2010) IDBA- A Practical Iterative de Bruijn Graph De Novo Assembler. RECOMB. Lisbon. |
| MaSuRCA (Maryland Super Read - Celera Assembler) | (large) genomes | Sanger, Illumina, 454 hybrid approach | Zimin, A. et al. The MaSuRCA genome Assembler. Bioinformatics (2013). doi: 10.1093/bioinformatics/btt476 |
| MIRA (Mimicking Intelligent Read Assembly) | genomes, ESTs | Sanger, 454, Solexa | Chevreux et al. (2004) Using the miraEST Assembler for Reliable and Automated mRNA Transcript Assembly and SNP Detection in Sequenced ESTs Genome Research 2004. 14: 1147-1159. |
| NextGENe | (small genomes) | 454, Solexa, SOLiD | Manion et al. De novo assembly of short sequence reads with nextgene ™ software & condensation tool. Application note//softgenetics.com/PDF/DenovoAssembly_SSR_AppNote.pdf |
| Newbler | genomes, ESTs | 454, Sanger(OLC) | Margulies M et al. Genome sequencing in microfabricated high-density picolitre reactors. *Nature.* 2005 Sep. 15; 437(7057): 376-80. |
| PADENA | genomes | 454, Sanger | Thareja, G.; Kumar, V.; Zyskowski, M.; Mercer, S. and Davidson, B. (2011). PadeNA: A PARALLEL DE NOVO ASSEMBLER. In *Proceedings of the International Conference on Bioinformatics Models, Methods and Algorithms - Volume 1: BIOINFORMATICS*, (BIOSTEC 2011) |
| PASHA | (large) genomes | Illumina | Liu, Y., Schmidt, B. & Maskell, D. L. Parallelized short read assembly of large genomes using de Bruijn graphs. *BMC Bioinformatics* 12, 354 (2011) |
| Phrap | genomes | Sanger, 454, Solexa (OLC) | Bastide and Mccombie, Assembling Genomic DNA sequences with PHRAP. Current protocols in Bioinformatics. Vol 17(1) March 2007. |
| TIGR Assembler | genomic | Sanger | Sutton G G, White O, Adams M D, Kerlavage A R (1995) TIGR Assembler: A new tool for assembling large shotgun sequencing projects. Genome Science and Technology 1: 9-19. |
| Ray | genomes | Illumina, mix of Illumina and 454, paired or not | Boisvert et al. Ray Meta: scalable de novo metagenome assembly and profiling. *Genome Biology* (BioMed Central Ltd). 13: R122, Published: 22 Dec. 2012 |
| Sequencher | genomes | traditional and next generation sequence data | Bromberg C. Gene Codes Corporation; 1995. Sequenche |
| SeqMan NGen | (large) genomes, exomes, transcriptomes, metagenomes, ESTs | Illumina, ABI SOLiD, Roche 454, Ion Torrent, Solexa, Sanger | Feldmeyer B et al. Short read Illumina data for the de novo assembly of a non-model snail species transcriptome (Radix balthica, Basommatophora, Pulmonata), and a comparison of assembler performance. *BMC Genomics.* 2011; 12: 317. Published 2011 Jun. 16. www.dnastar.com/t-products-seqman-ngen.aspx |
| SGA | (large) genomes | Illumina, Sanger (Roche 454, Ion Torrent?) | Simpson J T and Durbin R. Efficient de novo assembly of large genomes using compressed data structures. *Genome Res.* 2012; 22(3): 549-556 |

TABLE 2-continued

Non-limiting List of de novo Sequence Assemblers

| Name | Type | Technologies and algorithm | Reference/Link |
|---|---|---|---|
| SHARCGS | (small) genomes | Solexa | Dohm J C et al., Substantial biases in ultra-short read data sets from high-throughput DNA sequencing Nucleic Acids Res. 2008 Jul. 26. |
| SOPRA | genomes | Illumina, SOLiD, Sanger, 454 | Dayarian, A. et al., SOPRA: Scaffolding algorithm for paired reads via statistical optimization. BMC Bioinformatics 11, 345 (2010) |
| SparseAssembler | (large) genomes | Illumina, 454, Ion torrent | Ye, C., Ma, Z. S., Cannon, C. H. et al. Exploiting sparseness in de novo genome assembly. BMC Bioinformatics 13, S1 (2012). |
| SSAKE | (small) genomes | Solexa (SOLiD Helicos) | Warren R L, Sutton G G, Jones S J M, Holt R A, 2007 (epub 2006 Dec. 8). Assembling millions of short DNA sequences using SSAKE. Bioinformatics 23: 500 |
| SOAPdenovo | genomes | Solexa (DBG) | Luo, Ruibang et al. "SOAPdenovo2: an empirically improved memory-efficient short-read de novo assembler." GigaScience vol. 1, 1 18. 27 Dec. 2012, doi: 10.1186/2047-217X-1-18 |
| SPAdes | (small) genomes, single-cell | Illumina, Solexa | Bankevich A. et al., SPAdes: A New Genome Assembly Algorithm and Its Applications to Single-Cell Sequencing. Journal of Computational Biology, 2012 |
| Staden gap5 package | BACs (, small genomes?) | Sanger | Bonfield, James K. and Whitwham, Andrew. Gap5 - editing the billion fragment sequence assembly. Bioinformatics 26, 1699-1703, (2010) |
| Taipan | (small) genomes | Illumina | Bertil Schmidt et al, A fast hybrid short read fragment assembly algorithm, Bioinformatics, Volume 25, Issue 17, 1 Sep. 2009, Pages 2279-2280 |
| VCAKE | (small) genomes | Solexa (SOLiD, Helicos) | William R. Jeck et al., Extending assembly of short DNA sequences to handle error, Bioinformatics, Volume 23, Issue 21, 1 Nov. 2007, Pages 2942-2944, |
| Phusion assembler | (large) genomes | Sanger (OLC) | Mullikin, James C, and Zemin Ning. "The phusion assembler." Genome research vol. 13, 1 (2003): 81-90. doi: 10.1101/gr.731003 |
| Quality Value Guided SRA (QSRA) | genomes | Sanger, Solexa | Bryant, Douglas W Jr et al. "QSRA: a quality-value guided de novo short read assembler." BMC bioinformatics vol. 10 69. 24 Feb. 2009, doi: 10.1186/1471-2105-10-69 |
| Velvet | (small) genomes | Sanger, 454, Solexa, SOLiD (DBG) | Zerbino, Daniel R. "Using the Velvet de novo assembler for short-read sequencing technologies." Current protocols in bioinformatics vol. Chapter 11 (2010): Unit 11.5. doi: 10.1002/0471250953.bi1105s31 |

Figure 15:
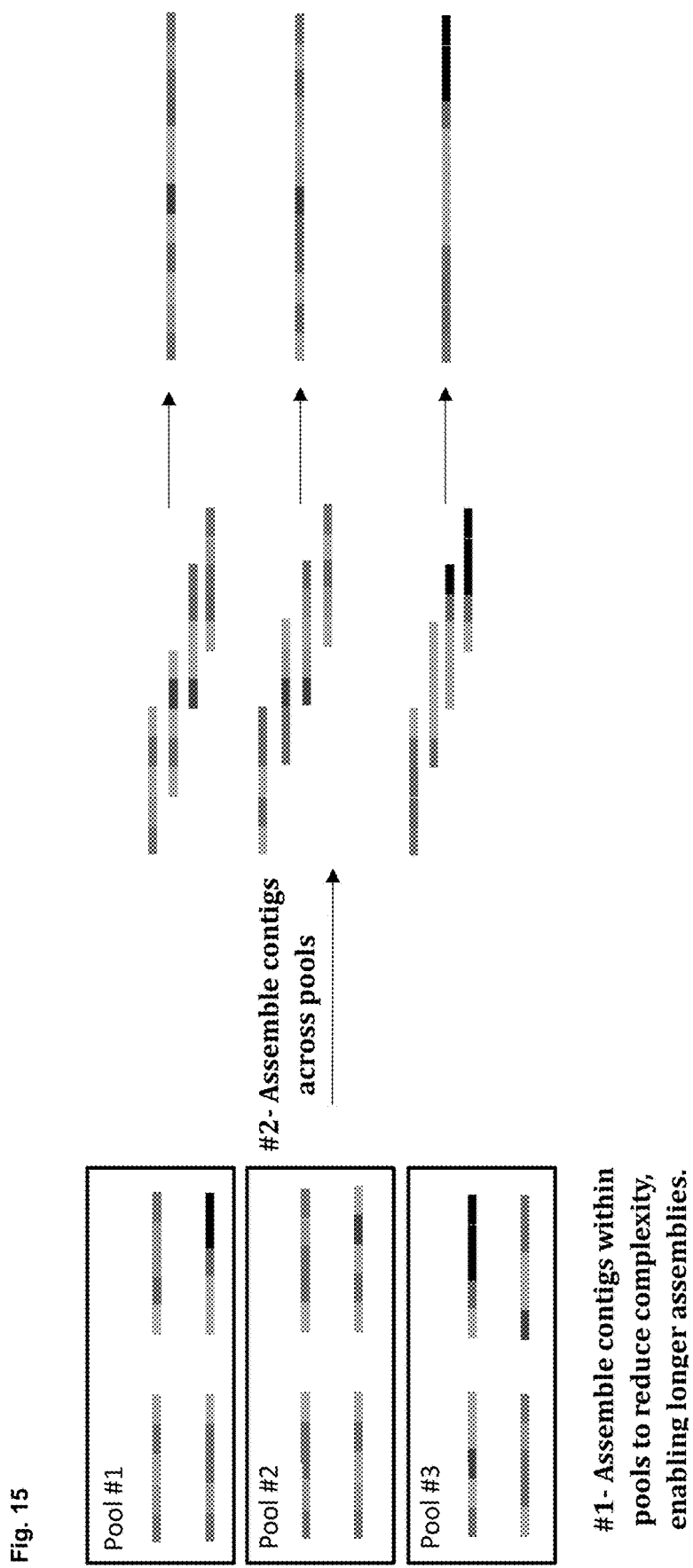
FIG. 15—depicts assembly steps of the digital metagenomic library of the present disclosure. In some embodiments, a two phased assembly method is used to obtain longer assemblies.

In some embodiments, the present disclosure teaches a sequential assembly technique comprising at least a first assembly and a second assembly. In some embodiments, the first assembly is an assembly of sequences from each silo pool (or if barcoded, to any distinctly barcoded group of sequences). This first assembly thus only builds sequences by combining reads obtained from within the same silo pool (or barcoded group). This first assembly benefits from a relatively lower complexity pool of reads, and is therefore able to align sequences with higher confidence (and thus generate longer assemblies compared to more complex pools). The resulting sequences from the first assembly consist of a plurality of mini metagenomes, each corresponding to a portion of one or more cosmids in the initial E. coli cosmid library. (See FIG. 15).

In some embodiments, the mini metagenomes from the first assembly produce a digital library with an N50 length of about 5 kb, 6 kb, 7 kb, 8 kb, 9 kb, 10 kb, 11 kb, 12 kb, 13 kb, 14 kb, 15 kb, 16 kb, 17 kb, 18 kb, 19 kb, 20 kb, 21 kb, 22 kb, 23 kb, 24 kb, 25 kb, 26 kb, 27 kb, 28 kb, 29 kb, 30 kb, 31 kb, 32 kb, 33 kb, 34 kb, 35 kb, 36 kb, 37 kb, 38 kb, 39 kb, or 40 kb, including all ranges and subranges therebetween. Thus, in some embodiments, the mini metagenomes from the first assembly produce a digital library with an N50 length of at least 5 kb, 6 kb, 7 kb, 8 kb, 9 kb, 10 kb, 11 kb, 12 kb, 13 kb, 14 kb, 15 kb, 16 kb, 17 kb, 18 kb, 19 kb, 20 kb, 21 kb, 22 kb, 23 kb, 24 kb, 25 kb, 26 kb, 27 kb, 28 kb, 29 kb, 30 kb, 31 kb, 32 kb, 33 kb, 34 kb, 35 kb, 36 kb, 37 kb, 38 kb, 39 kb, or 40 kb.

In some embodiments, the resulting assemblies from the first assembly are then used to prepare longer assemblies across different silo pools (or barcoded groups, if barcodes were used) in a second assembly. As described above, each of the silo pools (or barcoded groups) used for the first assembly are smaller portions of the starting metagenomic DNA sample. Thus, it is possible, and even likely, that sequences contained in one silo pool/barcode group may correspond (i.e., assemble, align) with sequences from one or more other silo pools/barcode groups. Thus, in some embodiments, each of the assembled mini metagenomes from the first assembly are provided as input for a second assembly. In some embodiments, mini metagenomes from the first assembly can be combined, and result in longer sequence assemblies. (See FIG. 15). In some embodiments, the second assembly also comprises assembling any unassembled reads remaining from each of the silo pools/barcode groups.

In some embodiments, the resulting cross-silo/barcode group assemblies produce even large sequence strings. The resulting assembled sequences from the first and second assembly steps are populated into a database and were referred to as a "digital metagenomics library," or "digital environmental library," depending on the source of the sequences.

In some embodiments, the resulting digital metagenomics or environmental library comprises an average sequence length of about 15 kb, 16 kb, 17 kb, 18 kb, 19 kb, 20 kb, 21 kb, 22 kb, 23 kb, 24 kb, 25 kb, 26 kb, 27 kb, 28 kb, 29 kb, 30 kb, 31 kb, 32 kb, 33 kb, 34 kb, 35 kb, 36 kb, 37 kb, 38 kb, 39 kb, 40 kb, 41 kb, 42 kb, 43 kb, 44 kb, 45 kb, 46 kb, 47 kb, 48 kb, 49 kb, 50 kb, 51 kb, 52 kb, 53 kb, 54 kb, 55 kb, 56 kb, 57 kb, 58 kb, 59 kb, 60 kb, 61 kb, 62 kb, 63 kb, 64 kb, 65 kb, 66 kb, 67 kb, 68 kb, 69 kb, 70 kb, 71 kb, 72 kb, 73 kb, 74 kb, 75 kb, 76 kb, 77 kb, 78 kb, 79 kb, 80 kb, 81 kb, 82 kb, 83 kb, 84 kb, 85 kb, 86 kb, 87 kb, 88 kb, 89 kb, 90 kb, 91 kb, 92 kb, 93 kb, 94 kb, 95 kb, 96 kb, 97 kb, 98 kb, 99 kb, 100 kb, 101 kb, 102 kb, 103 kb, 104 kb, 105 kb, 106 kb, 107 kb, 108 kb, 109 kb, 110 kb, 111 kb, 112 kb, 113 kb, 114 kb, 115 kb, 116 kb, 117 kb, 118 kb, 119 kb, 120 kb, 121 kb, 122 kb, 123 kb, 124 kb, 125 kb, 126 kb, 127 kb, 128 kb, 129 kb, or 130 kb, including all ranges and subranges therebetween. In some embodiments, the average sequence length of the digital metagenomics library is 32 kb.

In some embodiments, the resulting digital metagenomics or environmental library comprises an N50 of about 10 Kb, 11 Kb, 12 Kb, 13 Kb, 14, Kb, 15 kb, 16 kb, 17 kb, 18 kb, 19 kb, 20 kb, 21 kb, 22 kb, 23 kb, 24 kb, 25 kb, 26 kb, 27 kb, 28 kb, 29 kb, 30 kb, 31 kb, 32 kb, 33 kb, 34 kb, 35 kb, 36 kb, 37 kb, 38 kb, 39 kb, 40 kb, 41 kb, 42 kb, 43 kb, 44 kb, 45 kb, 46 kb, 47 kb, 48 kb, 49 kb, 50 kb, 51 kb, 52 kb, 53 kb, 54 kb, 55 kb, 56 kb, 57 kb, 58 kb, 59 kb, 60 kb, 61 kb, 62 kb, 63 kb, 64 kb, 65 kb, 66 kb, 67 kb, 68 kb, 69 kb, 70 kb, 71 kb, 72 kb, 73 kb, 74 kb, 75 kb, 76 kb, 77 kb, 78 kb, 79 kb, 80 kb, 81 kb, 82 kb, 83 kb, 84 kb, 85 kb, 86 kb, 87 kb, 88 kb, 89 kb, 90 kb, 91 kb, 92 kb, 93 kb, 94 kb, 95 kb, 96 kb, 97 kb, 98 kb, 99 kb, 100 kb, 101 kb, 102 kb, 103 kb, 104 kb, 105 kb, 106 kb, 107 kb, 108 kb, 109 kb, 110 kb, 111 kb, 112 kb, 113 kb, 114 kb, 115 kb, 116 kb, 117 kb, 118 kb, 119 kb, 120 kb, 121 kb, 122 kb, 123 kb, 124 kb, 125 kb, 126 kb, 127 kb, 128 kb, 129 kb, or 130 kb, including all ranges and subranges therebetween. In some embodiments, the resulting digital metagenomics or environmental library comprises an N50 of at least 15 kb, 16 kb, 17 kb, 18 kb, 19 kb, or 20 kb.

In some embodiments, the present disclosure teaches that the physical and/or digital sequence libraries described herein are representative of the environmental sample from which it was extracted. In some embodiments the digital sequence libraries can be assessed by reviewing the predicted taxonomic classification of the assembled sequences within the library. Persons having skill in the art will be familiar with ways of assessing taxonomic diversity within a sequence and assembled library. In some embodiments, taxonomic characterization of the digital metagenomics library can be done via a Krona plot. An illustrative description of how classification can take place is provided. Nucleotide sequences of the assembled contigs are used as input to the software tool Kaiju (github.com/bioinformatics-centre/kaiju; Menzel, P. et al. (2016) "Fast and sensitive taxonomic classification for metagenomics with Kaiju." Nat. Commun. 7:11257). The Kaiju tool predicts ORFs in all six reading frames on the contigs, and uses the predicted ORFs to perform a homology search against a reference database. Taxonomy is assigned to the source contig sequence based on assignment of taxonomy for each of the ORFs contained on it, based on the Least Common Ancestor (LCA). The reference database used is all protein sequences in the NCBI NR database. This includes sequence data from all cultured and environmental bacteria, archaea, as well as eukaryotes. The diversity determined using this method provides an overview of the composition of environmental DNA captured in the arrayed metagenomic library.

In Silico Identification of Natural Product-Encoding Clusters

Many natural products in microbes are produced by machinery encoded by multi-gene clusters (MGCs) that, in addition to encoding for the biosynthetic genes, typically also encode for expression control, self-resistance, and export (Walsh C T, and Fischbach M A 2010. Natural Products Version 2.0: Connecting Genes to Molecules. J Am Chem Soc 132:2469-2493; Kottmann et al., 2015. Minimum Information about a Biosynthetic Gene cluster. Nat Chem Biol 11:625-631; Tenconi E. and Rigali S. 2018. Self-resistance mechanisms to DNA-damaging antitumor antibiotics in Actinobacteria. Curr Opin Microbiol 45:100-108). Comparisons of multi-gene clusters across products/species have also revealed a series of conserved structural features capable of identifying various categories of MGCs amidst the background of other DNA regulatory and biosynthetic genes. The inventions of the present disclosure leverage the conserved structural, sequence, and organizational properties of natural product-encoding MGCs to produce new in silico natural product discovery workflows. (See FIG. 1). In in silico methods of the present disclosure can be broadly categorized into 1) resistance gene-based MGC searches, 2) untargeted resistance signal MGC searches, and 3) transitive MGC searches. Each of these is discussed in more detail below.

In some embodiments, the in silico methods of the present disclosure (i.e., methods 1-3 discussed above), are capable of leveraging (and exploring the diversity of) digital metagenomic libraries or digital environmental libraries. This document has outlined the many advantages of using metagenomic libraries for natural product discovery. In some embodiments, however, the in silico methods of the present disclosure can also be applied to other sequence libraries, such as libraries representing collections of strains or other private and publicly available databases, or digital environmental libraries, as described in earlier sections of this disclosure. Persons having skill in the art will thus recognize that descriptions of the methods below in the context of metagenomics libraries can also be applied to other sequence libraries. Application of the methods to these libraries is therefore also inherently disclosed.

In Silico Discovery of Natural Product Encoding MGCs—Resistance Gene Searches Theoretical Basis In some embodiments, the present disclosure teaches resistance-based search strategies for MGCs. These strategies are largely based on the resistance hypothesis of natural product evolution.

The resistance hypothesis states that within the MGC there is often at least one gene conferring resistance against the potentially harmful natural product ("NP") that the organism produces. Without wishing to be bound by any one theory, the instant inventors hypothesize that the presence of a resistance gene within MGCs is an evolutionary self-defense mechanism to ensure that the microbe producing the natural product has a way of delivering the new NP to its environment, or otherwise mitigating any negative effects stemming from its accumulation. This hypothesis also posits that most (but not all) resistance genes will be located within—or highly proximate to—the MGC. This genetic proximity increases the chances that the resistance gene will be co-inherited (and potentially-co-regulated) with the natural product-encoding MGC.

The resistance hypothesis encompasses a variety of resistance strategies that can be categorized into four notable mechanisms. (See FIG. 5). For example, in some embodiments, the resistance is NP export (efflux)-based resistance, as exemplified by the export of tetracycline from *Streptomyces*. In some embodiments, the resistance is NP modification-based resistance, as exemplified by the acetyltransferase modification of chloramphenicol in *Streptomyces*. In some embodiments, the resistance is target modification-based resistance, as exemplified by ribosome methylation of aminoglycosides in *Streptomyces*. In some embodiments, the resistance is target variant-based resistance, as exemplified by the encoding of RNA polymerase variants imparting resistance against rifamycin in *Amycolatopsis rifamycinica*. Persons having skill in the art will recognize that these mechanisms are illustrative, and not meant to limit the scope of the instant invention. Thus, in some embodiments, references to resistance genes in the present application will be broadly understood to cover genes falling under any of the mechanisms discussed above, or other mechanisms that result in the proximal location of resistance genes to their NP-encoding MGCs.

As an extension of the target variant-based strategies in the resistant hypothesis, the duplication hypothesis states that the resistance gene within a MGC will share sequence similarity with an essential gene that performs a primary function in the organism.

Figure 17:
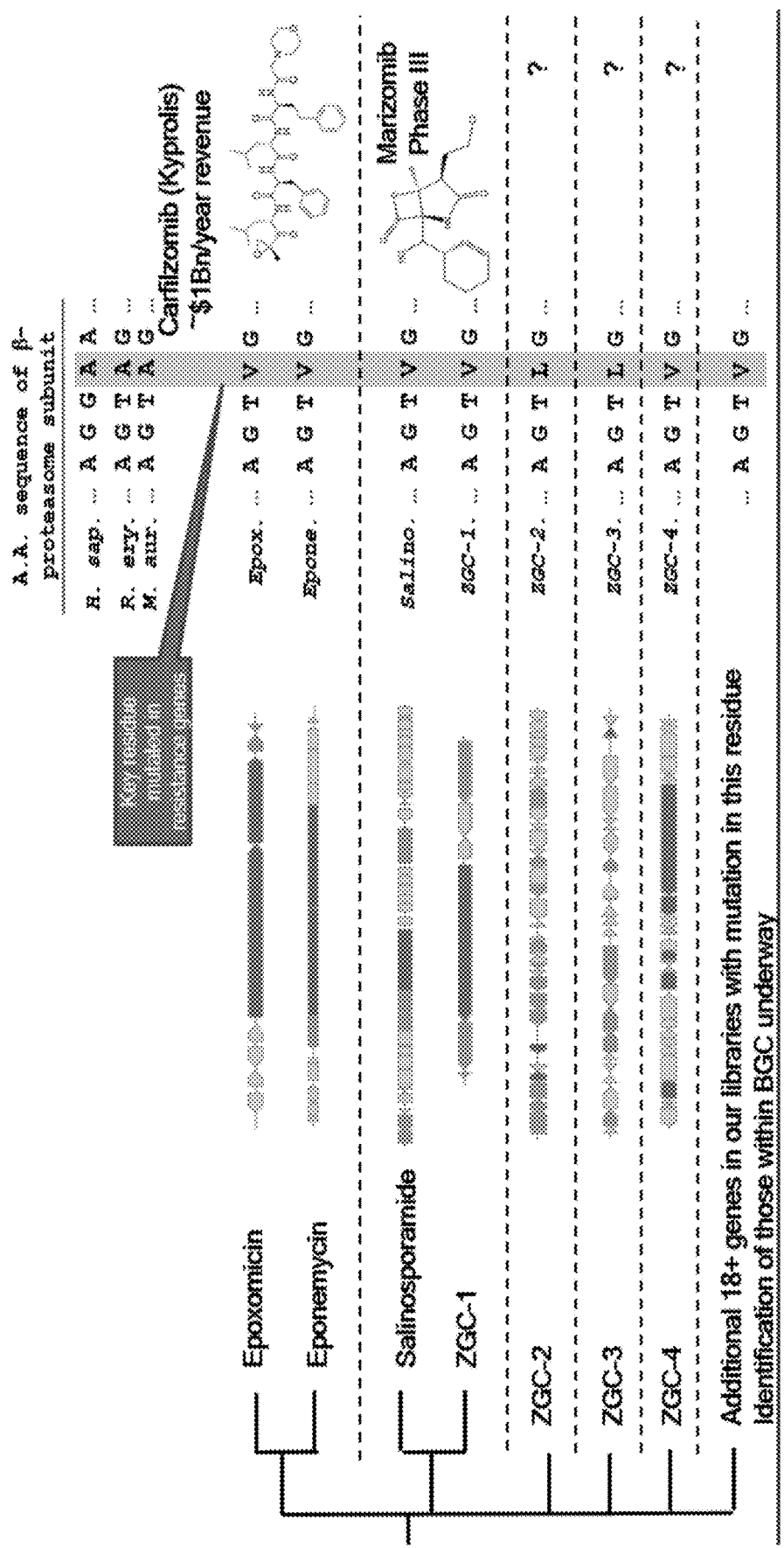
FIG. 17—depicts the results of a resistance gene-based multi-gene cluster search, according to methods of the present disclosure.
Figure 18:
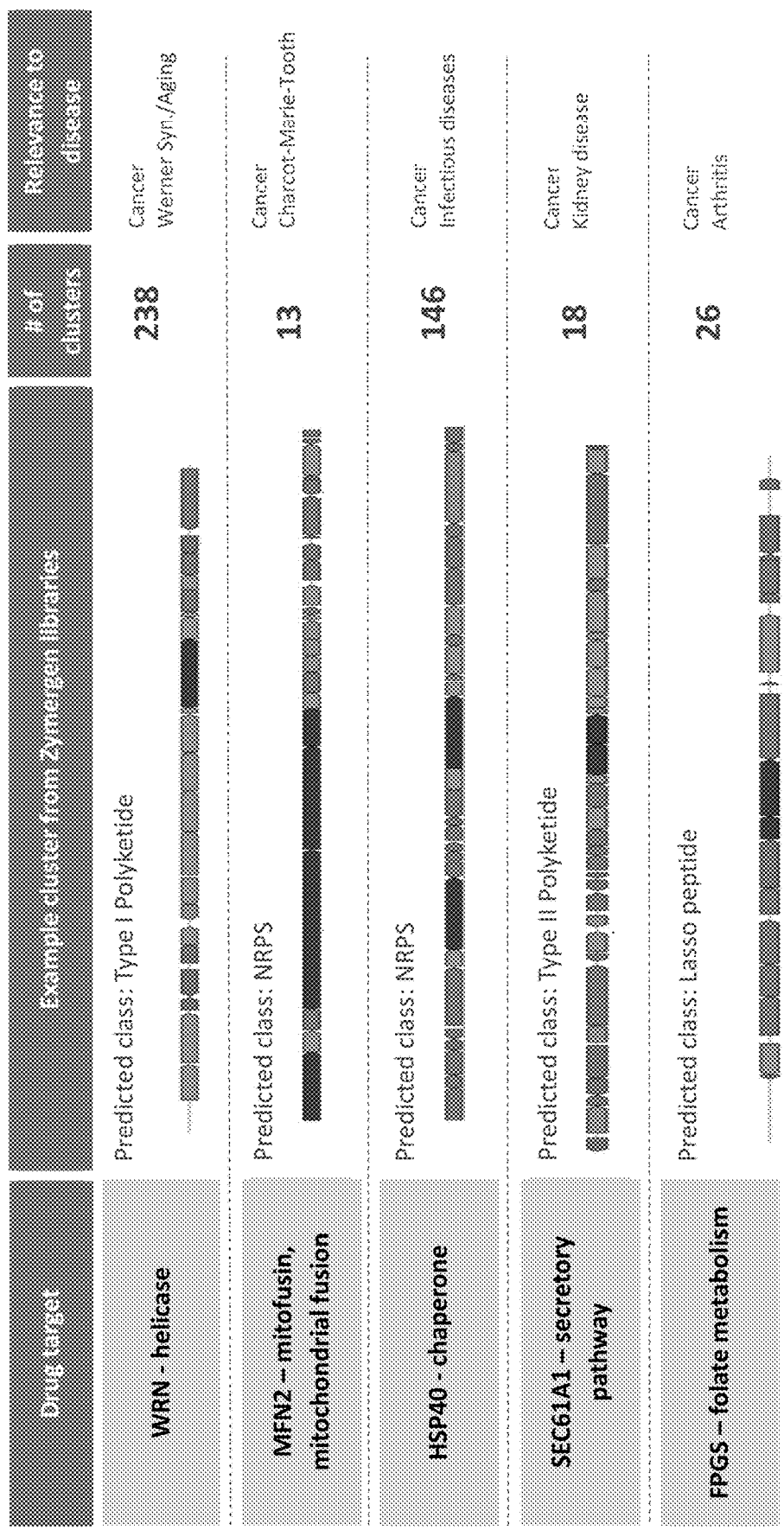
FIG. 18—depicts additional results of a resistance gene-based multi-gene cluster search, according to methods of the present disclosure. The workflows of the present disclosure were used to identify natural product encoding clusters for natural products targeting WRN-helicase, MFN2, HSP40, SEC61A1, and FPGS.

The duplication hypothesis arises from observations that many antibiotics' common target sites, such as DNA gyrase, are also found in the producing microbe. Thus, in order to protect itself, the producing microbe harbors a copy of the target sequence with a slight modification that renders the altered protein resistant to the effects of the toxic natural product. In some embodiments, the modification affects the ability of the natural product to bind to the protein, but does not affect the ability of the protein to carry out its normal role in the cell. (See e.g., Expoxomicin resistance illustrated in FIG. 17, and examples discussed below).

For example, *Salinispora tropica* produces salinosporamide A to inhibit the proteasome. The proteasome, however, is also present in *S. tropica*. The gene cluster encoding salinosporamide A encloses the SalI gene, which shares 58% sequence identity to the proteasome β-subunit gene on Strop_2244. However, at the protein level, the SalI subunit and the typical β-subunit differ in only two amino acids, at positions 45 and 49. Nevertheless, when combined with the α-subunit, SalI protein forms a proteasome complex that cannot be bound by salinosporamide A, thereby acting as an effective target variant-based resistance against salinosporamide A (Kale A J, McGlinchey R P, Lechner A, Moore B S. Bacterial self-resistance to the natural proteasome inhibitor salinosporamide A. ACS Chem Biol. 2011; 6(11):1257-1264).

At its core, target variant-based strategies and the duplication hypothesis describe very similar ideas. However, "target variant-based strategies" refers to a self-protective mechanism, whereas the duplication hypothesis describes one possible property of the MGCs that can be used to enhance MGC prediction. Indeed, certain embodiments of the present disclosure are based on the hypothesis that target-variants encoded within MGCs will exhibit homology to essential genes that are not only present in the producing microbe, but also in other organisms.

In some embodiments, the present disclosure thus teaches that conservation of a "resistance gene" across different organisms indicates that the conserved gene may be a target of the natural product encoded by the MGC. In some embodiments, the systems and methods of the present disclosure leverage the relationship between microbial MGC resistance genes and essential genes in other organisms to design natural product discovery programs focused on specific application targets.

For instance, examples within this application use the similarity of resistance genes identified in human cancers to identify novel natural products with potential anti-cancer properties, based on a likelihood of targeting the same essential gene. (See Example 2, and FIG. 17).

Specific discovery workflows based on the resistance gene hypotheses are discussed in more detail below.

Resistance Gene Search Workflow

In some embodiments, the present disclosure teaches in silico methods for searching a digital metagenomics library and identifying a natural product of interest. In some embodiments, the methods of the present disclosure comprise the steps of: a) querying a digital metagenomics library for a signal indicative of a natural product multi-gene cluster feature set; b) supplying the output of said query as a plurality of signal-associated (multi-gene cluster) digital feature sets; c) determining and assigning biologic relevancy to the signal-associated multi-gene cluster digital feature sets, by: 1) determining a computationally predicted biosynthetic functionality of a plurality of genes from a signal-associated multi-gene cluster digital feature set and digitally assembling a computationally determined natural product multi-gene cluster feature set comprising a biosynthetic operon; and/or ii) determining a computationally predicted biological resistance gene functionality of at least one gene from the signal-associated multi-gene cluster digital feature set, to thereby identify a computationally determined biological resistance gene; and d) identifying a natural product of interest based upon a computationally determined biological resistance gene being located within a threshold parameter of a computationally determined natural product multi-gene cluster feature set comprising a digitally assembled biosynthetic operon.

In some embodiments, resistance gene searching involves three steps: that of identifying a candidate resistance gene; that of identifying a candidate gene cluster; a finally, a determination that the candidate resistance gene and the candidate gene cluster are in proximity within a DNA fragment. Persons having skill in the art will recognize that the identification of candidate resistance genes sand candidate gene clusters can be conducted in any order. Both possible orders are encompassed by the instant claims, and are discussed in more detail below.

Figure 6:
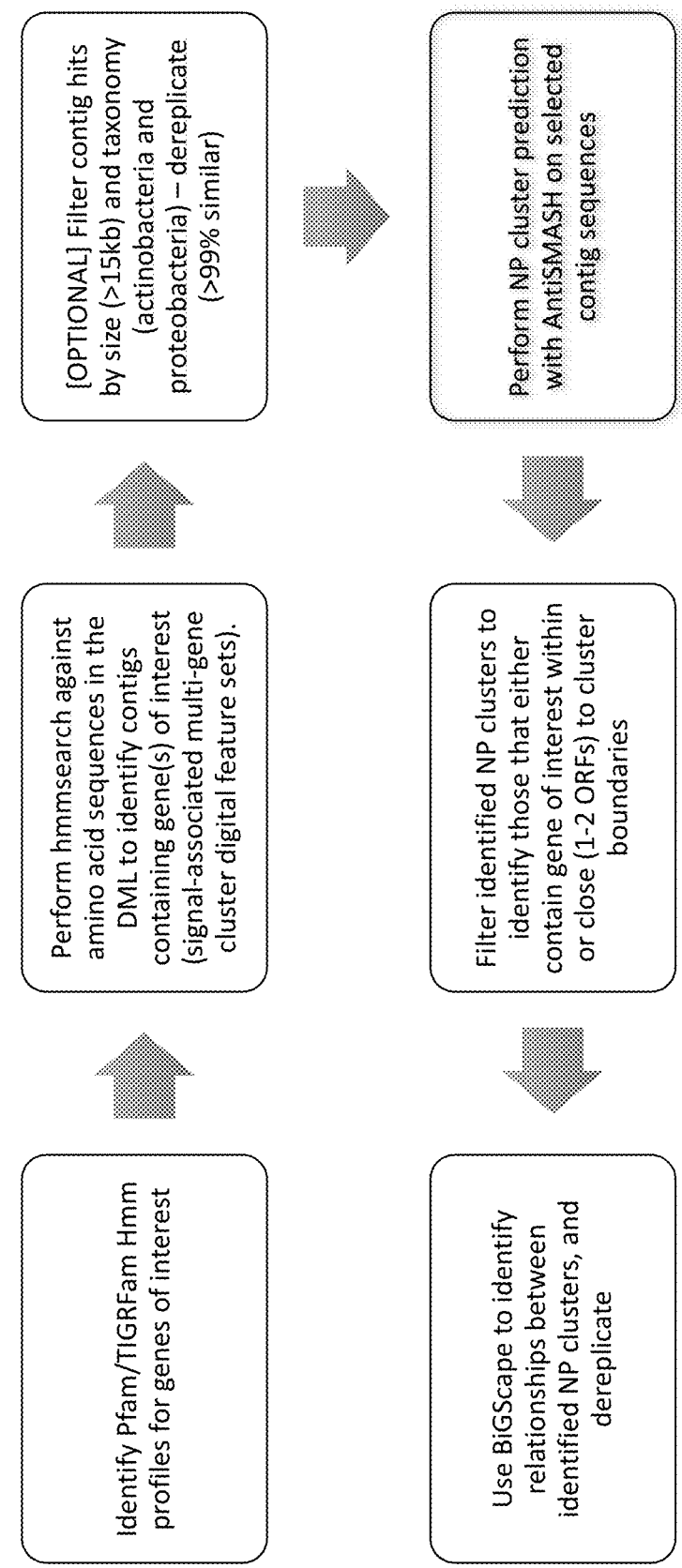
FIG. 6—depicts the steps of an embodiment of the in silico natural product multi-gene cluster discovery methods of the present disclosure. Candidate resistance genes may be identified in digital metagenomic libraries (DMLs) via HMMs selected based on selected target genes (e.g., resistance genes in other organisms or for related natural products). Metagenomic libraries can also be screened for the presence of multi-gene clusters. In some embodiments, the present disclosure teaches selecting MGCs that comprise candidate resistance genes within the MGC, or within 1-2 ORFS of said MGCs.

A visual representation of an embodiment of the workflow of the resistance gene MGC searches of the present disclosure is provided in FIG. 6. Briefly, the digital metagenomic library is queried for the presence of a homolog to a known or predicted resistance gene (i.e., resistance gene homology, corresponding to step a)). That is, in some embodiments, the initial "a) querying a digital metagenomics library for a signal indicative of a natural product multi-gene cluster feature set," comprises querying the digital metagenomics library for the presence of a candidate resistance gene.

Digital DNA sequence hits comprising the identified candidate resistance genes are optionally filtered, and then analyzed for the presence of natural product coding multi-gene clusters (i.e., cluster prediction, corresponding to step c)i)). That is, in some embodiments, the "determining and assigning biologic relevancy to a signal-associated multi-gene cluster digital feature sets," comprises identifying candidate gene clusters.

Finally, the location of identified candidate resistance genes is analyzed in comparison to the location of the identified candidate clusters, thereby identifying candidate clusters in which the candidate resistance gene is located within the predicted boundaries of the cluster, or within a predetermined distance from said boundaries (i.e., proximity analysis, corresponding to step d)).

As noted above, persons having skill in the art will recognize that the identification of candidate clusters and candidate resistance genes can be conducted in any order. For example, in some embodiments, the digital metagenomic library is queried for the presence of all predicted natural product coding multi-gene clusters (candidate clusters, corresponding to step a)). That is, in some embodiments, the initial a) "querying a digital metagenomics library for a signal indicative of a natural product multi-gene cluster feature set," comprises querying the digital metagenomics library for the presence of a candidate resistance gene.

Digital DNA sequence hits comprising the predicted natural product coding multi-gene clusters are further queried for the presence of a homolog to a known or predicted resistance gene (candidate resistance genes, corresponding to step c)ii)). That is, in some embodiments, the "determining and assigning biologic relevancy to a signal-associated multi-gene cluster digital feature sets," comprises identifying candidate resistance genes.

Finally, the location of identified candidate resistance genes is analyzed in comparison to the location of the identified candidate clusters, thereby identifying candidate clusters in which the candidate resistance gene is located within the predicted boundaries of the cluster, or within a predetermined distance from said boundaries (i.e., proximity analysis, corresponding to step d). Each of these steps is discussed in more detail, below.

Selecting Target Genes for Resistance Gene Searches

Figure 7:
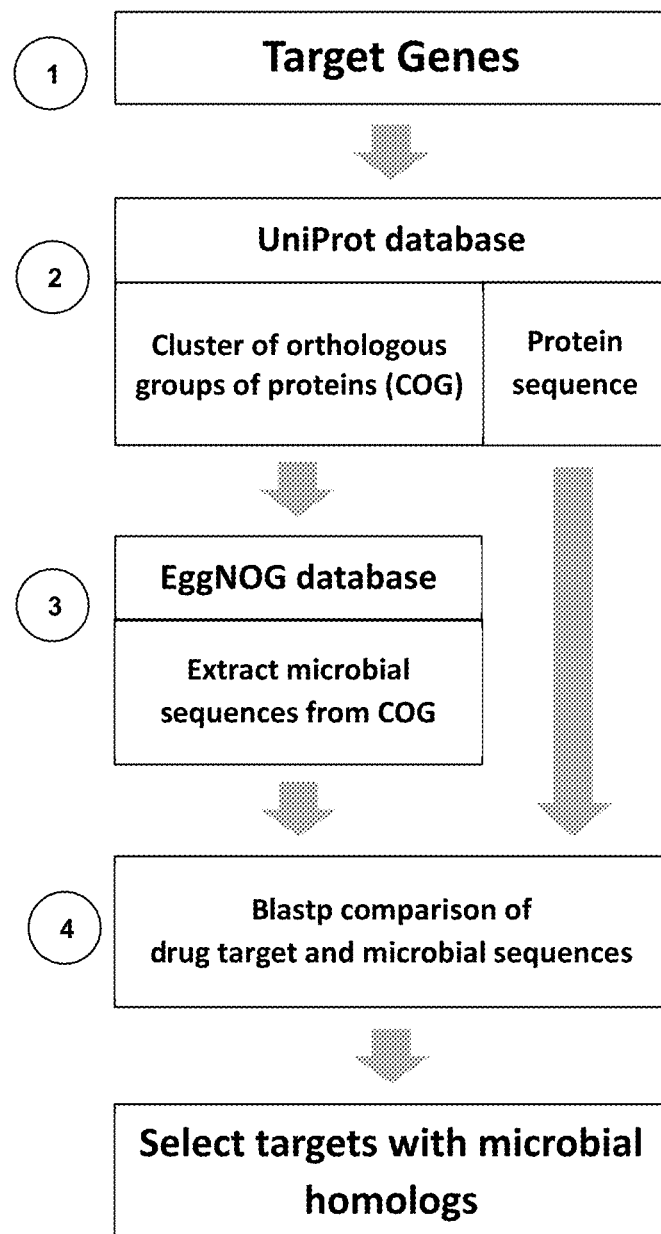
FIG. 7—illustrates a method for the identification of target resistance genes that could be used in the multi-gene discovery platforms of the present disclosure. For each target resistance gene of interest, the protein sequence and (if available) the ID of the corresponding cluster of orthologous group of proteins (COG) are retrieved from a sequence database (e.g., the Uniprot database). In some embodiments, the COGs are formed by EggNOG's clustering algorithm (e.g., database version 4.5.1). In some embodiments, sequences within the COG are compared to all microbial proteins in the same orthologous group, using diamond blastp. In some embodiments, relevant hits, i.e., e-value of $10^{-3}$ or lower, are selected for downstream analyses.

In some embodiments, the initial step of the discovery platform is to set a goal, and identify resistance genes designed to identify the desired natural products (FIG. 7). In some embodiments, the methods of the present disclosure can be customized to search for MGCs encoding particular classes of natural products. For example, in some embodiments, the goal may be to identify natural products that can interact with a human protein (i.e. the target gene/protein). In this illustrative example, the digital metagenomic library is queried for the presence of homologs of the human protein that are well-conserved in prokaryotes (i.e. querying the database for a resistance gene). By example, in some embodiments, the presently disclosed methods can be used to search for bacterial natural products encoding human proteasome inhibitors using a resistance gene search because the human proteasome is well-conserved in some prokaryotes.

Thus, the presently disclosed methods permit, for the first time, the exploration and identification of new natural products for specific therapeutic targets. For example, If the goal is to identify natural products capable of modulating the activity of a human cell cycle gene associated with cancer, then the target gene/protein would be the human cell cycle gene, and related genes. That is, in some embodiments, a search for natural products capable of modulating the activity of a cell cycle gene would utilize a predictive model (e.g., HMM, trained on the human cell cycle gene, and (possibly) other related genes (e.g., genes in the same pFAM or recognized to be within the same class by scientific reports). In some embodiments, application of the MGC discovery workflows to the presently disclosed long-assembly library exhibits unexpected synergies that allow the exploration of the broad genetic diversity of metagenomic samples for the first time. Indeed, experiments demonstrate that application of the discovery workflows is more than 10×, 20×, 30×, 40×, or 50× more effective at identifying MGCS than other large sequence databases.

In another illustrative example, the goal may be to identify variants of known antibiotics. In these embodiments, the digital metagenomics library could be queried for the presence of homologs to the gene(s) responsible for resistance of the known antibiotic (e.g., TEM-1 B-lactamase for ampicillin resistance). The resulting hits would be expected to be enriched in MGCs encoding for antibiotic variants, based on the presence of the candidate resistance gene sharing homology with the gene responsible for resistance of the known antibiotic. Thus, in some embodiments, the resistance gene searches of the present disclosure identify MGCs encoding for natural products that target the resistance gene (or homologs thereof), or whose effects are reduced/remediated by the presence of the resistance gene.

Persons having skill in the art will recognize however, that the methods of the present disclosure can be applied genes/proteins of any species, including those derived from plants, fungi, and bacteria.

In some embodiments the target gene sequences used for resistance gene searches are full gene sequences (e.g., from transcriptional start site to termination). In some embodiments the target gene sequences used for resistance gene searches are the coding sequences of genes (e.g., expressed gene minus UTRs). In some embodiments the target gene sequences used for resistance gene searches are partial genes, such as those comprising one or more relevant domains. In some embodiments the target gene sequences used for resistance gene searches are protein sequences, such as the sequence of a complete expressed protein. In some embodiments the target gene sequences used for resistance gene searches are protein sequences, such as the sequence of a complete expressed protein. In some embodiments the target gene sequences used for resistance gene searches are partial protein sequences, such as those belonging to a particular protein domain of interest. Thus, if the target resistance gene is a protein with a well-conserved DNA binding domain, the resistance gene searches of the present disclosure can be focused on the conserved DNA binding domain, as opposed to the entire protein sequence.

In some embodiments, the present disclosure teaches selecting resistance gene search targets using the following in silico workflow: 1) identify a desired natural product target gene (e.g., a gene that is hypothesized to be affected by a known or predicted natural product); 2) identify the Common Ortholog Group (COG) of the desired natural product target gene (e.g., as found in Uniprot); 3) determine if the identified COG contains microbial sequences; and 4) if so, conduct BLAST comparing the target gene to the microbial sequences from the same COG. In some embodiments, the resulting blast hits are; 5) further evaluated for conservation (e.g., an E-value of <0.001 indicates that there is significant conservation between the target gene/protein and microbial gene/proteins). In some embodiments, the present disclosure teaches selecting genes through blast, as described above. In some embodiments, the present disclosure teaches only selecting blast hits with an E-value of <0.001. In some embodiments, the selected target gene is used in the MGC search workflows described in this document.

Resistance Gene Homology Searches

In some embodiments, the present disclosure teaches querying a digital metagenomics library for a signal indicative of a natural product multi-gene cluster feature set. In some embodiments the querying step comprises searching the digital metagenomics library for homologs to a known or predicted resistance gene (both referred to as target resistance gene), thereby identifying a candidate resistance gene. As noted above, in some embodiments, the resistance gene searches can be conducted later in the method, in the step for assigning biological relevancy to the signal-associated multi-gene cluster digital feature set.

In some embodiments, the search for resistance genes is performed using traditional search methodologies. For example, in some embodiments, candidate resistance genes are identified based on sequence identity. In some embodiments, identity of related polypeptides or nucleic acid sequences can be readily calculated by any of the methods known to one of ordinary skill in the art. The "percent identity" of two sequences (e.g., nucleic acid or amino acid sequences) may, for example, be determined using the algorithm of Karlin and Altschul *Proc. Natl. Acad. Sci. USA* 87:2264-68, 1990, modified as in Karlin and Altschul *Proc. Natl. Acad. Sci. USA* 90:5873-77, 1993. Such an algorithm is incorporated into the NBLAST® and XBLAST® programs (version 2.0 or later) of Altschul et al., *J. Mol. Biol.* 215:403-10, 1990. BLAST® protein searches can be performed, for example, with the XBLAST program, score=50, wordlength=3 to obtain amino acid sequences homologous to the proteins described herein. Where gaps exist between two sequences, Gapped BLAST® can be utilized, for example, as described in Altschul et al., *Nucleic Acids Res.* 25(17):3389-3402, 1997. When utilizing BLAST® and Gapped BLAST® programs, the default parameters of the respective programs (e.g., XBLAST® and NBLAST®) can be used, or the parameters can be adjusted appropriately as would be understood by one of ordinary skill in the art.

In some embodiments, candidate resistance genes exhibit at least 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with a target resistance gene, including all ranges and subranges therebetween.

In some embodiments, candidate resistance genes are identified based on sequence similarity. Similarity of nucleic acid sequences and protein sequences can be assessed by a number of methods, including those known in the art, in accordance with the present disclosure.

Widely used similarity searching programs known to persons having skill in the art include: BLAST (Altschul S F, Madden T L, Schaffer A A, Zhang J, Zhang Z, Miller W, Lipman D J. Gapped BLAST and PSI-BLAST: a new generation of protein database search programs. Nucleic Acids Res. 1997; 25:3389-3402; units 3.3 and 3.4), PSI-BLAST (Id.), SSEARCH (Smith T F, Waterman M S. Identification of common molecular subsequences. J. Mol. Biol. 1981; 147:195-197; Pearson W R. Searching protein sequence libraries: Comparison of the sensitivity and selectivity of the smith-waterman and fasta algorithms. Genomics. 1991; 11:635-650, unit 3.10), FASTA (Pearson W R, Lipman D J. Improved tools for biological sequence comparison. Proc. Natl. Acad. Sci. USA. 1988; 85:2444-2448 unit 3.9), and MUSCLE (Edgar R C. MUSCLE: multiple sequence alignment with high accuracy and high throughput. *Nucleic Acids Res.* 2004; 32(5):1792-1797).

In some embodiments, candidate resistance genes exhibit at least 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence similarity with a target resistance gene, including all ranges and subranges therebetween.

In some embodiments, candidate resistance genes are identified via predictive engines. In some embodiments, the predictive engines are machine learning models. In some embodiments the predictive engines are HMM models.

Persons having skill in the art will recognize the compatibility of multiple machine learning predictive models to the workflows of the present disclosure. Thus, although HMMs are often used as the illustrative model, in some embodiments, it will be understood that reference to HMM can be generally understood as "predictive model", or "predictive machine learning model." In some embodiments, the predictive engine/model is selected from the group consisting of a HMM, a PSSM (Position specific scoring matrices), a SVM (Support Vector Machines), a Bidirectional LSTM (Long Short Term Memory), a CNN (Convolutional Neural Network), a RNN (Recurrent Neural Networks), a Dynamic Bayesian networks, artificial neural networks, including recurrent neural networks such as those based on Long Short Term Memory Models (LSTM), and combinations thereof.

Persons having skill in the art will be familiar with the various public sources for HMM sequence models, and/or with methods of generating new machine learning models for conducting the resistance gene searches. For example, in some embodiments, the present disclosure teaches the use of TIGRFam or PFam HMM models to identify candidate resistance genes. These HMMs are available for a wide range of types of proteins and protein domains, and can be applied directly the digital metagenomic libraries of the present disclosure.

TIGRFAM is a resource consisting of curated multiple sequence alignments, Hidden Markov Models (HMMs) for protein sequence classification, and associated information capable of searching for homologous proteins. Starting with release 10.0, TIGRFAMs models use HMMER3, which provides excellent search speed and search sensitivity (Haft D H, et al., TIGRFAMs: a protein family resource for the functional identification of proteins. Nucleic acids research. 2001-01-01; 29.1: 41-3.)

Pfam similarly contains multiple alignments and hidden Markov model based profiles (HMM-profiles) of complete protein domains. The definition of domain boundaries, family members and alignment is done semi-automatically based on expert knowledge, sequence similarity, other protein family databases and the ability of HMM-profiles to correctly identify and align the members (Sonnhammer E L, Eddy S R, Birney E, Bateman A, Durbin R. Pfam: multiple sequence alignments and HMM-profiles of protein domains. Nucleic Acids Res. 1998; 26(1):320-322). Illustrative examples of HMM searches for candidate resistance proteins are provided in later sections of this document.

Resistance Gene Search Output and Optional Filtering

In some embodiments, the output from the resistance gene homology searches is a plurality of candidate resistance gene sequences, contained within assembled sequence from the digital metagenomics library (i.e., signal-associated multi-gene cluster digital feature sets). In some embodiments, each candidate resistance gene sequence is associated with a confidence score related to the likelihood that the search model's prediction is accurate. Thus, candidate resistance gene sequences may be identified based on the confidence score assigned to the candidate sequence by the model (e.g., a machine learning model, e.g., an HMM).

In some embodiments, the present disclosure teaches keeping all predicted gene candidate sequences for the next workflow step. In some embodiments, the present disclosure teaches the use of pre-selected confidence cutoffs, so that only the hits with the best confidence proceed to subsequent steps of the analysis. The confidence score cutoff may vary based on the size of the database and other features of the particular implementation of the method. Alternatively, the method or system may employ other means for discriminating between candidate sequences and non-candidate sequences. In some embodiments, the candidate resistance gene sequences are ranked in order of highest confidence to lowest confidence by their confidence score and then a cutoff is employed to remove any sequences falling below a particular confidence threshold. For example, if the confidence score is an e-value, the candidate sequences may be ranked in order of ascending e-value: lowest e-value (highest confidence) to highest e-value (lowest confidence). Then, any sequences assigned an e-value above a selected threshold may be removed from the pool of candidate sequences. Analogously, if the confidence score is a bitscore, the candidate sequences may be ranked in order of descending bitscore: highest bitscore (highest confidence) to lowest bitscore (lowest confidence). Then, any sequences assigned a bitscore below a selected threshold may be removed from the pool of candidate sequences.

In some embodiments, following identification of the candidate resistance sequences from the sequence database, the candidate sequences are filtered to remove candidate sequences that are less likely to perform the function of the target resistance gene. In some embodiments, the candidate sequences are filtered based on their evaluation using one or more second "control" predictive models. The number of control predictive models employed may depend on the situation, the type of target resistance gene, the availability of relevant data, and other such features. In some embodiments, the number of control predictive models is between 1 and 100,000. In some embodiments, the number of control predictive models is at least 1, at least 10, at least 100, at least 1,000, at least 10,000, or at least 100,000.

In some embodiments, the candidate resistance sequences are evaluated by a first predictive model that determines the likelihood that the sequence performs the function of the target resistance gene, e.g., by assigning a confidence score; then, the candidate sequences are evaluated by a second predictive model or models that determine the likelihood that the sequence performs a different function, e.g., by assigning a confidence score. The relative likelihoods of the candidate sequence performing the target protein or target gene function or another function are then compared. In some embodiments, each candidate sequence is assigned a "target resistance gene confidence score" generated by the first predictive model and a "best match confidence score", wherein the best match confidence score is the best confidence score generated by a second predictive model evaluating the likelihood that the candidate sequence performs a different function than the target protein or target gene function. For example, if 500 control predictive models are employed to determine whether or not the sequence is likely to encode a protein or gene performing a function other than the target protein or target gene function, the "best match confidence score" would be the best confidence score (e.g., highest bitscore, lowest e-value) generated by any one of the 500 control predictive models.

Thus, in some embodiments, the target protein or target gene confidence score and the best match confidence score are compared. In some embodiments, the log of the target protein or target gene e-value and the log of the best match (e.g., from the second predictive machine learning model) e-value are compared. In some embodiments, the target protein or target gene bitscore and the best match bitscore are compared. In some embodiments, a threshold is established for the relative likelihood of performing the target protein or target gene function.

The number of control predictive machine learning models employed is not numerically limited, but is based on the ability to generate and/or availability of control models, such as those which may be generated based on the identification of orthology groups other than those to which the target protein or target gene belongs. In some embodiments, at least one secondary model is employed. In some embodiments, at least 5, 10, 50, 100, 200, 300, 400, 500, 600, 700, 800, 900, 1,000, or 10,000 control models are employed.

In some embodiments, candidate resistance sequences are only retained if the likelihood of performing the target protein or target gene function is greater than the likelihood of performing a different protein function (i.e. if the target match confidence score is the best match confidence score. In some embodiments, candidate resistance sequences are only retained if the likelihood of performing the target resistance gene function is greater than or approximately equal to the likelihood of performing a different protein function. In some embodiments, the candidate resistance sequence is retained if the relative likelihood of performing the target resistance gene function falls within a certain confidence interval. In some embodiments, the candidate resistance sequence is retained if the relative likelihood of performing the target resistance gene function exceeds a certain threshold value. In some embodiments, a candidate resistance sequence is retained if it meets the following criteria (or the equivalent for a target resistance gene):

$$\frac{\text{candidate resistance bit score}}{\text{best match bit score}} \frac{\text{(target resistance gene confidence score)}}{\text{(best match confidence score)}} \text{ or } \frac{\log(\text{candidate resistance } E \text{ value})}{\log(\text{best match } E \text{ value})} \frac{\text{(target resistance gene confidence score)}}{\text{(best match confidence score)}} > \text{threshold value.}$$

In some embodiments, the best match E value or best match bitscore is the best confidence score out of the control predictive models. In other embodiments, the best match is the best confidence score out of all tested predictive models, including the candidate resistance gene confidence score. In this second embodiment, if the candidate resistance gene confidence score (e.g. bitscore or E value) is the best match, then the ratio is 1. In other embodiments, in which the best match confidence score is selected from amongst the control predictive models, the ratio can exceed 1.

The threshold value for retaining a candidate resistance gene sequence may be modified based on the desired confidence range. In some embodiments the threshold value is between 0.1 and 0.99. In some embodiments, the threshold value is between 0.5 and 0.99. In some embodiments, the threshold value is 0.1, 0.2, 0.3, 0.4, 0.5, 0.6, 0.7, 0.8, or 0.9. In some embodiments, the threshold value is 0.5, 0.55, 0.6, 0.65, 0.7, 0.75, 0.8, 0.85, 0.9, or 0.95.

The threshold calculations above are illustrative, but in no way exhaustive. Persons having skill in the art will recognize how to apply various threshold cutoffs depending on how their confidence scores are calculated. For example, if the confidence score is such that a lower score indicates greater confidence, then a sequence may be retained if the ratio of the target protein or target gene confidence score to the best match confidence score is lower than a certain threshold value.

In some embodiments each of the output candidate resistance genes will be associated with a longer DNA sequence (i.e., each candidate resistance gene will be contained within a longer assembled DNA sequence within the digital metagenomic library). In some embodiments, the present disclosure teaches filtering out candidate resistance genes that are contained within assembled DNA sequences that are less than 10 kb, 15 kb, 20 kb, 25 kb, or 30 kb in length. In some embodiments, the sequence length cutoff is made based on the expected size of the multi-gene cluster. If the expected natural product is expected to be produced by a multi-gene cluster of at least 30 kb, it may not be relevant to further process candidate resistance genes of less than 10 kb in length.

In some embodiments, the outputs of the resistance gene searches may also be filtered based on the predicted taxonomy of the assembled DNA sequence. Thus, if the goal is to identify natural products from Actinobacteria, sequences which had been identified as belonging to other genus/species can be filtered out prior to subsequent workflow steps.

In some embodiments, the outputs of the resistance gene searches may also be filtered to remove duplicates, or highly related sequences. In some embodiments the resistance gene results may also be filtered to remove partial sequences.

In some embodiments, the outputs of the resistance gene searching can be prioritized based on the each candidate resistance sequence's homology to a corresponding target e gene from another organism. Thus, in some embodiments, candidate resistance genes are compared to a known database using BLAST, to determine whether the strongest matches are identified by blast as homologs to the desired target sequence. For example, in some embodiments, the search for natural products targeting the beta-subunit of the human proteasome would be compared against the human proteome using blast to ensure that the candidate sequence was capable of identifying the beta-subunit from the proteome database. These hits would, in some embodiments, be prioritized for further review.

In some embodiments, DNA digital sequences from the digital metagenomics library that are identified as comprising a candidate resistance gene, and which (optionally) further survive the filtering steps described above and herein referred to as "signal-associated multi-gene cluster digital feature sets."

In some embodiments, unfiltered sequences are permitted to proceed along the presently disclosed workflow.

Multi-Gene Cluster Prediction

In some embodiments, the present disclosure teaches a step of assigning biological relevancy to the signal—associated multi-gene cluster digital feature set. In some embodiments, assigning relevancy comprises determining a computationally predicted biosynthetic functionality of a plurality of genes from a signal-associated multi-gene cluster digital features set and digitally assemble a computationally determined natural product multi-gene cluster feature set comprising one or more biosynthetic operons (e.g., identification of biosynthetic gene clusters). In some embodiments, this step comprises computationally determining whether the signal-associated multi-gene cluster digital feature set comprises any natural product-encoding multi-gene clusters (MGCs).

As noted above, in some embodiments, the multi-gene cluster prediction can be conducted earlier in the method, in the step for querying a digital metagenomics library for a signal indicative of a natural product multi-gene cluster feature set. Thus, in some embodiments, the multi-gene cluster prediction produces the plurality of signal-associated multi-gene cluster digital feature sets.

The concept of genome mining for MGCs is facilitated by the development of many bioinformatics tools that utilize various approaches to tap into the pool of potential natural product (NP) encoding clusters. These tools often rely on algorithms designed to search for the presence of various genes and structures associated with MGCs discovered to date.

MGCs encoding for various biosynthetic classes of natural products include polyketides (PKS) (Hertweck C (2009) The biosynthetic logic of polyketide diversity. Angew Chem Int Ed Engl 48:4688-4716), nonribosomal peptides (NRPs) (Condurso H L, Bruner S D (2012) Structure and noncanonical chemistry of nonribosomal peptide biosynthetic machinery. Nat rod Rep 29:1099-1110), ribosomally synthesized and post-translationally modified peptides (RiPPs) (Dunbar K L, Mitchell D A (2013) Revealing nature's synthetic potential through the study of ribosomal natural product biosynthesis. ACS Chem Biol 8:473-487), saccharides (Mccranie E K, Bachmann B O (2014) Bioactive oligosaccharide natural products. Nat Prod Rep 31:1026-1042), terpenoids (Cane D E, Ikeda H (2012) Exploration and mining of the bacterial terpenome. Acc Chem Res 45:463-472), and hybrid structures.

Each of the aforementioned natural product classes may be further divided into subclasses. For example, polyketides are divided into three groups based on the architecture of their biosynthetic enzymes, polyketide synthases (PKSs). Minimally, PKSs comprise three activities: (1) acyltransferase (AT)—the decision gate that selects building blocks; (2) thiolation (T) or acyl carrier protein (ACP) onto which the building block is covalently tethered; and (3) ketosynthase (KS) that catalyzes condensation of activated carboxylic acid monomers ("head-to-tail," decarboxylative, Claisen-type reactions). Catalytic domains are fused in type I PKSs, whereas type II PKSs are a dissociable complex of discrete enzymes. Type III PKSs, which are mainly found in plants, are multifunctional enzymes that use malonyl-CoA directly, rather than first transferring it to a T domain. Moreover, type I PKSs can be further categorized into either iterative (i.e., each domain catalyzes more than one round of elongation), as it is typical for fungal polyketide biosynthesis, or multimodular, which is the archetype of bacterial type I PKSs. In addition, trans-AT PKSs (Piel J (2010) Biosynthesis of polyketides by trans-AT polyketide synthases. Nat Prod Rep 27:996-1047) are an evolutionarily distinct subtype of multimodular PKSs in which AT domains are free standing. Nonribosomal peptide synthetases (NRPSs) are organized in a similar fashion as multimodular PKSs. Adenylation (A)

domains select amino acid building blocks transferring them to T domains (also called peptidyl carrier protein, PCP, in NRPSs), and condensation (C) domains catalyze peptide bond formation.

These aforementioned features of known MGCs, together with their associated signature domains/genes can be used to develop search models for new MGCs within the digital metagenomic libraries of the present disclosure (e.g., through profile Hidden Markov Models (HMNI) for more or more of the signature domains).

In some embodiments, prediction of biosynthetic gene clusters can be automated using several developed algorithms. A non-limiting list of cluster prediction algorithms compatible with the methods of the present disclosure include: SBSPKS (Anand S, Prasad M V, Yadav G et al (2010) SBSPKS: structure based sequence analysis of polyketide synthases. Nucleic Acids Res 38: W487-W496), NP.searcher (Li M H, Ung P M, Zajkowski J et al (2009) Automated genome mining for natural products. BMC Bioinformatics 10:185), and BAGEL3 (Van Heel A J, De Jong A, Montalban-Lopez M et al (2013) BAGEL3: automated identification of genes encoding bacteriocins and (non-) bactericidal posttranslationally modified peptides. Nucleic Acids Res 41:W448-W453) focus on polyketides, polyketides, and NRPs and RiPPs, respectively. For a recent review of available in silico tools, see (Weber T (2014) In silico tools for the analysis of antibiotic biosynthetic pathways. Int J Med Microbiol 304:230-235). Table 1 of the present disclosure provides further MGC identification algorithms.

The most comprehensive computational tool for automatic identification and analysis of multi-gene clusters is antiSMASH (antibiotics and Secondary Metabolite Analysis Shell-current version 5.0) Kai Blin, Simon Shaw, Katharina Steinke, Rasmus Villebro, Nadine Ziemert, Sang Yup Lee, Marnix H Medema, & Tilmann Weber Nucleic Acids Research (2019)). In addition, Cimermancic et al. (Cimermancic P, Medema M H, Claesen J et al (2014) Insights into secondary metabolism from a global analysis of prokaryotic biosynthetic gene clusters. Cell 158:412-421) have recently developed ClusterFinder, an HMM-based probabilistic algorithm that can identify both known and unknown classes of natural products centered on Pfam domain frequencies. In some embodiments, the present disclosure utilizes Deep-BGC for the prediction of MGCs (See Geoffrey D Hannigan et al., A deep learning genome-mining strategy for biosynthetic gene cluster prediction, *Nucleic Acids Research*, Volume 47, Issue 18, 10 Oct. 2019, Page el 10). In some embodiments, the present disclosure uses any of the tools described in Table 1 for the MGC prediction step.

In some embodiments, the output from the multi-gene cluster prediction step is a plurality of computationally determined natural product multi-gene clusters within the digital metagenomics library. In some embodiments, the results are DNA sequences that were also identified as comprising a candidate resistance gene.

Proximity Analysis

Figure 8:
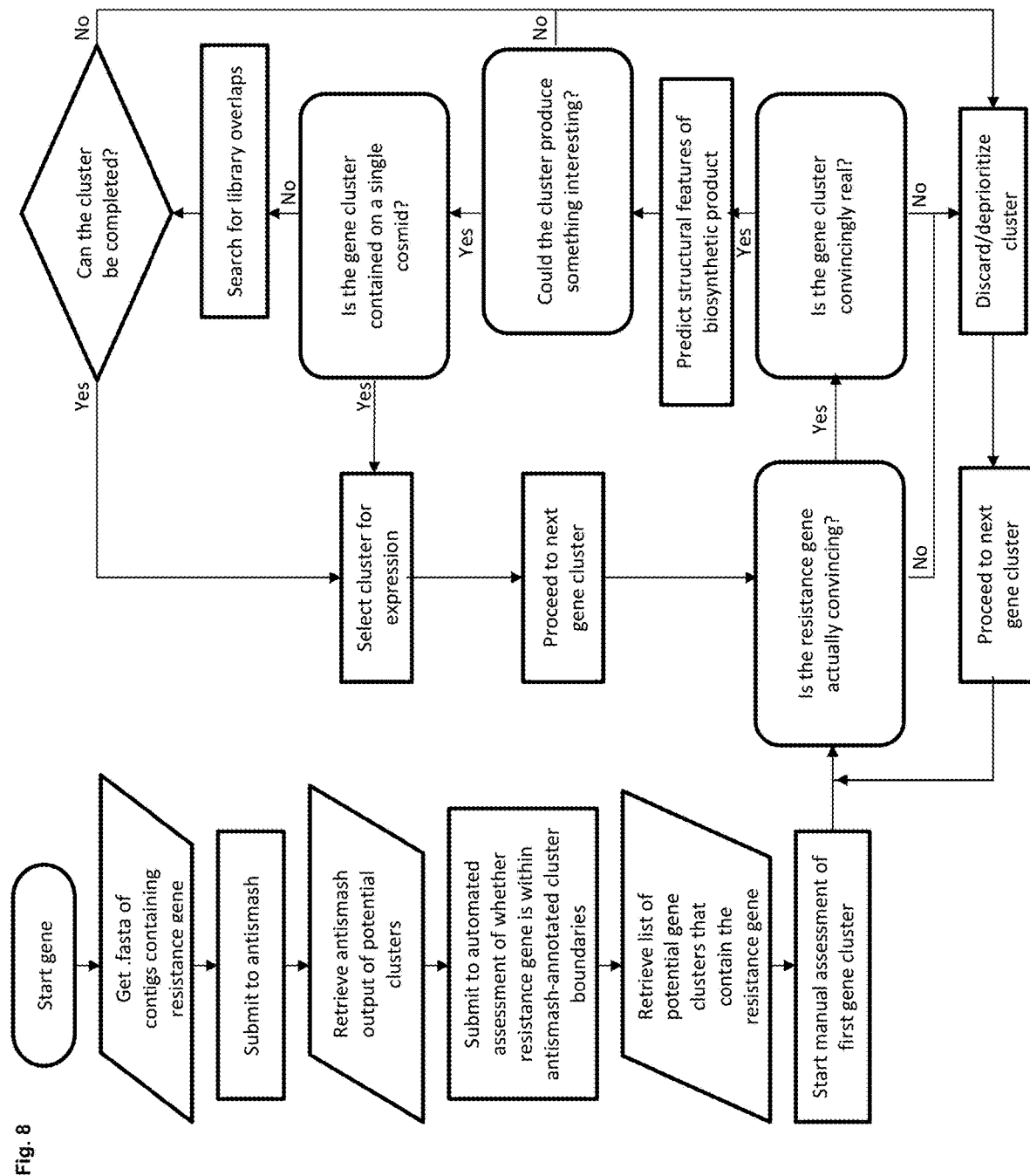
FIG. 8—depicts the steps of an embodiment of prioritizing the in silico natural product multi-gene cluster discovery methods of the present disclosure.

In some embodiments, the presently disclosed methods for identifying a natural product of interest comprise the step of identifying a natural product of interest based upon a computationally determined (candidate) biological resistance gene being located within a threshold parameter of a computationally determined (candidate) natural product multi-gene cluster feature set comprising a digitally assembled biosynthetic operon (or operons). In some embodiments, the present disclosure thus selects computationally determined natural product multi-gene clusters as described above (e.g., as identified through antiSMASH, or equivalent analysis) that contain at least one of the identified candidate resistance genes (i.e., computationally determined biological resistance genes) within its cluster boundaries, or within a pre-selected threshold of said boundaries. (See FIG. 6 and FIG. 8).

In some embodiments, a computationally determined multi-gene cluster is selected if it comprises the candidate resistance gene within its cluster boundaries. In some embodiments, a computationally determined multi-gene cluster is selected if it comprises the candidate resistance gene within 1 open reading frame (ORF) of either of the cluster boundaries (i.e., outside of the predicted cluster). That is, the cluster is selected if there is one or less computationally predicted open reading frames between the boundary of the cluster and the transcriptional start site for the candidate resistance gene. In some embodiments, a computationally determined natural product multi-gene cluster is selected if it comprises the candidate resistance gene within 2 ORFs of either of the cluster boundaries. In some embodiments, a computationally determined natural product multi-gene cluster is selected if it comprises the candidate resistance gene within 3, 4, 5, 6, or ORFs of either of the cluster boundaries.

In some embodiments, a computationally determined natural product multi-gene cluster is selected if it comprises the candidate resistance gene within 1 kb, 2 kb, 3 kb, 4 kb, 5 kb, 6 kb, 7 kb, 8 kb, 9 kb, or 10 kb of either of the cluster boundaries, including all ranges and subranges therebetween. That is, the computationally determined natural product multi-gene cluster is selected if either the start codon (if downstream of the MGC) or stop codon (if upstream of the MGC) of the candidate resistance gene is within 1 kb, 2 kb, 3 kb, 4 kb, 5 kb, 6 kb, 7 kb, 8 kb, 9 kb, or 10 kb of either of the cluster boundaries, including all ranges and subranges therebetween.

In some embodiments, the resulting selected natural product multi-gene cluster(s) may be further filtered or prioritized according to prediction confidence scores and/or sequence similarity. (See FIG. 6) For example, in some embodiments, the present disclosure teaches dereplicating sequences based on sequence similarity. In some embodiments, the present disclosure teaches dereplicating by filtering out sequences that are closely related (e.g., by sequence homology). In some embodiments the dereplication or prioritization is conducted using the Biosynthetic Gene Similarity Clustering and Prospecting Engine BiG-SCAPE (Navarro-Muñoz, J. C., Selem-Mojica, N., Mullowney, M. W. et al. A computational framework to explore large-scale biosynthetic diversity. Nat Chem Biol 16, 60-68 (2020)).

Manufacture and Validation

In some embodiments, the present disclosure envisions experimentally validating new multi-gene clusters identified via the methods of the present disclosure. That is, in some embodiments, the present disclosure teaches the manufacturing of cells that comprise the (candidate/selected) MGC encoding for the natural product or a refactored version thereof. In some embodiments, the present disclosure teaches the manufacturing of cells that comprise the computationally determined natural product multi-gene cluster feature set or a refactored version thereof. In some embodiments, the manufacturing step is also applied to other MGC discovery and resistance gene discovery workflows of the present disclosure In some embodiments the MGC-containing sequences recovered from the sequence library can be directly cloned into a host cell for expression. In some embodiments, the MGCs must be refactored (e.g., optimized) for expression into different cells. Persons having skill in the art will be familiar with methods of refactoring MGCs. For example, in some embodiments, refactoring an MGC includes codon optimizing encoded genes. In some embodiments, refactoring an MGC includes replacing one or more regulatory sequences with other sequences for better expression in a host cell. Guidance on common refactoring strategies can be found in Gao-Yi Tan, Tiangang Liu, Rational synthetic pathway refactoring of natural products biosynthesis in actinobacteria, Metabolic Engineering, Volume 39, 2017, Pages 228-236.

Resistance Gene Workflow Alternative Embodiments

The resistance gene workflow disclosed above followed the general order of first conducting resistance gene homology searches and later conducting the multi-gene cluster prediction. The present disclosure also envisions embodiments in which the search order is reversed, such that the multi-gene cluster prediction is conducted first, and the resistance gene homology searches are conducted second. Indeed, there may be some instances in which reversing the order may yield analysis efficiencies. For example, if the multi-gene cluster prediction tool is less computationally taxing than the resistance gene homology search, it may be computationally efficient to first narrow down the search space by conducing the multi-gene cluster prediction first. Similarly, if the user anticipates conducting searches for multiple target resistance genes within the same digital metagenomics library, it may be computationally efficient to conduct a global multi-gene cluster analysis over the entire library first, and then use those identified clusters to speed up subsequent resistance gene homology searches. Other situations might arise where reversing the order of these steps is desirable. Rather than identify all possible scenarios, the disclosure merely notes that in some embodiments, the order may be reversed.

Untargeted Resistance Signal Multi-gene Cluster Feature Set Discovery Workflow

The potential for Ag, drug and consumer product discoveries from natural product-encoding sequence libraries remains largely untapped. Metagenomic libraries in particular, represent a rich source of unexplored genetic diversity. Many of the undiscovered natural products contained within these metagenomic libraries however, are expected to be completely new molecules that lack significant relationships to existing natural products and their associated synthetic operons. The tools of the present disclosure, as illustrated in this section, exploit conserved structural properties of biosynthetic operons to identify new natural products, and where possible, their corresponding novel resistance genes (untargeted resistance signal multi-gene cluster feature set discovery platform).

In some embodiments, the untargeted resistance signal multi-gene cluster feature set discovery platform of the present disclosure follows the following general workflow: a) computationally predicting natural product multi-gene cluster feature sets within a long-assembly digital metagenomic library, b) annotating genes within the predicted natural product multi-gene cluster feature sets (or within 1-2 ORFs of the boundaries of said clusters), c) filtering annotated genes from the predicted natural product multi-gene cluster feature sets so as to focus on genes that i) do not have a predicted biosynthetic function, and ii) (optionally) are not recognized as homologs to known resistance genes, thereby producing a plurality of filtered genes of interest, and d) selecting one or more natural product multi-gene cluster features sets that comprise at least one of the plurality of filtered genes of interest, thereby creating a library of candidate MGC sequences. In some embodiments, the workflow further comprises the steps of: e) manufacturing one or more host cell(s), wherein each manufactured host cell comprises a natural product multi-gene cluster feature set from amongst the candidate MGC sequences, f) culturing the manufactured host cells of step (e), and g) analyzing spent cultures from the cultures of step (f) for the presence of a natural product, wherein said natural product is not present in cultures of control host cells lacking the natural product multi-gene cluster feature set present in the manufactured host cell. Each step of this workflow is discussed in more detail below.

In some embodiments, a gene is predicted to have a biosynthetic function if it has greater than 10, 9, 8 7, 6, 5, 4, 3, or 2 BLAST hits in MiBig as assessed by anti SMASH.

In some embodiments the method comprises filtering out genes that are not within or immediately adjacent to a biosynthetic operon. In some embodiments the method comprises filtering out genes that are not within 1 kb, 2 kb, 3 kb, 4 kb, 5 kb, or 10 kb of a core biosynthetic gene. In some embodiments the method comprises filtering out genes that are not an essential gene (e.g. as listed in www.essentialgene.org) or which have a BLAST result bitscore lower than 250, 200, 150, 100, or 50 with an essential gene. In some embodiments the method comprises filtering out genes that are annotated as transport-related or regulatory genes. In some embodiments the annotation is handled by any annotation engine, including for example, antiSMASH.

Filtering by Resistance Mechanism

Figure 5:
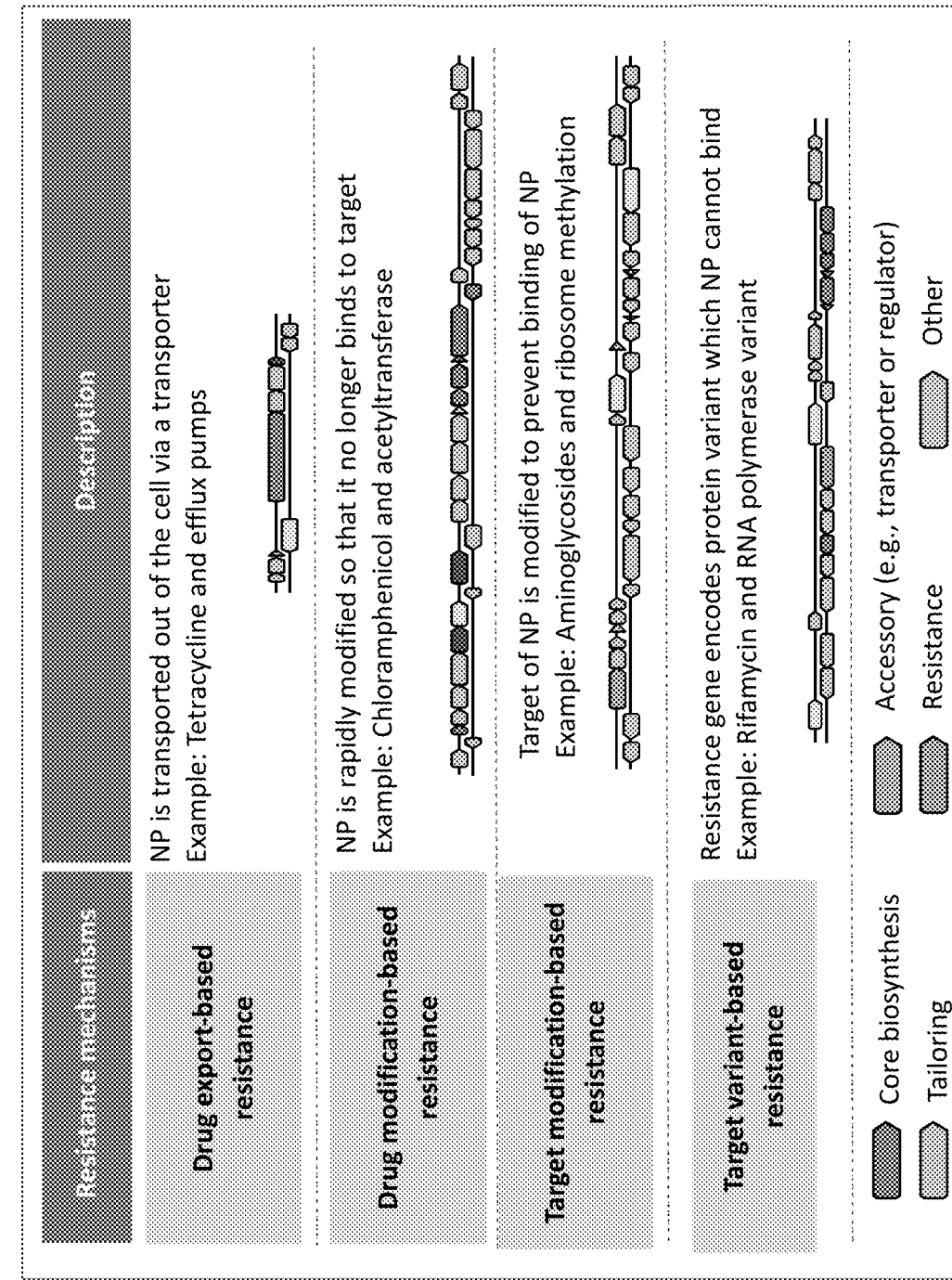
FIG. 5—depicts a non-limiting list of mechanisms of action for multi-gene cluster-associated resistance genes. Resistance genes can function by transporting out natural products that are toxic to the producing cell. Resistance genes can modify natural products that accumulate within the producing cell to reduce or abrogate toxicity within the cell. Resistance genes can act on endogenous genes, modifying them so that they are no longer affected by a natural product. Resistance genes can be variants of targets of natural products, such that the variants allow the producing cell to continue functioning.

Resistance genes can impart resistance to natural products via a variety of resistance mechanisms see e.g., FIG. 5. While identifying MGCs with resistance genes of all resistance mechanisms can be valuable, in some applications, it may be beneficial to search for MGCs/resistance genes that are predicted to function via one or more resistance mechanisms.

Therefore, in some embodiments, the method comprises filtering out genes that are predicted to have different resistance mechanisms from the desired resistance mechanism. Thus, in some embodiments, the method comprises filtering out genes that exhibit similarity to resistance genes with a different resistance mechanism from the desired resistance mechanism. In some embodiments, the method comprises filtering all genes except those that exhibit similarity to resistance genes with the desired resistance mechanism.

In some embodiments, the determination of resistance gene mechanism is assessed via analysis of a gene with resfam models for each mechanism.

In some embodiments, the desired resistance mechanism is the target variant-based resistance. This is because variant-based resistance mechanism provides information about the biological target of the encoded natural product. That is, presence of a variant-based resistance gene indicates that the non-variant equivalent of the resistance gene (i.e., the gene that the variant replaces) is likely the target of the natural product encoded by the MGC. Thus, filtering by mechanism can, in some embodiments, also provide information about the functionality of the newly discovered natural product.

Additional Untargeted Workflows

In some embodiments, the present disclosure teaches an in silico method for identifying a candidate multi-gene cluster feature set with a predicted resistance gene, said method comprising the steps of: a) computationally predicting natural product multi-gene cluster feature sets within a digital metagenomic library; b) assigning a biosynthetic potential score to genes within the multi-gene cluster feature sets; said biosynthetic potential score based on the calculated likelihood that a gene is a biosynthetic enzyme; c) optionally assigning a known resistance gene score to genes within the multi-gene cluster feature sets, said known resistance score based on the shared sequence identity of a gene with a known resistance gene; and d) selecting a candidate multi-gene cluster feature set comprising a predicted resistance gene, said predicted resistance gene exhibiting a pre-set combination score threshold, said combination score based on the combination of the biosynthetic potential score and the known resistance gene score (if assigned).

In some embodiments, the method comprises assigning a biosynthetic operon score to genes within the multi-gene cluster feature sets, said biosynthetic operon score based on a gene's proximity to a biosynthetic operon within its multi-gene cluster feature set; and wherein the combination score is also based on the biosynthetic operon score.

In some embodiments, the method comprises assigning a core biosynthetic gene distance score to genes within the multi-gene cluster feature sets, said a core biosynthetic gene distance score based on a gene's proximity to a core biosynthetic gene within its multi-gene cluster feature set; and wherein the combination score is also based on the core biosynthetic gene distance score.

In some embodiments, the method comprises assigning an essential gene score to genes within the multi-gene cluster feature sets, said essential gene score based on a gene's highest sequence identity to a list of known essential gene sequences; and wherein the combination score is also based on the essential gene score. In some embodiments, the predicted resistance gene within the selected candidate multi-gene cluster feature set shares at least 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, or 70% sequence identity with an essential gene.

In some embodiments, the predicted resistance gene within the selected candidate multi-gene cluster feature set shares less than 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, or 70% sequence identity with a known resistance gene.

In some embodiments, the predicted resistance gene within the selected candidate multi-gene cluster feature set shares more than 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, or 70% sequence identity with a known resistance gene. In some embodiments, this strategy represents a further narrowing/improvement of a resistance gene workflow.

In some embodiments, the predicted resistance gene within the selected candidate multi-gene cluster feature set shares less than 90%, 89%, 88%, 87%, 86%, 85%, 84%, 83%, 82%, 81%, 80%, 79%, 78%, 77%, 76%, 75%, 74%, 73%, 72%, 71%, or 70% sequence identity with a biosynthetic enzyme. In some embodiments, the biosynthetic enzyme is a biosynthetic enzyme for the natural product encoded by multi-gene cluster feature set containing the predicted resistance gene. In some embodiments, the biosynthetic enzyme is a biosynthetic enzyme associated with natural product encoded by multi-gene cluster feature sets (e.g., MiBig). In some embodiments, the predicted resistance gene within the selected candidate multi-gene cluster feature set returns fewer than 8, 6, 4, or 2 BLAST hits in miBIG, as assessed by antismash.

In some embodiments, the predicted resistance gene within the selected candidate multi-gene cluster feature set has a combination score wherein the calculated likelihood that a gene is a biosynthetic enzyme is low and wherein the shared sequence identity with a known resistance gene is low when compared to known biosynthetic enzymes or known resistance genes, respectively. In some embodiments, the predicted resistance gene within the selected candidate multi-gene cluster feature set has a combination score wherein the calculated likelihood that a gene is a biosynthetic enzyme is low and wherein the shared sequence identity with a known resistance gene is high when compared to known biosynthetic enzymes or known resistance genes, respectively.

In some embodiments, the predicted resistance gene within the selected candidate multi-gene cluster feature set is located within or immediately adjacent (i.e. no other ORFs in between) to a biosynthetic operon within the selected candidate multi-gene cluster feature set. In some embodiments, the predicted resistance gene within the selected candidate multi-gene cluster feature set is located inside of a biosynthetic operon or within 500 bp of a biosynthetic operon contained in the selected candidate multi-gene cluster feature set.

In some embodiments the predicted resistance gene within the selected candidate multi-gene cluster feature set is located within 1 kB, 2 kb, 3 kb, 4 kb, or 5 kb of a core biosynthetic enzyme.

In some embodiments, the method comprises assigning a transport gene potential score to genes within the multi-gene cluster feature sets, said transport gene potential score based on a gene's likelihood of being a transport-related gene (e.g., via sequence identity) and wherein the combination score is also based on the core biosynthetic gene distance score. In some embodiments, transport gene potential is assessed via an annotation engine, such as antiSMASH.

In some embodiments, the method comprises assigning a regulatory gene potential score to genes within the multi-gene cluster feature sets, said regulatory gene potential score based on a gene's likelihood of being a regulatory gene (e.g., via sequence identity) and wherein the combination score is also based on the core biosynthetic gene distance score. In some embodiments, regulatory gene potential is assessed via an annotation engine, such as anti SMASH.

In some embodiments, the method comprises the step of: assigning a resistance mechanism score to genes within the multi-gene cluster feature sets, said resistance mechanism score assigned based on a gene's similarity to resistance genes with different resistance mechanisms from the desired resistance mechanism, and wherein the combination score is also based on the resistance mechanism score.

In some embodiments, the method comprises the step of: assigning a resistance mechanism score to genes within the multi-gene cluster feature sets, said resistance mechanism score assigned based on a gene's similarity to resistance genes with the desired resistant mechanism, and wherein the combination score is also based on the resistance mechanism score.

In some embodiments, the desired resistance mechanism is target variant-based resistance.

Computationally Predicting MGCs

In some embodiments the untargeted resistance signal multi-gene cluster feature set discovery platform comprises the step of a) computationally predicting natural product multi-gene cluster feature sets within a long-assembly digital metagenomic library. In some embodiments, this step is conducted as described above, under the header "Multi-Gene Cluster Prediction." Briefly, sequences within the digital metagenomics library are analyzed with a MGC prediction algorithm to identify natural product multi-gene cluster feature sets. In some embodiments, the identification of natural product multi-gene cluster feature sets is done with antiSMASH.

Annotating Genes Within MGC Feature Sets

In some embodiments the untargeted resistance signal multi-gene cluster feature set discovery platform comprises the step of b) annotating genes within the predicted natural product multi-gene cluster feature sets (or within 1-2 ORFs of the boundaries of said clusters). Other filtering steps are also recited, based on various annotations (e.g., regulatory or transport genes). In some embodiments, the annotation of the predicted natural product multi-gene cluster feature sets is done based on homology of sequences in the MGC to known genes using one or more annotation engines.

In some embodiments, the annotation is conducted via antiSMASH, whose identification of MGCs also includes an annotation of genes within each MGC. In some embodiments, the annotation step is done through comparison of sequences within the MGC with known biosynthetic enzymes contained in public databases.

For example, in some embodiments, annotation is based on homology to biosynthetic enzymes contained in a public database of natural product gene clusters, such as MIBiG (//mibig.secondarymetabolites.org/download). Thus, in some embodiments, amino acid sequences for biosynthetic enzymes from the MIBiG database are queried via annotations "biosynthetic" and "biosynthetic-additional", and extracted from the sequence genbank file. The resulting set of amino acid sequences are clustered using CD-HIT to reduce redundancy. In some embodiments, the resulting non-redundant set of amino acid sequences represents the biosynthetic enzyme database, which can be used to query against a larger set of sequences within the MGCs to identify biosynthetic enzyme homologs.

Persons having skill in the art will be familiar with the various other gene annotation tools compatible with the workflows of the present disclosure. A non-limiting list of annotation tools is provided as Table 3 below.

TABLE 3

Non-limiting List of Sequence Annotation Tools

| Name | Can be Used For | Algorithm | References |
| --- | --- | --- | --- |
| GeneMark | Archaea, Metagenomes, Eukaryotes, Viruses, Phages, Plasmids, EST and cDNA | hidden Markov model | Besemer J. and Borodovsky M. Nucleic Acids Research, 2005, Vol. 33, Web Server Issue, pp. W451-454 |
| GeneHacker | Microbial genomes | Markov model | Yada. T, Hirosawa. M DNA Res., 3, 335-361 (1996). Syst. Mol. Biol. pp. 252-260 (1996). Syst. Mol. Biol. pp. 354-357 (1997). |
| Gene Walker HMMgene (v. 1.1) | Human vertebrate and C. elegans | Hidden Markov model Hidden Markov model | A. Krogh: In Proc. of Fifth Int. Conf. on Intelligent Systems for Molecular Biology, ed. Gaasterland, T. et al., Menlo Park, CA: AAAI Press, 1997, pp. 179-186. |
| Chemgenome2.0 | Prokaryotes | Ab-initio Method | Poonam Singhal, B. Jayaram, Surjit B. Dixit and David L. Beveridge. Prokaryotic Gene Finding based on Physicochemical Characteristics of Codons Calculated from Molecular Dynamics Simulations. Biophysical Journal, 2008, Volume: 94 Issue: 11, 4173-4183] |
| Softberry Server | Bacteria, Viruses and eukaryotes | HMM and similarity based searches | Solovyev V. V., Salamov A. A., Lawrence C. B. (Nucl. Acids Res., 1994, 22, 24, 5156-5163). |
| Gene ID | Animal, Human, Plants fungus, Protists | Neural Network | Blanco et. al., Genome Research 6(4): 511-515 (2000). |
| GenScan | Vertebrates, Arabidopsis, Maize | Ab-inito Method | Burge and Karlin (1998) Curr. Opin. Struct. Biol. 8, 346-354. |
| GenomeThreader | Plants | Similarity-based gene prediction program where additional cDNA/EST and/or protein sequences are used to predict gene structures via spliced alignments | Gremme et al Information and Software Technology, 47(15): 965-978, 2005 |
| JIGSAW(formerly "Combiner") | Eukaryotes | multiple sources of evidence (output from gene finders, splice site prediction programs and sequence alignments to predict gene models) | Allen et al. Genome Biology 2007, 7(Suppl): S9.; Allen and Salzberg Bioinformatics 21(18): 3596-3603, 2005; Allen et al. Genome Research, 14(1), 2004. |
| GlimmerHMM | Eukaryotes | GlimmerHMM is based on a Generalized Hidden Markov Model (GHMM). Although the gene finder conforms to the overall mathematical framework of a GHMM, additionally it incorporates splice site models adapted from | Majoros et al. Bioinformatics 20 2878-2879, 2004 |

TABLE 3-continued

Non-limiting List of Sequence Annotation Tools

| Name | Can be Used For | Algorithm | References |
|---|---|---|---|
| | | the GeneSplicer program and a decision tree adapted from GlimmerM. It also utilizes Interpolated Markov Models for the coding and noncoding models. Currently, GlimmerHMM's GHMM structure includes introns of each phase, intergenic regions, and four types of exons (initial, internal, final, and single). | |
| GenZilla | Eukaryotes | GeneZilla is based on the Generalized Hidden Markov Model (GHMM). It evolved out of the ab initio eukaryotic gene finder TIGRscan, which was developed at The Institute for Genomic Research. | GeneZilla (formerly "TIGRscan") is briefly described in: Majoros W, et al. (2004) Bioinformatics 20, 2878-2879 The novel decoding algorithm used by GeneZilla is described in: Majoros W. et al. (2005) BMC Bioinformatics 5: 616. |
| Twinscan/N-SCAN (Ver 4.1.2) | | TWINSCAN extends the probability model of GENSCAN, allowing it to exploit homology between two related genomes. Separate probability models are used for conservation in exons, introns, splice sites, and UTRs, reflecting the differences among their patterns of evolutionary conservation. | TWINSCAN: Gross and Brent. J Comput Biol. 2006 Mar; 13(2): 379-93. Korf I, N-SCAN: Flicek et al Bioinformatics. 2001; 17 Suppl 1: S140-8. |
| Manatee | prokaryotic and eukaryotic genomes | Manatee is a web-based gene evaluation and genome annotation tool that can view, modify, and store annotation for prokaryotic and eukaryotic genomes. The Manatee interface allows biologists to quickly identify genes and make high qualify functional assignments using a multitude of genome analyses tools. These tools consist of, but are not limited to GO classifications, BER and blast search data, paralogous families, and annotation suggestions generated from automated analysis. | NA |
| EvoGene | NA | alignment of multiple genomic sequences | Pedersen and Hein. Bioinformatics (in press) |
| CRITICA(Coding Region Identification Tool Invoking Comparative Analysis) | Prokaryotic | CRITICA combines traditional approaches to the problem with a novel comparative analysis. If, in a nucleotide alignment, a pair of ORFs can be found in which the conceptual translated products are more conserved than would be expected from the amount of conservation at the nucleotide level, this is evolutionary evidence that the DNA sequences are protein coding. Regions found by this method are used to generate traditional dicodon frequencies for further analysis and give the prediction about a probable protein coding region. | Badger and Olsen. Molecular Biology and Evolution, 16(4): 512-524. 1999. |
| sgp2 | | Sgp2 predict genes by comparing anonymous genomic sequences from two different species. Further it combines tblastx, a sequence similarity search program, with geneid, an "ab initio" gene prediction program. | Parra et al. Genome Research 13(1): 108-117(2003) |

TABLE 3-continued

Non-limiting List of Sequence Annotation Tools

| Name | Can be Used For | Algorithm | References |
| --- | --- | --- | --- |
| Phat | Eukaryotes (Homo sapiens, Plasmodium falciparum, Plasmodium vivax) | Phat is a HMM-based genefinder, originally developed for genefinding in Plasmodium falciparum. | Unpublished |
| EuGene | Eukaryotes | Eugene exploit probabilistic models like Markov models for discriminating coding from non-coding sequences or to discriminate effective splice sites from false splice sites (using various mathematical models). | LNCS 2066, pp. 111-125, 2001 |
| AUGUSTUS | Eukaryotic genomic sequences | It allows to use protein homology information and travel in the prediction. | Stanke and Waack (2003) Bioinformatics, Vol. 19, Suppl. 2, pages ii215-ii225 |

Filtering out Biosynthetic Genes

In some embodiments the untargeted resistance signal multi-gene cluster feature set discovery platform comprises the step of c) filtering annotated genes from the predicted natural product multi-gene cluster feature sets so as to focus on genes that i) do not have a predicted biosynthetic function, and ii) (optionally) are not homologs to known target resistance genes, thereby producing a plurality of filtered genes of interest.

Genes that do not have a Biosynthetic Role

Thus, in some embodiments, the present disclosure teaches filtering out genes from the predicted natural product multi-gene cluster feature sets, wherein said filtered out (i.e, removed from consideration) genes were annotated by the annotation step as having a biosynthetic role.

In some embodiments the method comprises filtering out genes that are not within or immediately adjacent to a biosynthetic operon. In some embodiments the method comprises filtering out genes that are not within 1 kb, 2 kb, 3 kb, 4 kb, 5 kb, or 10 kb of a core biosynthetic gene. In some embodiments the method comprises filtering out genes that are not an essential gene (e.g. as listed in www.essentialgene.org) or which have a BLAST result bitscore lower than 250, 200, 150, 100, or 50 with an essential gene. In some embodiments the method comprises filtering out genes that are annotated as transport-related or regulatory genes.

Genes that are not homologs of known target resistance genes in other MGCs.

In some embodiments, the present disclosure teaches filtering out genes from the predicted natural product multi-gene cluster feature sets, wherein said filtered out (i.e., removed from consideration) genes are homologs of known target resistance genes in other MGCs. Thus, in some embodiments, the present disclosure teaches comparing genes within MGCs to lists of known target resistance genes, and identifying homologs thereof.

In some embodiments, the lists of known target resistance genes are from a ResFam from the ResFam database that includes resistance genes that do not provide resistance by encoding a variant of the target protein. In some embodiments, databases of resistance genes include the Dantas Lab Resfam (Gibson M K, Forsberg K J, Dantas G. Improved annotation of antibiotic resistance functions reveals microbial resistomes cluster by ecology. The ISME Journal. 2014, doi:ISMEJ.2014.106). In some embodiments, evaluation of homology is conducted in the same manner as the identification of candidate resistance genes based on target resistance (i.e., as described in this document under the header "Resistance Gene Homology Searches."). Briefly, homology can be determined based on sequence identity, sequence similarity, and/or through HMM predictive models.

In some embodiments, a sequence is considered a homolog of a known resistance gene if it shares more than 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity with a known resistance gene, including all ranges and subranges therebetween. In some embodiments, a sequence is considered a homolog of a known resistance gene if the ratio of its candidate resistance bitscore to best match bitscore is greater than 0.6, 0.7, 0.8, or 0.9, including all ranges and subranges therebetween.

Genes that are Co-Regulated with at Least One Biosynthetic Gene/Enzyme in the Cluster In some embodiments, the present disclosure further teaches additional step of c)iii) of filtering annotated genes from the predicted natural product multi-gene cluster feature sets to leave only genes that: comprises a gene with no predicted biosynthetic function that also is co-regulated with another gene within the multi-gene cluster feature set that has a predicted biosynthetic function. In some embodiments, the present disclosure further teaches filtering away genes so as to focus on genes that are co-regulated with at least one of the biosynthetic genes of the natural product multi-gene cluster feature set. That is, in some embodiments, the present disclosure teaches that the plurality of filtered genes of interest are co-regulated with at least one biosynthetic gene/enzyme in the natural product multi-gene cluster feature set.

In some embodiments, the present disclosure further teaches filtering away genes that are not within or immediately adjacent to a biosynthetic operon so as to focus on genes that are co-regulated with at least one of the biosynthetic genes of the natural product multi-gene cluster feature set. That is, in some embodiments, the present disclosure teaches that the plurality of filtered genes of interest are co-regulated (e.g., via a biosynthetic operon) with at least one biosynthetic gene/enzyme in the natural product multi-gene cluster feature set.

Persons having skill in the art will be aware of the various ways of empirically determining or computationally predicting whether two genes are co-regulated. For example, in some embodiments, two genes will be considered to be co-regulated if the structure of the multi-gene cluster indicates that the two genes are co-regulated (e.g., the genes are comprised within an operon, or are part of a predicted polycistronic mRNA. In some embodiments, two genes will be considered to be co-regulated if expression of the first gene is empirically determined to correlate with the production of the second gene (e.g., if both genes are activated/ repressed under similar conditions). In some embodiments, two genes will be considered to be co-regulated if their promoters contain binding sites that are predicted or shown to bind to the same transcription factor.

In some embodiments, the resulting plurality of filtered genes of interest is used to select one or more natural product multi-gene cluster features sets that comprise at least one of the plurality of filtered genes of interest, thereby creating a library of candidate MGC sequences.

Transitive Multi-gene Cluster Feature Set Discovery Workflow

In some embodiments, the present disclosure teaches transitive methods of identifying novel natural product-encoding multi-gene clusters. In some embodiments, the transitive methods of the present disclosure represent a horizontal exploration of MGCs based on the features of a known/predicted MGC of interest. Transitive searches are based, in part, on the inventor's discovery that homologs/ orthologs of a known MGC may exist in other portions of a host cell's genome, or in different microbial species, wherein said homolog/ortholog lacks the hallmark resistance gene of the original known MGC, or contains a resistance gene that bears little resemblance to the original gene.

Thus, in some embodiments, the present disclosure teaches an in silico method for identifying a candidate multi-gene cluster (MGC) comprising the steps of: a) providing the sequence of a known or predicted MGC; b) computationally predicting natural product multi-gene cluster feature sets within a long-assembly digital metagenomic library and supplying the output of said prediction as a plurality of signal-associated multi-gene cluster digital feature sets; c) selecting a candidate MGC from amongst the plurality of signal-associated multi-gene cluster digital feature sets of step (b) said candidate MGC comprising at least one similarity factor selected from the group consisting of: i) sequence homology amongst the biosynthetic enzymes within the known or predicted MGC and the candidate MGC; ii) same number of each type of biosynthetic module(s) within the known or predicted MGC and the candidate MGC; and iii) similarity with the known or predicted MGC is determined by similarity of the predicted chemical structures of natural products produced by the known/predicted MGC and the candidate MGC; thereby identifying the candidate MGC that does not encode for a resistance gene or contains a resistance gene that does not resemble the original gene. In some embodiments, only similarity factor (i) is used. In some embodiments MGCs are selected based on them comprising at least two similarity factors (e.g., comprising (i) and (ii) or (i) and (iii), or (ii) and (iii)).

In some embodiments, the transitive (horizontal) search for novel candidate MGCs is based on similarity of a MGC candidate to a known or predicted MGC. That is, in some embodiments, the methods of the present disclosure include the step of "providing the sequence of a known or predicted MGC." In some embodiments, known MGCs are those which have been experimentally validated, and demonstrated to produce a natural product (e.g., through empirical data held or known by the person carrying out the method, or as reported in a journal). In some embodiments, predicted MGCs are those which are predicted to encode for natural products by any one of the MGC discovery methods of the present disclosure. In some embodiments, predicted MGCs are those which comprise i) a resistance gene, and ii) are identified as encoding a multi-gene cluster based, at least in part, on the presence of MGC features such as PKS, NRPs, RiPPs, as discussed in the "Multi-Gene Cluster Prediction" section of this document.

In some embodiments, the present transitive searching workflow comprises the step of identifying candidate MGCs comprising similarity factors with the known or predicted MGC. In some embodiments, similarity with the known or predicted MGC is determined by sequence homology between biosynthetic enzymes in the clusters (e.g., as determined for example by BLAST, HMM, or by other tools such as anti SMASH annotation engine). In some embodiments, similarity with the known or predicted MGC is determined by sequence homology between core biosynthetic enzymes in the clusters (e.g. anACAD in the candidate MGC has significant similarity to an ACAD in the known or predicted MGCs, as determined for example by BLAST or an HMM, and discussed in more detail below). In some embodiments, the present disclosure teaches that the candidate MGCs will contain homologs for all of the biosynthetic enzymes of the known or predicted MGC. In some embodiments, the candidate MGCs contain homologs for at least 1, 2, 3, 4, 5, 6, 7, 8, 9, 10, 11, 12, 13, 14, 15, 16, 17, 18, 19, biosynthetic enzymes of the known or predicted MGC. In some embodiments, the candidate MGCs contain homologs for at least 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%, of the biosynthetic enzymes of the known or predicted MGC, including all ranges and subranges therebetween.

In some embodiments, biosynthetic genes/enzymes comprises expressed proteins (or the nucleic acid sequences encoding them, depending on the context) capable of catalyzing a biochemical synthesis reaction or which are part of a complex that catalyzes the reaction. That is, a sequence that does not have catalytic activity alone, but which complexes with one or more other enzymes capable of catalyzing a biochemical reaction are considered biosynthetic enzymes. For example, protein TfuA does not have catalytic activity by itself, but complexes with YcaOs in the production of natural products. In some embodiments, biosynthetic enzymes are identified by one or more annotation engines. In some embodiments a gene is considered a biosynthetic gene/enzyme, if it is annotated as such by antiSMASH. In some embodiments a gene is considered a biosynthetic gene/enzyme, if it is listed as such in the MiBIG database.

In some embodiments, the present disclosure teaches that the candidate MGCs will contain homologs for all of the core biosynthetic enzymes of the known or predicted MGC. Persons having skill in the art will readily be able to identify genes that define related MGCs (i.e., identifying the "core biosynthetic enzymes"). In some embodiments, "core biosynthetic enzymes" vary by MGC. For example, in one case, it might be two biosynthetic enzymes that generate the molecular scaffold. In another case, it might be the presence of a core biosynthetic enzyme as well as enzyme involved in utilizing a unique precursor. In another case, the tailoring enzymes that catalyze a characteristic modification might be what is characteristic of the cluster. In some embodiments, a gene is considered a "core biosynthetic enzyme" if it is annotated as such by an annotation engine. In some embodiments, a gene is considered a "core biosynthetic enzyme" if it is annotated as such by antiSMASH. The present disclosure teaches methods of identifying "core biosynthetic" enzymes or genes. In some embodiments, core biosynthetic genes are genes encoding enzymes within the MGC that have a biosynthetic role in the production of the natural product, and that form moieties critical to the molecule's structure or function that are not shared by all members of the molecule's class. In some embodiments these enzymes produce either a scaffold or a warhead. For example in the epoxomicin cluster the ACAD gene would be one of these (forms the epoxyketone that is integral to the molecules function), but the NRPS gene would not (the NRPS gene is shared amongst all NRPS clusters). In some embodiments, these enzymes are tailoring enzymes that introduce functional groups and moieties that, whilst they may impact target binding and the pharmacokinetic properties, do not form clear structural scaffolds or warheads. Examples would be the TfuA gene catalyzing thioamide formation, and HopA1-like gene catalyzing serine/threonine dehydration in thioviridamide biosynthesis. These are both tailoring reactions that some non-thioviridamide clusters have (semi-unique), but an intersect of the two will enrich greatly for thioviridamide-like clusters.

In some embodiments, the further selection of a "core biosynthetic" enzyme allows the user to further enrich the pool of candidate MGCs to those most likely to encode the NP of interest by filtering for the presence of enzymes that are important to the production of the NP, and are believed to be enriched or unique within the NPs of interest. In some embodiments, enzymes that would not qualify as "core biosynthetic" enzymes are common biosynthesis or tailoring enzymes. Common biosynthesis enzymes are those that build the class-defining scaffold for a class of metabolites. An example would be the chalcone/stilbene synthase gene in a type III PKS. Common tailoring enzymes are those that build class-defining functional groups. Examples would be O-methyltransferases or hydroxylases. Not only are these common across many different clusters, but their presence in cluster analogues is often unreliable. Thus, in some embodiments, common biosynthetic and tailoring enzymes would not, in isolation, be expected to enrich the pool of candidate MGCs for those encoding NPs of interest (e.g., in the case of transitive search-encoding for similar NPs to those encoded by the initial known or predicted MGC). The term "core biosynthetic enzyme" is used interchangeably with the term "core biosynthetic gene."

In some embodiments, the candidate MGCs contain homologs for at least 1, 2, 3, 4, 5, 6, 7, 8, 9, 10, 11, 12, 13, 14, 15, 16, 17, 18, 19, core biosynthetic enzymes of the known or predicted MGC. In some embodiments, the candidate MGCs contain homologs for at least 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%, of the core biosynthetic enzymes of the known or predicted MGC, including all ranges and subranges therebetween.

In some embodiments, evaluation of homology is conducted in the same manner as the identification of candidate resistance genes based on target resistance (i.e., as described in this document under the header "Resistance Gene Homology Searches."). Briefly, homology can be determined based on sequence identity, sequence similarity, and/or through HMM predictive models.

In some embodiments, a sequence is considered a homolog of a biosynthetic or core biosynthetic gene/enzyme if it shares more than 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity with the biosynthetic gene/enzyme of the initial known or predicted MGC, including all ranges and subranges therebetween. In some embodiments, a sequence is considered a homolog of a known resistance gene if the ratio of its candidate resistance bitscore to best match bitscore is greater than 0.6, 0.7, 0.8, or 0.9, including all ranges and subranges therebetween.

In some embodiments, the present disclosure teaches additional similarity factors with the known or predicted MGC that can be used to identify new MGCs. In some embodiments, similarity is determined by identifying a similar complement of genes in both clusters (e.g. same sets of tailoring enzymes encoded in both clusters).

In some embodiments, similar complements of genes means that the candidate MGC contains the same number (or plus or minus 1-2) of each type of biosynthetic module in the known or predicted MGC. For example, a candidate MGC would have a similar complement of genes, if it had three PKS-like modules, and four NRS-like modules, where the predicted MGC had three PKS-like modules, and three NRS-like modules.

In some embodiments, similarity with the known or predicted MGC is determined by similarity of the predicted chemical structures of natural products produced by the known/predicted MGC and the candidate MGC. Persons having skill in the art will be aware of how to predict chemical structures from MGCs. A non-limiting list of tools capable of predicting NP chemical structures from MGCs is provided in Table 4, below. Additional discussion on chemical structure elucidation from gene sequences is provided in the "Structure Elucidation—From Genes to Chemistry" section of this document.

TABLE 4

Non-limiting List of Chemical Structure Prediction Tools

| | |
|---|---|
| antiSMASH | See Kai Blin et al. "antiSMASH 5.0: updates to the secondary metaboline genome mining pipeline" *Nucleic Acids Research* (2019), tool available at //antismash.secondarymetabolites.org/#!/start |

TABLE 4-continued

Non-limiting List of Chemical Structure Prediction Tools

| | |
|---|---|
| NP.searcher | M. H. T. Li, P. M. U. Ung, J. Zajkowski, S. Garneau-Tsodikova, D. H. ShermanAutomated genome mining for natural products. BMC Bioinformatics, 10(2009), p. 185 |
| ClustScan | A. Starcevic, J. Zucko, J. Simunkovic, P. F. Long, J. Cullum, D. HranueliClustScan: an integrated program package for the semi-automatic annotation of modular biosynthetic gene clusters and in silico prediction of novel chemical structures Nucleic Acids Res., 36 (2008), pp. 6882-6892 |
| NRPS-PKS/SBPKS | S. Anand, M. V. Prasad, G. Yadav, N. Kumar, J. Shehara, M. Z. Ansari, D. MohantySBSPKS: structure based sequence analysis of polyketide synthases Nucleic Acids Res., 38 (2010), pp. W487-W496 |
| PRISM | Skinnider, M. A., Johnston, C. W., Gunabalasingam, M. et al. Comprehensive prediction of secondary metabolite structure and biological activity from microbial genome sequences. *Nat Commun* 11, 6058 (2020). https://doi.org/10.1038/s41467-020-19986-1 |

In some embodiments, the similarity of predicted chemical structures is done by human inspection. Thus, in some embodiments, two predicted chemical structures will be considered similar, if they share the same core structural elements. In other embodiments, chemical structure similarity is determined by any algorithmic/computational method known to persons having skill in the art, including those disclosed in Nikolova, N. and Jaworska, J. (2003), Approaches to Measure Chemical Similarity—a Review. QSAR Comb. Sci., 22: 1006-1026.

In some embodiments, structural similarity of the NP is evaluated by calculating the pairwise NP structure similarity from NP-corresponding fingerprints, based on the Tanimoto coefficient and using the python library RDKit (www.rdkit.org). Briefly, morgan fingerprints are prepared for the NP synthesized (or predicted to be synthesized) and for the NPs synthesized (or predicted to be synthesized) by the plurality of signal-associated multi-gene cluster digital feature sets (e.g., MGCs identified by antiSMASH). These fingerprints are then compared to identify the most similar NP structures, and their corresponding candidate MGCs.

In some embodiments, the Tanimoto coefficient is calculated with the formula for dichotomous variables.

$$S_{AB} = \frac{C}{A + B - C}$$

In some embodiments, the Tanimoto Coefficient is calculated using the following formula for continuous variables.

$$S_{A,B} = \frac{\left[\sum nj = 1\, x_{jA}x_{jB}\right]}{\left[\sum nj = 1(XjA)2 + \sum nj = 1(XjB)2 - \sum nj = 1XjAXjB\right]}$$

Wherein the $S_{AB}$ similarity score between molecules A and B is calculated by dividing the "C" features in common between two molecules, by the "A" the features of a first molecule plus the "B" features of a second molecule, minus C. That is, A is the number of on bits in molecule A, B is number of on bits in molecule B, while C is the number of bits that are on in both molecules. $x_{jA}$ means the j-th feature of molecule A. $x_{jB}$ means the j-th feature of molecule B. For more information on how to calculate the Tanimoto coefficient, see Bajusz, D., Rácz, A. & Héberger, K. Why is Tanimoto index an appropriate choice for fingerprint-based similarity calculations?. *J Cheminform* 7, 20 (2015).

In some embodiments Tanimoto coefficients range from 0 to 1 with 0 being no similarity and 1 being an identical molecule. In some embodiments. In some embodiments, two natural product structures are considered similar if they have a Tanimoto similarity coefficient of at least 0.6, 0.7, 0.8, 0.9, or 0.95, including all ranges and subranges therebetween.

In some embodiments, similarity is assessed by the combination of two or more methods described above (e.g., by sequence homology between all or core biosynthetic enzymes, by containing a similar complement of genes in both MGCs, or by similarity of predicted chemical structures). In some embodiments, the transitive searches of the present disclosure are capable of assigning a putative function to the candidate MGC, despite this MGC lacking a resistance gene within its boundaries.

In some embodiments, the present disclosure teaches a modified transitive MGC discovery workflow. For example, in some embodiments, the present disclosure teaches an in silico method for identifying a candidate multi-gene cluster (MGC), said method comprising the steps of: a) identifying the biosynthetic gene/enzymes of a known or predicted MGC; b) querying a digital metagenomics library for homologs of each of the biosynthetic gene/enzymes identified in (a), wherein said digital metagenomics library comprises digitally assembled contigs; and c) identifying a new candidate MGC based on the presence of homologs of the biosynthetic enzymes within single contig of the digital metagenomics library. In some embodiments, the biosynthetic gene/enzymes of this workflow are core biosynthetic gene/enzymes, as described supra in this document.

In some embodiments, the present disclosure teaches an in silico method for identifying a candidate multi-gene cluster (MGC), said method comprising the steps of: a) providing a known or predicted MGC with a set of core biosynthetic gene/enzymes; b) querying a digital metagenomics library for homologs of each of the core biosynthetic gene/enzymes of (a), wherein said digital metagenomics library comprises digitally assembled contigs; and c) identifying a new candidate MGC based on the presence of homologs of each of the core biosynthetic gene/enzymes within a single digitally assembled contig of the digital metagenomics library. In some embodiments, the biosynthetic genes of this workflow are core biosynthetic gene/enzymes, as described supra in this document.

This section of the disclosure describes the identification of a new candidate MGC based on the presence of homologs of the biosynthetic enzymes within single contig of the digital metagenomics library. In some embodiments, the present disclosure teaches identification of candidate MGCs that contain homologs for all of the biosynthetic enzymes of the known or predicted MGC. In some embodiments, the candidate MGCs contain homologs for at least 1, 2, 3, 4, 5, 6, 7, 8, 9, 10, 11, 12, 13, 14, 15, 16, 17, 18, 19, biosynthetic enzymes of the known or predicted MGC, including all ranges and subranges therebetween. In some embodiments, the candidate MGCs contain homologs for at least 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%, of the biosynthetic enzymes of the known or predicted MGC, including all ranges and subranges therebetween.

In some embodiments, the candidate MGCs contain homologs for at least 1, 2, 3, 4, 5, 6, 7, 8, 9, 10, 11, 12, 13, 14, 15, 16, 17, 18, 19, core biosynthetic enzymes of the known or predicted MGC, including all ranges and subranges therebetween. In some embodiments, the candidate MGCs contain homologs for at least 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%, of the core biosynthetic enzymes of the known or predicted MGC, including all ranges and subranges therebetween.

Thus, in some embodiments, the present disclosure teaches screening digitally assembled contigs for the presence of homologs to biosynthetic or core biosynthetic gene/enzymes of a known or predicted MGC. In some embodiments homologs of biosynthetic genes or core biosynthetic gene/enzymes are identified one by one, and then a second step confirm that the identified homologs are in a single contig (i.e. that at least one complete "set" of homologs are within a digitally assembled contig). In other embodiments, the homologs of biosynthetic genes or core biosynthetic gene/enzymes are searched and confirmed to be in a single digitally assembled contig in a single step.

In some embodiments, homology of biosynthetic genes or core biosynthetic gene/enzymes is conducted in the same way as other homology steps of the present disclosure and this section specifically (i.e. by sequence identity or by HMM, by the cutoffs described above). In some embodiments, tools such as Multi-GeneBlast is used (www.ncbinlmnih.gov/pmc/articles/PMC3670737/).

In some embodiments, the transitive search methods of the present disclosure are conducted following any of the other MGC discovery platforms disclosed in this document. Thus, in some embodiments, transitive searches can be used to identify additional candidate MGCs based on MGCs identified through the resistance gene-based search methods discussed above. In some embodiments, the transitive search methods can be used to identify additional related MGCs based on known clusters reported in the literature, or otherwise identified via other methods not disclosed herein.

Construction of HMMs

Several of the homology searches described in this document can be conducted via HMM searches. In some embodiments, the HMM searches are based on existing HMM models, such as those available in Pfam and TIGRfam. In other embodiments, the present disclosure teaches methods of constructing new HMMs designed to search for candidate homolog genes. Methods of constructing custom HMMs for searching candidate homolog genes are discussed in more detail below.

The present disclosure, in some embodiments, provides methods and systems making use of Hidden Markov Models (HMMs) for the prediction of candidate homolog genes (e.g., candidate resistance genes, or for the purpose of annotation through homology to a gene with a known function). For the sake of simplicity however, sections below will generically refer to use of HMMs to identify homologs to a target gene/protein.

The following provides an exemplary workflow for generating an HMM for use in the present methods and systems. In some embodiments, an HMM generation workflow comprises the following steps:

1) Identify sequences to be used in a training data set corresponding to the target resistance gene;
2) Align the sequences;
3) Evaluate the alignment;
4) Generate the HMM predictive machine learning model from the multiple sequence alignment;
5) Evaluate the HMM.

Each of these exemplary steps is elaborated on herein.

1. Identify Sequence to be Used in Training Data Set

To construct an HMM to make predictions about whether or not a given sequence is a homolog to a target gene/protein, it is necessary to have a set of target sequences (at least one) that exhibits the desired properties (i.e., has been determined to belong to an annotation category of interest, such as belonging to a genus of target resistance genes). This is the initial training data set that will be used to train the machine learning model (e.g., HMM) in the present methods and systems: the data set comprises input genetic data (nucleic acid and/or amino acid sequences) and output phenotypical data (that the sequence performs the desired function). The list may be generated from either an existing orthology group (e.g., a KEGG orthology group) identified as having the desired function, or by identifying a sequence performing the desired function in Uniprot and finding homologs of that sequence (e.g. via a review of published validations of said homologs, or via traditional BLAST methods). In some embodiments, the list may be compiled from a publicly available sequence database. In some embodiments, the list may be compiled from a proprietary database. In some embodiments, the list may be compiled from a commercial database. In some embodiments, the list may be compiled from empirical data, such as validation experiments.

In some embodiments, the present disclosure teaches that the predictive ability of the HMM can be improved by providing the model with diverse sequences encoding proteins performing the desired function, i.e., the target protein function, or diverse sequences encoding genes performing the desired function, i.e., the target gene function. A very similar sequence set may train the HMM to identify similar sequences, similar to BLAST. Diverse sequences allow the HMM to capture which positions (e.g., amino acids) can vary and which are important to conserve. In some embodiments, it is desirable to include as many sequences as possible that are reasonably expected to perform the desired target function.

In some embodiments, the present disclosure teaches that the sequences in the training data set should share one or more sequence features. If sequences in the training data set do not share any common sequence features, they are likely not orthologs and should be excluded from the training data set. In some embodiments, the present disclosure teaches the creation of a primary HMM trained solely on high confidence training data sets, and a separate HMM trained on sequences selected with more lenient guidelines, such as outlier sequences that are believed to have the desired function, but do not share many of the sequence features present within the rest of the training data set. This permits the users to the analysis results with high vs. low confidence training data, providing flexibility for any downstream analysis.

For the purposes of illustration, the guidance for the identification of an initial training data set of sequences is applied to the target protein O-acetylhomoserine sulfhydrylase. These steps may be followed by an individual or may be programmed into software as a part of a method or system. To find an initial sequence training data set for the target protein O-acetylhomoserine sulfhydrylase, one may start by looking for an existing orthology group annotated with the desired function, e.g., as follows:

a. Search KEGG orthology database for the desired term (www.genome.jp/dbget-bin/www_bfind_sub?mode=bfind&max_hit=1000&dbkey=kegg&keywords=O-acetylhomoserine+sulfhydrylase).
b. Select the KEGG Orthology link.
c. Scroll down to Genes and select the Uniprot link to get a list of Uniprot IDs for this function.
d. Cut and paste the list of Uniprot IDs into Excel to get a column of the IDs separate from the descriptions.
e. Go to Retrieve/ID at Uniprot.
f. Paste the set of Uniprot IDs retrieved in step (e). This will return a list of Uniprot entries. Select the download link to retrieve a list sequences of these entries in FASTA format.

It is also possible to compile an initial training data set by searching Uniprot for a desired sequence, e.g., as follows:

a. Search UniprotKB for a protein performing the function of the target protein in any organism, e.g., an organism of interest. For this example, the search begins with the exemplary O-acetylhomoserine sulfhydrylase found at www.uniprot.org/uniprot/A4WQL8.
b. In the upper left corner, there is a button to do a BLAST search of this sequence against the full UniprotKB. Click this, and select the advanced option.
c. Set Threshold to 0.1 and Hits to 1000; this will provide a large number of hits while removing very different sequences. Then run the search. It will take a few minutes to complete the search.
d. Click the download link to download all sequences as a FASTA file.

2. Align the Sequences

The sequences accumulated in step 1 may be aligned using any available multiple sequence alignment tool. Multiple sequence alignment tools include Clustal Omega, EMBOSS Cons, Kalign, MAFFT, MUSCLE, MView, T-Coffee, and WebPRANK, among others. For the purposes of this illustrative example, Clustal Omega is employed. Clustal Omega may be installed on a computer and run from the command line, e.g., with the following prompt:

$ clustalo-infile=uniprot-list.fasta-type=protein-output=fasta-outfile=aligned.fasta 3. Evaluate the Alignment (Optional)

The multiple sequence alignment performed in step 2 may be evaluated and filtered for poor matches. As described in the foregoing, sequences that do not share sequence features are likely not in the same orthology group and may be detrimental to the quality of the HMM.

For assisting in the evaluation of the alignment, exemplary in-browser alignment tools are http://msa.biojs.net/ and/github.com/veidenberg/wasabi. Both can be downloaded and run locally.

Sequences that do not match the rest of the training data set may be removed from the training data set before proceeding to the next step. Such sequences may be removed in an automated fashion based on objective criteria of the quality of the alignment, such as not possessing one or more sequence features common to most other members of the orthology group. In some embodiments, sequences that do not match the orthology group may be removed by other means, e.g., visual inspection.

4. Generate the HMM Predictive Machine Learning Model Based on the Training Data Set The HMM can be generated by any HMM building software. Exemplary software may be found at, or adapted from: mallet.cs.umass.edu; www.cs.ubc.cal-murphyk/Software/HMM/hmm.html; cran.r-project.org/web/packages/HMM/index.html; www.qub.buffalo.edu; //ccb.jhu.edu/software/glimmerhmm/. In some embodiments, the HMMER tool is employed.

For the purposes of this illustrative example, HMMbuild is used and may be downloaded and run locally with the following command:

$ hmmbuild test.hmm aligned.fasta

5. Evaluate the HMM (Optional)

To evaluate the HMM generated in step 4, it may be run on an annotated database to evaluate its ability to correctly recognize sequences. In this illustrative example, the HMM is used to query the SwissProt database, for which all annotations are presumed to be true. The results of this test run may be checked to see if the annotations of the search result match the function the HMM should represent.

With a fasta file (or files) of a search database of protein sequences (e.g., protein_db.fasta), the following command can be run to get an output file of HMM matches with a corresponding E-value.

$ hmmsearch-A 0—cpu 8-E1e-20—noali—notextw test.hmm protein_db.fasta>hmm.out

This command can also be used on the translated proteome of a genome to find all hits matching a functional motif The various options in this command correspond to the following:
-A 0: do not save multiple alignment of all hits to a file
—cpu 8: use 8 parallel CPU workers for multithreads
-E1e-20: report sequences<=1e-20 e-value threshold in output
—noali: don't output alignments, so output is smaller
—notextw: unlimit ASCII text output line width In some embodiments, custom-built HMMs built according to this and other known methods can be used to establish homology for any of the workflow steps of this disclosure (e.g., identifying candidate resistance genes, or annotating genes). In some embodiments, the HMMs are built around "complete" target sequences (e.g., target genes for resistance searching, biosynthetic genes or "core biosynthetic gene/ enzymes", or others, described in this disclosure). In some embodiments, the HMMS are built around specific domains of said target sequences (e.g., a domain found to be representative for the particular target gene/protein of interest).

Structure Elucidation—From Genes to Chemistry

In some embodiments, the presently disclosed natural product discovery workflow (e.g. FIG. 1), comprises a step of in silico structure elucidation. That is, in some embodiments, the present disclosure teaches methods of predicting natural product chemical structure based on the sequences of natural product multi-gene clusters identified through methods disclosed herein (e.g., computationally determined natural product multi-gene cluster feature set). (See FIG. 3).

In some embodiments, computationally predicted natural product (NP) structures can be helpful for prioritizing NP discovery efforts. For example, an MGC predicted to produce an NP with a known structure may be de-prioritized in the discovery pipeline compared to an MGC that is predicted to produce an NP of higher interest to the goals of the program. In some embodiments, in silico predictions about NP structure can facilitate subsequent detection of the NP (e.g., via mass spec).

Predicting the small molecule products of a wide range of biosynthetic pathways directly from genome sequence data is a computational and data-intensive process. There exist an enormous variety of enzymes involved in synthesizing and tailoring natural product scaffolds, and innumerable variations on known chemical themes. From a computational perspective, the problem can largely be reduced to the question of how to acquire a sufficiently comprehensive training dataset to cover this diversity and complexity.

A range of algorithms have been developed to predict the substrate specificities of NRPS adenylation domains and PKS acyltransferase domains. (See e.g., Khayatt B I, Overmars L, Siezen R J, Francke C. Classification of the adenylation and acyl-transferase activity of NRPS and PKS systems using ensembles of substrate specific hidden Markov models. PLoS One. 2013; 8:e62136, and Baranagie D, et al. Predicting substrate specificity of adenylation domains of nonribosomal peptide synthetases and other protein properties by latent semantic indexing. J Ind Microbiol Biotechnol. 2014; 41:461-7). The Minimum Information about a Biosynthetic Gene cluster (MIBiG) also includes annotated information about all enzyme functions and specificities for known MGCs, as well as the level of evidence available for each observation (Medema MH. The Minimum Information about a Biosynthetic Gene cluster (MIBiG) specification. Nat Chem Biol. 2015).

These and other individual monomer predictions are combined by tools like NP.searcher and anti SMASH to give a rough idea of the core scaffold of a polyketide or nonribosomal peptide. (Li M H, Ung P M, Zajkowski J, Garneau-Tsodikova S, Sherman D H. Automated genome mining for natural products. BMC Bioinforma [computer file] 2009; 10:185, Medema M H, et al. antiSMASH: rapid identification, annotation and analysis of secondary metabolite biosynthesis gene clusters in bacterial and fungal genome sequences. Nucleic Acids Res., and Blin K, et al. antiSMASH 2.0—a versatile platform for genome mining of secondary metabolite producers. Nucleic Acids Res. 2013). For some classes of RiPPs, intramolecular cross-links can also be predicted (Blin K, Kazempour D, Wohlleben W, Weber T. Improved lanthipeptide detection and prediction for antiSMASH. PLoS One. 2014; 9:e89420).

Another structure prediction tool contemplated by the present disclosure is the PRediction Informatics for Secondary Metabolomes (PRISM) software. PRISM uses chemical graphs to model natural product scaffolds of various cluster types (Michael A. Skinnider et al., PRISM 3: expanded prediction of natural product chemical structures from microbial genomes, Nucleic Acids Research, Volume 45, Issue W1, 3 Jul. 2017, Pages W49-W54, and US Pub. No. 2018/0373833, each of which is hereby incorporated by reference). Additional examples of structure-predicting software tools is provided in Table 4, above.

Matching Genes to Molecules Using Analytical Chemistry Techniques

In some embodiments, the structure elucidation steps of the natural product discovery platform comprise synthesizing and analyzing natural products from identified MGCs. In some embodiments, the present disclosure teaches methods of analyzing data from empirical analysis of new natural products by leveraging in silico predictions about the natural product's structure. (See FIG. 3).

For example, the peptidogenomics and glycogenomics methodologies combine the power of tandem mass spectrometry to profile the fragment composition of molecules with MGC predictions of chemical sub-structures that may correspond to these fragments. (See Kersten R D, et al. A mass spectrometry-guided genome mining approach for natural product peptidogenomics. Nat Chem Biol. 2011; 7:794-802, and Kersten R D, et al. Glycogenomics as a mass spectrometry-guided genome-mining method for microbial glycosylated molecules. Proc Natl Acad Sci USA. 2013; 110:E4407-16). In some embodiments, the computational coupling of mass spectrometric and genomic data for peptidogenomics has been entirely automated by a number of algorithms. This provides an unprecedentedly rapid method to connect gene clusters to molecules.

The RiPPQuest and NRPQuest algorithms both use a molecular networking approach to identify potential gene clusters for observed tandem mass spectra of lanthipeptides (a class of RiPPs) and nonribosomal peptides (NRPs), respectively (Mohimani H, et al. Automated genome mining of ribosomal peptide natural products. ACS Chem Biol. 2014; Mohimani H, et al. NRPquest: Coupling Mass Spectrometry and Genome Mining for Nonribosomal Peptide Discovery. J Nat Prod. 2014; and Guthals A, Watrous J D, Dorrestein P C, Bandeira N. The spectral networks paradigm in high throughput mass spectrometry. Mol Biosyst. 2012; 8:2535-2544).

The search database for RiPPquest is compiled by finding all short open reading frames (ORFs) near each detected lanthionine synthetase-encoding gene in a genome, while NRPquest creates a database of possible NRPs by generating all possible orders of NRPS assembly-lines within each detected NRP MGC and then predicting the amino acids encoded by each NRPS module using NRPSPredictor2 (Röttig M, et al. NRPspredictor2—a web server for predicting NRPS adenylation domain specificity. Nucleic Acids Res. 2011; 39:W362-7). A spectral networking approach enables multiple variants of a molecule to be assessed, which reduces the likelihood of a false negative result from unanticipated tailoring modifications. Also, it allows immediate identification of previously unknown variants of known peptides.

An alternative method, Pep2Path, uses a probabilistic framework to predict the likelihood that each NRPS module selects every possible amino acid as a substrate, and then calculates combined probabilities for all possible NRPS assembly lines to match a mass spectrometry-derived mass shift sequence tag: a sequence of fragment molecular weight differences that is representative for the amino acid sequence of the peptide under study (Medema M R, et al. Pep2Path: Automated Mass Spectrometry-Guided Genome Mining of Peptidic Natural Products. PLoS Comput Biol. 2014; 10:e1003822). Even though Pep2Path is based on the same algorithm for substrate specificity prediction as NRPquest (i.e., NRPSPredictor2), the advantage of this approach is that the algorithm will not fail to predicted a peptide-MGC link if a few modules are slightly mispredicted: e.g., if a module is specific for tyrosine, and a phenylalanine is observed, the probability of the module to be responsible for the observed amino acid will still be high. Pep2Path also has a tool for RiPP MGC identification, which searches all possible ORFs in a genome for hits to an observed mass shift sequence tag.

Workflow for Prioritizing Resistance Genes and Clusters

The present disclosure provides a workflow describing embodiments of prioritization of resistance genes and clusters. (See FIG. 8).

In some embodiments, the presently disclosed workflow is designed to filter out clusters where the putative resistance gene has a significant chance of playing a different role in the cluster (e.g. biosynthetic vs. resistance) as well as filter out clusters with additional technical issues such as being incomplete, or having low-confidence as being a true cluster based on the lack of certain biosynthetic genes.

In some embodiments, the present workflow includes a checkpoint to determine whether a resistance gene is convincing. The resistance gene is convincing if it is in an operon with biosynthetic genes (for example known tailoring such as methyltransferases, glycosyltransferases, and oxidases/reductases), or orphaned within two genes of biosynthetic genes. If the resistance gene could have a biosynthetic role, this is assessed in concert with the associated genes (for example, a target resistance gene that is involved in fatty acid metabolism is less convincing if it is associated with a fatty acid-containing gene cluster). Unconvincing resistance genes are in operons with or near other primary metabolic/housekeeping genes (for example: multiple enzymes involved in amino acid metabolism). They are also less convincing if they are near other parts of a multipart complex (for example, if the target resistance gene was a ribosome subunit, and it was associated with other ribosome subunits).

In some embodiments, the present workflow includes a checkpoint to determine if the gene cluster is convincingly real. A convincing gene cluster contains multiple biosynthetic genes capable of producing a scaffold. For example, this may include genes that code for modular assembly lines (PKS/NRPS), structural peptides (RiPPs), or terpene synthases. Isolated genes without surrounding biosynthetic tailoring genes are often unconvincing, for example bacteriocin clusters called because of the presence of a protease, with no other associated genes, are discarded. In some embodiments, this quality control step is addressed by ensuring that the computationally determined biological resistance gene is located within a threshold parameter of a computationally determined natural product multi-gene cluster feature set.

In some embodiments, the present workflow includes a checkpoint to determine if a cluster could produce something interesting. The 'interestingness' of a gene cluster is assessed with a number of metrics. If the gene cluster looks identical to a previously identified gene cluster, the cluster is discarded. If it looks similar to a previously identified gene cluster, then the value of an analogue of the previously identified gene cluster is assessed (for example, an analogue of a molecule that has no bioactivity is not interesting). The characteristics of the predicted molecule that may produce is assessed, for example bacteriocins will may have poor pharmacokinetics, and therefore they are less interesting. In some embodiments. possibly interesting molecular features are also assessed, for example if a halogenase is present this may produce a molecule that is easier to identify and that may have more valuable pharmacokinetics.

In some embodiments, the present workflow includes a checkpoint to determine if a gene cluster is contained in a single cosmid. A cluster is be guessed to be on a single cosmid if there are no operons of biosynthetic genes running on or off of the cosmid.

In some embodiments, the present workflow includes a checkpoint to determine if a cluster can be completed. A cluster that is not contained on a single cosmid is compared against other contigs in our library. If an overlapping contig (or multiple contigs) can be found that complete the gene cluster (so that there are no operons of biosynthetic genes running on or off of the cosmid), then the cluster is deemed completable. If the assembled sequence of the cosmid is short (<30 kb), indicating that it is incomplete, then it may be completable if the cosmid is retrieved from the physical cosmid library and resequenced. Therefore, if it is particularly interesting and is worth the risk that it won't be completed, it may still be continued with.

Methods, Systems, and Tools of the Present Natural Product Analoging Platform

Portions of the present disclosure provide various methods for the discovery of novel natural products from metagenomic libraries. These novel natural products have the potential to drastically increase the available NP diversity for a variety of applications ranging from small-molecule drug treatments, agricultural products, such as pesticides or insect pheromones, and or other consumer food, cosmetic, and cleaning products, among others.

In some instances however, natural products with high potential for a desired application are still considered inviable for other reasons. The natural product, for example, may lack necessary shelf life, may cause adverse reactions in some populations of patients, or may simply have an undesirable flavor or smell that prevents widespread adoption. Natural products may also have poor bioavailability or poor absorption, distribution, metabolism and excretion (ADME) profiles. Other reasons that might prevent an otherwise beneficial natural product from achieving commercial success may be cost of production, or the lack of patent protection for naturally-occurring compounds. In these instances, it may be beneficial to modify natural products to produce molecules that alleviate perceived downsides and/or instill desired properties.

An example of a natural product that benefited from modification is salicylic acid (SA). This natural product had originally been discovered in willow, as a common plant stress hormone. This natural product was valued in classical antiquity, and referenced in clay tablets from Sumer and papyrus from Egypt as a treatment for pain. (Diarmuid Jeffreys. Aspirin: The Remarkable Story of a Wonder Drug. Chemical Heritage Foundation, 2008). Salicylic acid however, was difficult to synthesize, and was disliked by some patients, who complained about the irritating effects that the natural product had on the stomach. In 1897, scientists at Bayer® developed an acetylsalicylic acid variant of SA, which mitigated the irritating effects of the original drug, and was easier to synthesize (Id.). This drug is now commonly known as aspirin.

In some embodiments the present disclosure teaches methods for improving newly discovered natural products. Thus, in some embodiments, the present disclosure teaches methods of analoging natural products. Analoging, as used herein, describes the modification of a natural product to create variant molecules with improved, or otherwise desirable properties. In some embodiments, analoging comprises adding or removing various chemical groups to the central core structure of the natural product.

In some embodiments, the present disclosure teaches biosynthetic methods of natural product analoging. Thus, in some embodiments, the present disclosure generates variants of natural products by either modifying existing biosynthetic pathways, or by post-synthesis processing of natural products with one or more enzyme catalysts. In some embodiments, the present disclosure refers to biosynthetic-based analoging as "bioconversion." A comparison of the presently disclosed bioconversion strategies to traditional chemical approaches to analoging is provided in FIG. 11.

In some embodiments, the analoging methods of the present disclosure comprise modifications that occur either during, or after the synthesis of the natural product. That is, in some embodiments, the analoging methods of the present disclosure begin to modify the natural product after it has been synthesized (e.g., after extraction, in a separate reaction, or through the incorporation of additional biosynthetic steps). In some embodiments, the analoging methods of the present disclosure modify the biosynthetic steps of the natural product itself to produce a variant (e.g., replacing or modifying a gene within the biosynthetic pathway of the natural product to create a variant). In some embodiments, the present disclosure also teaches methods of analoging natural products by adding intermediary steps to the biosynthetic pathway.

Figure 9:
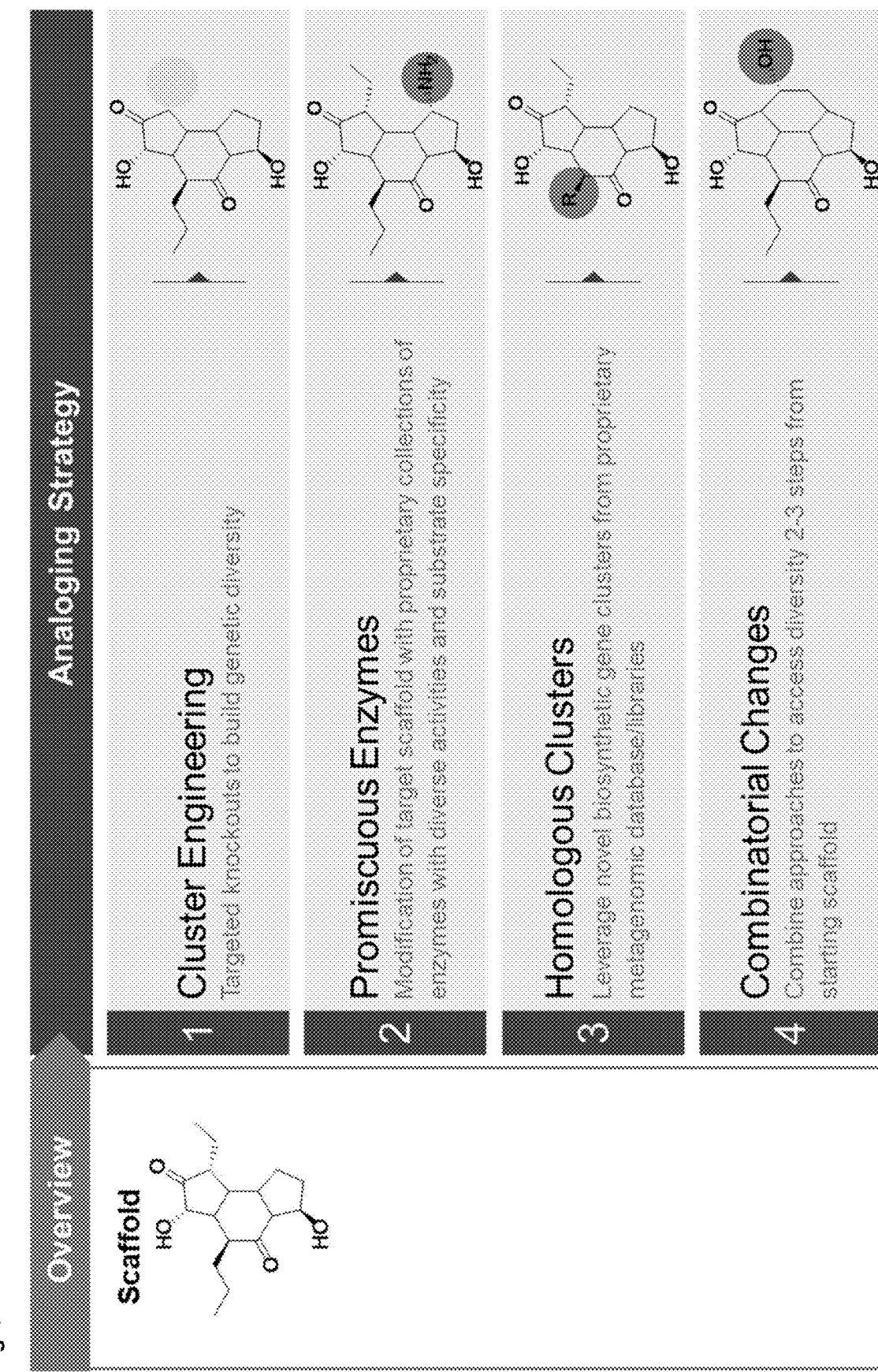
FIG. 9—depicts various strategies of the natural product analoging platform of the present disclosure. In some embodiments, the present disclosure teaches analoging natural products by engineering MGCs (e.g., modifying or knocking out one or more genes involved in the biosynthesis of said natural product). In some embodiments, the present disclosure teaches methods of analoging natural products through enzyme panels (e.g., promiscuous enzymes known or predicted to catalyze a desired reaction). In some embodiments, the present disclosure teaches method of leveraging homologous clusters to analog natural products. Combinations of these techniques is also within the envisioned embodiments of the present disclosure.

In some embodiments, the presently disclosed analoging methods fall into at least three broad categories representing: 1) cluster engineering (e.g., disrupting or otherwise modifying existing biosynthetic genes/biosynthetic pathways), 2) enzyme panels (e.g., use of promiscuous enzymes), and 3) the exploitation of homologous clusters (e.g., biosynthetic engineering through swapping of portion or the entire MGC). (See FIG. 9). In some embodiments, the present disclosure also teaches analoging through combination of one or more of the three broad strategies described above. Each of these strategies is discussed in more detail below.

Natural Product Analoging—Cluster Engineering

In some embodiments, the present disclosure teaches cluster engineering methods of analoging natural products. Thus, in some embodiments, the present disclosure teaches a method for producing an analog of a target natural product, said method comprising the steps of: a) providing a base microbial host cell comprising a multi-gene cluster known to produce the target natural product; b) perturbing the genome of the base microbial host cell to mutate or knock out the expression of one or more genes within the multi-gene cluster, thereby creating a library of mutated microbial host cells; c) culturing a microbial host cell from the library of mutated microbial host cells; d) analyzing spent media from the cultures of step (c), for the presence of (or to identify) the target natural product and/or analogs of said target natural product, and e) selecting a microbial host cell from the microbial host cells cultured in step (c), wherein the selected microbial host cell produces an analog of the target natural product as determined by the analysis of step (d), thereby producing an analog of the target natural product.

In some embodiments, the step of perturbing the genome can be done via any known methods of modifying DNA sequences. In some embodiments, the present disclosure teaches perturbing the genome by replacing all (or a portion) of a multi-gene cluster with corresponding DNA comprising desired mutations. In some embodiments, the present disclosure teaches for example, use of loop in/out techniques. In some embodiments, the present disclosure teaches the use of gene editing tools to make the desired modifications.

In some embodiments, the molecules of a genome-editing system may include, for example, a) an enzyme and an RNA, b) the RNA and a nucleic acid encoding the enzyme, c) the enzyme and a nucleic acid encoding the RNA, or d) nucleic acid encoding both the enzyme and the RNA. In some embodiments, the genome-editing system comprises a designer nuclease (or a nucleic acid encoding the designer nuclease, such as an mRNA or a DNA plasmid), such as a zinc-finger nuclease (ZFN), a transcription activator-like effector nuclease (TALEN), a homing endonuclease (such as an ARC Nuclease™) or a nucleic acid-guided endonuclease (NGEN), such as an RNA-guided endonuclease (RGEN, e.g., Cas9) or a DNA-guided endonuclease (DGEN). In some embodiments, the genome-editing system further comprises a guide nucleic acid (gNA) (or a nucleic acid encoding the guide nucleic acid, such as an mRNA or a DNA plasmid), such as a guide RNA (gRNA) or a guide DNA (gDNA). In some embodiments, the genome-editing system is a clustered regularly interspaced short palindromic repeat (CRISPR) system (including, for example, CRISPR-associated proteins and/or nucleic acids, or nucleic acids encoding one or more of CRISPR-associated proteins and/or nucleic acids). In some embodiments, the genome-editing system comprises a ZFN. In some embodiments, the genome-editing system comprises a TALEN. In some embodiments, the genome-editing system comprises a homing endonuclease. In some embodiments, the genome-editing system comprises an integrase (or a nucleic acid encoding the integrase, such as an mRNA or a DNA plasmid). In some embodiments, the genome-editing system further comprises a donor nucleic acid comprising a recombination site recognized by the integrase.

The engineering (i.e., genome perturbation) methods of the present disclosure can be done in isolation, or can be part of a larger strain engineering program. For example, in some embodiments, MGC engineering of the present disclosure can be done according to the methods of U.S. Pat. No. 9,988,624, which is hereby incorporated in its entirety.

Natural Product Analoging—Enzyme Panel and Promiscuous Enzymes

In some embodiments, the present disclosure teaches enzyme panel methods of analoging natural products. Thus, in some embodiments, the present disclosure teaches the use of one or more enzymes to modify a natural product or a precursor of the natural product.

In some embodiments, the present disclosure teaches a method for biosynthetic analoging of a target natural product, said method comprising the steps of: a) providing a plurality of enzymes known or predicted to catalyze a type of reaction for analoging of the target natural product, thereby creating an analoging enzyme panel library; b) incubating individual enzymes from the analoging enzyme panel with the target natural product, or a precursor to the target natural product, thereby producing reaction mixtures; c) analyzing at least one of the reaction mixtures of step (b), for the presence of the target natural product and/or analogs of said target natural product; and d) selecting an enzyme from the analoging enzyme panel, wherein the selected enzyme produces an analog of the target natural product, as determined by the analysis of step (c), thereby analoging the target natural product.

In some embodiments, the enzymes from the analoging enzyme panel are purified enzymes. In some embodiments, enzymes of step (a) are provided in the form of lysates from microbial strains heterologously expressing said enzymes.

In some embodiments, the enzymes from the enzyme panels are comprised within strains. Thus, in some embodiments, the present disclosure teaches a method for biosynthetic analoging of a target natural product, said method comprising the steps of: a) providing a plurality of microbial strains, each expressing an enzyme known or predicted to catalyze a type of reaction for analoging of the target natural product, thereby creating an analoging enzyme panel library of microbial strains; b) contacting individual microbial strains from the analoging enzyme panel library of microbial strains with the target natural product, or a precursor to the target natural product, thereby creating a mixture (e.g., culturing individual microbial strains from the analoging enzyme panel library of microbial strains, in growth media comprising the target natural product, or a precursor to the target natural product); c) analyzing the mixture of strains and the target natural product or precursor of step (b) (e.g., spent media from the cultures of step (b)) for the presence of the target natural product and/or analogs of said target natural product; and d) selecting a microbial strain from the analoging enzyme panel library of microbial strains, wherein the selected microbial strain produces a desired analog of the target natural product, as determined by the analysis of step (c), thereby analoging the target natural product; wherein the enzyme expressed by the selected microbial strain is a selected enzyme.

In some embodiments, the strains within an enzyme panel are lysed prior to being contacted with the target natural product or precursor thereof. Thus, in some embodiments, the present disclosure teaches a method for biosynthetic analoging of a target natural product, said method comprising the steps of: a) providing a plurality of microbial strain lysates, each lysate from a microbial strain expressing an enzyme known or predicted to catalyze a type of reaction for analoging of the target natural product, thereby creating an analoging enzyme panel library; b) contacting individual lysates from the analoging enzyme panel library with the target natural product, or a precursor to the target natural product, thereby creating enzyme mixtures; c) analyzing the enzyme mixtures of step (b) for the presence of the target natural product and/or analogs of said target natural product; and d) identifying a lysate from the analoging enzyme panel library, that produces a desired analog of the target natural product, as determined by the analysis of step (c), thereby analoging the target natural product; wherein the enzyme expressed by the microbial strain corresponding to the identified lysate is a selected enzyme.

In some embodiments, the method further comprises the step of: perturbing the genome of a first base microbial strain to express the selected enzyme, wherein the first base microbial strain is capable of synthesizing the target natural product.

In other embodiments, the enzyme panel is a series of sequences that are added to a microbe that is already capable of producing the natural product. Thus, in some embodiments, the present disclosure teaches A method for biosynthetic analoging of a target natural product, said method comprising the steps of: a) providing a plurality of genetic sequences, each encoding an enzyme known or predicted to catalyze a type of reaction for a first analoging of the target natural product; b) perturbing the genome of one or more cells of a first base microbial strain to each express an enzyme encoded by one or more of the plurality of genetic sequences of step (a), wherein the first base microbial strain is capable of synthesizing the target natural product, thereby creating an analoging enzyme panel library of microbial strains; c) culturing individual microbial strains from the analoging enzyme panel library of microbial strains; d) analyzing spent media or lysates from the cultures of step (c), for the presence of the target natural product and/or analogs of said target natural product; and e) selecting a microbial strain from the analoging enzyme panel of microbial strains, wherein the selected microbial strain produces a desired analog of the target natural product, as determined by the analysis of step (d), thereby analoging the target natural product. In some embodiments, the strains of the present disclosure can be further modified to comprise additional enzymes, by repeating the steps of the method above with a second plurality of genetic sequences.

In some embodiments, the enzymes encoded by the plurality of genetic sequences are added to a strain to catalyze an additional reaction (i.e., in addition to the reactions already encoded by the original MGC). Thus, in some embodiments the present disclosure teaches adding a nucleic acid encoding an enzyme encoded by the plurality of genetic sequences to an existing MGC.

In some embodiments, the enzymes encoded by the plurality of genetic sequences are added to a strain to replace a reaction in the biosynthetic pathway of the natural product of interest. Thus, in some embodiments, steps of perturbing the genome of a host cell comprises replacing one or more of the biosynthetic genes of the original MGC with a sequence encoding for the enzyme encoded by the one or more of the first or second plurality of genetic sequences.

In some embodiments, the enzymes encoded by the plurality of genetic sequences are identified from a metagenomic library. Thus, in some embodiments, at least one of the enzymes is from a metagenomic library, and was predicted to catalyze the type of reaction by a machine learning model populated by a training data set comprising a genetic sequence input variable and a phenotypic performance output variable; i) wherein the genetic sequence input variable comprises one or more amino acid sequences of enzymes that catalyze the type of reaction for analoging of the target natural product; and ii) wherein the phenotypic performance output variable comprises one or more phenotypic performance features that are associated with the one or more amino acid sequences.

In some embodiments, the present disclosure teaches a method for biosynthetic analoging of a target natural product, said method comprising the steps of: a) accessing a training data set comprising a genetic sequence input variable and a phenotypic performance output variable; i) wherein the genetic sequence input variable comprises one or more amino acid sequences of enzymes that are known or predicted to catalyze a type of reaction for analoging of the target natural product, and ii) wherein the phenotypic performance output variable comprises one or more phenotypic performance features that are associated with the one or more amino acid sequences; b) developing a first predictive machine learning model that is populated with the training data set; c) applying, using a computer processor, the first predictive machine learning model to a digital metagenomic library containing amino acid sequences (e.g., a list of amino acids encoded by the assembled contigs within the DMLs of the present disclosure) from one or more organisms to identify a pool of candidate sequences within the digital metagenomic library, wherein said candidate sequences are predicted with respective first confidence scores to catalyze the type of reaction for analoging of the target natural product, by the first predictive machine learning model; d) removing from the pool of candidate sequences, any sequence that is predicted to perform a different function by a second predictive machine learning model with a second confidence score if the ratio of the first confidence score to the second confidence score falls beyond a preselected threshold, thereby producing a filtered pool of candidate sequences; e) manufacturing one or more microbial cells to each express a sequence from the filtered pool of candidate sequences from step (d), f) culturing the manufactured host cells of step (e), and lysing the cultured cells, thereby creating an analoging enzyme panel library; g) incubating individual enzymes from the analoging enzyme panel library with the target natural product, or a precursor to the target natural product, thereby producing reaction mixtures; h) analyzing at least one of the reaction mixtures of step (g), for the presence of the target natural product and/or analogs of said target natural product; and i) selecting an enzyme from the analoging enzyme panel, wherein the selected enzyme produces a desired analog of the target natural product, as determined by the analysis of step (h), thereby analoging the target natural product.

Many embodiments of the analoging methods of the present disclosure recite the step of analyzing the spent media, lysates, incubations, reactions, mixtures or equivalents of earlier steps for the presence of the target natural product and/or analogs of said target natural product. In some embodiments this analysis step comprises direct measurements for the presence of said target natural product or analog. Persons having skill in the art will be aware of the many ways of detecting chemical entities, including HPLC, GC, NMR, IR, etc.

In some embodiments, this analysis step comprises proxy measurements indicative of the presence of an analog of the target natural product. For example, in some embodiments the present disclosure teaches the use of various colorimetric assays for identifying either the presence of a desired molecule or the consumption of a molecule. In some cases, the colorimetric assays directly measure the presence of the analog. In other embodiments, the colorimetric assay measures a different compound, which is used to infer the presence of the first. For example, in some embodiments, the presence or consumption of an enzyme co-factor is measured to infer enzymatic conversion of a target natural product. In some embodiments the presence or consumption of a reactant is measured to infer enzymatic conversion of a target natural product. One illustrative example is the use of a colorimetric assay monitoring the consumption of reduced nicotinamide adenine dinucleotide (phosphate), over time. This colorimetric assay can be used in instances in which the enzymatic reduction (analoging) of a substrate requires NAD(P)H to be oxidized; therefore, the activity of this enzyme panel is coupled to the consumption of NAD(P)H which can be monitored by the reduction of absorbance at 340 nm.

Natural Product Analoging—Exploitation of Homologous Clusters

In some embodiments, the present disclosure teaches exploitation of homologous MGCs for analoging natural products.

In some embodiments, the present disclosure teaches methods of analoging by identifying homologous MGCs that are predicted to produce the same, or very similar natural products. This approach leverages the existing diversity within one or more metagenomic libraries to identify natural product variants with superior qualities to those of the originally identified natural product. In some embodiments, the newly identified MGCs would be expected to comprise one or more slightly different biosynthetic enzymes that would result in a corresponding modification of the natural product, thereby producing an analog.

In some embodiments, the present disclosure teaches a method for producing an analog of a target natural product, said method comprising the steps of: a) providing a first multi-gene cluster known to produce the target natural product; b) developing a predictive model based on said first multi-gene cluster; c) querying, in silico, a digital metagenomics library for new multi-gene clusters, wherein said new multi-gene clusters are predicted, by the predictive model, to produce the target natural product or a variant of the target natural product, thereby producing a pool of candidate multi-gene clusters; d) manufacturing one or more microbial host cells to each express at least one multi-gene cluster from the pool of candidate multi-gene clusters; e) culturing at least one of the microbial host cells manufactured in step (d); f) analyzing spent media from the cultures of step (e), for the target natural product and/or analogs of said target natural product; and g) selecting a microbial host cell from the microbial host cells cultured in step (e), wherein the selected microbial host cell produces an analog of the target natural product as determined by the analysis of step (f), thereby producing an analog of the target natural product.

In some embodiments, the predictive models of the present disclosure determine whether a new multi-gene cluster produces the target natural product or a variant of the target natural product, as described in the "Transitive Multi-gene Cluster Feature Set Discovery Workflow" section of this document (e.g., using tools described in Table 4, or their equivalents).

In some embodiments, known MGCs are those which have been experimentally validated, and demonstrated to produce a natural product (e.g., through empirical data, or as reported in a journal).

Figure 12:
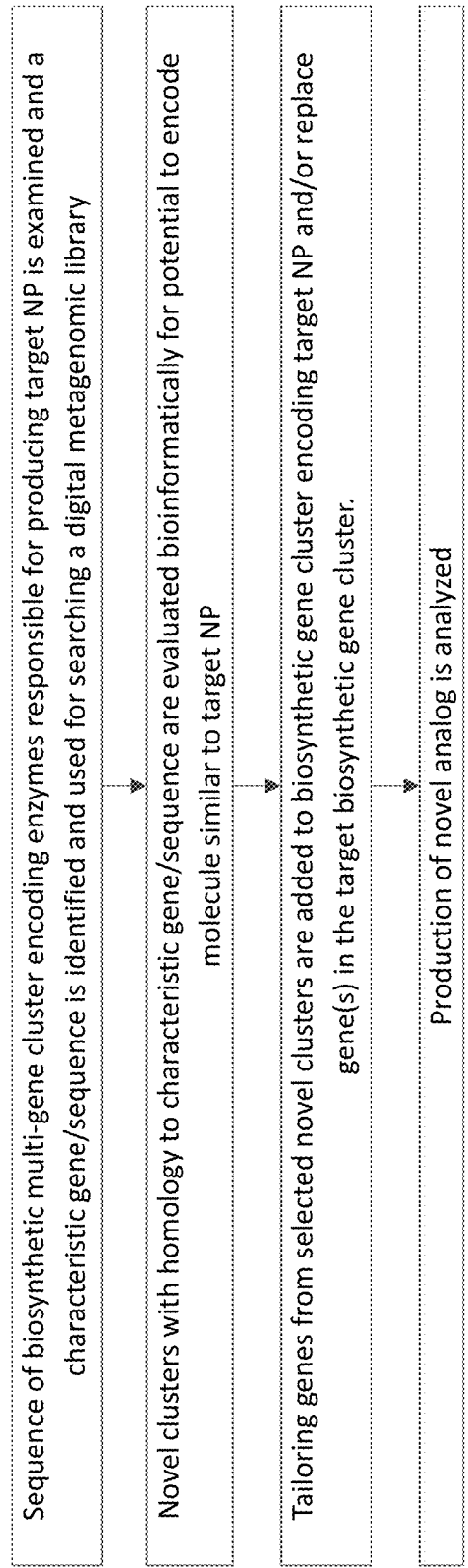
FIG. 12—depicts a workflow for one of the biosynthetic analoging methods of the present disclosure.

In some embodiments, the present disclosure teaches methods for identifying homologous MGCs, and mining those MGCs for analoging enzymes. In some embodiments, the present disclosure teaches engineering of the original natural product-encoding MGC to add one or more parts from a homologous MGC. In some embodiments, the present disclosure teaches engineering of the original natural product-encoding MGC to replace one or more genes within that original MGC, with one or more parts from a homologous MGC. (See FIG. 12).

Thus, in some embodiments, the present disclosure teaches a method for producing an analog of a target natural product, said method comprising the steps of: a) providing a first multi-gene cluster known to produce the target natural product; b) developing a predictive model based on said first multi-gene cluster; c) querying, in silico, a digital metagenomics library for new multi-gene clusters, wherein said new multi-gene clusters are predicted, by the predictive model, to produce the target natural product or a variant of the target natural product, thereby producing a pool of candidate multi-gene clusters; d) identifying, in silico with an annotation engine, individual genes encoding biosynthetic enzymes within one or more of the new multi-gene clusters of the pool of candidate multi-gene clusters of step (c), thereby producing an analoging enzyme panel library comprising biosynthetic genes from the new multi-gene clusters; e) perturbing the genome of a base microbial host cell to express a gene from the analoging enzyme panel library, wherein the base microbial host cell comprises the first multi-gene cluster, thereby manufacturing a cell; f) culturing at least one of the microbial host cells manufactured in step (e); g) analyzing spent media or lysate from the cultures of step (f), for the target natural product and/or analogs of said target natural product; and h) selecting a microbial host cell from the microbial host cells cultured in step (f), wherein the selected microbial host cell produces an analog of the target natural product as determined by the analysis of step (g), thereby producing an analog of the target natural product.

In some embodiments, the step of developing a predictive model based on said first multi-gene cluster is identifying a set of biosynthetic genes that can be used to search for similar biosynthetic cluster. In some embodiments, the biosynthetic genes used to search of similar biosynthetic clusters are core biosynthetic enzymes.

In some embodiments, the step of querying, in silico, a digital metagenomics library for new multi-gene clusters is conducted as described in the Transitive Multi-gene Cluster Feature Set Discovery Workflow section of the present disclosure. That is, in some embodiments, the "querying step" comprises identifying MGCs that contain homologs for all the biosynthetic genes of the MGC predictive model of the previous step. In some embodiments, the candidate MGCs contain homologs for at least 1, 2, 3, 4, 5, 6, 7, 8, 9, 10, 11, 12, 13, 14, 15, 16, 17, 18, 19, biosynthetic genes of the MGC predictive model, including all ranges and subranges therebetween. In some embodiments, the candidate MGCs contain homologs for at least 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%, of the biosynthetic genes of the MGC predictive model. As noted above, in some embodiments the MGC predictive model comprises all biosynthetic genes of the first MGC. In some embodiments the MGC predictive model comprises only core biosynthetic gene/enzymes of the first MGC, including all ranges and subranges therebetween.

In some embodiments, the present disclosure teaches a method for producing an analog of a target natural product, said method comprising the steps of: a) providing a plurality of multi-gene clusters known or predicted to produce the target natural product or related natural products; b) identifying, in silico with an annotation engine, individual genes encoding biosynthetic enzymes within the plurality of multi-gene clusters of step (a), thereby producing an analoging enzyme panel library comprising biosynthetic genes from the plurality of multi-gene clusters; c) perturbing the genome of a base microbial host cell to express a gene from the analoging enzyme panel library, wherein the base microbial host cell comprises a first multi-gene cluster capable of producing the target natural product, thereby manufacturing a microbial cell; d) culturing at least one of the microbial host cells manufactured in step (c); e) analyzing spent media or lysate from the cultures of step (d), for the target natural product and/or analogs of said target natural product; and f) selecting a microbial host cell from the microbial host cells cultured in step (d), wherein the selected microbial host cell produces an analog of the target natural product as determined by the analysis of step (e), thereby producing an analog of the target natural product.

Natural Product Analoging—Combination Strategies

In some embodiments, the present disclosure teaches analoging through a combination of the disclosed strategies. Thus in some embodiments, the present disclosure teaches combining the strategies of cluster engineering and enzyme panels. In some embodiments, the present disclosure teaches combining the strategies of cluster engineering and exploitation of homologous clusters. In some embodiments, the present disclosure teaches combining the strategies of enzyme panels and exploitation of homologous clusters. In some embodiments, the present disclosure teaches combining the strategies of cluster engineering, enzyme panels, and exploitation of homologous clusters.

Systems for Carrying out the Disclosed Methods

Those skilled in the art will understand that some or all of the elements of embodiments of the disclosure, and their accompanying operations, may be implemented wholly or partially by one or more computer systems including one or more processors and one or more memory systems. Some elements and functionality may be implemented locally and others may be implemented in a distributed fashion over a network through different servers, e.g., in client-server fashion, for example. In particular, server-side operations may be made available to multiple clients in a software as a service (SaaS) fashion.

Those skilled in the art will recognize that, in some embodiments, some of the operations described herein may be performed by human implementation, or through a combination of automated and manual means. When an operation is not fully automated, appropriate components of embodiments of the disclosure may, for example, receive the results of human performance of the operations rather than generate results through its own operational capabilities.

The present description is made with reference to the accompanying drawings and Examples, in which various example embodiments are shown. However, many different example embodiments may be used, and thus the description should not be construed as limited to the example embodiments set forth herein. Rather, these example embodiments are provided so that this disclosure will be thorough and complete. Various modifications to the exemplary embodiments will be readily apparent to those skilled in the art, and the generic principles defined herein may be applied to other embodiments and applications without departing from the spirit and scope of the disclosure. Thus, this disclosure is not intended to be limited to the embodiments shown, but is to be accorded the widest scope consistent with the principles and features disclosed herein.

EXAMPLES

The following examples are given for the purpose of illustrating various embodiments of the disclosure and are not meant to limit the present disclosure in any fashion. Changes therein and other uses which are encompassed within the spirit of the disclosure, as defined by the scope of the claims, will be recognized by those skilled in the art.

A brief table of contents is provided below solely for the purpose of assisting the reader. Nothing in this table of contents is meant to limit the scope of the examples or disclosure of the application.

TABLE 4.1

Table of Contents for Example Section

| Example | Description |
|---|---|
| 1 | Analysis of Metagenomic Library Features<br>Describes generating a variety of metagenomic libraries from samples of similar complexity to determine the optimum N50 assembly length for natural product-encoding Multi-Gene Cluster (MGC) discovery. Assemblies with greater than about 15,000 bp exhibit excellent MGC discovery rates. |
| 2 | Analysis of Consequences of Changes in Cosmid Pooling on Final Library Properties<br>Describes assembly simulations conducted to identify the optimum amount of cosmid pooling to generate digital metagenomics libraries amenable to MGC discovery (i.e., with N50s of at least 15,000 bp, as determined in Example 1). The simulations indicate that, at 10x coverage, pooling of 6,000 to 15,000 cosmid yields optimum libraries for MGC discovery. It is possible to pool up to 34,000 cosmids while still producing libraries with N50 lengths of at least 15 Kb. Smaller pools fail to fully capitalize on sequencer throughput, and produce fewer 15+ Kb contigs per 500 Mb of sequence. In addition, pooling of greater than 15,000 cosmids results in lower number of 15+ Kb contigs per 500 Mb of sequence. |
| 3 | Creation of Digital Metagenomics Library with Features Described in Earlier Examples.<br>Describes the steps taken to produce a soil physical metagenomic library and DML. The library was created according to the information gleaned from Examples 1 and 2. 6,000 to 10,000 cosmids were pooled to create sequencing silos that were then sequenced using Next Gen sequencing. Sequential assemblies were used to generate the DML. The resulting DML had an N50 of greater than 15,000 bp. |
| 4 | Demonstrating Benefits of DML Over other Sequence Libraries<br>Compares the Digital Metagenomic Libraries (DML) prepared according to the present disclosure to the largest publicly-available soil metagenomics library from the Joint Genome Institute.<br>Even though the JGI metagenomic library is over 4 times larger, the DML of the present disclosure is capable of identifying higher numbers of natural product-encoding contigs. Overall, the libraries of the present disclosure are over 50x better at identifying clusters. |
| 5 | Resistance Gene Searching Workflow to Identify Salinosporamide A-Like Natural Products<br>Is an illustration of the Resistance Gene Searching workflows of the present disclosure, as applied to Digital Metagenomic Libraries. The workflow was used to identify new MGC's expected to encode Salinosporamide A-like natural products. |
| 6 | Transitive Searching Workflows to Identify Eponemycin-Like Natural Products<br>Is an illustration of the Transitive Searching workflows of the present disclosure, as applied to Digital Metagenomic Libraries. The workflow was used to identify new MGC's expected to encode eponemycin-like natural products, without the need to search by resistance gene. |
| 7 (Prophetic) | Untargeted Resistance Signal Searching (or de novo MGC discovery) Workflows<br>Is an illustration of the Untargeted Resistance Signal Searching (or De Novo MGC discovery) workflows of the present disclosure, as applied to Digital Metagenomic Libraries. Example workflow was described for identifying new MGCs. |
| 8 | Analoging Enzyme Discovery and Use-Aldo Keto Reductase (in silico)<br>Is an illustration of a natural product analoging method of the present disclosure. The example describes the use of predictive machine learning models to identify and compile panels of enzymes from metagenomic libraries. The creation of an aldo-keto reductase enzyme panel is exemplified. Lysates of microbes expressing sequences coding for the enzyme panel can be used to analog the natural product. |
| 9 and 10 | Analoging Enzyme Discovery and Use-Aldo Keto Reductase (in silico)<br>Examples 9 and 10 utilize the methods of the present disclosure to identify novel candidate analoging enzymes with Aldo Keto Reductase (AKR) activity. Specifically, these examples describe how to create and use predictive machine learning models of the present disclosure to identify and compile panels of candidate enzymes from sequence libraries. |
| 11 | Analoging Enzyme Discovery and Use-Aldo Keto Reductase (Wet Lab Validations)<br>Experimentally validates the in silico analoging enzyme panels generated in Examples 9 and 10. Descriptions of sequence recovery from physical libraries, and subsequent enzyme cloning and activity tests. |
| 12 | Analoging Enzyme Discovery and Use-Dehydrogenase (Enrichment by Searching Within MGC)<br>Experiments demonstrated enrichment in validated analoging enzymes when sequence searches are filtered based on their presence within an MGC. |

TABLE 4.1-continued

Table of Contents for Example Section

| Example | Description |
|---|---|
| 13 | Analoging Enzyme Discovery and Use-P450 BM3 (Use of Predictive Models Based on Sequence Fragments) Illustration of Analoging platform from in silico machine learning model creation and application, to validation. Experiments demonstrated ability to use predictive models that are based on sequence fragments as opposed to whole-enzymes. enrichment in validated analoging enzymes when sequence searches are filtered based on their presence within an MGC. |
| 14 | Analoging Enzyme Discovery and Use-Methyltransferases Illustration of Analoging platform from in silico machine learning model creation and application, to validation. Experiments demonstrated ability to use predictive models to discover novel methyltransferase enzymes. Enzymes can use multiple natural product substrates. |
| 15 | Analoging Enzyme Discovery and Use-Haloperoxidase (Comparison Against Traditional BLAST Approaches) Comparison of the discovery rates of new analoging enzymes using the machine learning-based analoging discovery platform of the present disclosure against traditional BLASTp searching. |
| 16 | Analoging Enzyme Discovery and Use-Aldo Keto Reductase (Comparison Against Other Search Strategies) Comparison of the discovery rates of new analoging enzymes using the machine learning-based analoging discovery platform of the present disclosure against traditional BLASTp searching. |
| 17 | Untargeted MGC Discovery Workflow- Identification of Resistance Genes Without the Need for any Sequence Information about the Gene. Illustration of the in silico Untargeted MGC Discovery workflows of the present disclosure. Specifically, the example illustrates the various scoring metrics used to identify candidate resistance genes (and their related MGCs). |
| 18 | Resistance Gene Searching Workflow to Identify Natural Products Capable of Modulating New Therapeutic Target Is an illustration of the Resistance Gene Searching workflows of the present disclosure, as applied to Digital Metagenomic Libraries. The example demonstrates in silico discovery of MGCs likely to encode natural products targeting a desired therapeutic target. Wet lab validation confirms modulation of HDAC1 therapeutic target. |
| 19 | Resistance Gene Searching Workflow to Identify Natural Products Capable of Modulating New Therapeutic Target Is an illustration of the Resistance Gene Searching workflows of the present disclosure, as applied to Digital Metagenomic Libraries. The example demonstrates in silico discovery of MGCs likely to encode natural products targeting a desired therapeutic target. Wet lab validation confirms modulation of SOD2 therapeutic target. |
| 20 | DML Versioning and Updates Illustrates metagenomic library assembly and versioning. This example provides a more detailed workflow for generating Digital Metagenomic Libraries of the present disclosure. |

Example 1

Modeling to Establish Optimum Metagenomic Library Parameters

The present invention is based, in part, on the inventor's discovery of metagenomic library parameters that enable in silico natural product discovery. The authors hypothesized that prior attempts to generate metagenomic libraries that would be useful for MGC discovery had failed by creating libraries that either i) failed to produce sufficiently long assemblies due to overly-complex DNA mixtures, or ii) failed to capture meaningful diversity within an environmental sample, due to the selection of only a few cells/cosmids for sequencing. That is, prior attempts had either not taken sufficient steps to reduce complexity, or had reduced complexity so much that it failed to capture the diversity of the sample.

As an initial step, the inventors analyzed the rate of MGC discovery with libraries of different N50 lengths. A variety of digital metagenomic libraries (DML) from samples of similar complexity were sequenced to varying levels of coverage in order to produce DMLs with different N50s ranging from ~1000 bp to ~25,000 bp. The DML assembly metrics of N50, total assembly length, and number of contigs were calculated for each DML using metaQUAST. These test DMLs were then analyzed with anti SMASH to identify multi-gene clusters present within the assemblies. For the purpose of this analysis, only clusters of greater than 10 kb were searched, as this has been determined to be the lowest average cluster size encoding natural products of interest (see R. Baltz. Natural product drug discovery in the genomic era; realities, conjectures, misconceptions, and opportunities. J. of Industrial Microbiology and Biotechnology 2019 March; 46(3-4):281-299, which demonstrated that clusters of at least ~10 kb were most associated with useful biological activity). Finally, for each DML, the number of MGC>10 kb per Mbp of assembled sequence was calculated.

Figure 22:
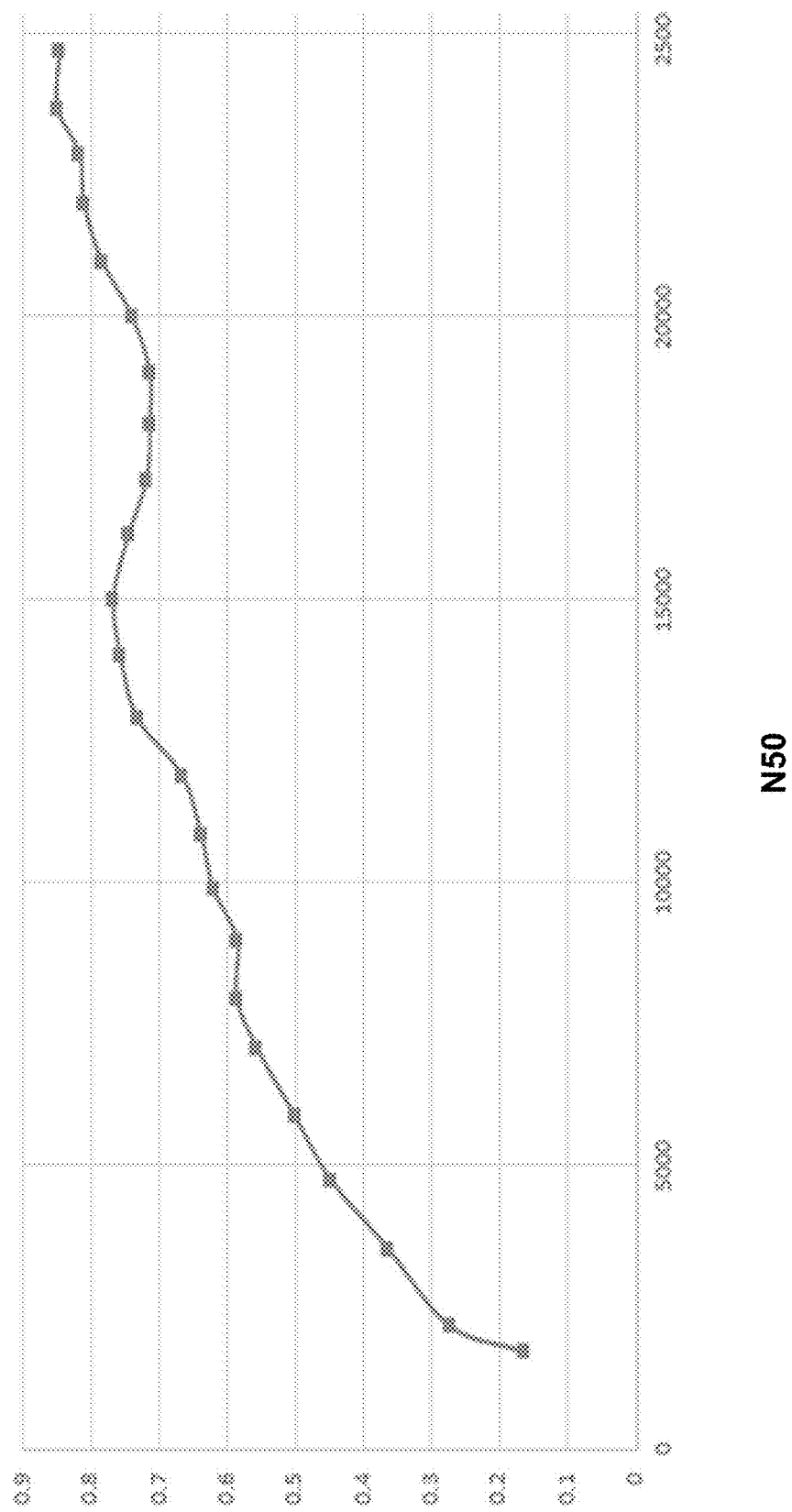
FIG. 22—depicts the results of an analysis leveraging sequencing assemblies from highly similar samples that have been sequenced to produce a range of N50 and testing the effect of library assembly quality (as measured by N50), on MGC discovery rate. The number of MGCs per Kb of sequence increases rapidly until about N50 of 15 Kb, and then begins to level off.
Figure 23:
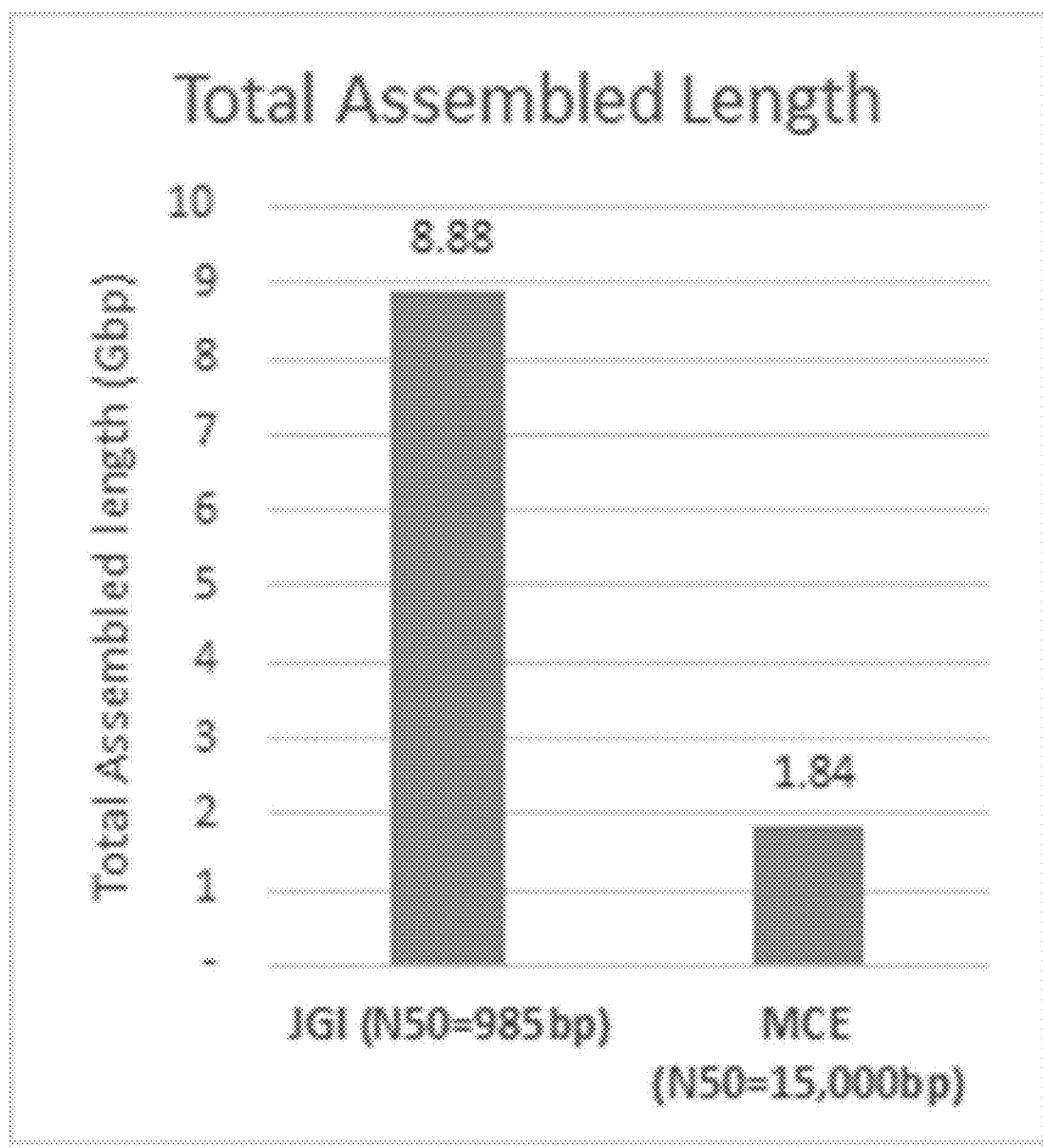
FIG. 23—depicts the size differences between the Joint Genome Institute (JGI) soil metagenome library (Project 1077706), and a digital metagenomics library (MCE) produced according to the methods of the present disclosure from a soil sample (see Example 4). The JGI has over 4 times more total assembled sequence than the MCE produced according to methods of the present disclosure. The MCE however, has an N50 of about 15 Kbp, compared to the JGI N50 of 985 bp.

The results of these experiments are shown in Table 5, and are also illustrated in FIG. 22. The rate of MGC discovery per mega base pair of assembled sequence in FIG. 22 is depicted as a function of N50 of the test DML. The overall rate of MGC discovery increases rapidly with increasing N50, but begins to flatten out at N50 of about 15,000 bp. Libraries with N50 of 15,000 bp.

TABLE 5

Rate of MGC discovery in Test DMLs

| DML | N50 (bp) | # contigs | Total assembly length (bp) | # of clusters >10 kb | # of clusters >10 kb/ Mbp of assembly length | N50 moving average | # of clusters >10 kb/ Mbp of assembly length moving average |
|---|---|---|---|---|---|---|---|
| DML01 | 923 | 24893 | 16,205,185 | 0 | 0 | | |
| DML02 | 1343 | 69045 | 46,576,495 | 6 | 0.128820342 | | |
| DML03 | 1606 | 66923 | 54,262,162 | 10 | 0.184290482 | 1721 | 0.164887334 |
| DML04 | 3012 | 65230 | 89,481,968 | 31 | 0.346438514 | 2496 | 0.275204816 |
| DML05 | 4023 | 88442 | 129,172,637 | 57 | 0.441269926 | 3541.5 | 0.366227363 |
| DML06 | 5525 | 70456 | 123,754,711 | 61 | 0.492910528 | 4766.25 | 0.449913884 |
| DML07 | 6505 | 84506 | 157,985,015 | 82 | 0.519036568 | 5890.5 | 0.502302005 |
| DML08 | 7509 | 59186 | 106,116,826 | 59 | 0.555990998 | 7088.25 | 0.557900582 |
| DML09 | 8814 | 149489 | 189,855,041 | 126 | 0.663664232 | 7965 | 0.588315553 |
| DML10 | 9032 | 57879 | 109,019,241 | 67 | 0.614570413 | 8992.5 | 0.587070459 |
| DML11 | 10615 | 170132 | 204,257,825 | 105 | 0.514056193 | 9902.75 | 0.622617723 |
| DML12 | 11150 | 106873 | 181,901,502 | 127 | 0.698180051 | 10876.25 | 0.640260872 |
| DML13 | 12708 | 123263 | 181,140,464 | 133 | 0.73423683 | 11904 | 0.668668084 |
| DML14 | 13143 | 124471 | 218,346,829 | 159 | 0.728199263 | 12908 | 0.734176905 |
| DML15 | 14631 | 60896 | 158,486,472 | 123 | 0.776091476 | 14008 | 0.758934729 |
| DML16 | 15550 | 51381 | 120,419,761 | 96 | 0.797211348 | 15034.25 | 0.76936696 |
| DML17 | 16813 | 68380 | 154,646,000 | 120 | 0.775965754 | 16144.5 | 0.747321457 |
| DML18 | 17584 | 133563 | 229,681,310 | 147 | 0.640017248 | 17116 | 0.720668082 |
| DML19 | 18517 | 108635 | 238,992,178 | 160 | 0.669477978 | 18091.75 | 0.715373741 |
| DML20 | 19453 | 97830 | 150,766,593 | 117 | 0.776033985 | 19024.75 | 0.715826535 |
| DML21 | 20545 | 46375 | 158,143,030 | 123 | 0.777776928 | 20023.25 | 0.74229864 |
| DML22 | 21578 | 88269 | 176,966,077 | 132 | 0.745905669 | 20968.25 | 0.7854003 |
| DML23 | 22297 | 76375 | 171,044,816 | 144 | 0.84188462 | 21993 | 0.811871956 |
| DML24 | 23552 | 107709 | 206,367,782 | 182 | 0.881920609 | 22891.75 | 0.818539227 |
| DML25 | 24140 | 69408 | 167,817,353 | 135 | 0.80444601 | 23697.25 | 0.851384676 |
| DML26 | 24800 | 69763 | 166,422,075 | 146 | 0.877287463 | 24700.25 | 0.847783723 |

Note that because the complexity of each sample is similar, a lower N50 also results in a lower total assembled length for the DML (total assembled length is the total amount of non-overlapping sequence information contained within the contigs of the DML).

The results from this experiment suggested that libraries with N50s below 5,000 bp are insufficient for practical MGC discovery. In some embodiments, the results suggest that DMLs with N50s of at least 15 Kb are optimal for MGC discovery.

Example 2

Modeling to Establish Optimum Pooling Parameters

The present disclosure teaches methods of pooling clones from environmental samples into separate silos as a way to reduce complexity of metagenomic libraries for subsequent assembly. Pooling also allows for greater sampling of the environmental sample, and for more efficient use of the sequencer's bandwidth and can result in larger overall libraries per run. In order to determine the optimal level of pooling to produce DMLs for natural product discovery, a series of simulations were conducted.

In order to generate simulated sequencing and sequencing assembly of pools of cosmids of different sizes (1, 5, 10, 100, 200, 6,000, 12,000, and 60,000 cosmids), raw paired-end fasq (Illumina) data generated from multiple empirically sequenced metagenomic libraries of different sizes were concatenated to yield the desired simulated number of cosmids. The raw fastq files for these simulated pools were first trimmed using bbduk from the BBtools package (//sourceforge.net/projects/bbmap/). The total reads in the trimmed fastq files were then subsampled to normalize to a target read depth of 5× and 10× using bbnorm in the BBtools package. After normalization and subsampling, reads matching E. coli gDNA and pWEB cloning vector backbone were removed from the fastq filed using bbduk, followed by merging of the paired end reads using bbmerge. The merged and unmerged paired-end fastq reads (for each normalized depth) were provided. as input to SPAdes assembler (v.3.10.1), and assembly was run with default parameters, without read error correction. This process resulted in simulated assemblies from pools of cosmids sequenced at 5× and 10× coverage. Assembly quality metrics for the contigs from each assembly were generated using metaQUAST (v.5.0.0), including N50's and number of contigs greater than 15 kb in length. The 15 kb N50 cutoff was based on the results of Example 1, which had identified contig lengths of greater than 15 kb as optimal for natural product-encoding MGCs. Finally, the number of MGC's encoded on these contigs were identified by inputting the contigs into antiSMASH 5.0.

Figure 21B:
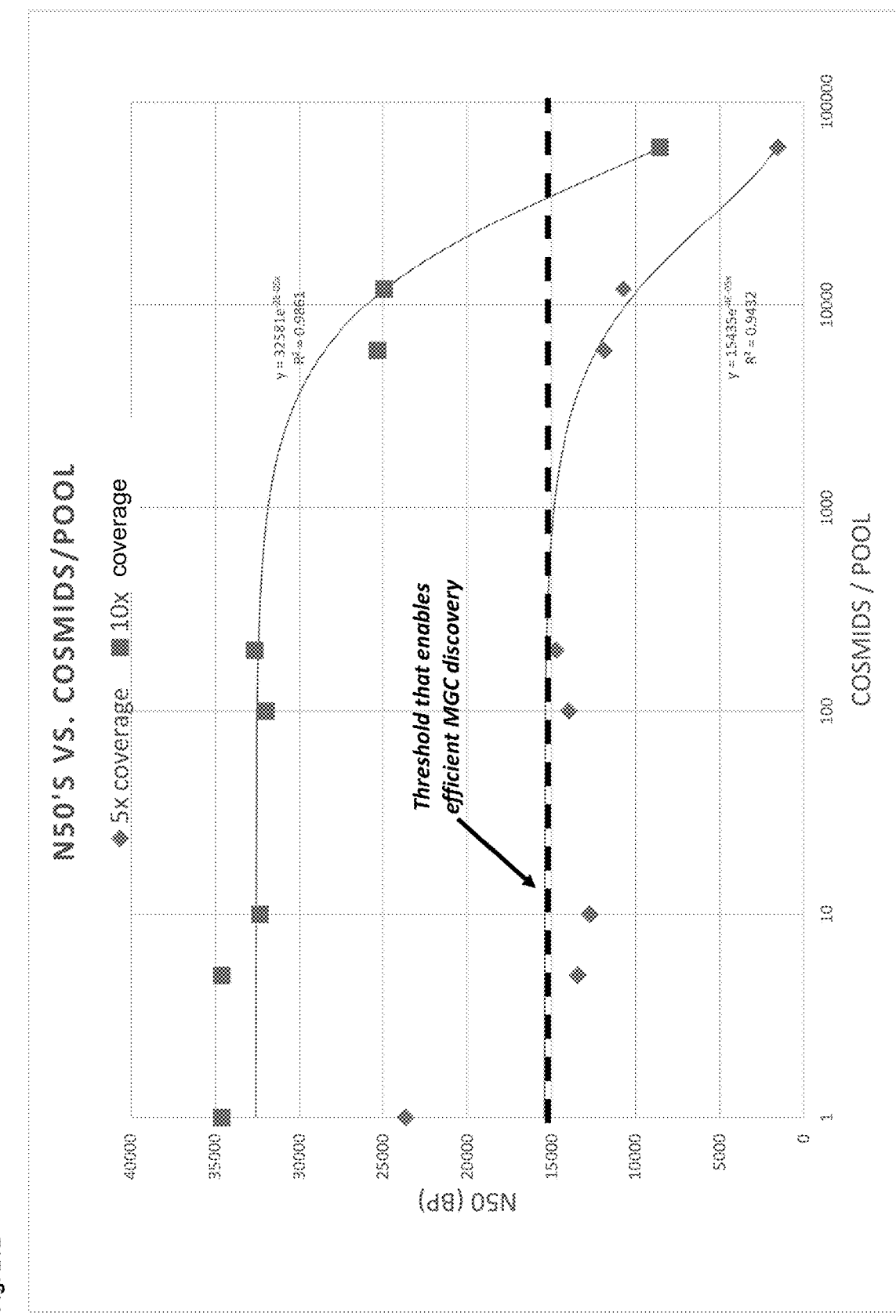
Figure 21C:
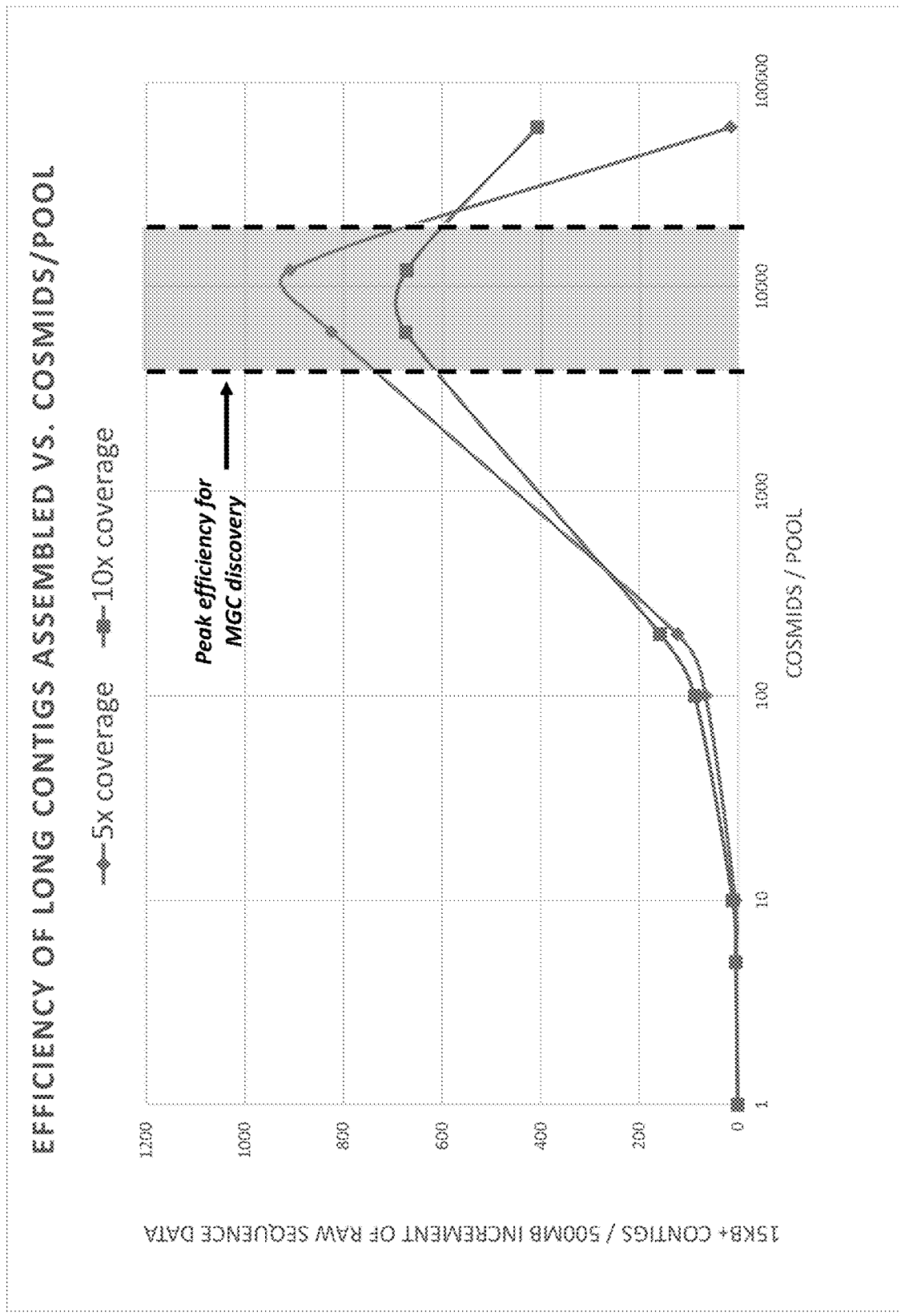

The results of these simulations are depicted in Table 6, and illustrated on FIG. 21A and FIG. 21B. The simulations show that, at 10× coverage, it is possible to produce digital metagenomic libraries suited for MGC discovery (i.e., with N50s of greater than 15,000 bp) by pooling up to ~34,000 clones per sequencing silo. This result was unexpected, as the general thinking was that while pools of <100 cosmids the have been sequenced simultaneously can yield sequence assemblies of sufficient length to enable MGC annotation, cosmid pools of higher levels of complexity (e.g. >1000 cosmids), without a way to demultiplex samples from the pool (e.g., through the use of individual barcodes), would result in failed or low quality assemblies that could not be used for MGC annotation.

TABLE 6

N50 Length of Libraries Generated from Cosmid Pooling

| Cosmid Pool Size | N50 at 5x coverage | N50 at 10x coverage |
|---|---|---|
| 1 | 23678 | 34601 |
| 5 | 13419 | 34601 |
| 10 | 12707 | 32333 |
| 100 | 13973 | 31961 |
| 200 | 14753 | 32645 |
| 6000 | 11856 | 25331 |
| 12000 | 10713 | 24952 |
| 60000 | 1566 | 8546 |

While the simulations indicate that cosmids pools of up to ~34,000 could yield sequence assemblies of sufficient length to contain MGCs, that complexity may not be the most efficient pool size for MGC discovery. To further optimize the complexity of pools for this application, the simulated data was analyzed to determine the efficiency of long-contig (>15 kb) assembly per 500 MB increment of raw sequence data (as calculated from 5x or 10x raw sequence coverage). 500 MB was chosen because it is on the order of the amount of data generated from an Illumina MiSeq run. The results from these simulations are depicted in Table 7 below, and also illustrated in FIG. 21C.

TABLE 7

Efficiency of Lone Contigs Assembled vs. Cosmids per Silo Pool

| | Number of 15+ Kb contigs per 500 MB of raw sequence. | |
|---|---|---|
| Cosmid Pool Size | 5x Coverage | 10x Coverage |
| 1 | 1.0 | 1.0 |
| 5 | 4.0 | 5.0 |
| 10 | 6.0 | 11.0 |
| 100 | 66.0 | 88.0 |
| 200 | 123.0 | 158.0 |
| 6000 | 824.7 | 674.2 |
| 12000 | 909.4 | 672.0 |
| 60000 | 14.6 | 407.5 |

The results show that the number of contigs>15 kb generated per 500 MB of raw sequence data increases significantly when moving from 1 cosmid to ~10,000 cosmids in the pool, indicating that pooling cosmids at that degree of complexity is more efficient use of sequencing capacity for MGC annotation. However, as the complexity of the pool increases to 60,000, the number of contigs>15 kb generated per 500 MB of raw sequence data dramatically drops. In these highly complex pools, the assemblies may still yield a higher absolute number of contigs>15 kb, but each contig requires more sequencing in order to be generated, and as a result fewer contigs of that length per sequencing run are generated Thus, for this application, the simulations indicate that a cosmid pool of ~6,000-15,000 yields the optimal libraries for MGC discovery. These simulations were repeated for 20x coverage sequencing runs, and yielded similar results as those reported above.

Based on the results from Examples 1 and 2 above, Applicant then set out to produce an optimized metagenomic library from soil environmental DNA by pooling 6,000 to 10,000 cosmids per silo sequencing run, as discussed in more detail in Example 3, below.

Example 3

Preparation of Metagenomic Libraries

Collection

Approximately 1 kg of soil sample from a private field was collected and rocks, branches, and other non-soil matter were removed by passing the soil through a 2 mm wire sieve. DNA was extracted from ~250 g of soil by first adding 300 mL of a CTAB-based lysis buffer (100 mM Tris-HCl, 100 mM EDTA, 1.5M NaCl, 1% (w/v) CTAB, 2% (w/v) SDS, pH 8.0), followed by incubation at 70° C. for 2 h with consistent inversion to mix. The sample was centrifuged at 4,000 g for 20 min. at 4° C. Supernatant was transferred to a clean bottle and centrifuged a second time at 4,000 g for 20 min. at 4° C. The resulting lysate was transferred to a new bottle and 0.7 volumes of isopropanol was added and gently mixed for 30 min. Precipitated DNA was pelleted by two rounds of centrifugation at 4,000 g for 30 min. at 4° C., washed with 70% ethanol between the first and second centrifugation. The supernatant was discarded, the DNA pellet was allowed to dry, and the dry DNA was resuspended in 10 mL of TE. The extracted DNA was quantified using an Epoch spectrophotometer, and saved for further processing.

Size Selection

Figure 13:
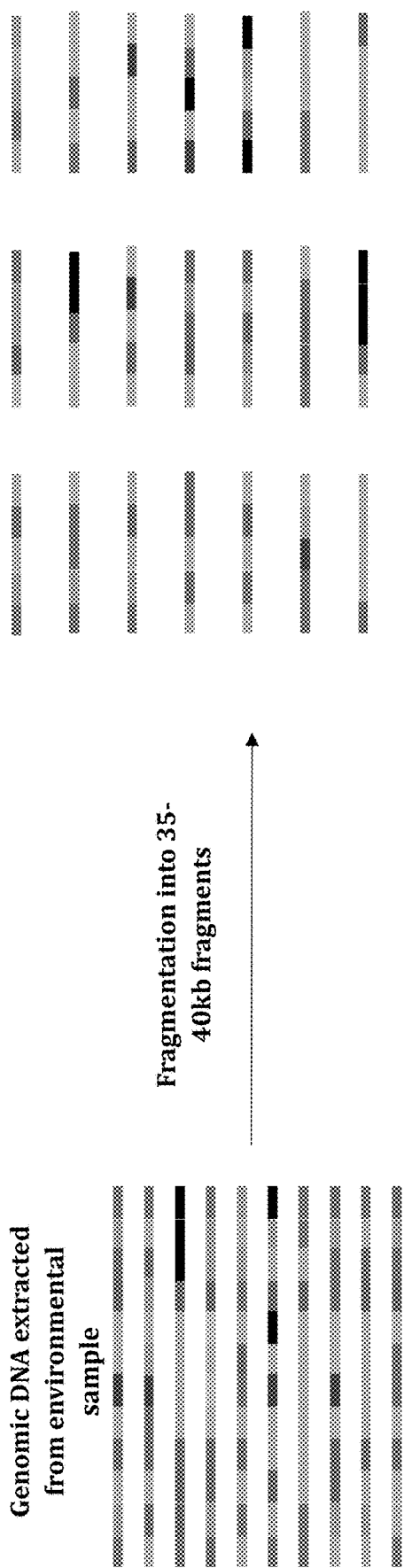
FIG. 13—depicts initial steps of the library preparation methods of the present disclosure. DNA extracted from an environmental sample is cloned into a cosmid backbone, packaged via phage, and transduced into an E. coli host to create a metagenomics DNA library.

Extracted DNA comprising the genomes of the microorganisms in the soil sample was loaded on an unstained 0.75% agarose gel and separated at constant voltage of 3V/cm for 12-16 hrs. The edges of the gel containing DNA sizing markers were excised and stained. Subsequently, a gel band containing DNA around 35-50 kb was excised. The gel slice containing DNA was placed inside a 12 kD MWC dialysis tubing with 1× TAE buffer and DNA was electroeluted for 3 hrs at 3V/cm constant voltage. Following electroelution, DNA was concentrated and buffer exchanged into 0.5× TE buffer using a CentriCon ultrafiltration device with 30kD MWC membrane. (See FIG. 13).

Cosmid Packaging

DNA was blunt ended using End-It DNA End-Repair kit (Lucigen, ER0720) and isopropanol precipitated. Approximately 10 ligation reactions containing 250 ng of blunt-ended DNA was combined with 500 ng of a blunt-ended cosmid vector (T4 ligase, NEB, M0202) and cloned into a cosmid backbone. The cloned DNA was packaged into phages and transduced into *E. coli* using a MaxPlax™ packaging kit (Lucigen, MP5120) following the manufacturer's instructions. (See FIG. 13). Briefly, packaging extract solution comprising phages were mixed with fragmented DNA by pipetting several times without introducing air bubbles. Reactions were incubated for 90 minutes at 30 Celsius. An additional 25 ul of thawed packaging extract solution was added, and the reactions were incubated for an additional 90 minutes at 30 Celsius. The incubated samples were diluted with Phage Dilution Buffer and gently vortexed. Unincorporated phage proteins were precipitated by adding chloroform a mixing the sample gently. Dilutions were mixed with host *E. coli* cells, incubated at room temperature for 20 min for phage attachment. The transfected cells were recovered at 37 Celsius for 75 min and plated on LB agar containing appropriate antibiotic selection. Efficiency of packaging was measured for a portion of the packaging reactions according to the manufacturer's instructions.

Pooling and Sequencing

Example 2 had demonstrated that, at 10× coverage, it would be possible to pool up to ~34,000 clones while still producing DMLs amenable to natural product discovery (e.g., having N50s of at least 15,000 bp), though maximal efficiency would be achieved in the range of ~6,000-~15,000 clones per pool. In an effort to produce the best possible library within the budgetary limitations, E. coli containing transduced cosmids were combined into pools of roughly 6,000-10,000 cosmids each ("E. coli cosmid pool") based on the measured efficiency of phage packaging. Each E. coli cosmid pool was prepped for sequencing using Nextera XT® DNA Library Prep kit, and sequenced on a HiSeq 4000 or NovaSeq 6000 Illumina® sequencer. (See FIG. 14)

Sequential Assemblies

Reads from pooled samples were trimmed, quality filtered, and paired end reads were merged using BBTools. Contaminating sequences (e.g. cloning vector, host genome) were also removed using BBTools. Clean, merged and unmerged paired end reads were assembled using SPAdes version 3.10.1. The resulting contig assemblies, of an N50 length ~18 kb were used to prepare longer assemblies across different contigs and pools. (See FIG. 15). The resulting cross-pool assemblies produced large sequence strings, with an N50 of ~32 kb. The assembled sequences were populated into a database and were referred to as a "digital metagenomics library".

Arraying Physical Pools

E. coli cosmid pools were stored in glycerol in individual cryovials for long term storage. Duplicate E. coli cosmid pools were stored in 96-well format as both glycerol stock of E. coli cells or as isolated DNA from said stock. (See FIG. 16). These were referred to as the "metagenomic physical library." Each sequence in the digital metagenomics library was associated, via a database, to the location of the corresponding physical DNA fragment within the stored metagenomic physical library.

Example 4

MGC Discovery Comparison Using Digital Metagenomic Libraries of the Present Disclosure and Publicly Available Assembled Metagenomic Libraries A digital metagenomic library, prepared following the same protocols as those described in Example 3. The library was produced according to the recommendations gleaned from simulations conducted in Examples 1 and 2. The resulting library was broadly representative of the soil environmental sample from which it was derived (see e.g., FIG. 28A-28D), and exhibited N50s>15,000 bp for improved MGC discovery.

In order to validate these above-referenced library design choices, the inventors conducted a real world comparison of the DML from this example, with that of one of the largest publicly available soil metagenomes (the Joint Genome Institute soil metagenome library from Project ID Gp0051441, hereby referred to as "the JGI soil metagenome"). The JGI soil metagenome was based on soil gathered from Kansas, Wisconsin and Iowa native prairie soil samples, and is publicly available at the Joint Genome Institute Genome portal at //img.jgi.doe.gov/cgi-bin/m/main.cgi?section=TaxonDetail&page=taxonDetail&taxon_oid=3300000956 (see also Adina Chuang Howe, Janet K. Jansson, Stephanie A. Malfatti, Susannah G. Tringe, James M. Tiedje, C. Titus Brown. "Tackling soil diversity with the assembly" Proceedings of the National Academy of Sciences March 2014, 201402564; DOI: 10.1073/pnas.1402564111).

The JGI metagenome library had a total assembled length of 8.88 Giga base pairs, compared to only 1.84 of the DML of the present disclosure. The DML produced in Example 3 had an average N50 of greater than 15,000 bp, while the JGI metagenome had an average N50 of 985.

Figure 24:
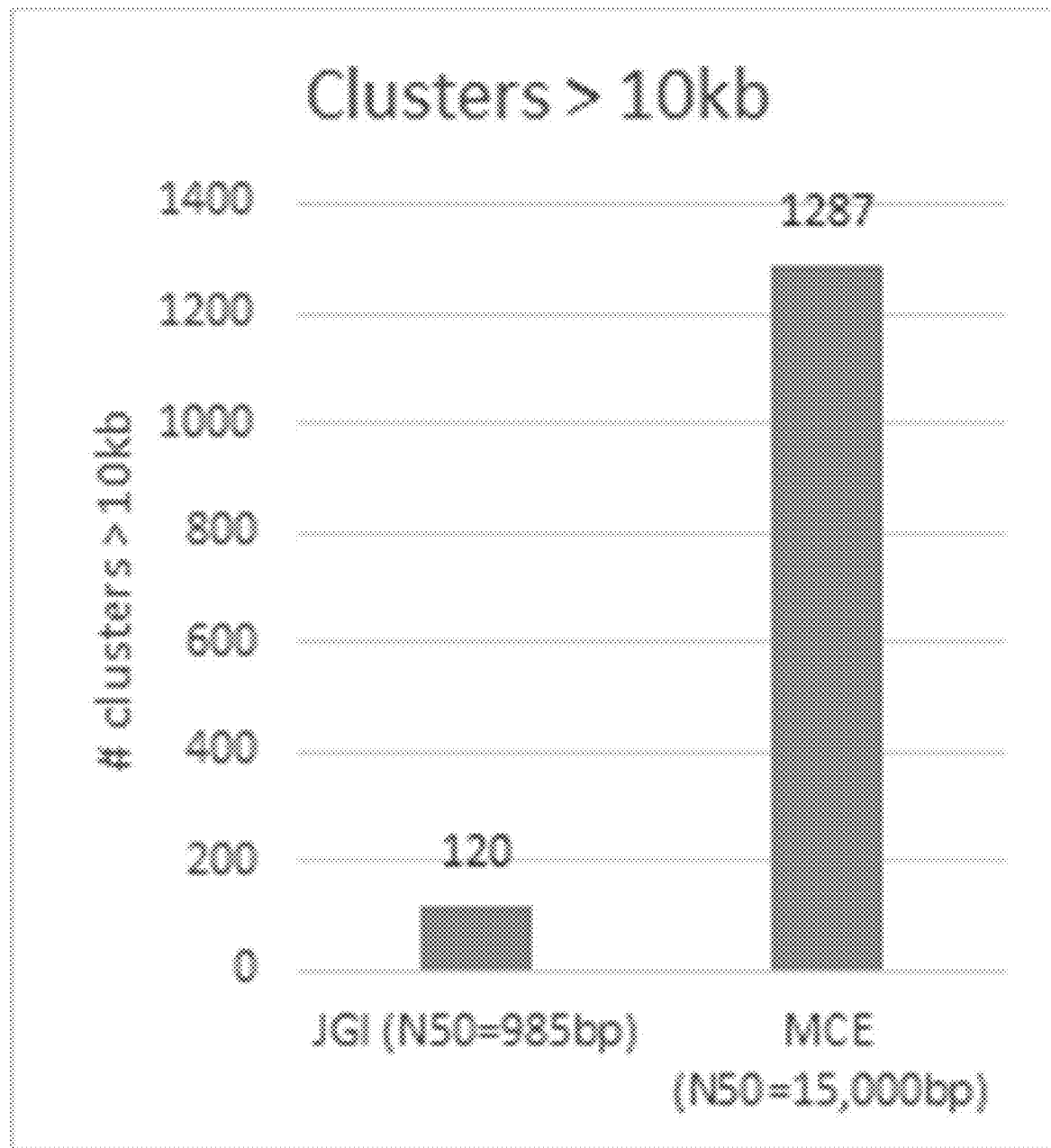
FIG. 24—depicts the number of clusters identified in the JGI and MCE libraries using the digital searching methodologies of the present disclosure. Only 120 MGCs were identified in the JGI database, compared to 1287 in the MCE. It was thus possible to identify 10× more MGCs in the MCE database, which is four times smaller in size than the JGI soil metagenome database (i.e. MCE exhibits over 50 times more effective at identifying MGCs).
Figure 25:
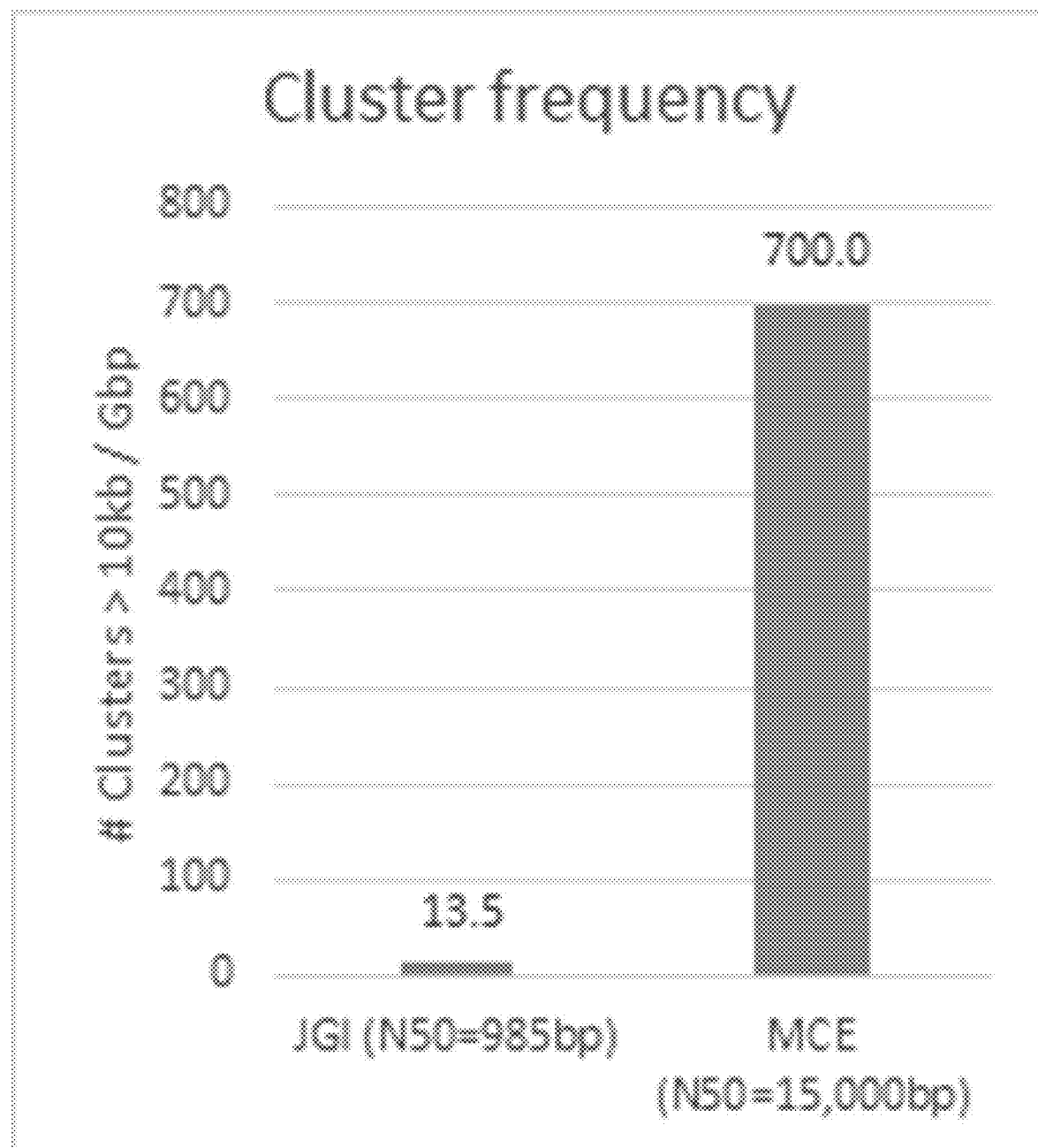
FIG. 25—depicts the number of clusters identified in the JGI and MCE libraries using the digital searching methodologies of the present disclosure. Results are shown as number of MGCs identified per Gigabase of sequence. The MCE, with N50 of about 15 kbp, is over 50 times more efficient at identifying MGCs.
Figure 26:
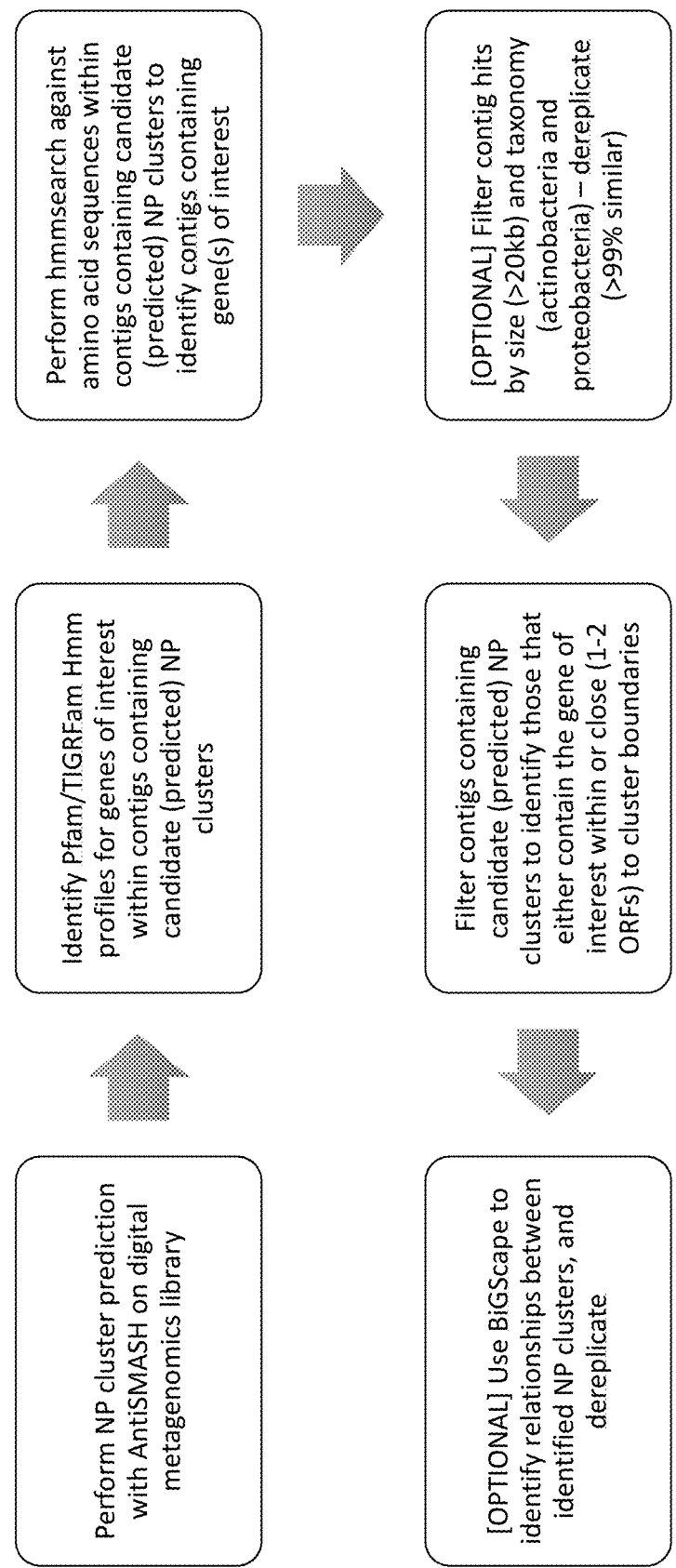
FIG. 26—depicts the steps of an embodiment of the in silico natural product multi-gene cluster discovery methods of the present disclosure. Digital metagenomic libraries are queried for the presence of multi-gene clusters. Candidate resistance genes may be identified in digital metagenomic libraries via HMMs selected based on known or predicted target resistance genes (e.g., resistance genes in other organisms or for related natural products). In some embodiments, the present disclosure teaches selecting MGCs that comprise candidate resistance genes within the MGC, or within 1-2 ORFS of said MGCs.
Figure 28A:
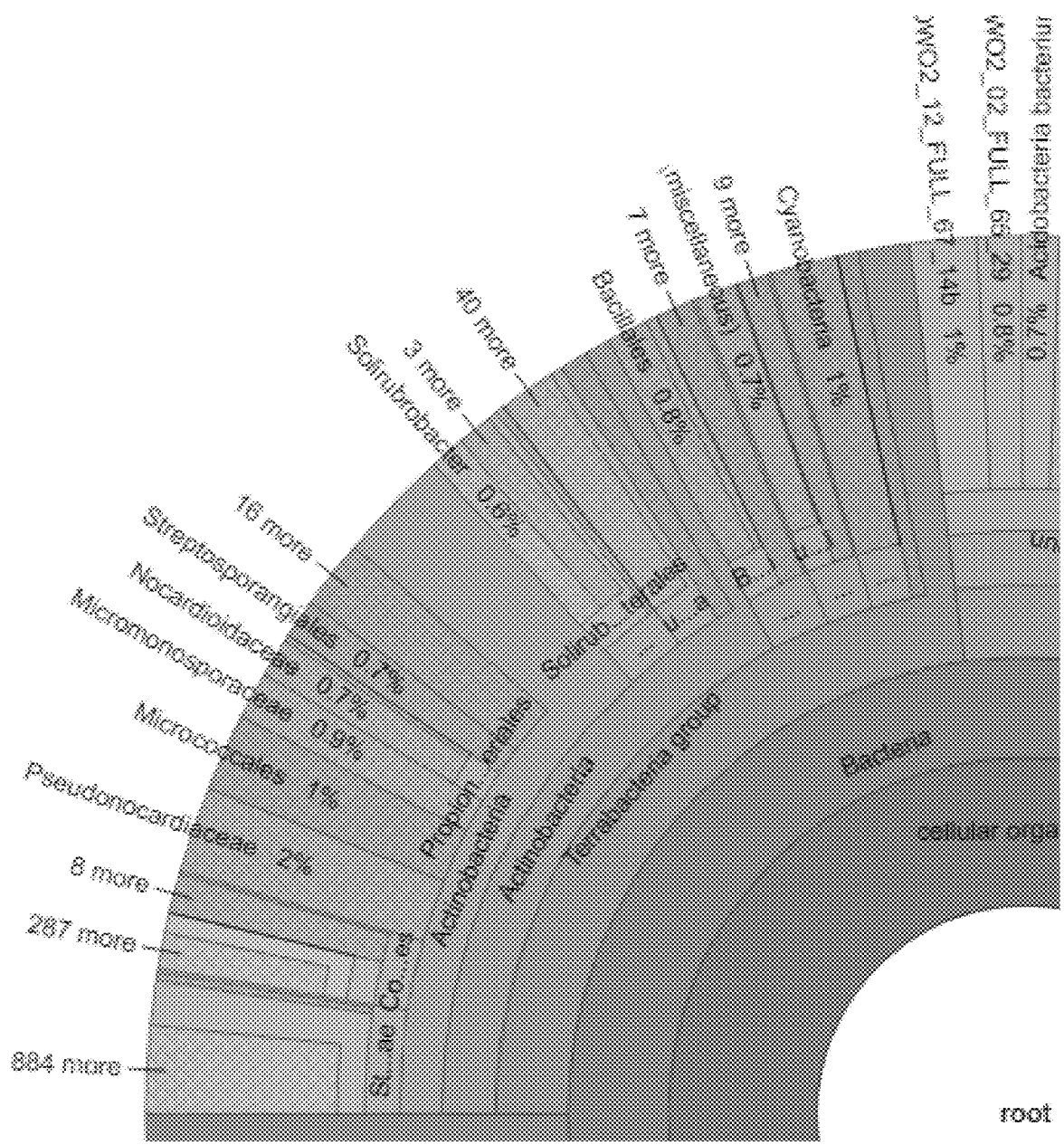
FIG. 28A-28D—Krona plot illustrating taxonomic characterization of a digital metagenomics library (MCE) produced according to the methods of the present disclosure from a soil sample (see Example 4). The MCE exhibited a taxonomic diversity representative of the original environmental soil sample.
Figure 28B:
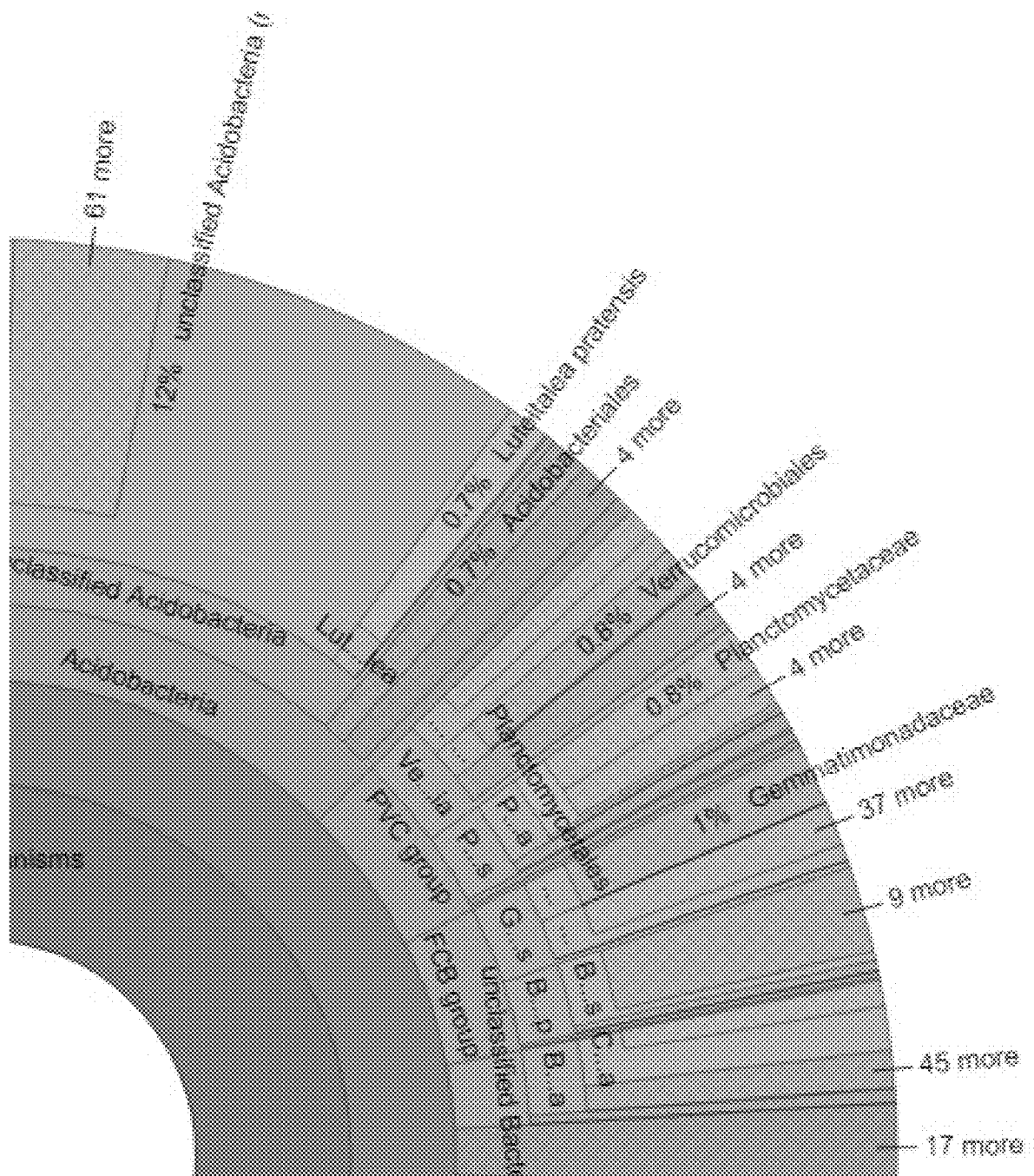
Figure 28C:
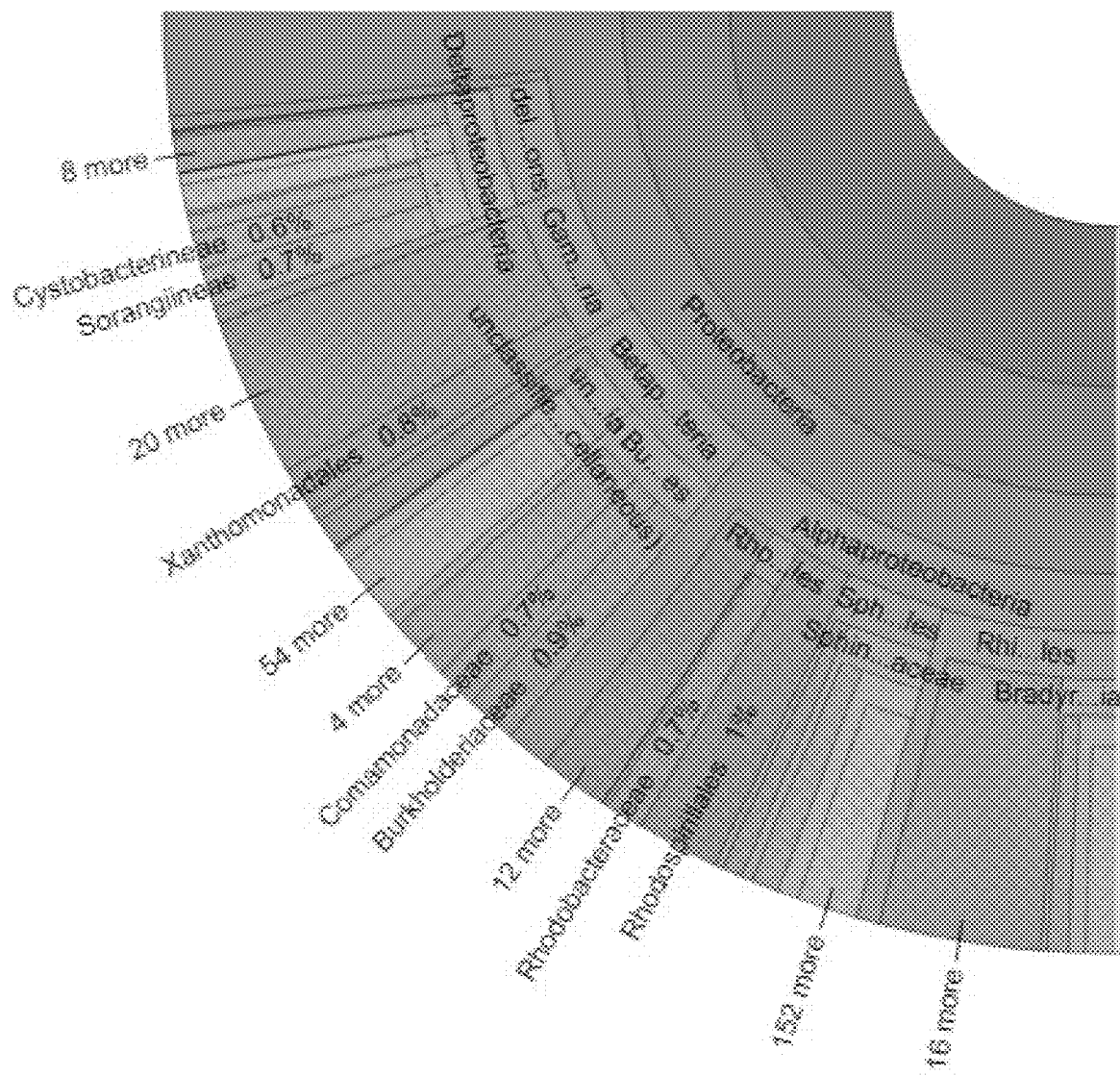
Figure 28D:
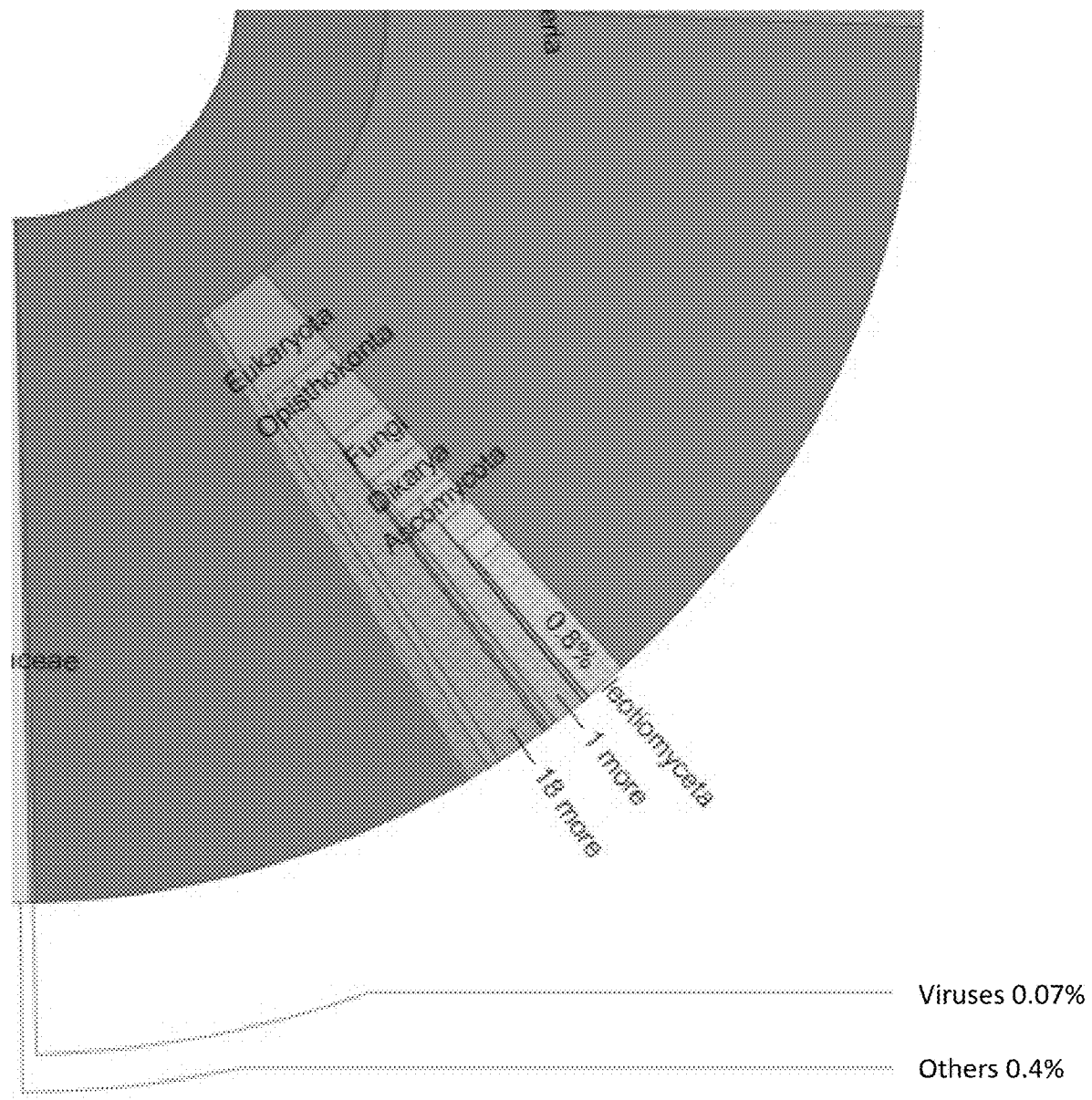

The JGI metagenome library and the DML were both analyzed using antiSMASH 5.0, to identify number of putative multi-gene clusters of greater than 10 kb in length. This results of this analysis are summarized in FIG. 24. AntiSMASH identified 1287 putative clusters in the DML, but only 120 putative clusters in the JGI metagenome library. These results are better represented in FIG. 25, which provides the number of clusters identified per Gigabase of sequence. The JGI metagenome library yielded 13.5 putative clusters per Gigabase, while the DML of the present disclosure yielded 700 putative clusters per Gigabase of sequence.

Thus, when compared against publicly available metagenomic libraries, the DML of the present disclosure was over 50× better at yielding putative cluster hits.

Example 5

Identification of Natural Product in Metagenomic Libraries (Resistance Signal Searching)

Having designed, and validated the digital metagenomic library (DML) in Example 3, we next sought to apply the product discovery workflows to this DML. This example illustrates the resistance signal based searches of multi-gene cluster feature sets for identifying novel natural products, as discussed in the "Resistance Gene Search Workflow" section of this document. This example used putative target variant-based resistance sequences as signals indicative of natural product multi-gene cluster feature sets. This example applies the resistance gene search workflow to identify new natural products that are related to existing natural products, by using known resistance genes as the target gene for identifying candidate resistance genes.

Application Target

Inhibitors of the proteasome are both approved anti-cancer drugs (e.g. Carfilzomib) as well as anti-cancer drugs in clinical development (e.g. Marizomib). Both Carfilxomib and Marizomib are based on bacterial natural products, epoxomicin and salinosporamide A respectively. The biosynthetic gene cluster that encodes Salinosporamide A in certain species of Salinospora bacteria contains all the biosynthetic enzymes needed to produce Salinosporamide A. In addition to these enzymes, the biosynthetic gene cluster contains a gene (resistance gene) that encodes a variant of the beta-subunit of the proteasome which is resistant to the effects of Salinosporamide A. Expression of this protein variant allows the producing bacteria to survive in the presence of Salinosporamide A. Novel natural product small molecule proteasome inhibitors may be encoded by biosynthetic gene clusters that contain resistance genes that encode a variant of the beta-subunit of the proteasome. These novel natural product proteasome inhibitors can serve as the scaffold for novel anti-cancer drugs.

Selection of HMM

HMM libraries (PFAM and TIGRFAM) were searched to identify an appropriate HMM for the beta-subunit of the proteasome. TIGR03690 was selected and used as the search query.

Searching for Resistance Genes in Metagenomic Libraries—Querying a Digital Metagenomics Library for a Signal Indicative of a Natural Product Multi-Gene Cluster Feature Set.

The HMM model identified above was used to search for microbial genes encoding the beta-subunit of the proteasome (target gene, resistance gene) in the digital metagenomics library produced by Example 3. The search identified a series of sequences termed "candidate sequences." Each candidate sequence was associated with a confidence score assigned by the model. A maximum E value of 1e-10 was established to select top hits for further analysis. In some instances, sequences were de-replicated at 97% identity.

Supplying the Output of the HMM Query as a Plurality of Signal-Associated (Multi-Gene Cluster) Digital Feature Sets.

Assembled sequences encoding for the one or more candidate sequences identified above (i.e., gene encoding the beta-subunit of the proteasome), were downloaded into a new file representing signal-associated (multi-gene cluster) digital feature sets.

Multi-Gene Cluster Identification—Determining and Assigning Biologic Relevancy to the Signal-Associated Multi-Gene Cluster Digital Feature Sets.

These digital feature sets were analyzed for the presence of multi-gene cluster feature sets using an antiSMASH cluster analysis tool. (See Kai Blin et al. "antiSMASH 5.0: updates to the secondary metabolite genome mining pipeline" *Nucleic Acids Research* (2019), tool available at// antismash.secondarymetabolites.org/#!/start). The identification of MGCs based on the presence of biosynthetic and other sequence based signals associated with gene clusters (e.g., using antiSMASH) is also referred to as determining a computationally predicted biosynthetic functionality of a plurality of genes from a signal-associated multi-gene cluster digital feature set and digitally assembling a computationally determined natural product multi-gene cluster feature set comprising a biosynthetic operon.

Identifying MGCs Encoding a Natural Product of Interest Based Upon a Computationally Determined Biological Resistance Gene Being Located within a Threshold Parameter of a Computationally Determined Natural Product Multi-Gene Cluster Feature Set The location of the resistance genes identified in earlier steps (candidate sequences) was compared against the location of MGCs identified via antiSMASH, above. 20 predicted natural product multi-gene clusters containing a candidate sequence within its predicted borders or within 5-10 kb from these borders were selected for further analysis.

Optional Prioritization of Multi-Gene Clusters

The goal of this example was to identify MGCs encoding novel variants of natural products with potential anti-cancer properties, with structural similarities to epoxomicin. To enrich for natural product multi-gene clusters that contain a bonafide resistance gene, additional criteria were used to select for the clusters of greatest interest. Putative resistance genes (candidate genes) were compared to the human proteome utilizing BLAST to confirm that the strongest protein matches to the putative resistance gene are to the components of the beta-subunit of the proteasome. It is noted that this could have also been achieved by merely increasing the stringency of the resistance gene homology search in the step of "querying a digital metagenomics library for a signal indicative of a natural product multi-gene cluster feature set."

Hits from antiSMASH analysis were also analyzed via BIGScape to identify relationships between the identified multi-gene clusters and group the multi-gene clusters accordingly. (See Navarro-Muñoz et al. "A computational framework for systematic exploration of biosynthetic diversity from large-scale genomic data" BioRxiV 2018, said tool available at omictools.com/big-scape-tool). In some workflows, the list of multi-gene clusters were further filtered by 1) predicted length of the multi-gene cluster and 2) predicted taxonomy of the multi-gene cluster as assigned by Kaiju.

Multi-gene clusters containing a gene encoding the beta-subunit of the proteasome adjacent to a gene encoding the alpha-subunit of the proteasome were deemed less likely to be serving as a resistance gene and were removed from the set.

These steps prioritized the pool of candidate clusters to three priority multi-gene clusters selected for validation.

A flow chart outlining the in silico steps of this method is provided in FIG. 6.

NP Validation

The workflow steps of this example identified an MGC already reported in the literature as producing eponemycin (1,2-Epoxy-2-hydroxymethyl-4-(N-isooctanoylserylamino)-6-methylhept-6-ene-3-one). The identification of the eponemycin cluster thus validated the in silico portions of the resistance gene search workflow.

Additional candidate MGCs identified in this example will be validated via wet lab techniques. DNA comprising sequences identified above as comprising multi-gene clusters in proximity to candidate sequences are recovered from the metagenomic physical library. Briefly, the location of the desired DNA sequence that comprise the multi-gene cluster is obtained from the metagenomic database, which indicates the plate(s) and well(s) where each sequence is physically located (i.e., location within the metagenomic physical library). The identified DNA sequences are then recovered from the physical library (e.g., via dilution series to isolate the sequences of interest from the pool), and the DNA sequences that comprise the multi-gene cluster are cloned and reassembled in a plasmid vector using Transformation Assisted Recombination (TAR) in *S. cerevisiae*. The vectors were used to introduce the multi-gene cluster into a *Streptomyces* sp. Microbial host. The modified microbial host cells are then cultured, and tested for the production of natural products, wherein said natural products either i) binds or otherwise interacts with the proteasome in vivo or in vitro and/or ii) would be toxic to the cell via inhibition of the proteasome, save for the expression of the candidate resistance gene identified in (or in proximity to) the identified multi-gene cluster.

Example 6

Identification of Natural Product Produced by Clusters without Resistance Gene Existence/Knowledge (Transitive Searching Workflow)

This example illustrates methods for the discovery of multi-gene cluster feature set that lack readily identifiable resistance genes, as discussed in the "Transitive Multi-gene Cluster Feature Set Discovery Workflow" section of this document. This approach can be used to identify novel multi-gene clusters based on their similarity to other known clusters, including known clusters with known or predicted resistance genes.

The multi-gene clusters identified in Example 5 were further analyzed to identify distinctive enzymatic components common to said clusters. A cluster known to produce eponemycin was selected for additional analysis. Sequence analysis of the eponemycin encoding cluster identified an acyl CoA dehydrogenase (ACAD) gene (AHB38508.1), associated with non-ribosomal peptide synthetase and polyketide synthase genes, that are essential to the formation of the distinctive epoxyketone found in eponemycin (i.e., "core biosynthetic gene/enzyme"). To identify clusters that encode molecules structurally related to eponemycin, the AHB38508.1 sequence was used to BLAST search the digital metagenomic library of Example 3 to identify other ACAD genes with high identity scores. The top 250 hits were then further analyzed by creating a database of DNA immediately surrounding the putative ACAD gene. This was accomplished by taking the entire contig that contained the ACAD gene for further analysis. The DML contained 20 kb upstream and 20 kb downstream of each of the 250 putative ACAD genes identified in the metagenomic database. These selected sequences containing the ACAD genes were then analyzed using antiSMASH to identify ACAD genes that were contained within putative multi-gene clusters. Specifically, hits associated with NRPS and PKS containing gene clusters were identified. A total of 22 hits were identified as putative novel multi-gene clusters capable of encoding eponemycin-like natural products.

These 22 putative hits were further filtered for hits that exhibited i) similar size to the original eponemycin clusters (i.e. a range of about 20 kb to 40 kb), and ii) similar complement of core biosynthetic gene/enzymes (e.g., the presence of one to two PKS-like modules, two to five NRPS-like modules, and the aforementioned ACAD gene). These filters did not remove sequences from consideration, but instead were used to prioritize hits for experimental validation.

When we examined the 22 hits, we identified two clusters in the database that encode an epoxyketone-containing molecule called expoxomicin or a closely related analog. Despite the lack of a resistance gene within the epoxomicin cluster, epoxomicin has been characterized as an inhibitor of the beta-subunit of the proteasome.

Example 7

Identification of Natural Product in Metagenomic Libraries (Untargeted Resistance Signal Searching)

This example illustrates methods for de novo multi-gene cluster feature set discovery, said methods not requiring pre-selection of a putative resistance gene to begin the search. This example generally follows the workflow outlined in the "Untargeted Resistance Signal Multi-gene Cluster Feature Set Discovery Workflow" section of this document. In some cases, the methods of this example are capable of identifying novel resistance genes, without relying on sequence identity of said novel resistance gene to known resistance genes.

Creation of a Biosynthetic Database of Enzymes Involved in the Biosynthesis of Natural Products Biosynthetic enzymes contained in a public database of natural product gene clusters (MIBiG//mibig.secondarymetabolites.org/download) are identified. Amino acid sequences for these biosynthetic enzymes are queried via annotations "biosynthetic" and "biosynthetic-additional", and extracted from the sequence genbank file. The resulting set of amino acid sequences are clustered using CD-HIT to reduce redundancy. The resulting non-redundant set of amino acid sequences represents the biosynthetic enzyme database, and can be used to query against a larger set of sequences to identify biosynthetic enzyme homologs.

Multi-Gene Cluster Identification in Metagenomic Libraries (PROPHETIC)—Computationally Predicting Natural Product Multi-Gene Cluster Feature Sets Within a Long-Assembly Digital Metagenomic Library;

The digital metagenomics library produced by Example 3 is analyzed for the presence of multi-gene cluster feature sets using an antiSMASH cluster analysis tool. (See Kai Blin et al. "antiSMASH 5.0: updates to the secondary metaboline genome mining pipeline" *Nucleic Acids Research* (2019), tool available at Hantismash.secondarymetabolites.org/#!/start). The resulting antiSMASH output includes a list of identified gene clusters, as well as functional annotation of key biosynthetic enzymes within those clusters.

Identification of Putative Resistance Genes within Identified MGCs (PROPHETIC)—Annotating Genes Within the Predicted Natural Product Multi-Gene Cluster Feature Sets and Filtering Annotated Genes from the Predicted Natural Product Multi-Gene Cluster Feature Sets.

Putative resistance genes within the identified multi-gene clusters is done via process of elimination. The annotations of genes within the multi-gene clusters are filtered to remove any sequences predicted with a high degree of confidence to be involved in the biosynthesis of the natural products, either predicted by antiSMASH or contained in our biosynthetic database. Remaining genes within the multi-gene clusters without a predicted biosynthetic function are considered "candidate resistance genes," and are analyzed further.

HMMs from the ResFam database that identify resistance genes that do not provide resistance by encoding a variant of the target protein were used to identify non-protein variant resistance genes and removed from the analysis. The remaining candidate resistance genes are investigated in silico, by identifying putative orthologs of said genes in public databases. The identified orthologs provide the putative target of the encoded natural product.

NP and Resistance Validation (PROPHETIC)

DNA comprising sequences identified above as comprising multi-gene clusters in proximity to candidate sequences are recovered from the metagenomic physical library. Briefly, the location of the desired DNA sequence that comprise the multi-gene cluster is obtained from the metagenomic database, which indicates the plate(s) and well(s) where each sequence is physically located (i.e., location within the metagenomic physical library). The identified DNA sequences are then recovered from the physical library (e.g., via dilution series to isolate the sequences of interest from the pool), and the DNA sequences that comprise the multi-gene cluster are cloned and reassembled in a plasmid vector using Transformation Assisted Recombination (TAR) in *S. cerevisiae*. The vectors were used to introduce the multi-gene cluster into a *Streptomyces* sp. microbial host. The modified microbial host cells are then cultured, and tested for the production of a natural product that is not found in an empty-vector control.

The natural product is semi-purified and its toxicity to an unmodified microbial host cell is verified by a disk diffusion assay. When the putative resistance gene is expressed in the unmodified microbial host, the natural product is no longer toxic. Binding assays demonstrate that the natural product interacts with the hypothesized target protein.

Example 8

Analoging Natural Products

This example illustrates several of the presently disclosed methods for analoging natural product molecules. Specifically, the example describes the use of predictive machine learning models to identify and compile panels of enzymes from metagenomic libraries. These panels are then applied to natural product molecules (or are integrated into the genomes of strains producing the natural products) to produce novel analogs.

Selection of Enzymes from Metagenomic Library

An HMM was developed to identify 384 aldo-keto reductase genes that were selected to 1) sample metagenomic diversity broadly and/or 2) contain sequence characteristics believed to enrich for the enzyme-substrate activity of interest.

Construction of Enzyme Panel

The locations of the desired DNA sequences that comprise the enzyme panel were obtained from the metagenomic database, which indicates the plate(s) and well(s) where each sequence is physically located (located (i.e., location within the metagenomic physical library). The identified sequences are then recovered from the physical library (e.g. via PCR) ad are cloned into an expression plasmid and transformed into a microbial host cell. These host cells are then arrayed into 96-well or 384-well format.

Assay and Identification of Active Enzyme

To express enzymes of interest, microbial strains containing the expression plasmid are cultured in autoinduction media under antibiotic selection. After induction, microbial cultures are harvested, lysed and clarified to release overexpressed enzymes of interest for characterization.

To characterize the activity of enzyme panels, clarified lysate is incubated in a reaction mixture containing substrate, buffer and other relevant additives with a distinct marker (e.g. co-factor with known absorbance). Activity is measured by the change in absorption intensity over the course of a reaction. Active enzyme variants will show a delta absorbance below control throughout the duration of the reaction.

As an example, the aldo-keto reductase enzyme panel is characterized by an end-point colorimetric assay, monitoring the consumption of reduced nicotinamide adenine dinucleotide (phosphate), over time. The enzymatic reduction (analoging) of a substrate requires NAD(P)H to be oxidized; therefore, the activity of this enzyme panel is coupled to the consumption of NAD(P)H which can be monitored by the reduction of absorbance at 340 nm.

Clarified lysate containing over-expressed enzyme variants were mixed with a set concentrations of substrate (geldanamycin), phosphate buffer and NAD(P)H. Absorbance of the reaction mixture is taken at the beginning and end of the reaction to determine the delta absorbance. Controls are also used to determine background absorbance. Reaction mixtures containing variants with a positive delta absorbance, above background, are analyzed to confirm the production of the desired analog, reduced geldanamycin.

In Vivo Activity

Figure 10:
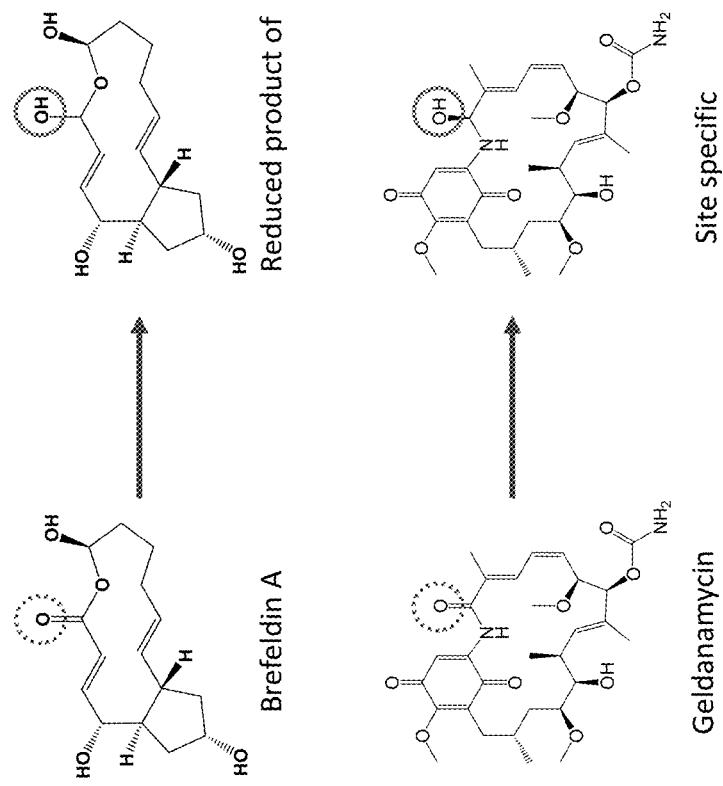
FIG. 10—depicts a panel of metagenomic-sourced aldo-keto reductases that was screened to generate modifications of brefeldin A and geldanamycin, as described in Example 5. Using the methods of the present disclosure 3 enzymes that can modify brefeldin and 1 enzyme that can modify geldanamycin were identified.

The enzyme variant that is able to act on geldanamycin identified via the in vitro enzyme panel screen will be cloned into an expression plasmid and transformed into the native producer of geldanamycin, *Streptomyces hygroscopicus*. Following fermentation and mass spec analysis, the reduced form of geldanamycin identified in the in vitro assay will be identified in the transformed microbial cell. (See FIG. 10).

Example 9

Using Training Data Sets to Generate Predictive Machine Learning Models that are Applied to Metagenomic Databases to Generate Pools of Candidate Sequences for Analoging—Custom AKR HMM Approach These examples describe the use of predictive machine learning models to identify and compile panels of candidate enzymes from metagenomic libraries. The aim of this selection was to A) sample diversity broadly across a large sequence library (e.g., the metagenomic library of the present disclosure) and/or B) demonstrate the ability of the presently described predictive models to enrich for enzyme-substrate activity of interest.

Examples 9 and 10 thus represent the in silico portions of the analoging platform. Example 11 later clones and expresses the identified pools of candidate analoging enzymes and tests them against natural product molecules to produce novel analogs. Additional details of the pursued strategies are discussed below.

An initial training data set of canonical aldo-keto reductases (AKR) sequences was produced from a review of literature and annotated databases. This is referred to in the specification as "accessing a training data set comprising a genetic sequence input variable and a phenotypic performance output variable."

These training data set sequences were used to generate a multiple sequence alignment (MSA) which was further used to develop a custom predictive machine learning HMM model, as described in this document. This is referred to in the specification as "developing a first predictive machine learning model that is populated with the training data set."

The custom AKR HMM was then run against (or applied to) the digital metagenomic library of Example 3 to identify a pool of candidate AKR sequences, which are herein referred to as the HMM output sequences. This is referred to in the specification as "applying, using a computer processor, the first predictive machine learning model to a metagenomic library containing amino acid sequences from one or more organisms to identify a pool of candidate sequences within the metagenomic library." A total of 110,232 initial sequences were identified by the HMM.

In order to further enrich for sequences of interest, these HMM output sequences were filtered by size (establishing an acceptable min/max length of 150 to 1,500 amino acids, respectively). This limitation was to ensure that any identified sequences represented a complete AKR enzyme. The result of this filtering step left 107,838 number of hits.

Results were further clustered by 40% ID using CD-HIT in order to group candidate sequences based on their sequence similarities in order to better sample the diversity of hits in the subsequent validation stages. The 2,404 clusters generated by CD-HIT were sorted by their size (cluster size is the number of sequences per cluster). Subsequently, 177 clusters out of the 2,404 were chosen to represent the 107,828 sequences by cluster size, namely the biggest 177 CDHIT clusters. In order to identify representative sequences of each of the 177 clusters, cluster centroids were selected as follows: First, all sequences of the cluster were aligned using the MAFFT algorithm. Next, the resulting multiple sequence alignment was converted to an HMM using the HMMBUILD software. Following this step, this HMM was run vs. all the sequences of the cluster. The highest scoring sequence was finally selected as a CDHIT cluster representative. This step was conducted to provide as broad a picture as possible of the sequences identified by the model, but is not necessarily required for discovery of new enzymes.

177 candidate AKR sequences were selected for further validation from amongst the hits of this search. Two of the 177 tested hits were validated as being capable of analoging Brefeldin A in an initial screen. These enzymes also exhibited activity on Erythromicin and Salinomycin. A more detailed discussion of the results is provided in Example 16 of this disclosure.

Example 10

Using Training Data Sets to Generate Predictive Machine Learning Models That are Applied to Metagenomic Databases to Generate Pools of Candidate Sequences for Analoging—Custom HMM Library This example describes an alternative approach for selecting genes from amongst the HMM result set to sample the diversity of the results. In Example 9, the results were sampled by clustering the results based on sequence identity. In this example, we generated a set of sequences that represent the 107,838 HMM output sequences from Example 9. This was achieved by calculating "cluster centroids" for all 2,404 CDHIT clusters. In addition, we ran the custom HMM mentioned above against the public UniProtKB SwissProt database; this resulted in an additional 378 sequences that were added to the 2,404 CDHIT40 cluster centroids. We combined these sets into a single sequence set that includes 2,722 sequences. This set was used to generate a sequence similarity network. This was achieved by running all-by-all BLAST for all these 2,722 sequences, yielding a pairwise similarity matrix for all these sequences. This matrix was then represented as a network using the Cytoscape software; each node represents a sequence, and edges represent pairwise BLAST similarity. The Perfused forced-directed layout was used for visualizing clusters.

Following this step, several edge inclusion cutoffs (as represented by pairwise BLAST bitscores) were manually sampled for this network. This step was guided by the information available from the sequences originating in the UniProtKB SwissProt database. Namely, an edge inclusion cutoff of 80 (pairwise BLAST bitscore) was selected to generates sequence clusters that include AKR homologs that belong to different sub-families of the AKR superfamily (as defined by SwissProt). This procedure resulted in 39 sequence similarity clusters.

We then used these 39 broad sequence similarity clusters to create a set of 39 custom HMM's as follows. The 39 sets of sequences, one of each cluster, were aligned using the MAFFT algorithm and were then used to generate HMMs using the HMMBUILD software. This provided an expanded series of HMM models based on sequences beyond those which are identified in publications or annotated databases.

All these 39 Custom HMM Library models were then used for searching the metagenomics library of Example 3. Specific HMM bits core cutoffs were then manually determined, so that the hits of a given HMM will not include hits of any of the other HMMs (the bitscore values were 150, 160, 170, 180, 190, 190, 260, 260, 270, 280, 290, 290, 300, 300, 300, 300, 300, 310, 310, 340, 340, 340, 350, 370, 370, 370, 370, 380, 390, 400, 410, 410, 430, 430, 430, 440, 490, 520 and 610). Since many hits were still found for each HMM, the CDHIT algorithm was used to cluster each and every of these 39 sets of hits, using 40% ID. Centroid sequences see 7 above of the largest clusters were then selected to represent each of the 39 sequence sets.

168 candidate AKR sequences were selected for further validation from amongst the hits of this search. One of the 168 tested hits were validated as being capable of analoging Geldanamycin, as described in Example 16, below.

Example 11

Experimental Validation of Candidate AKR Sequences Against a Natural Product

This example discloses the "wet lab" portion of the analoging methods of the present disclosure, wherein candidate sequences identified via the predictive engines described above are experimentally validated.

The pool of 345 candidate AKR sequences identified in Examples 9-10 were PCR amplified from existing physical libraries of the metagenomic library utilized in the earlier examples. Primer3 was used to design fixed-end primers for the amplification. To clone in high throughput, homologous sequences were inserted onto each gene amplicon for effective gibson assembly within the multiple cloning site of pET24a expression plasmid (Sigma Aldrich). 20 uL PCRs were performed with Q5 Hot Start High-Fidelity 2× Master Mix (New England Biolabs) under touch-down PCR thermocycler conditions (Touch down at 72° C. annealing temp with −1° C./cycle for 8 cycles, followed by 64C annealing for 28 cycles). PCR products were purified using a magbead clean up protocol (DNA clean up and concentrator Magbead kit, Zymo Research).

The expression plasmid was digested with EcoRI-HF/NotI-HF (New England Biolabs) and purified (QiAquick PCR purification kit, Qiagen) prior to assembly. Gibson assembly (NEBuilder HiFi DNA assembly) and chemical transformation (10-beta competent E. coli High Fidelity, NEB) protocols were adapted for high-throughput automation in 96-well and 384-well plate format. 228/345 genes were successfully cloned. Successful clones were miniprepped (Qiagen, Plasmid Plus 96 kits) and transformed into an expression host (BL21-DE3, NEB).

For optimal expression, 1 mL of BL21-DE3 pET24a-AKR strains were cultured in 96-deep well plates using autoinduction media+kanamycin at 25° C. induction. After overnight induction, cultures are harvested at 5000 rpm for 10 minutes at 10° C. Pellets are resuspended and lysed using 250 uL of BugBuster Master Mix (Sigma Aldrich). Lysed cells are then pelleted and run through desalting plates (Zeba Spin Desalting Plates-7K MWCO, Thermo Fisher) to buffer exchange and clarify the over-expressed enzyme lysates for characterization.

To characterize the cloned AKR library activity against Geldanamycin, Erythromycin, Brefeldin A, and Salinomycin natural products, an end-point colorimetric assay, monitoring the consumption of reduced nicotinamide adenine dinucleotide (phosphate), was developed. The enzymatic reduction of a substrate requires NAD[P]H to be oxidized; therefore, the activity of this enzyme panel is coupled to the consumption of NAD[P]H which can be monitored by the reduction of absorbance at 340 nm. Absorbance of the reaction mixture is taken at the beginning and end of the reaction to determine the delta absorbance. Controls are also used to determine background absorbance. Reaction mixtures containing variants with a positive delta absorbance, above background, are analyzed to confirm the production of the desired analog, e.g., reduced Brefeldin A. 96-well plate, 200 uL reactions, containing 180 uL master mix 100 uM NAD[P]H, 200 uM natural product (e.g., Brefeldin A) in 175 mM phosphate buffer, pH7) and 20 uL of clarified lysate were shaking over 1.5 hrs at 22C.

After screening 228 enzyme variants from Examples 9-10, three active variants, showing significant delta absorbances below control were submitted for analog confirmation. The identified enzymes exhibited activity against Geldamycin, Erythromycin, Brefeldin A, and Salinomycin.

Additional characterization was performed on reactions that generated a significant positive delta absorbance. 100 uL aliquots were mixed with acetonitrile in a 1:1 ratio to crash out proteins and buffer salts; after agitation, a liquid extraction of the organic layer is carried out. 5 uL of extracted solvent were injected on to the LC-MS (Thermo Q-Exactive) for analysis. In the case of Brefeldin A, the putative reaction product was observed at 281.1747 m/z and a retention time of 1.69 min/This mass to charge ratio and dehydrogenase dataset was further partitioned as "cluster associated" and "not cluster associated". If a biosynthetic gene cluster of any class was predicted on a contig, it was categorized as "within an MGC", and if no cluster could be predicted, it was categorized as "outside an MGC."

These in silico methods identified 451 dehydrogenase sequences within MGCs, and 523 dehydrogenase sequences outside MGCs.

Of the identified dehydrogenase sequences, 143 sequences "within an MGC" and 270 sequences "outside an MGC" were chosen for experimental validation. The experimental wet lab validation was conducted by obtaining the full candidate sequences from the physical copies of the digital metagenomics library, and cloning them into expression vectors, as described in Example 11. Dehydrogenase activity was tested on Geldanamycin, Salinomycin, and Brefeldin A natural product substrates.

The results of these assays are shown in Table 8, below.

TABLE 8

| | Dehydrogenase analoging validation Dehydrogenases | | | |
| --- | --- | --- | --- | --- |
| strategy | # tested (# recommended) | Geldanamycin | Salinomycin | Brefeldin A |
| Within an MGC | 143 (451) | 2 | 1 | 1 |
| Outside an MGC | 270 (523) | 0 | 1 | 1 |
| | Results showing identified enzymes with their substrate specificity | | | |
| Enzyme 1 (within an MGC) | | 1 | | |
| Enzyme 2 (outside an MGC) | | | 1 | 1 |
| Enzyme 3 (within and MGC) | | 1 | 1 | 1 | retention time were consistently observed in reaction mixtures where colorimetric results suggested the desired enzymatic activity. As a control, an empty strain (pET24a) was also analyzed and the putative product was not detected. This was consistent with other AKR variants that the appropriate activity was not observed. Thus, Geldamycin, Erythromycin, Brefeldin A, and Salinomycin analogs were identified using the methods of the present disclosure.

Example 12

Analoging Enzyme Discovery—Enrichment by Searching within MGC

This example demonstrates that analoging enzyme discovery can be enhanced by defining the location of the encoding gene.

Amino acid sequences annotated as "Dehydrogenase" in the MIBIG database (//mibig.secondarymetabolites.org/) were retrieved to be used as query sequences. A total of ~200 amino acid sequences were retrieved. These sequences were used as queries to search against predicted CDS sequences in the metagenomic database of Example 3.

Next, we tested whether the location of the candidate dehydrogenase sequences can be used to further enrich for the analoging enzymes of interest. The contigs containing the candidate dehydrogenase sequences identified above were retrieved. Biosynthetic gene clusters were predicted on the contigs using antiSMASH 4. Depending on whether a biosynthetic gene cluster could be predicted on the contig containing the candidate dehydrogenase sequence or not, the The validation experiments identified a total of three enzymes capable of using one of the three tested natural products as substrates. The results showed that the analoging enzyme discovery methods of the present disclosure could be further improved/enriched for validated enzymes by focusing the search on candidate dehydrogenase sequences located within predicted MGC sequences. The results identified two enzymes located within MGCs, and only one enzyme located outside of the MGC. The enrichment for validated dehydrogenases within MGCs is further seen in the rate of discovery, where 2 enzymes were validated out of 143 tested in the "within an MGC" group, and only 1 out of 270 enzymes were validated in the "outside an MGC" category (about 4× better enrichment within MGC).

Example 13

Analoging Enzyme Discovery-Searches Based on Whole Sequences or Individual Domains The present disclosure teaches that the HMM search strategies of the present disclosure can be based on whole target sequences of interest. In some embodiments, the present disclosure teaches that the HMM search strategies of the present disclosure can be based on one or more domains of interest of the target sequence. These various strategies were compared.

Flavocytochrome P450 BM3 is a natural fusion protein constructed of cytochrome P450 and NADPH-cytochrome P450 reductase domains. P450 BM3 binds and oxidizes several mid- to long-chain fatty acids, typically hydroxylating these lipids at the ω-1, ω-2 and ω-3 positions.

BM3 is a natural fusion enzyme comprising two major domains: a cytochrome P450 (heme-binding) catalytic domain and a NADPH-cytochrome P450 reductase (CPR) domain containing FAD and FMN cofactors in distinct domains of the CPR. HMM models based on the entire BM3 sequence ("full HMM"), and HMM models based on the PFAM database, in particular four HMMs with the following identifiers: PF00067, PF00258, PF00667 and PF00175, corresponding with regions of the protein ("partial HMMS") were obtained.

The HMMs above were then run against (or applied to) the digital metagenomic library of Example 3 as follows. The full HMM was used to search the digital metagenomic library and hits were categorized as either "higher bitscore" or "lower bitscore" candidate BM3 sequences. The partial HMMs of the protein were then individually used to search the library. Candidate BM3 sequences identified by each of the four of the partial HMMS were then selected for validation ("Higher bitscore HMM hits of multiple HMM models").

Of the identified candidate BM3 sequences, 130 sequences of the "higher bitscore HMM hits of multiple HMM models", 4 sequences of the "higher bitscore HMM hits of one HMM model", and 64 sequences of the "lower bitscore HMM hits of one HMM model" were chosen for experimental validation. The experimental wet lab validation was conducted by obtaining the full candidate sequences from the physical copies of the digital metagenomics library, and cloning those into an expression vector as described in Example 11.

Dehydrogenase activity was tested on a Geraniol natural product substrate. The results of these assays are shown in Table 9, below.

TABLE 9

BM3 analoging validation
BM3

| Strategy | # tested (# recommended) | Geraniol |
|---|---|---|
| Higher bitscore HMM hits of multiple HMM models | 130 (272) | 4 |
| Higher bitscore HMM hits of one HMM model | 4 (14) | 0 |
| Lower bitscore HMM hits of one HMM model | 64 (217) | 1 |

The validation experiments identified a total of five active enzymes on the Geraniol natural product substrate. This was thus another validation of the analoging methods of the present disclosure. In addition, the results showed that the analoging enzyme discovery methods of the present disclosure can be conducted using HMM models trained on partial sequences, such as sequences to domains of interest of a particular enzyme. It also shows that the analoging discovery platforms of the present disclosure can utilize a combination of HMMs.

Example 14

Analoging Enzyme Discovery—Application to Methyltransferases

This example demonstrates that analoging enzyme discovery platform can be applied to any analoging enzyme of interest, including methyltransferases.

An initial training data set of 53 methyltransferase enzyme sequences with validated or predicted methyltransferase function was produced. This corresponds the claimed step of "accessing a training data set comprising a genetic sequence input variable and a phenotypic performance output variable."

These training data set sequences were used to generate a multiple sequence alignment (MSA) which was further used to develop a custom predictive machine learning HMM model, as described infra. This is referred to in the specification as "developing a first predictive machine learning model that is populated with the training data set."

The custom HMM was then run against (or applied to) the digital metagenomic library of Example 3 to identify a pool of candidate methyltransferase sequences, which are herein referred to as the HMM output sequences. This corresponds to the claimed element of "applying, using a computer processor, the first predictive machine learning model to a metagenomic library containing amino acid sequences from one or more organisms to identify a pool of candidate sequences within the metagenomic library." 742 sequences were selected for further analysis ("HMM output sequences" or specifically, "candidate [methyltransferase] sequences").

Of the identified candidate methyltransferase sequences, 233 were chosen for experimental validation. The experimental wet lab validation was conducted by obtaining the full candidate sequences from the physical copies of the digital metagenomics library, and cloning those into an expression vector as described in Example 11.

Methyltransferase activity was tested on Rifamycin and Demeclocycline natural product substrates. The results of these assays are shown in Table 10, below.

TABLE 10

Methyltrasferase analoging validation
Methyltransferases

| Strategy | # tested (# recommended) | Erythromycin | Brefeldin A |
|---|---|---|---|
| Custom library of 53 HMMs | 233 (742) | 7 | 4 |

The validation experiments identified a total of eleven enzymes capable of using at least one of the two tested natural products as substrates. This was thus another validation of the analoging methods of the present disclosure.

Example 15

Analoging Enzyme Discovery—Comparison of HMM Algorithms Against Traditional BLAST SEARCH This example demonstrates that machine-learning based analoging enzyme discovery platform of the present disclosure is superior at identifying enzymes for analoging than traditional BLAST searches.

Two types of HMM models were created for searching the metagenomic database. The first type of model was a LIMS HMMSCAN fully-automated LIMS search. We identified four haloperoxidase enzyme families in the KeGG database, as defined by KeGG orthology groups K00433, K17990, K20206 and K00431. The sequences associated with each these groups were aligned to create four multiple sequence alignments using the MAFFT software, and then each alignment was used to generate an HMM using the HMMBUILD software.

All these HMMs were run against the metagenomic database of Example 3 to find haloperoxidase analoging enzymes. The results were then filtered by "removing from the pool of candidate sequences, any sequence that is predicted to perform a different function by a second predictive machine learning model with a second confidence score if the ratio of the first confidence score to the second confidence score falls below a preselected threshold."

The removal of irrelevant hits was thus conducted as follows. First, an HMM library was constructed for all available KeGG orthology groups (thousands of HMMs for different enzyme functions). The generation of these HMMs was the same as the generation of the four HMMs described above. This library of HMMs was run vs. all the hits of the LIMS HMMSCAN, and all hit that have a bitscore for any of the thousands HMMs that is higher than 120% of the bitscore of each of the LIMS HMMSCAN HMMs, were removed.

The second HMM model was a Custom HMM library created according to the methods of the present disclosure. Briefly, an initial training data set of haloperoxidase enzyme sequences known or predicted to exhibit haloperoxidase activity was produced. This corresponds the claimed step of "accessing a training data set comprising a genetic sequence input variable and a phenotypic performance output variable."

These training data set sequences were used to generate a multiple sequence alignment (MSA) which was further used to develop a custom predictive machine learning HMM model, as described infra. This is referred to in the specification as "developing a first predictive machine learning model that is populated with the training data set."

The custom HMM machine learning models were then run against (or applied to) the digital metagenomic library of Example 3 to identify a pool of candidate haloperoxidase sequences, which are herein referred to as the HMM output sequences. This corresponds to the claimed element of "applying, using a computer processor, the first predictive machine learning model to a metagenomic library containing amino acid sequences from one or more organisms to identify a pool of candidate sequences within the metagenomic library." A total 1141 sequences identified from this Custom HMM Library were selected for further analysis, while 277 were selected for further analysis from the LIMS HMMSCAN HMMs.

As a comparison, a control search using traditional BLAST protein algorithms was conducted on the digital metagenomics library of Example 3. The BLAST searches were run using the same enzymes used to create the Custom HMM Library described above. The same selection procedure was applied for each of the 24 BLAST query canonical sequences. First, the best BLAST hit (a single sequence) was selected for screening. Second, for each of the 24 sets of BLAST hits, a specific bitscore cutoff was manually determined. Since sorted BLAST bitscores are characterized by very high values, followed by a sharp drop in these bitscore values, the bitscore determined was the one corresponding for the lowest bitscore of that sharp drop. Since there were typically many BLAST hits for each of these queries, the BLAST hits were clustered by CDHIT with 40% ID, and cluster centroids were selected as described in the examples above. A total of 101 top BLAST hits were saved.

Of the identified candidate haloperoxidase sequences, 182 of the LIMS HMM SCAN hits, 368 of the Custom HMM Library hits, and 57 of the BLAST hits were chosen for experimental validation and successfully cloned. The experimental wet lab validation was conducted by obtaining the full candidate sequences from the physical copies of the digital metagenomics library, and cloning those into an expression vector as described in Example 11.

Haloperoxidase activity was tested on Rifamycin and Demeclocycline natural product substrates. The results of these assays are shown in Table 11, below.

TABLE 11

| Haloperoxidase analoging validation Haloperoxidase | | | |
|---|---|---|---|
| strategy | # tested (# recommended) | Rifamycin | Demeclocycline |
| LIMS HMMSCAN | 182 (277) | 1 | 0 |
| Custom HMM library | 368 (1141) | 3 | 3 |
| Best BLAST hits of 'canonical' enzymes | 57 (101) | 0 | 0 |

The validation experiments identified a total of seven enzymes capable of using at least one of the two tested natural products as substrates. This was thus another validation of the analoging methods of the present disclosure for haloperoxidases. This example was also an illustration of the HMM filtering methods of the present disclosure, which utilize the scores of other HMMs to filter results.

The results also showed that the machine learning platforms of the present disclosure (e.g., LIMS HMMSCAN and Custom HMM Library) are substantially superior to traditional BLAST approaches, which failed to identifying even a single analoging enzyme.

Example 16

Analoging Enzyme Discovery

This example demonstrates that advantages of the machine-learning based analoging enzyme discovery platform of the present disclosure compared to other approaches.

Five search strategies were compared in this example.

The first model was a position profiling model generated as follows. First, the structure of literature-documented AKRs was studied to identify positions that are responsible for substrate recognition. Second, a structure-based multiple sequence alignment of AKRs, including sequences of the crystal-solved structures was generated using the MAFFT algorithm and manual curation. Third, eleven positions that correspond with the residues in the positions identified in the first stage were identified in the alignment. Forth, each of the 107,828 AKR sequences were individually added to the multiple sequence alignment using the MAFFT-add algorithm. Fifth, the predicted location of the 11 amino acids in each of the 107,828 sequences that correspond with the 11 positions were saved. Sixth, each of the 11 positions was then mapped to 20 sequences (selected from 107,828 set), each representing a different amino acid present in that position. For some cases, not all the 20 amino acid variants were available.

The second model was the Custom HMM library created according to the methods described in Example 10.

The third model was a Custom AKR HMM created according to the methods described in Example 9.

The fourth model was an indel variants model. The structure of a multiple crystal-solved structures of AKR enzymes were studied, particularly near the active site. The structural alignment of these structures (PSB codes: 1PZ1, 4PMJ, 1PYF, 1GVE, 1LQA, 1YNP and 1OG6) suggests that all these proteins are share similar overall structure (all share the α/βtIM barrel fold), but differ near the region that binds the substrate. Two particular locations in the common fold were identified near the substrate binding site, where different AKR structures had different loops that were "decorating" the common fold. This indicated that substrate specificity of particular AKRs is, at least partially, determined by the sequence and lengths of two loops found near the active site. The two pairs of loop start and end positions were consistent among all the examined structures, as indicated by their structure-based sequence alignment.

Loop lengths can thus be used as a motivation for sampling variation in the substrate recognition part of AKRs. Next, the position profiling approach was used to recognize the loop length for each of the 107,828 sequences found in the metagenomic repository. This was achieved by identifying the start-end positions in the multiple sequence alignment, and identifying the start and end position of the two loops in the query sequences. This step has yielded a mapping of the length of the two loops for each of the 107,828 sequences found in the metagenomic repository. Finally, 91 sequences were selected from this set, such they sample different combinations of the lengths of the loops, for example "short loop 1" (1-10 amino acids) and "medium loop2" (11-20 amino acids).

The fifth model was a position combination profiling model. This model is based of the position profiling model. The motivation here was that different combinations of the 11 positions found in the position profiling model play a potentially significant role in substrate recognition. To sample different combinations of the 11 positions, the following steps were followed: a mapping was created between each of the 107,828 AKR homologs found in the metagenomic library, and the combination of the 11 amino acids predicted to reside in each of the of the 11 positions identified for the position profiling model. The frequency of each of these combinations was calculated, and then a list of 11-amino acid combinations was sorted by their frequency. Finally, 64 sequences, each including the most frequent 64 combinations were selected for screening.

The five models described above were then run against (or applied to) the digital metagenomic library of Example 3 to identify a pool of candidate AKR sequences, which are herein referred to as the HMM output sequences. This corresponds to the claimed element of "applying, using a computer processor, the first predictive machine learning model to a metagenomic library containing amino acid sequences from one or more organisms to identify a pool of candidate sequences within the metagenomic library." A total of 180 initial sequences were identified by the position profiling model, a total of 168 initial sequences were identified by the Custom HMM of the present disclosure, a total of 177 initial sequences were identified from the Custom AKR HMM model, 91 initial sequences were identified from the indel variants model, and 64 sequences were identified from the position combination profiling model ("HMM output sequences" or specifically, "candidate [AKR] sequences").

Of the identified candidate AKR sequences, 94 initial sequences in the position profiling model, a total of 92 initial sequences in the Custom HMM of model, a total of 136 initial sequences in the Custom AKR HMM model, a total of 49 initial sequences in the indel variants model, and a total of 35 sequences in the position combination profiling model were chosen for experimental validation. The experimental wet lab validation was conducted by obtaining the full candidate sequences from the physical copies of the digital metagenomics library, and cloning those into an expression vector as described in Example 11.

AKR activity was tested on Geldamycin, Erythromycin, Brefeldin A, and Salinomycinnatural product substrates. The results of these assays are shown in Table 12, below.

TABLE 12

AKR analoging validation
AKRs

| strategy | # tested (# recommended) | Geldanamycin | Erythromycin | Brefeldin A | Salinomycin |
|---|---|---|---|---|---|
| position profiling (single positions) | 94 (180) | 0 | 0 | 0 | |
| Custom HMM library | 92 (168) | 1 | 0 | 0 | |
| Custom AKR HMM | 136 (177) | 0 | 1 | 2 | 2 |
| Indel variants | 4 (91) | 0 | 0 | 1 | |
| Position combination profiling | 3 (64) | 0 | 0 | 0 | |
| Results showing identified enzymes with their substrate specificity | | | | | |
| Enzyme 1 (Custom AKR HMM) | | | 1 | 1 | 1 |
| Enzyme 2 (Custom HMM library) | | 1 | | | |
| Enzyme 3 (indel) | | | | 1 | |
| Enzyme 4 (Custom AKR HMM) | | | | 1 | 1 |

The results confirmed that the predictive machine learning models of the present disclosure are capable of identifying novel analoging enzymes, including AKRs.

Example 17

Untargeted MGC Discovery Workflow

This example is a working illustration of the untargeted MGC discovery workflows of the present disclosure. In some embodiments the untargeted workflow describes assigning genes within predicted MGCs a biosynthetic potential score, a resistance gene score, and (in some embodiments) one or more of a biosynthetic operon score, a core biosynthetic gene distance score, and an essential gene score. The application of these scoring elements are illustrated below.

The goal of this example was to test whether the workflow of the present disclosure could be used to enrich the resistance genes through a process of elimination that filters out genes that are less likely to be resistance genes. Although this example uses known resistance genes in order to be able to validate results, the same steps can be applied to any number of predicted MGCs to identify yet unknown resistance genes.

The DNA sequences containing the borrelidin (AJ580915), thiomarinol (FN689524), kalimantacin (GU479979), eponomycin (KF647220), bengamide (KP143770), griselimycin (KP211414), salinosporamide (NC_009380), pentalenolactone (NZ_BJTV01000007), and albomycin (NZ_CP029361) gene clusters were submitted to antiSMASH. All of these are known to contain a target-copy resistance gene. This resulted in 9 gene clusters being identified, with a total of 388 genes. Of those 388 genes, 9 of them are resistance genes, meaning the resistance genes made up 2.3% of the total genes.

First, all genes were analyzed and assigned a biosynthetic potential score, a transport-related potential and regulatory potential score. All genes annotated as having a biosynthetic function (partial biosynthetic potential score), a transport related function, or a regulatory gene function by antiSMASH were given low priority scores and were removed from consideration entirely. As noted above, the biosynthetic potential transport-related potential and regulatory potential were calculated by the annotation given by antiSMASH using the MiBig database. This left 149 genes out of the original 388. Of those 149 genes, 8 are resistance genes, meaning the resistance genes made up 5.4% of the remaining genes. This step resulted in a greater than two-fold enrichment for resistance genes.

Figure 29:
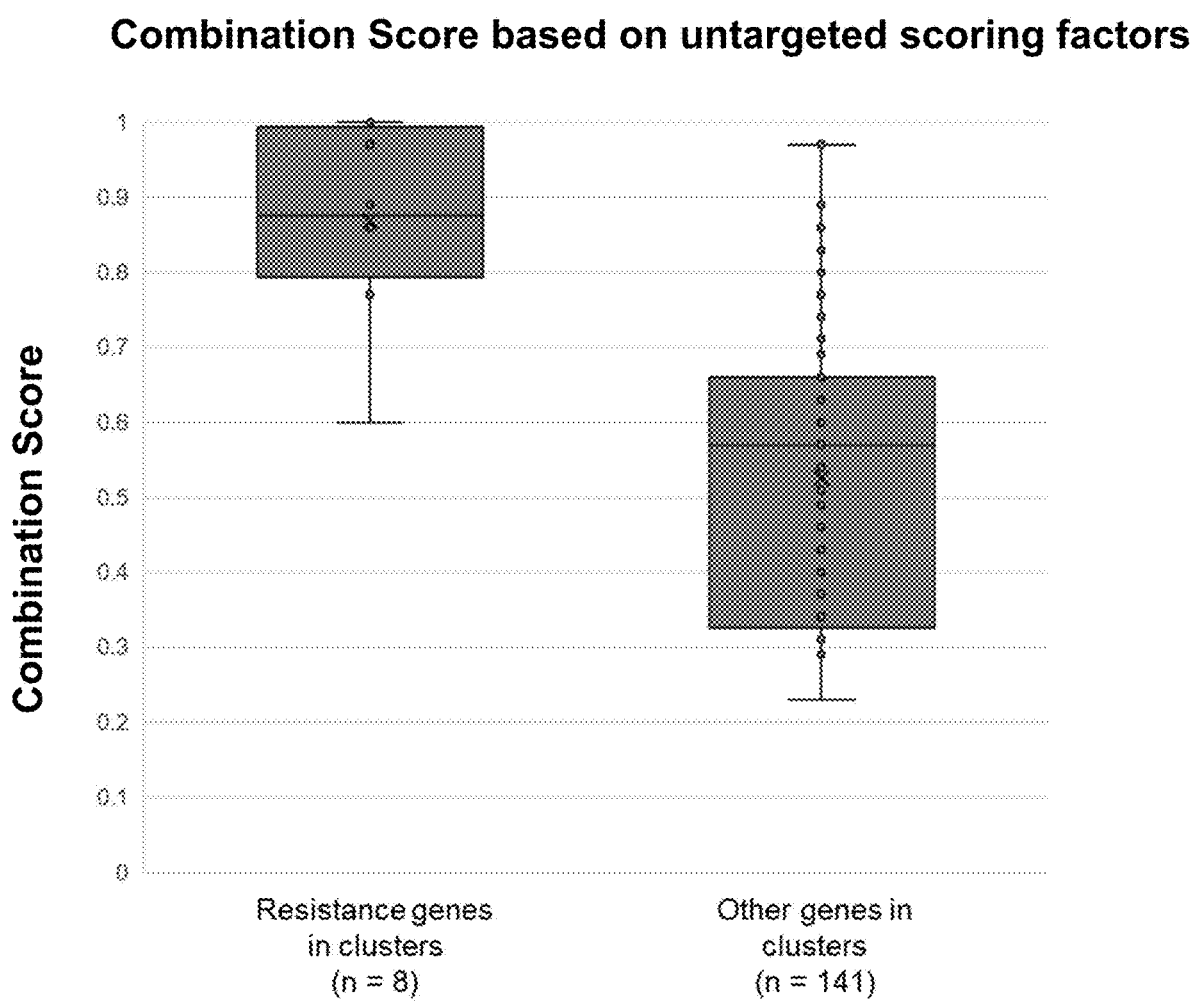
FIG. 29—shows Combination Scores of genes within predicted MGCs, as part of the untargeted MGC discovery workflows of Example 17.

The remaining 149 genes were then analyzed and given a biosynthetic potential score, a biosynthetic operon score, a core biosynthetic gene distance score, and an essential gene score, which were then combined into a combination score, as shown in FIG. 29. For the purpose of this example, no resistance gene score was given, as the data set included known resistance genes that would have been filtered out. All genes annotated as having a biosynthetic function given low priority scores and/or removed from consideration entirely. The biosynthetic potential was calculated by the annotation given by antiSMASH using the MiBig database. Genes with more BLAST hits with MiBig genes (higher biosynthetic potential) were given lower scores than those with fewer hits (less likely to have biosynthetic potential). Combination scores of less than 0.85 were eliminated, while combination scores greater than 0.85 were kept. Of the 10 genes that survived our scoring, 6 are the known resistance genes for the 9 MGCs used in this example (~60% of genes being resistance genes). Thus, the untargeted workflow of the present disclosure was able to enrich the incidence of resistance genes more than thirty-fold using the scoring factors of the present disclosure.

Example 18

Additional Example of Resistance Gene Workflow (HDAC1) Target Gene

This example illustrates the ability to use the resistance gene workflows of the present disclosure to identify natural-product-encoding multi-gene clusters that target a specific therapeutic target. This example shows the identification of candidate MGCs predicted to produce natural products targeting the human HDAC1 gene.

HDAC1 is responsible for the deacetylation of lysine residues on the N-terminal part of the core histones (H2A, H2B, H3 and H4). Histone deacetylation gives a tag for epigenetic repression and plays an important role in transcriptional regulation, cell cycle progression and developmental events. HDACs enzymes have been recognized as potentially useful therapeutic targets for a broad range of human disorders. Emerging studies have demonstrated that different types of HDAC inhibitors show beneficial effects in various experimental models of neurological disorders.

To identify MGCs encoding for natural products targeting HDAC1, we applied the resistance gene workflow using the HDAC1 (PFAM PF00850) as the target resistance gene. An HMM corresponding to this PFAM was built as disclosed herein. The resulting HMM model was used to search of the metagenomic database of Example 3, to return homologous amino acid sequences using a bitscore cutoff of 50. Sequences matching this cutoff were dubbed "candidate resistance genes" which were identified via the step of "querying a digital metagenomics library for a signal indicative of a natural product multi-gene cluster feature set."

The contigs that contained candidate resistance genes are referred to as "a plurality of signal-associated multi-gene cluster digital feature sets." These multi-gene cluster digital feature sets encode predicted HDAC1 homologs from the HMM searches above and were were then run through antiSMASH v5 to identify feature sets that were within computationally determined natural product multi-gene cluster feature sets ("determining a computationally predicted biosynthetic functionality of a plurality of genes from a signal-associated multi-gene cluster digital feature set and digitally assembling a computationally determined natural product multi-gene cluster (MGC) feature set comprising one or more biosynthetic operon(s)"). contain a predicted BGC.

This workflow identified 87 potential MGCs that contain a candidate HDAC1 resistance gene that is within or directly adjacent to the borders of the MGC as predicted by antiSMASH. We selected a cluster named internally dubbed ZGCHDAC11789 for downstream analysis.

After an individual *E. coli* isolate containing the desired MGC encoding the ZGCHDAC11789 was successfully retrieved from the physical copy of the metagenomic library, the DNA coding the biosynthetic pathway of interest was cloned into an *S. cerevisiae/E. coli/Streptomyces* shuttle vector via TAR (transformation-associated recombination) cloning in *S. cerevisiae*. After DNA transformation and recombination in *S. cerevisiae*, the assembled plasmid DNA was extracted from *S. cerevisiae* and transformed into *E. coli* for propagation. The sequence of the resulting plasmid was confirmed by next-generation sequencing.

Next, this plasmid was introduced into the heterologous expression host *Streptomyces albus* J1074 (wildtype or engineered strain) via conjugal transfer. Specifically, *E. coli* S17 strain containing the plasmid of interest was co-cultured with the spores of *S. albus* to stimulate the conjugation process. After growth selection on solid media containing the desired antibiotic markers, *S. albus* exconjugant colonies were propagated to generate glycerol spore stocks and the presence of gene clusters confirmed by colony PCR.

For initial small-scale plate screen to detect novel compound production, to each single well of a 24-deepwell plate, 3 mL TSB seed culture containing the appropriate selection antibiotic was added and inoculated with *S. albus* spores with and without the cluster to a final $OD_{450}$~0.05. The plate was sealed with two layers of air-permeable seals and incubated at 30° C. with 250 rpm (2.5 cm throw) and 80-85% humidity for 2-3 days until dense culture formation. The culture was then inoculated at 10% (v/v) inoculum into 3 mL each of the fermentation media (mO42, O42, R5A, and ISP4) containing the appropriate selection antibiotic in a new set of 24-deepwell plate. This main plate culture was incubated for seven days before harvesting.

Once the fermentation completes, the culture in the plate was extracted with equal volume of ethyl acetate twice and the combined organic layer was concentrated to dryness before subjected to LC/MS analysis to verify the production of a novel molecule(s).

Once novel molecule production was confirmed, we utilized a large-scale fermentation in DASGIP bioreactors (Eppendorf) to generate semi-purified material. Spores (0.05 OD) were first inoculated into 250 mL baffled flasks (×8) each containing 75 ml of Terrific Soy Broth (TSB), APRA (50 ug/mL) and antifoam (PD-602) and grown for 24 hours at 30 degrees Celsius. Each seed culture was then split equally into two DASGIPs (16 total) and grown for 96 hours at 30 degrees Celsius with agitation ranging from 200-800 RPM. Fermentation broth from individual reactors was pooled and centrifuged at 4000 RPM (4° C.) for 20 min. The clarified broth was carefully decanted from the cell pellet, and subsequently extracted with activated Dianion HP20 resin (Alfa Aesar) (5% w/v) for approximately 16 h. Aqueous media was removed from the resin via filtration through cheese cloth and discarded. The resin was washed thoroughly with ultrapure water (~12 L) to ensure removal of any highly water-soluble media components. The washed resin was then extracted 2× with 2 L of HPLC acetone followed by 2× L HPLC methanol, by adding solvent directly to the resin and gently stirring for 15-30 min. Organic solvent was filtered from the resin via vacuum filtration, pooled, and concentrated in-vacuo until only water remained. This aqueous layer was extracted 3× with equal volumes ethyl acetate. Organic layers were pooled, dried over anhydrous $MgSO_4$, filtered, and dried to completion in-vacuo yielding a brown oil (855.1 mg).

This crude extract was brought up in minimal methanol (~2 mL), loaded onto silica and subsequently fractionated using a Biotage Selekt automated chromatography Instrument fixed with a Biotage Sfär Silica HC-D high capacity duo column (10 g) and a Biotage Isolera tray rack compatible with 240 mL collection bottles. Fractionation was accomplished using a three-solvent stepwise gradient, consisting of heptane (solvent A), ethyl acetate (solvent B), and methanol (solvent C). Material was eluted with a flow rate of 20 mLmin$^{-1}$, collecting 4 CV fractions (60 mL) for each step. The initial step of the gradient consisted of 7:3 (A:B), this was followed by six additional steps consisting of 1:1 (A:B), 1:4 (A:B), 100% B, 1:9 (B:C), 3:7 (B:C), and finally 1:4 (B:C) yielding 7 fractions (F1-F7) with increasing polarity. Fractions were concentrated in-vacuo and analyzed for the ion of interest (m/z 811.5828) via LCMS using a ThermoFisher Q-Exactive orbitrap MS and a vanquish LC with an analytical Agilent Eclipse 2.1×50 mm C18 column at a flow rate of 0.5 mLmin$^{-1}$. The compound was identified in F6 (245.8 mg).

F6 was further fractionated on an Agilent 1260 Infinity II Series prep HPLC using a reversed-phase Phenomenex 10 µm C18(2) 100 Å column (250×10.00 mm) run at a flow rate of 8 mL/min, collecting 12 mL fractions. The sample was dissolved in HPLC grade methanol to a final concentration of 100 mgmL$^{-1}$. Purification was accomplished by injecting 500 µL aliquots of this solution (using a 500 µL loop). Material was eluted using $H_2O$ (solvent A) and acetonitrile (solvent B). The gradient used an initial isocratic step of 10% acetonitrile for 2 min. This was followed by a linear increasing gradient from 10% to 95% acetonitrile over 28 min (30 min total). The column was washed with an isocratic step of 95% acetonitrile for an additional 10 min (40 min total), finally followed by an isocratic equilibration step of 10% acetonitrile for 10 min (50 min total). Fractions were analyzed for the ion of interest by LCMS (as previously described). Fractions containing the appropriate m/z were pooled and dried yielding 3.7 mg of off-white solid. Purified compounds were analyzed via LCMS and ELSD (Agilent 1290 Infinity II LC-ELSD) detection for purity assessments.

HDAC1 activity was measured using a commercially available fluorogenic activity assay kit (HDAC1 Fluorogenic kit, BPS Bioscience). Controls and test reactions were set up as follows. All relevant reagents were thawed to room temperature prior to experiment. HDAC1 was diluted with HDAC assay buffer to 1.4 ng/ul and 25× HDAC substrate 3 was diluted to a 200 µM solution. Enzyme was prepared immediately before beginning assay to limit time HDAC1 and HDAC Developer were not in use. The commercial inhibitor, Trichostatin A, was also diluted 10-fold in HDAC assay buffer. Three controls were prepared: 35 µL of HDAC assay buffer+5 uL of BSA (1 mg/ml)+5 uL of HDAC substrate 3+5 uL of 100% DMSO (blank), 30 µL of HDAC assay buffer+5 uL of BSA (1 mg/ml)+5 uL of HDAC substrate 3+5 uL of HDAC1+5 uL of 100% DMSO (positive control) and 30 µL of HDAC assay buffer+5 uL of BSA (1 mg/ml)+5 uL of HDAC substrate 3+5 uL of HDAC1+5 uL of Trichostatin A (inhibitor control). An additional control was set up to monitor inhibitor fluorescence: 45 uL of HDAC assay buffer+5 uL of test compound. Finally the inhibition samples were prepared containing 30 µL of HDAC assay buffer+5 uL of BSA (1 mg/ml)+5 uL of HDAC substrate 3+5 uL of HDAC1+5 uL of test compound (inhibition sample) in triplicates.

Figure 30:
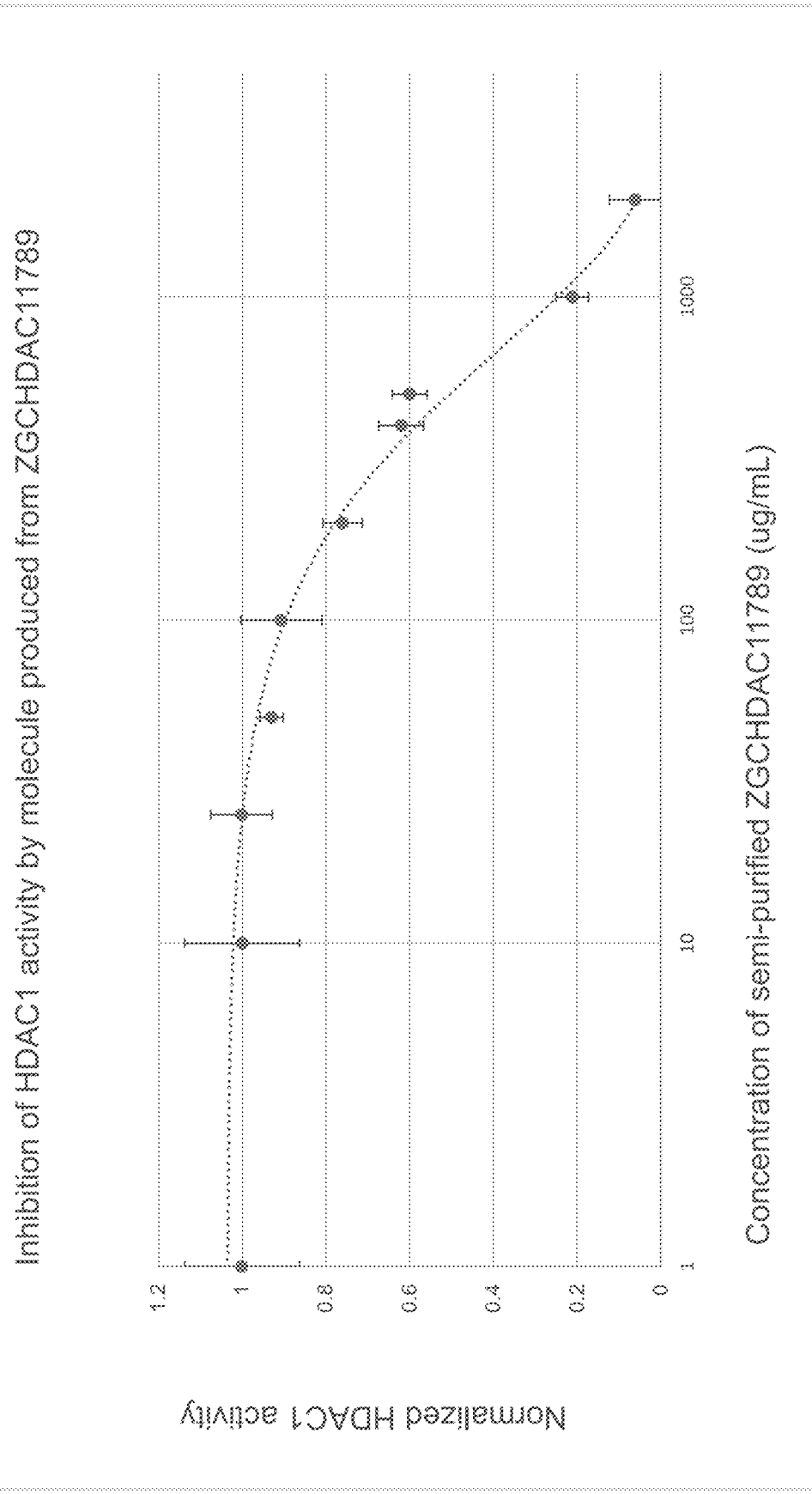
FIG. 30—depicts an activity curve of a newly identified natural product encoded by a MGC identified via the resistance gene workflow using HDAC1 as the target gene. The methods of the present disclosure are able to identify natural products specifically targeting selected therapeutic targets.

All controls and samples were mixed and incubated at 37° C. for 30 min. After incubation, 50 uL of 2× HDAC Developer was added to each reaction and incubated at 22° C. for 15 min; fluorescent measurements were then taken. The results of this assay are shown in FIG. 30.

HDAC1 activity was inhibited with increasing concentration of the semi-purified molecule derived from ZGCH-DAC11789. Thus, the resistance gene workflow of the present disclosure was able to identify MGCs encoding for natural products capable of affecting/targeting a desired therapeutic target.

Example 19

Additional Example of Resistance Gene Workflow for SOD2 (Superoxide Dismutase)

This example provides another illustration of how to use the resistance gene workflows of the present disclosure to identify natural-product-encoding multi-gene clusters that target a specific therapeutic target. This example shows the identification of candidate MGCs predicted to produce natural products targeting the human SOD2 gene.

Superoxide Dimutase 2 (SOD2) is a member of the iron/manganese superoxide dismutase family. It encodes a mitochondrial protein that forms a homotetramer and binds one manganese ion per subunit. This protein binds to the superoxide byproducts of oxidative phosphorylation and converts them to hydrogen peroxide and diatomic oxygen. Mutations in this gene have been associated with idiopathic cardiomyopathy (IDC), premature aging, sporadic motor neuron disease, and cancer.

To identify MGCs encoding for natural products targeting SOD2, we applied the resistance gene workflow using the SOD2 (PFAM PF00081) as the target resistance gene. An HMM corresponding to this PFAM was built as disclosed herein. The resulting HMM model was used to search of the metagenomic database of Example 3, to return homologous amino acid sequences using a bitscore cutoff of 50. Sequences matching this cutoff were dubbed "candidate resistance genes" which were identified via the step of "querying a digital metagenomics library for a signal indicative of a natural product multi-gene cluster feature set."

The contigs that contained candidate resistance genes are referred to as "a plurality of signal-associated multi-gene cluster digital feature sets." These multi-gene cluster digital feature sets encode predicted SOD2 homologs from the HMM searches above and were then run through antiSMASH v5 to identify feature sets that were within computationally determined natural product multi-gene cluster feature sets ("determining a computationally predicted biosynthetic functionality of a plurality of genes from a signal-associated multi-gene cluster digital feature set and digitally assembling a computationally determined natural product multi-gene cluster (MGC) feature set comprising one or more biosynthetic operon(s)").

This workflow identified 96 potential MGCs that contain a homolog of SOD2 that is within or directly adjacent to the borders of the MGC as predicted by antiSMASH. We selected a cluster named ZGCSOD21789 for downstream analysis.

After an individual E. coli isolate containing the desired cosmid encoding the ZGCSOD21789 was successfully retrieved from the metagenomic library, the DNA coding the biosynthetic pathway of interest was cloned into an S. cerevisiae/E. coli/Streptomyces shuttle vector via TAR (transformation-associated recombination) cloning in S. cerevisiae. After DNA transformation and recombination in S. cerevisiae, the assembled plasmid DNA was extracted from S. cerevisiae and transformed into E. coli for propagation. The sequence of the resulting plasmid was confirmed by next-generation sequencing.

Next, this plasmid was introduced into the heterologous expression host Streptomyces albus J1074 (wildtype or engineered strain) via conjugal transfer. Specifically, E. coli S17 strain containing the plasmid of interest was co-cultured with the spores of S. albus to stimulate the conjugation process. After growth selection on solid media containing the desired antibiotic markers, S. albus exconjugant colonies were propagated to generate glycerol spore stocks and the presence of gene clusters confirmed by colony PCR.

For initial small-scale plate screen to detect novel compound production, to each single well of a 24-deepwell plate, 3 mL TSB seed culture containing the appropriate selection antibiotic was added and inoculated with S. albus spores with and without the cluster to a final $OD_{450}$~0.05. The plate was sealed with two layers of air-permeable seals and incubated at 30° C. with 250 rpm (2.5 cm throw) and 80-85% humidity for 2-3 days until dense culture formation. The culture was then inoculated at 10% (v/v) inoculum into 3 mL each of the fermentation media (mO42, O42, RSA, and ISP4) containing the appropriate selection antibiotic in a new set of 24-deepwell plate. This main plate culture was incubated for seven days before harvesting.

Once the fermentation completes, the culture in the plate was extracted with equal volume of ethyl acetate twice and the combined organic layer was concentrated to dryness before subjected to LC/MS analysis to verify the production of a novel molecule(s).

Once novel molecule production was confirmed, we utilized a larger scale fermentation in 2.8 L UltraYield (Thomson) shake flasks to generate crude lysate for assays. To do this, the seed train was started in 25 mL TSB media in a baffled 250 mL shake flask. After the culture was inoculated with the spore stock to a $OD_{450}$~0.04, the seed flask was incubated at 30° C. with 175 rpm (5 cm throw) and 80-85% humidity for at least 24 hours until dense culture formation. Then this entire seed culture was inoculated into 0.5 L of fermentation media in a 2.8 L UltraYield shake flask at 5% inoculum. The UltraYield shake flasks were sealed with a vent cap or double air-permeable seals and incubated under the same condition for seven days before harvesting.

The fermentation broth was extracted using Dianion HP20 resin (Alfa Aesar) by adding 5% w/v to cultures 16 hours prior harvest. Resin and biomass were collected by transferring contents of the cultures to 500 mL centrifuge bottles (Corning) followed by centrifugation at 3000 rpm for 10 minutes using an Avanti J-E centrifuge. Culture supernatant was decanted and discarded. Cell and resin pellet was washed 2x by adding 250 mL ultrapure water directly to the bottles and shaking, centrifuging, then decanting off the supernatant waste. Washed cell and resin pellet was then extracted 2x with 250 mL HPLC acetone and 2x250 mL methanol, sequentially, by adding solvent directly to the bottles, sonicating for 15 minutes, centrifuging, decanting, and pooling all solvent extract. Organic extract was concentrated in-vacuo down to remaining aqueous extract. This aqueous extract was extracted 2x with equal volumes ethyl acetate, pH adjusted to 5, then extracted two additional times with ethyl acetate. Pooled ethyl acetate extract was concentrated in-vacuo.

Superoxide dismutase 2 (SOD2) activity was determined using a commercially available colorimetric activity kit (*Superoxide Dismutase Colorimetric Activity kit, ThermoFisher*). Controls and test reactions were set up as follows. All relevant reagents were thawed to room temperature prior to mixing. The 10x substrate concentrate and 25x Xanthine Oxidase concentrate were diluted in their respective buffers supplied in the kit; SOD2 (Sigma Aldrich) was diluted to 1 U/mL with the supplied assay buffer. The enzyme was diluted immediately before beginning assay to limit time SOD2 and Xanthine Oxidase is not in use. Two commercial inhibitors, 2-Methoxyestradiol and LCS-1 (Sigma Aldrich), were also diluted to 30 µM in assay buffer. Three controls were prepared: 8 uL of SOD2+50 uL of 1x substrate+2 uL of assay buffer (positive control), 100%

DMSO (vehicle control) or commercial inhibitor (inhibitor control). In addition, two controls were prepped containing 10 uL of assay buffer+50 uL of 1× substrate (substrate control) or 58 ul of assay buffer+2 uL of test compound (test compound control). Finally, 8 uL of SOD2+50 uL of 1× substrate+2 uL of test compound (ZGCSOD21789 crude lysate or WT crude lysate) were prepared; all controls and samples were made in triplicates. Once all controls and samples were ready, 25 uL of 1× Xanthine Oxidase was added to initiate the superoxide generation; reactions were incubated at 22° C. for 20 min.

Figure 31:
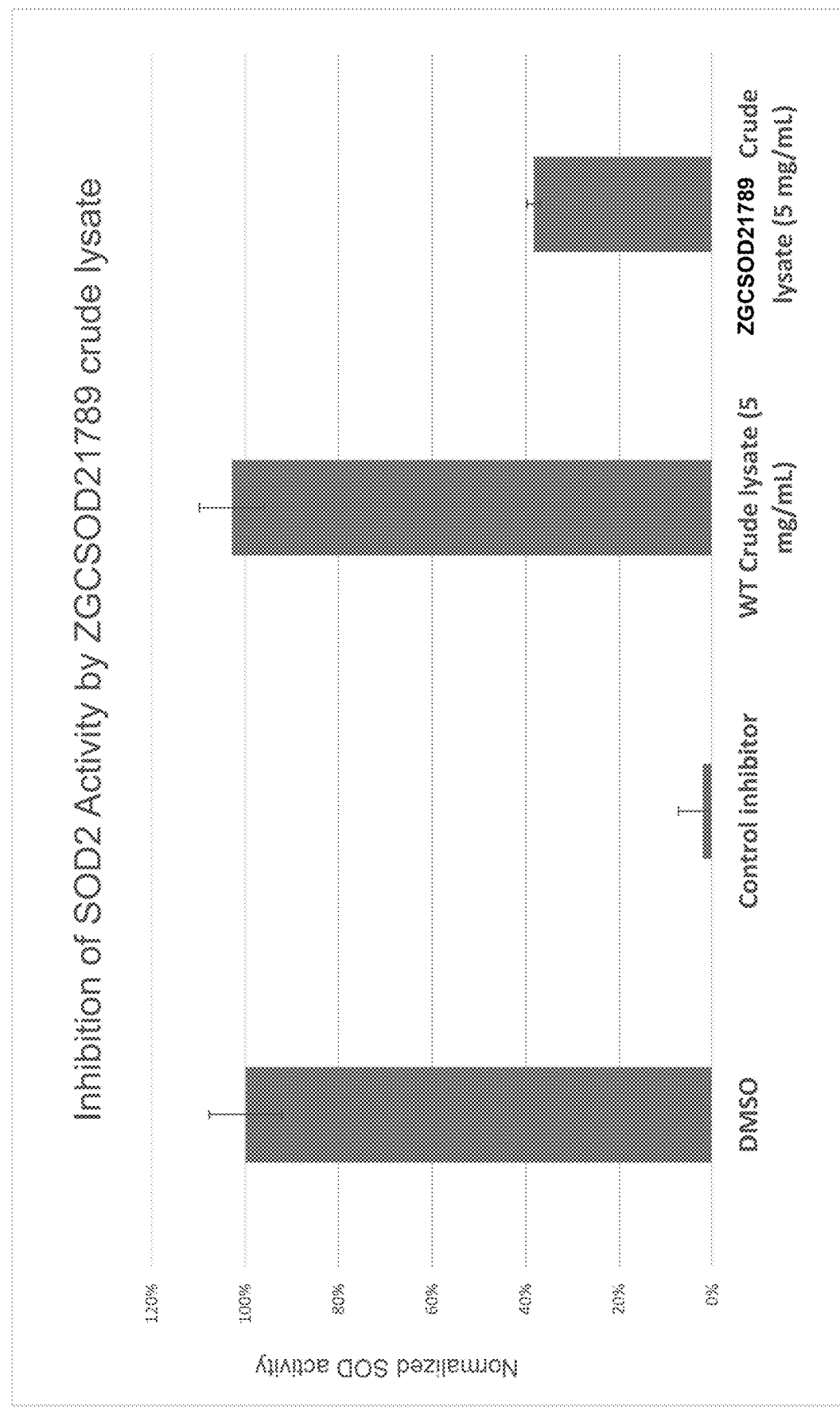
FIG. 31—depicts normalized SOD activity of a newly identified natural product encoded by a MGC identified via the resistance gene workflow using SOD2 as the target gene. The methods of the present disclosure are able to identify natural products specifically targeting selected therapeutic targets.

Absorbance measurements were taken at 0 min (prior to Xanthine Oxidase addition) and 20 min. The results of this assay are shown in FIG. 31.

Crude lysate from the ZGCSOD21789 fermentation broth inhibited SOD2 activity whereas crude lysate from a WT control did not. Thus, the resistance gene workflow of the present disclosure was able to identify MGCs encoding for natural products capable of affecting/targeting a desired therapeutic target.

Example 20

Metagenomic Library Assembly and Versioning

Advances in next-generation sequencing (NGS) have allowed scientists to study and profile microbial communities by direct sequencing of microbial DNA. Raw NGS data, known as sequence reads, can be directly compared to reference sequences to identify features and genes of interest computationally. Sequence reads can also be assembled into longer sequences, known as contigs, by identifying overlaps in those sequences. The contigs can subsequently be annotated to identify genes and features of interest. The collection of sequences derived from microbial communities is often referred to as a metagenomic library.

Figure 19:
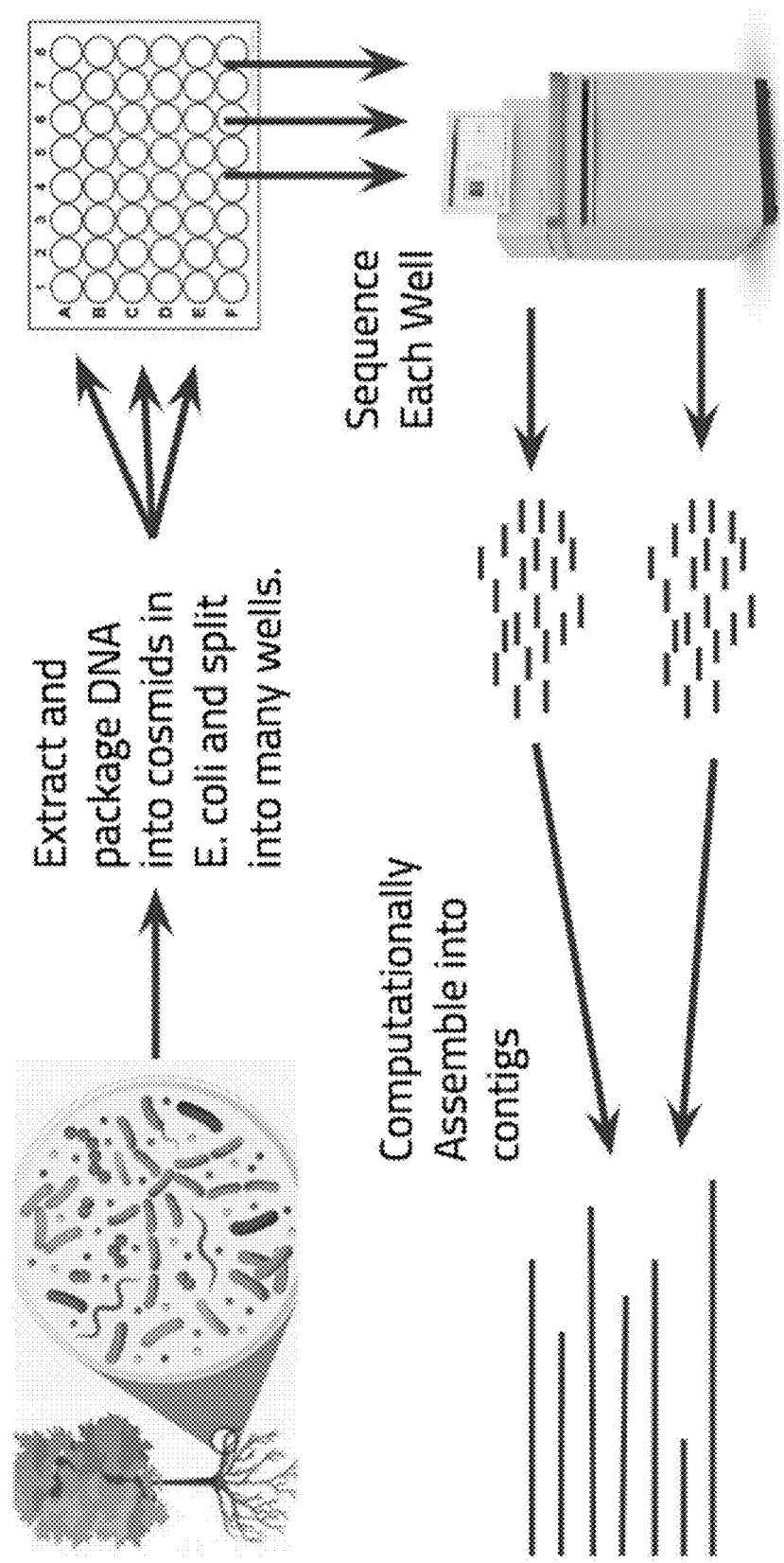
FIG. 19—is a schematic of a cosmid-based digital metagenomic library construction.

Instead of direct sequencing, metagenomic libraries can also be constructed by packaging microbial DNA into cosmids, which are then cloned and replicated by a host organism, often *Escherichia coli*, and split across multiple physical samples thereby reducing the complexity of any single physical sample. Once a physical cosmid metagenomic library is prepared, the cosmid and microbial community DNA can be sequenced and analyzed per sample, and the results computationally combined to produce a digital representation of the physical metagenomic library (FIG. 19).

A key challenge in analyzing and building metagenomics libraries lies in tracking data provenance through the computational analysis in a way that scales to large amounts of sequence data generated over time.

The methods described here addresses the problem of running a metagenomic assembly and annotation pipeline at scale in such a way as to produce consistent collections of sequences where each individual sequence can be linked to the specific bioinformatics tools used to generate the data, the specific physical samples that were sequenced, and the microbial community that was under investigation.

This example describes a computational infrastructure and system designed to assemble and annotate metagenomic cosmid libraries at scale, although any metagenomic or isolate sequence data can be processed with the same mechanism.

NGS Data Processing Pipeline

The process consists of processing raw sequence data through 5 steps:

1) Data Preparation and Sample ID Assignment

Raw NGS data is generated using NGS sequencers such as the Illumina NovaSeq. Prior to sequencing, individual samples and the sequencing run are labeled with unique IDs. Once new NGS data is generated, they are stored either on on-premise clusters or with cloud providers, such as Amazon Web Services. Importantly, the invention specifies how this data is labeled and stored such that subsequent steps can consume that data at scale. Namely, data is organized by NGS sequencing run, and then individual sequence data files (FASTQ) are labeled by unique sample IDs either automatically generated or assigned manually.

Additionally, metadata for the samples is provided in a separate file that maps individual sample IDs to unique identifiers for the original microbial community source, which can be later used to associate environmental or experimental conditions with each sample.

At this step, a unique "Data Build" ID is also generated that will associate all the intermediate and final data files during processing together. See the "Data Artifact Tracking System" below for details on the file and data tracking component of the invention.

2) Preprocessing and NGS Reads Filtering

Raw NGS data for each sequenced sample is preprocessed to filter out reads based on data quality or contamination. A range of bioinformatics tools can be used for this step depending on the specific metagenomic preparation, such as FastQC or bbtools. The overall invention is indifferent to tool selection as long as it produces a new FASTQ file for the sample.

In order to run this step at scale (hundreds or more samples), the bioinformatics tools are executed in containers (specifically with Docker, although any containerization system with versioned images would work). The workload is batched by first identifying the sequencing run and Data Build IDs, accessing the metadata for those samples to be processed, then distributing the work to run in parallel per sample using a batch execution system. The particular choice of which batch execution system to use is not critical to the invention, so long as individual compute nodes have access to the sequence data and shared file system or store.

A key part of the invention is that the provenance information for each sample is provided to the preprocessing step, indicating both which input data files to process and also the version of the tools used and metadata describing each sample. That information is then saved together with the output files of the preprocessing step before being indexed and versioned using the "Data Artifact Tracking System" described later. The combined output of this step is then available for both downstream processing and manual inspection.

3) Sequence Assembly

The filtered raw sequence data can then be assembled separately per sample to produce much longer consensus sequences known as contigs. There are many bioinformatics tools that can assemble sequence reads data into contigs, including Spades and MegaHit.

This step is triggered by launching a container that first identifies the Data Build ID, uses the Data Artifact Tracking System to identify inputs, and runs in a massively parallel way across all samples using a batch execution system. Assembled contigs are then stored with metrics in a set of files that are then indexed by the Data Artifact Tracking System.

Another important aspect to the invention is that individual contigs are labeled with a universally unique ID (UUID), which can be generated in parallel with no central ID provider and still are guaranteed to be unique, which is an important consideration in large scale assembly.

4) Sequence Annotation

Contigs can then be analyzed to identify locations of predicted genes or other genomic features, such as promoter sites. Contigs can also be analyzed to assign a predicted taxonomy of the organism. As for previous steps, there are many bioinformatics tools available to annotate DNA sequences, including Prodigal and kaiju.

Like sequence assembly, this step is triggered by launching a container that first identifies the data build in progress using the Data Build ID, uses the Data Artifact Tracking System to identify inputs, and is run in a massively parallel way across all samples using a batch execution system.

Also like previous steps, the output data is indexed and versioned with the Data Artifact Tracking System.

5) Sequence Merging into a Versioned Data Build

The final step is the aggregation of data across samples into a single collection for the Data Build. This step is similarly started by launching a container that uses the unique Data Build ID to combine output files from multiple steps into a single set of files that form the final output of the system. These files include combined FASTA files of each contig sequence, GenBank and FASTA files for genomic feature annotations, CSV files of taxonomic predictions for each contig sequence, and a set of CSV files associating each contig and annotation to a unique Data Build ID, sample ID, and metagenomic library with any additional metadata that may be available.

At this point, the Data Build is considered complete and immutable for this collection of data and Data Build ID.

Data Artifact Tracking System

One of the core components for the system to operate is a Data Artifact Tracking System which associates groups of files with metadata in a searchable way so that output data can be quickly cataloged and input data readily identified.

The Data Artifact Tracking System groups a set of files together with a JSON file containing provenance metadata (including, among other information, a creation timestamp, Data Build ID, checksums of included files, and container versions of bioinformatics tools used to generate the files) and a UUID that uniquely identifies the set of files. This group of files is then referred to as a Data Artifact.

Data Artifacts, once indexed, are considered immutable and therefore provide a searchable record of how that data was generated together with that data.

Data Artifacts are created in a two-step process. A common file system that is writable by compute jobs allows output to be written and grouped into folders. This virtual space is considered the Data Artifact Staging Area. It allows files to be written and created on this file system in parallel. These Data Artifacts are not yet searchable, but are considered indexable as soon as an "artifact.json" file containing the required metadata information is created.

In the second step, an indexer crawls the Data Artifact Staging Area for any new Data Artifacts that have an associated "artifact.json" file. This indexer is run as a separate job either manually or launched at some regular time interval. During indexing, the metadata and files are validated. If valid, the Data Artifact files are then moved to a separate permanent location on the file system, backed up as appropriate to other cloud storage locations, and metadata is indexed in a document based database, such as MongoDB.

Critically, this now allows other compute jobs to uniquely identify each Data Artifact and search for data by querying that document database.

To illustrate by example, an assembly task would look up all Data Artifacts containing filtered FASTQ sequence data for a specific sample, run the assembly tool, then create an output folder in the Data Artifact Staging Area to store the resultant FASTA files. Finally the task will write an "artifact.json" file indicating the Data Artifact is ready for processing. The indexer task would then move the Data Artifact to a permanent location to make those files available for downstream steps. Then, an annotation task could look up the assembled contigs for one or more samples from the Data Artifact database, and similarly process those contigs to identify genes or other genomic features.

Operation of the Assembly and Annotation Pipeline Over Time

Often when building complex metagenomic libraries over hundreds of samples, individual samples may not be sequenced as well as desired due to normal experimental variance, experimental mistakes, or other similar issues. Sequencing at this scale is still relatively expensive, so it can be cost prohibitive to resequence or reprepare the entire library. Instead, individual samples of cosmid DNA may be reprepared or simply resequenced to add additional data and improve the quality of the final assemblies. This is complicated by the fact that resequencing is not always done immediately during primary analysis, but may be called for months or years later if there is new interest in particular samples or it is later determined that certain samples are not of high enough quality.

This poses a computational challenge in data tracking and processing that our invention addresses. Traditional systems without built-in provenance or means for effective versioning at the sample, contig, or gene level will struggle with combining the results over time across many metagenomic libraries in a way that maintains the integrity of existing data while still augmenting the results with recent new data.

The invention described here, however, by using the Data Artifact tracking system, allows for incremental building of a metagenomic library over time effectively. As new samples are resequenced, new Data Build IDs are created, the pipeline steps are rerun on select samples using the new data or combinations of new and old data together as appropriate. In the final data aggregation steps, select information is pulled from previous Data Builds and combined in a way that preserves untouched samples, but replaces or aggregates new results, into a new Data Build that can be used immediately.

Figure 20:
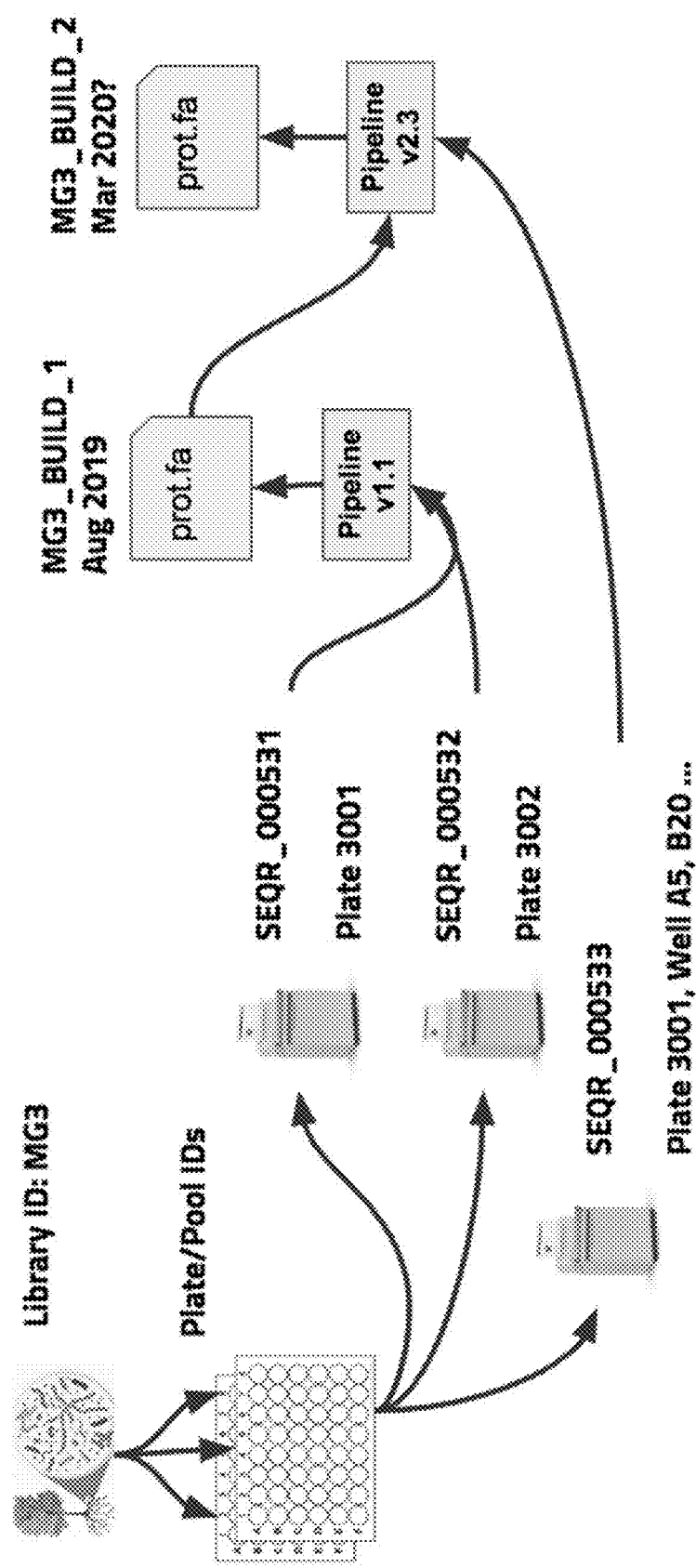
FIG. 20—is an illustration of how the system can aggregate new information in a streamlined, cost-effective way from resequencing of specific samples over a long period of time to generate a single new searchable metagenomic library.

This process is illustrated in FIG. 20. Take a metagenomic library named MG3, that is prepared as a cosmid library over hundreds of samples across a set of plates. Each sample on those plates is then sequenced. Due to the large number of samples, these samples are split into two sequencing runs at a remote sequencing center. The system assigns unique IDs SEQR_000531 and SEQR_000532 to uniquely identify which samples were sequenced on which sequencing run. The preprocessing, assembly, and annotation steps are run combining that data into a single Data Build that is given Data Build ID MG3_BUILD_1. That result is now usable downstream for sequence search or other applications. Let's assume in the future that several dozen samples have been requested to be resequenced because of data quality issues detected later. Those samples are prepped and resequenced with a different sequencing center. That new sequencing run is assigned a unique ID as well, and the pipeline processes those samples together with past information from those samples to create improved assemblies and new annotations. The data collectively now is aggregated from MG3_BUILD_1 and results for the new samples to generate MG3_BUILD_2, which in turn is available for downstream analysis. This process can be repeated indefinitely with this invention to produce single or combined metagenomic or other libraries incrementally over time while still tracking the provenance of each specific contig and annotation to the specific pipeline version, sequencing run, and metagenomic library.

Further Embodiments of the Invention

Other subject matter contemplated by the present disclosure is set out in the following numbered embodiments:

1. An in silico method for searching a multi-gene cluster feature set digital metagenomics library and identifying a natural product of interest, comprising:
  a) querying a digital metagenomics library for a signal indicative of a natural product multi-gene cluster feature set;
  b) supplying the output of said query as a plurality of signal-associated multi-gene cluster digital feature sets;
  c) determining and assigning biologic relevancy to the signal-associated multi-gene cluster digital feature sets, by:
    determining a computationally predicted biosynthetic functionality of a plurality of genes from a signal-associated multi-gene cluster digital feature set and digitally assembling a computationally determined natural product multi-gene cluster (MGC) feature set comprising one or more biosynthetic operon(s); and/or
    determining a computationally predicted biological resistance gene functionality of at least one gene from a signal-associated multi-gene cluster digital feature set to thereby identify a computationally determined biological resistance gene; and
  d) identifying an MGC encoding for the natural product of interest based upon a computationally determined biological resistance gene being located within a threshold parameter of a computationally determined natural product multi-gene cluster feature set comprising a digitally assembled biosynthetic operon.

2. The method according to embodiment 1, wherein the multi-gene cluster feature set digital metagenomics library is a long-assembly digital metagenomics library comprising an N50 length of at least about 10 kb, 15 kb, 20 kb, 25 kb, 30 kb, 35 kb, or 40 kb.

3. The method according to any one of embodiments 1-2, wherein the digital metagenomics library is at least about 50 Mb, 75 Mb, 100 Mb, 200 Mb, 300 Mb, 400 Mb, 500 Mb, 600 Mb, 700 Mb, 800 Mb, 900 Mb, 1000 Mb, 1100 Mb, 1200 Mb, 1300 Mb, or 1400 Mb in size.

4. The method according to embodiment 1, wherein the multi-gene cluster feature set digital metagenomics library comprises an N50 length of at least about 10 kb, 15 kb, or 20 kb and the digital metagenomics library is at least about 500 MB in size.

5. The method according to embodiment 1, wherein the multi-gene cluster feature set digital metagenomics library comprises: sequenced and digitally assembled contig sequences having an N50 length of at least about 10 kb, 15 kb, or 20 kb and the digital metagenomics library is at least about 1 TB in size.

6. The method according to embodiment 1, wherein the multi-gene cluster feature set digital metagenomics library comprises: sequenced and digitally assembled sequences having an N50 length of at least about 10 kb, 15 kb, or 20 kb and the digital metagenomics library is about 500 MB to about 1 TB in size.

7. The method according to embodiment 1, wherein the multi-gene cluster feature set digital metagenomics library comprises: sequenced and digitally assembled contig sequences having an N50 length of at least about 10 kb 15 kb, or 20 kb, wherein a majority of the assembled sequence in the library is from uncultured microorganisms.

8. The method according to embodiment 1, wherein the multi-gene cluster feature set digital metagenomics library comprises: sequenced and digitally assembled contig sequences having an N50 length of at least about 10 kb, 15 kb, or 20 kb, wherein substantially all of the sequence in the library is from uncultured microorganisms.

9. The method according to embodiment 1, wherein the multi-gene cluster feature set digital metagenomics library comprises: sequenced and digitally assembled contig sequences having an N50 length of at least about 10 kb, 15 kb, or 20 kb, wherein a majority of the sequence in the library is from uncultured microorganisms, physical copies of said digitally assembled contig sequences being arrayed into a corresponding physical cosmid, fosmid, BAC, YAC, or a combination thereof, library.

10. The method according to embodiment 1, wherein the multi-gene cluster feature set digital metagenomics library comprises: sequenced and digitally assembled contig sequences having an N50 length of at least about 10 kb, 15 kb, or 20 kb, wherein a majority of the sequence in the library is from uncultured microorganisms, at least some of which are derived from a soil sample, physical copies of said digitally assembled contig sequences being arrayed into a corresponding physical cosmid library.

11. The method according to embodiment 1, wherein the querying in step a) comprises: utilizing a HMM model to search the digital metagenomics library for a gene of interest, and wherein step c) comprises determining a computationally predicted biosynthetic functionality of a plurality of genes from a signal-associated multi-gene cluster digital feature set and digitally assembling a computationally determined natural product multi-gene cluster feature set comprising one or more biosynthetic operons.

11.1. The method according to embodiment 1, wherein the querying in step a) comprises identifying contigs within the digital metagenomics library that contain a homolog of a gene of interest wherein homology is determined based on a candidate sequence exhibiting at least 95%, 90%, 85%, 80%, 79%, 78%, 77%, 76%, 75%, 74%, 73%, 72%, 71%, or 70% sequence identity with the gene of interest, and wherein step c) comprises determining a computationally predicted biosynthetic functionality of a plurality of genes from a signal-associated multi-gene cluster digital feature set and digitally assembling a computationally determined natural product multi-gene cluster feature set comprising one or more biosynthetic operons.

12. The method according to embodiment 1, wherein the querying in step a) comprises: utilizing a predictive model to search the digital metagenomics library for a homolog of a gene of interest, and wherein step c) comprises determining a computationally predicted biosynthetic functionality of a plurality of genes from a signal-associated multi-gene cluster digital feature set and digitally assembling a computationally determined natural product multi-gene cluster feature set comprising one or more biosynthetic operons.

13. The method according to embodiment 1, wherein the querying in step a) comprises: utilizing a predictive model to search the digital metagenomics library for a homolog of a gene of interest, or genes of interest, wherein the encoded protein of said gene(s) does not have a biosynthetic function in producing the natural product of interest, and wherein step c) comprises determining a computationally predicted biosynthetic functionality of a plurality of genes from a signal-associated multi-gene cluster digital feature set and digitally assembling a computationally determined natural product multi-gene cluster feature set comprising one or more biosynthetic operons.

13.1 The method according to any embodiment 12 or 13, wherein the predictive model is selected from the group consisting of a HMM, a PSSM (Position specific scoring matrices), a SVM (Support Vector Machines), a Bidirectional LSTM (Long Short Term Memory), a CNN (Convolutional Neural Network), a RNN (Recurrent Neural Networks), a Dynamic Bayesian networks, artificial neural networks, including recurrent neural networks such as those based on Long Short Term Memory Models (LSTM), and combinations thereof.

13.1.1 The method according to embodiment 12 or 13, wherein the predictive model is a HMM 13.2 The method according to embodiment 13.1.1, wherein the homolog exhibits a bitscore greater than 30, 40, 50, 60, 70, 80, 90, 100, 110, 120, or 130 on the HMM model.

13.3. The method according to embodiment 1, wherein the querying in step a) comprises: identifying contigs within the digital metagenomics library that contain a homolog of a gene of interest wherein homology is determined based on a candidate sequence exhibiting at least 95%, 90%, 85%, 80% 79%, 78%, 77%, 76%, 75%, 74%, 73%, 72%, 71%, or 70% sequence identity with the gene of interest, wherein the encoded protein of said gene of interest does not have a biosynthetic function in producing the natural product of interest, and wherein step c) comprises determining a computationally predicted biosynthetic functionality of a plurality of genes from a signal-associated multi-gene cluster digital feature set and digitally assembling a computationally determined natural product multi-gene cluster feature set comprising one or more biosynthetic operons.

14. The method according to embodiment 1, wherein the querying in step a) comprises: utilizing a predictive model to search the digital metagenomics library for a known resistance gene, or variant, or homolog thereof, and wherein step c) comprises determining a computationally predicted biosynthetic functionality of a plurality of genes from a signal-associated multi-gene cluster digital feature set and digitally assembling a computationally determined natural product multi-gene cluster feature set comprising one or more biosynthetic operons.

14.1 The method according to embodiment 14, wherein the predictive model is selected from the group consisting of a HMM, a PSSM (Position specific scoring matrices), a SVM (Support Vector Machines), a Bidirectional LSTM (Long Short Term Memory), a CNN (Convolutional Neural Network), a RNN (Recurrent Neural Networks), a Dynamic Bayesian networks, artificial neural networks, including recurrent neural networks such as those based on Long Short Term Memory Models (LSTM), and combinations thereof.

14.1.1 The method according to embodiment 14, wherein the predictive model is a HMM 14.2 The method according to embodiment 14.1.1, wherein the homolog exhibits a bitscore greater than 30, 40, 50, 60, 70, 80, 90, 100, 110, 120, or 130 on the HMM model.

14.3. The method according to embodiment 1, wherein the querying in step a) comprises: identifying contigs within the digital metagenomics library that contain a homolog of a known resistance gene, or variant, or homolog thereof wherein homology is determined based on a candidate sequence exhibiting at least 95%, 90%, 85%, or 80% sequence identity with the known resistance gene or variant or homolog thereof, and wherein step c) comprises determining a computationally predicted biosynthetic functionality of a plurality of genes from a signal-associated multi-gene cluster digital feature set and digitally assembling a computationally determined natural product multi-gene cluster feature set comprising one or more biosynthetic operons.

15. The method according to embodiment 1, wherein the querying in step a) comprises: utilizing a predictive model to search the digital metagenomics library for a computationally predicted or hypothesized resistance gene, or variant, or homolog thereof, and wherein step c) comprises determining a computationally predicted biosynthetic functionality of a plurality of genes from a signal-associated multi-gene cluster digital feature set and digitally assembling a computationally determined natural product multi-gene cluster feature set comprising one or more biosynthetic operons.

15.1 The method according to embodiment 15, wherein the predictive model is selected from the group consisting of a HMM, a PSSM (Position specific scoring matrices), a SVM (Support Vector Machines), a Bidirectional LSTM (Long Short Term Memory), a CNN (Convolutional Neural Network), a RNN (Recurrent Neural Networks), a Dynamic Bayesian networks, artificial neural networks, including recurrent neural networks such as those based on Long Short Term Memory Models (LSTM), and combinations thereof.

15.1.1 The method according to embodiment 15, wherein the predictive model is a HMM 15.2 The method according to embodiment 15.1.1, wherein the homolog exhibits a bitscore greater than 30, 40, 50, 60, 70, 80, 90, 100, 110, 120, or 130 on the HMM model.

15.3. The method according to embodiment 1, wherein the querying in step a) comprises: identifying contigs within the digital metagenomics library that contain a homolog of a computationally predicted or hypothesized resistance gene wherein homology is determined based on a candidate sequence exhibiting at least 95%, 90%, 85%, or 80% sequence identity with the computationally predicted or hypothesized resistance gene, and wherein step c) comprises determining a computationally predicted biosynthetic functionality of a plurality of genes from a signal-associated multi-gene cluster digital feature set and digitally assembling a computationally determined natural product multi-gene cluster feature set comprising one or more biosynthetic operons.

16. The method according to embodiment 1, wherein the querying in step a) comprises: utilizing a predictive model to search the digital metagenomics library for a gene of interest contained on a single contig, and wherein step c) comprises determining a computationally predicted biosynthetic functionality of a plurality of genes from a signal-associated multi-gene cluster digital feature set and digitally assembling a computationally determined natural product multi-gene cluster feature set comprising one or more biosynthetic operons.

16.1 The method according to embodiment 16, wherein the predictive model is selected from the group consisting of a HMM, a PSSM (Position specific scoring matrices), a SVM (Support Vector Machines), a Bidirectional LSTM (Long Short Term Memory), a CNN (Convolutional Neural Network), a RNN (Recurrent Neural Networks), a Dynamic Bayesian networks, artificial neural networks, including recurrent neural networks such as those based on Long Short Term Memory Models (LSTM), and combinations thereof.

16.1.1 The method according to embodiment 16, wherein the predictive model is a HMM.

16.2 The method according to embodiment 16.1.1, wherein the homolog exhibits a bitscore greater than 30, 40, 50, 60, 70, 80, 90, 100, 110, 120, or 130 on the HMM model.

17. The method according to embodiment 1, wherein the signal-associated multi-gene cluster digital feature sets comprise a database of a plurality of contigs that are computationally predicted to contain multi-gene clusters, comprising one or more biosynthetic operons.

18. The method according to embodiment 1, wherein the querying in step a) comprises: identifying all sequences that are computationally predicted to contain multi-gene clusters, comprising one or more biosynthetic operons (e.g., comprising MGCs), and wherein step c) comprises determining a computationally predicted biological resistance gene functionality of at least one gene from a signal-associated multi-gene cluster digital feature set to thereby identify a computationally determined biological resistance gene.

19. The method according to embodiment 1, wherein the signal-associated multi-gene cluster digital feature sets comprise a database of a plurality of single contigs containing a putative resistance gene.

20. The method according to any one of embodiments 1-19, wherein the signal-associated multi-gene cluster digital feature sets are filtered to eliminate contigs that are less than about 15 kb in size.

21. The method according to any one of embodiments 1-19, wherein the signal-associated multi-gene cluster digital feature sets are filtered to eliminate contigs that are less than about 15 kb in size and also eliminate duplicate contig results that share greater than about 99%, 98%, 97%, 96%, 95%, 94%, 93%, 92%, 91% or 90% sequence identity with a first contig within the signal-associated multi-gene cluster digital feature set.

21.1 The method according to any one of embodiments 1-19, wherein the MGC encoding for the natural product of interest are filtered to eliminate duplicate MGCs that share greater than about 99%, 98%, 97%, 96%, 95%, 94%, 93%, 92%, 91% or 90% sequence identity with a first identified MGC identified in step (d).

22. The method according to any one of embodiments 1-21.1, wherein assembling a computationally determined natural product multi-gene cluster feature set comprising one or more biosynthetic operon(s) in step c) is performed with a genetic algorithm.

23. The method according to any one of embodiments 1-21.1, wherein assembling a computationally determined natural product multi-gene cluster feature set comprising one or more biosynthetic operon(s) in step c) is performed with a genetic cluster prediction algorithm.

24. The method according to any one of embodiments 1-21.1, wherein assembling a computationally determined natural product multi-gene cluster feature set comprising one or more biosynthetic operon(s) in step c) is performed with a multi-gene cluster (MGC) prediction algorithm (e.g., such as those listed in Table 1).

25. The method according to any one of embodiments 1-21.1, wherein assembling a computationally determined natural product multi-gene cluster feature set comprising one or more biosynthetic operon(s) is performed with the antibiotics and secondary metabolite analysis shell (AntiSMASH) algorithm and pipeline or the DeepBGC algorithm and pipeline.

26. The method according to any one of embodiments 1-25, wherein determining a computationally predicted biological resistance gene functionality of at least one gene from a signal-associated multi-gene cluster digital feature set to thereby identify a computationally determined biological resistance gene is performed after assembling a computationally determined natural product multi-gene cluster feature set comprising a biosynthetic operon, utilizing a biosynthetic gene cluster (BGC) prediction algorithm.

26.1 The method according to any one of embodiments 1-25, wherein assembling a computationally determined natural product multi-gene cluster feature set comprising a biosynthetic operon, utilizing a biosynthetic gene cluster (BGC) prediction algorithm is performed after determining a computationally predicted biological resistance gene functionality of at least one gene from a signal-associated multi-gene cluster digital feature set, to thereby identify a computationally determined biological resistance gene a computationally determined natural product multi-gene cluster feature set comprising a biosynthetic operon has been assembled utilizing a biosynthetic gene cluster (BGC) prediction algorithm.

27. The method according to any one of embodiments 1-26.1, further comprising:
e) identifying a plurality of computationally determined natural product multi-gene cluster feature sets within the digital metagenomics library that do not comprise the computationally determined biological resistance gene.

28. The method according to any one of embodiments 1-26.1, further comprising:
e) identifying a plurality of computationally determined natural product multi-gene cluster feature sets that do not comprise the computationally determined biological resistance gene, but which have a predetermined degree of genetic relatedness to a computationally determined natural product multi-gene cluster feature set that comprises the computationally determined biological resistance gene, to thereby create a transitive resistance gene natural product multi-gene cluster feature set.

29. The method according to any one of embodiments 1-26.1, further comprising:
e) identifying a plurality of computationally determined natural product multi-gene cluster feature sets that do not comprise the computationally determined biological resistance gene, but which have a predicted degree of genetic relatedness to an identified computationally determined natural product multi-gene cluster feature set that comprises the computationally determined biological resistance gene, to thereby create a transitive resistance gene natural product multi-gene cluster feature set; and
f) identifying a natural product of interest from the transitive resistance gene natural product multi-gene cluster feature set.

29.1 The method according to any one of embodiment 1-29, wherein the computationally determined biological resistance gene is under the regulatory control of a biosynthetic operon within the multi-gene cluster feature set.

29.2 The method of any one of embodiments 1-29.1, comprising step:
e) manufacturing a host cell, wherein the host cell comprises the MGC encoding for the natural product of interest identified in step (d), or a refactored version thereof;

29.3 The method embodiment 29.2, comprising step:
f) culturing the manufactured host cells of step (e).

29.4 The method of embodiment 29.3, comprising step:
g) analyzing spent cultures from the cultures of step (f) for the presence of a natural product, wherein said natural product is not present in cultures of control host cells lacking the MGC sequence present in the manufactured host cell.

29.5 The methods of any one of embodiments 1-29.4, wherein the digital metagenomics library was produced according to the methods of any one of embodiments 32-61.

29.6 The method of any one of embodiments 27-28, comprising step:

f) manufacturing a host cell, wherein the host cell comprises at least one of the computationally determined natural product multi-gene cluster feature sets identified in step (e), or a refactored version thereof;

29.7 The method embodiment 29.6, comprising step:

g) culturing the manufactured host cells of step (0.

29.8 The method of embodiment 29.7, comprising step:

h) analyzing spent cultures from the cultures of step (g) for the presence of a natural product, wherein said natural product is not present in cultures of control host cells lacking the MGC sequence present in the manufactured host cell.

30. An in silico method for identifying candidate multi-gene cluster (MGC) feature sets with unknown putative resistance genes or no resistance genes, said method comprising the steps of:

a) computationally predicting natural product multi-gene cluster feature sets within a digital metagenomic library;

b) annotating genes within the predicted natural product multi-gene cluster feature sets, each multi-gene cluster feature set comprising left and right boundaries, wherein the annotation step optionally comprises annotating genes located within 1-2 open reading frames (ORFs) of the boundaries of said multi-gene cluster feature sets;

c) filtering annotated genes from the predicted natural product multi-gene cluster feature sets to leave only genes that:

i) do not have a predicted biosynthetic function, and ii) are optionally not homologs to known target resistance genes, thereby producing a plurality of filtered genes of interest; and d) selecting a natural product multi-gene cluster features set that comprises at least one of the plurality of filtered genes of interest, thereby identifying a candidate MGC sequence with a putative resistance gene or no resistance gene.

30.1 An in silico method for identifying a candidate multi-gene cluster feature set with a predicted resistance gene, said method comprising the steps of:

a) computationally predicting natural product multi-gene cluster feature sets within a digital metagenomic library;

b) assigning a biosynthetic potential score to genes within the multi-gene cluster feature sets; said biosynthetic potential score based on the calculated likelihood that a gene is a biosynthetic enzyme;

c) assigning a known resistance gene score to genes within the multi-gene cluster feature sets, said known resistance score based on the shared sequence identity of a gene with a known resistance gene;

d) selecting candidate multi-gene cluster feature set comprising a predicted resistance gene, said predicted resistance gene exhibiting a pre-set combination score threshold, said combination score based on the combination of the biosynthetic potential score and the known resistance gene score.

30.2 The method of embodiment 30.1, comprising the step of: assigning a biosynthetic operon score to genes within the multi-gene cluster feature sets, said biosynthetic operon score based on a gene's proximity to a biosynthetic operon within its multi-gene cluster feature set; and wherein the combination score is also based on the biosynthetic operon score.

30.3 The method of any one of embodiments 30.1 and 30.2, comprising the step of: assigning a core biosynthetic gene distance score to genes within the multi-gene cluster feature sets, said a core biosynthetic gene distance score based on a gene's proximity to a core biosynthetic gene within its multi-gene cluster feature set; and wherein the combination score is also based on the core biosynthetic gene distance score.

30.4 The method of any one of embodiments 30.1-30.3, comprising the step of: assigning an essential gene score to genes within the multi-gene cluster feature sets, said essential gene score based on a gene's highest sequence identity to a list of known essential gene sequences; and wherein the combination score is also based on the essential gene score.

30.5 The method of any one of embodiments 30.1-30.4, wherein the predicted resistance gene within the selected candidate multi-gene cluster feature set shares less than 99%, 98%, 97%, 96%, 95%, 94%, 93%, 92%, 91%, 90%, 89%, 88%, 87%, 86%, 85%, 84%, 83%, 82%, 81%, or 80% sequence identity with a known resistance gene.

30.6 The method of any one of embodiments 30.1-30.5, wherein the predicted resistance gene within the selected candidate multi-gene cluster feature set shares less than 90%, 89%, 88%, 87%, 86%, 85%, 84%, 83%, 82%, 81%, or 80% sequence identity with a biosynthetic enzyme.

30.6.1 The method of any one of embodiments 30.1-30.6, wherein biosynthetic enzyme is a biosynthetic enzyme for the natural product encoded by multi-gene cluster feature set containing the predicted resistance gene.

30.6.2 The method of any one of embodiments 30.1-30.6.1, wherein biosynthetic enzyme is a homolog of a biosynthetic enzyme associated with natural product encoded by multi-gene cluster feature sets (e.g., MiBig).

30.7 The method of any one of embodiments 30.1-30.6.2 wherein the predicted resistance gene within the selected candidate multi-gene cluster feature set returns fewer than 8, 6, 4, or 2 BLAST hits in miBIG, as assessed by antismash.

30.8 The method of any one of embodiments 30.1-30.7 wherein the predicted resistance gene within the selected candidate multi-gene cluster feature set has a combination score wherein the calculated likelihood that a gene is a biosynthetic enzyme is low and wherein the shared sequence identity with a known resistance gene is low when compared to known biosynthetic enzymes or known resistance genes, respectively.

30.9 The method of any one of embodiments 30.1-30.8 wherein the predicted resistance gene within the selected candidate multi-gene cluster feature set is located within or immediately adjacent (i.e. no other ORFS in between) to a biosynthetic operon within the selected candidate multi-gene cluster feature set.

30.10 The method of any one of embodiments 30.1-30.9 wherein the predicted resistance gene within the selected candidate multi-gene cluster feature set is located inside of a biosynthetic operon or within 500 bp of a biosynthetic operon contained in the selected candidate multi-gene cluster feature set.

30.11 The method of any one of embodiments 30.1-30.10 wherein the predicted resistance gene within the selected candidate multi-gene cluster feature set is located within 1 kB, 2 kb, 3 kb, 4 kb, or 5 kb of a core biosynthetic enzyme.

30.12 The method of any one of embodiments 30.1-30.11, wherein the predicted resistance gene within the selected candidate multi-gene cluster feature set shares at least 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, or 70% sequence identity with an essential gene.

30.12.1 The method of any one of embodiments 30.1-30.12, wherein the method comprises assigning a transport gene potential score to genes within the multi-gene cluster feature sets, said transport gene potential score based on a gene's likelihood of being a transport-related gene (e.g., via sequence identity) and wherein the combination score is also based on the core biosynthetic gene distance score.

30.12.2 The method of any one of embodiments 30.1-30.12.1, wherein the method comprises assigning a regulatory gene potential score to genes within the multi-gene cluster feature sets, said regulatory gene potential score based on a gene's likelihood of being a regulatory gene (e.g., via sequence identity) and wherein the combination score is also based on the core biosynthetic gene distance score.

30.12.3 The method of any one of embodiments 30.1-30.12.2, comprising the step of: assigning a resistance mechanism score to genes within the multi-gene cluster feature sets, said resistance mechanism score assigned based on a gene's similarity to resistance genes with different resistance mechanisms from the desired resistance mechanism, and wherein the combination score is also based on the resistance mechanism score.

30.12.4 The method of any one of embodiments 30.1-30.12.3, comprising the step of: assigning a resistance mechanism score to genes within the multi-gene cluster feature sets, said resistance mechanism score assigned based on a gene's similarity to resistance genes with the desired resistant mechanism, and wherein the combination score is also based on the resistance mechanism score.

30.12.5 The method of embodiments 30.1-30.12.4, wherein the desired resistance mechanism is target variant-based resistance.

30.13 An in silico method for identifying a resistance gene for a natural product encoded by a multi-gene cluster, said method comprising the steps of:
a) computationally predicting natural product multi-gene clusters within a digital metagenomic library;
b) assigning a biosynthetic potential score to genes within the multi-gene cluster feature sets; said biosynthetic potential score based on the calculated likelihood that a gene is a biosynthetic enzyme;
c) assigning a known resistance gene score to genes within the multi-gene cluster feature sets, said known resistance score based on the shared sequence identity of a gene with a known resistance gene;
d) selecting a predicted resistance gene that exhibits a pre-set combination score threshold, said combination score based on the combination of the biosynthetic potential score and the known resistance gene score.

30.14 The method of embodiment 30.13, comprising the step of: assigning a biosynthetic operon score to genes within the multi-gene cluster feature sets, said biosynthetic operon score based on a gene's proximity to a biosynthetic operon within its multi-gene cluster feature set; and wherein the combination score is also based on the biosynthetic operon score.

30.15 The method of any one of embodiments 30.13 and 30.14, comprising the step of: assigning a core biosynthetic gene distance score to genes within the multi-gene cluster feature sets, said a core biosynthetic gene distance score based on a gene's proximity to a core biosynthetic gene within its multi-gene cluster feature set; and wherein the combination score is also based on the core biosynthetic gene distance score.

30.16 The method of any one of embodiments 30.13-30.15, comprising the step of: assigning an essential gene score to genes within the multi-gene cluster feature sets, said essential gene score based on a gene's highest sequence identity to a list of known essential gene sequences; and wherein the combination score is also based on the essential gene score.

30.17 The method of any one of embodiments 30.13-30.16, wherein the predicted resistance gene shares less than 99%, 98%, 97%, 96%, 95%, 94%, 93%, 92%, 91%, 90%, 89%, 88%, 87%, 86%, 85%, 84%, 83%, 82%, 81%, or 80% sequence identity with a known resistance gene.

30.18 The method of any one of embodiments 30.13-30.17, wherein the predicted resistance gene shares less than 90%, 89%, 88%, 87%, 86%, 85%, 84%, 83%, 82%, 81%, or 80% sequence identity with a biosynthetic enzyme.

30.19 The method of any one of embodiments 30.13-30.18, wherein biosynthetic enzyme is a biosynthetic enzyme for the natural product encoded by multi-gene cluster feature set containing the predicted resistance gene.

30.19.1 The method of any one of embodiments 30.13-30.19, wherein biosynthetic enzyme is a biosynthetic enzyme associated with natural product encoded by multi-gene cluster feature sets (e.g., MiBig).

30.20 The method of any one of embodiments 30.13-30.19.1 wherein the predicted resistance gene returns fewer than 8, 6, 4, or 2 BLAST hits in miBIG, as assessed by antismash.

30.21 The method of any one of embodiments 30.13-30.20 wherein the predicted resistance gene has a combination score wherein the calculated likelihood that a gene is a biosynthetic enzyme is low and wherein the shared sequence identity with a known resistance gene is low.

30.22 The method of any one of embodiments 30.13-30.21 wherein the predicted resistance gene is located within or immediately adjacent (i.e. no other ORFS in between) to a biosynthetic operon within the selected candidate multi-gene cluster feature set.

30.23 The method of any one of embodiments 30.13-30.22 wherein the predicted resistance gene is located inside of a biosynthetic operon or within 500 bp of a biosynthetic operon.

30.24 The method of any one of embodiments 30.13-30.23 wherein the predicted resistance gene is located within 1 kB, 2 kb, 3 kb, 4 kb, or 5 kb of a core biosynthetic enzyme.

30.25 The method of any one of embodiments 30.13-30.24, wherein the predicted resistance gene within the selected candidate multi-gene cluster feature set shares at least 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, or 70% sequence identity with an essential gene.

30.26 The method of any one of embodiments 30.13-30.25, wherein the method comprises assigning a transport gene potential score to genes within the multi-gene cluster feature sets, said transport gene potential score based on a gene's likelihood of being a transport-related gene (e.g., via sequence identity) and wherein the combination score is also based on the core biosynthetic gene distance score.

30.27 The method of any one of embodiments 30.13-30.26, wherein the method comprises assigning a regulatory gene potential score to genes within the multi-gene cluster feature sets, said regulatory gene potential score based on a gene's likelihood of being a regulatory gene (e.g., via sequence identity) and wherein the combination score is also based on the core biosynthetic gene distance score.

30.28 The method of any one of embodiments 30.13-30.27, comprising the step of: assigning a resistance mechanism score to genes within the multi-gene cluster feature sets, said resistance mechanism score assigned based on a gene's similarity to resistance genes with different resistance mechanisms from the desired resistance mechanism, and wherein the combination score is also based on the resistance mechanism score.

30.29 The method of any one of embodiments 30.13-30.27, comprising the step of: assigning a resistance mechanism score to genes within the multi-gene cluster feature sets, said resistance mechanism score assigned based on a gene's similarity to resistance genes with the desired resistant mechanism, and wherein the combination score is also based on the resistance mechanism score.

30.30 The method of embodiments 30.28 or 30.29, wherein the desired resistance mechanism is target variant-based resistance.

31. The method according to any one of embodiments 30-30.30, wherein the digital metagenomic library is a long assembly digital metagenomics library comprising an N50 length of at least about 10 kb, 15 kb, 20 kb, 25 kb, 30 kb, 35 kb, or 40 kb.

31.1 The method according to any one of embodiment 30-31, wherein the digital metagenomic library is at least about 50 Mb, 75 Mb, 100 Mb, 200 Mb, 300 Mb, 400 Mb, 500 Mb, 600 Mb, 700 Mb, 800 Mb, 900 Mb, 1000 Mb, 1100 Mb, 1200 Mb, 1300 Mb, or 1400 Mb in size.

31.2 The method according to any one of embodiments 30-30.30, wherein the digital metagenomic library comprises: sequenced and digitally assembled contig sequences having an N50 length of at least about 10 kb, 15 kb, or 20 kb and the digital metagenomics library is at least about 500 MB in size.

31.3 The method according to any one of embodiments 30-30.30, wherein the digital metagenomic library comprises: sequenced and digitally assembled contig sequences having an N50 length of at least about 10 kb, 15 kb, or 20 kb and the digital metagenomics library is at least about 1 TB in size.

31.4 The method according to any one of embodiments 30-30.30, wherein the digital metagenomic library comprises: sequenced and digitally assembled sequences having an N50 length of at least about 10 kb, 15 kb, or 20 kb and the digital metagenomics library is about 500 MB to about 1 TB in size.

31.5 The method according to any one of embodiments 30-30.30, wherein the digital metagenomic library comprises: sequenced and digitally assembled contig sequences having an N50 length of at least about 10 kb 15 kb, or 20 kb, said assembled contig sequences; wherein a majority of the sequence in the library is from uncultured microorganisms.

31.6 The method according to any one of embodiment 30-30.30, wherein the digital metagenomic library comprises: sequenced and digitally assembled contig sequences having an N50 length of at least about 10 kb, 15 kb, or 20 kb, wherein substantially all of the sequence in the library is from uncultured microorganisms.

31.7 The method according to any one of embodiment 30-30.30, wherein the digital metagenomic library comprises: sequenced and digitally assembled contig sequences having an N50 length of at least about 10 kb, 15 kb, or 20 kb, wherein a majority of the sequence in the library is from uncultured microorganisms, physical copies of said digitally assembled contig sequences being arrayed into a corresponding physical cosmid, fosmid, BAC, YAC, or a combination thereof, library.

31.8 The method according to any one of embodiment 30-30.30, wherein the digital metagenomic library comprises: sequenced and digitally assembled contig sequences having an N50 length of at least about 10 kb, 15 kb, or 20 kb, wherein a majority of the sequence in the library is from uncultured microorganisms, at least some of which are derived from a soil sample, physical copies of said digitally assembled contig sequences being arrayed into a corresponding physical cosmid library.

31.9 The method according to any one of embodiments 30-31.8, wherein step (c) further filters annotated genes so as to leave only genes that iii) are co-regulated with another gene within the multi-gene cluster feature set that has a predicted biosynthetic function.

31.10 The method of any one of embodiments 30-31.9, comprising step:
e) manufacturing a host cell, wherein the host cell comprises the candidate MGC sequence of step (d), or a refactored version thereof.

31.10.1 The method of any one of embodiments 30-31.9, comprising step:
e) manufacturing a host cell, wherein the host cell comprises the selected candidate multi-gene cluster feature set of step (d), or a refactored version thereof.

31.10.2 The method of any one of embodiments 30-31.9, comprising step:
e) manufacturing a host cell, wherein the host cell comprises the multi-gene cluster feature set comprising the selected predicted resistance gene of step (d), or a refactored version thereof.

31.11 The method of embodiment 31.10-31.10.2, comprising step:
f) culturing the manufactured host cells of step (e).

31.12 The method of embodiment 31.11, comprising step:
g) analyzing spent cultures from the cultures of step (f) for the presence of a natural product, wherein said natural product is not present in cultures of control host cells lacking the candidate MGC sequence(s) present in the manufactured host cell.

31.13 The methods of any one of embodiments 30-31.12, wherein the digital metagenomics library was produced according to the methods of any one of embodiments 32-61.

32. A method for assembling a long-assembly DNA contig metagenomic library, comprising:
a) providing an unsequenced and unassembled metagenomic DNA sample comprising unique whole genomes;
b) reducing the genomic complexity of the metagenomic DNA sample by:
i) cloning DNA fragments from the metagenomic DNA sample into a plurality of vectors to create a metagenomic vector fragment library;
ii) pooling the vectors from the metagenomic vector fragment library into a plurality of discrete mini-metagenome subunits that comprise from about 1,000 to about 30,000 pooled vectors each, to create a mini-metagenome library that comprises, within the plurality of mini-metagenome subunits, DNA from the unsequenced and unassembled metagenomic DNA sample;
c) performing intra-pool sequencing and assembly of the metagenomic DNA contained in the pooled vectors present in the plurality of discrete mini-metagenome subunits of the mini-metagenome library, to create a first-pass long-assembly DNA contig metagenomic library comprising sequenced and assembled DNA contigs; wherein the first-pass long-assembly DNA contig metagenomic library has an N50 length of at least about 10 kb.

32.1 The method of embodiment 32, comprising the step:
d) performing inter-pool DNA contig assembly, by further assembling a plurality of sequenced and assembled DNA contigs from the first-pass long-assembly DNA contig metagenomic library to create a second-pass long-assembly DNA contig metagenomic library.

33. The method according to embodiment 32 or 32.1, wherein the unsequenced and unassembled metagenomic DNA sample comprises at least about 50, 100, 500, 1000, or 10000, unique whole genomes.

34. The method according to any one of embodiments 32-33, wherein the average size of the unique whole genomes in the unsequenced and unassembled metagenomic DNA sample is at least about 1 MB, 2 MB, 3 MB, 4 MB, or 5 MB or between 1-5 MB.

35. The method according to any one of embodiments 32-34, wherein the long-assembly DNA contig metagenomic library comprises a plurality of sequenced and assembled DNA contigs with a length of at least about 10 kb, 15 kb, 20 kb, 25 kb, 30 kb, 35 kb, 40 kb, 45 kb, 50 kb, or 100 kb.

36. The method according to any one of embodiments 32-35, wherein the long-assembly DNA contig metagenomic library has an N50 length of at least about 10 kb, 15 kb, 20 kb, 25 kb, 30 kb, 35 kb, 40 kb, 45 kb, 50 kb, or 100 kb.

36.1. The method according to any one of embodiments 32-36, comprising: arraying the DNA from the mini-metagenome subunit.

37. The method according to any one of embodiments 32-36, comprising: arraying physical copies of the long-assembly DNA contig length metagenomic library.

38. The method according to any one of embodiment 32-36, comprising: arraying physical copies of the intermediary DNA contig length mini-metagenome library, or the long DNA contig length metagenomic library, in a bacterial cell or DNA form.

39. The method according to any one of embodiments 32-36, comprising: arraying the plurality of discrete mini-metagenome subunits into a real coordinate space and assigning identifiers to each subunit.

40. The method according to any one of embodiments 32-36, comprising: arraying the plurality of discrete mini-metagenome subunits into a multi-well microtiter plate.

41. The method according to any one of embodiments 32-36, comprising: arraying the plurality of discrete mini-metagenome subunits into a 96-well microtiter plate 42. The method according to any one of embodiments 32-41, wherein the vectors comprise plasmids.

43. The method according to any one of embodiments 32-41, wherein the vectors comprise cosmids, fosmids, BACs, YACs, or a combination thereof.

44. The method according to any one of embodiments 32-41, wherein the vectors comprise cosmids.

45. The method according to any one embodiments 32-44, wherein the metagenomic vector fragment library in step (b) comprises at least about 1M, or 10M vectors.

46. The method according to any one of embodiments 32-44, wherein the vectors comprise cosmids, and the metagenomic vector fragment library in step (b) comprises at least about 10M cosmids.

47. The method according to any one of embodiments 32-44, wherein the vectors comprise cosmids, and the metagenomic vector fragment library in step (b) comprises at least about 20M cosmids.

48. The method according to any one of embodiments 32-47, comprising in step (b): cloning DNA fragments of less than about 200 kb, from the metagenomic library into a plurality of vectors.

49. The method according to any one of embodiments 32-47, comprising in step (b): cloning DNA fragments of less than about 100 kb, from the metagenomic DNA sample into a plurality of vectors.

50. The method according to any one of embodiments 32-47, comprising in step (b): cloning DNA fragments of less than about 50 kb, from the metagenomic DNA sample into a plurality of vectors.

51. The method according to any one of embodiments 32-47, comprising in step (b): cloning DNA fragments of about 20 kb to about 50 kb, from the metagenomic DNA sample into a plurality of vectors.

52. The method according to any one of embodiments 32-47, comprising in step (b): cloning DNA fragments of about 30 kb to about 45 kb, from the metagenomic DNA sample into a plurality of cosmids.

53. The method according to any one of embodiments 32-52, wherein the discrete mini-metagenome subunits in step (b) comprise from about 3,000 to about 15,000 pooled vectors each.

54. The method according to any one of embodiments 32-52, wherein the discrete mini-metagenome subunits in step (b) comprise from about 5,000 to about 12,000 pooled cosmid vectors each.

55. The method according to any one of embodiments 32-54, wherein the second-pass long-assembly DNA contig metagenomic library has an N50 length of at least about 10 kb, 15 kb, 20 kb, 25 kb, or 30 kb.

56. The method according to any one of embodiments 32-55, wherein step (c) comprises: simultaneously assembling all the DNA contigs contained in the pooled vectors present in an individual discrete mini-metagenome subunit from the plurality.

57. The method according to any one of embodiment 32-56, wherein in step (c) intra-pool sequencing is performed utilizing single molecule sequencing.

58. The method according to any one of embodiments 32-56, wherein in step (c) intra-pool sequencing is performed utilizing sequencing by synthesis (SBS).

59. The method according to any one of embodiments 32-56, wherein in step (c) intra-pool sequencing is performed utilizing single molecule, real-time (SMRT) sequencing.

60. The method according to any one of embodiments 32-56, wherein in step (c) intra-pool sequencing is performed utilizing nanopore sequencing.

60.1 The method according to any one of embodiments 32-56, wherein in step (c) intra-pool sequencing is performed utilizing synthetic long read sequencing.

60.2 The method according to embodiment 60.1 wherein the synthetic long read is based on proximity ligation strategies, and/or optical mapping 60.3 The method according to any one of embodiments 32-56, wherein in step (c) intra-pool sequencing is Hi-C sequencing.

61. The method according to any one of embodiments 32-60.3, wherein the discrete mini-metagenome subunits in step b) comprise from about 5,000 to about 12,000 pooled cosmid vectors each, and wherein step (c) comprises: simultaneously assembling all the sequenced DNA present in an individual discrete mini-metagenome subunit from the plurality.

62. A method for biosynthetic analoging of a target natural product, said method comprising the steps of:

a) providing a plurality of enzymes known or predicted to catalyze a type of reaction for analoging of the target natural product, thereby creating an analoging enzyme panel library;

b) incubating individual enzymes from the analoging enzyme panel with the target natural product, or a precursor to the target natural product, thereby producing reaction mixtures;

c) analyzing at least one of the reaction mixtures of step (b), for the presence of the target natural product and/or analogs of said target natural product; and d) selecting an enzyme from the analoging enzyme panel, wherein the selected enzyme produces a desired analog of the target natural product, as determined by the analysis of step (c), thereby analoging the target natural product.

63. The method of embodiment 62, wherein the enzymes of step (a) are provided in the form of lysates from microbial strains heterologously expressing said enzymes.

64. A method for biosynthetic analoging of a target natural product, said method comprising the steps of:

a) providing a plurality of microbial strains, each expressing an enzyme known or predicted to catalyze a type of reaction for analoging of the target natural product, thereby creating an analoging enzyme panel library of microbial strains;

b) contacting individual microbial strains from the analoging enzyme panel library of microbial strains with the target natural product, or a precursor to the target natural product, thereby creating a mixture;

c) analyzing the mixture of step (b) for the presence of the target natural product and/or analogs of said target natural product; and d) selecting a microbial strain from the analoging enzyme panel library of microbial strains, wherein the selected microbial strain produces a desired analog of the target natural product, as determined by the analysis of step (c), thereby analoging the target natural product; wherein the enzyme expressed by the selected microbial strain is a selected enzyme.

65. The method of any one of embodiments 62-64, further comprising the step of: perturbing the genome of a first base microbial strain to express the selected enzyme, wherein the first base microbial strain is capable of synthesizing the target natural product.

66. A method for biosynthetic analoging of a target natural product, said method comprising the steps of:

a) providing a plurality of genetic sequences, each encoding an enzyme known or predicted to catalyze a type of reaction for a first analoging of the target natural product;

b) perturbing the genome of one or more cells of a first base microbial strain to each express an enzyme encoded by one or more of the plurality of genetic sequences of step (a), wherein the first base microbial strain is capable of synthesizing the target natural product, thereby creating an analoging enzyme panel library of microbial strains;

c) culturing individual microbial strains from the analoging enzyme panel library of microbial strains;

d) analyzing spent media from the cultures of step (c), for the presence of the target natural product and/or analogs of said target natural product; and e) selecting a microbial strain from the analoging enzyme panel of microbial strains, wherein the selected microbial strain produces a desired analog of the target natural product, as determined by the analysis of step (d), thereby analoging the target natural product.

67. The method of embodiment 66, further comprising the steps of:

f) providing a second plurality of genetic sequences, each encoding an enzyme known or predicted to catalyze a type of reaction for a second analoging of the target natural product or the desired analog of step (e);

g) perturbing the genome of one or more cells of a second base microbial strain to each express an enzyme encoded by one or more of the second plurality of genetic sequences of step (0, wherein the second base microbial strain is capable of synthesizing the desired analog of step (e), thereby creating a second analoging enzyme panel library of microbial strains;

h) culturing individual microbial strains from the second analoging enzyme panel library of microbial strains;

i) analyzing spent media from the cultures of step (h), for the target natural product and/or analogs of said target natural product; and j) selecting a microbial strain from the second analoging enzyme panel of microbial strains, wherein the selected microbial strain of this step produces a second desired analog of the target natural product, as determined by the analysis of step (i), thereby analoging the target natural product.

68. The method of embodiment 66 or 67, wherein the target natural product is produced by a biosynthetic pathway in the first or second base microbial strain, said biosynthetic pathway comprising a plurality of biosynthetic genes, and wherein steps (b) and/or (g) comprise replacing one or more of the biosynthetic genes with one or more of the first or second plurality of genetic sequences of step (a) or (f), respectively.

69. The method of any one of embodiments 62-68, wherein at least one of the enzymes is from a sequence library (e.g. a metagenomic library), and was predicted to catalyze the type of reaction by a machine learning model populated by a training data set comprising a genetic sequence input variable and a phenotypic performance output variable;

i) wherein the genetic sequence input variable comprises one or more amino acid sequences of enzymes that catalyze the type of reaction for analoging of the target natural product; and ii) wherein the phenotypic performance output variable comprises one or more phenotypic performance features that are associated with the one or more amino acid sequences.

70. The method of embodiment 69, wherein the training data set comprises amino acid sequences of proteins that have either been:

i) empirically shown to catalyze the type of reaction for analoging of the target natural product; or ii) predicted with a high degree of confidence through other mechanisms to catalyze the type of reaction for analoging of the target natural product.

71. The method of any one of embodiments 62-70, wherein the enzymes are promiscuous enzymes.

71.1 The method of any one of embodiments 62-70, wherein the selected enzyme is capable of modifying more than one substrate.

72. A method for biosynthetic analoging of a target natural product, said method comprising the steps of:

a) accessing a training data set comprising a genetic sequence input variable and a phenotypic performance output variable;

i) wherein the genetic sequence input variable comprises one or more amino acid sequences of enzymes that are known or predicted to catalyze a type of reaction for analoging of the target natural product, and ii) wherein the phenotypic performance output variable comprises one or more phenotypic performance features that are associated with the one or more amino acid sequences;

b) developing a first predictive machine learning model that is populated with the training data set;

c) applying, using a computer processor, the first predictive machine learning model to a sequence library (e.g., a metagenomic library) containing amino acid sequences from one or more organisms, to identify a pool of candidate sequences within the metagenomic library, wherein said candidate sequences are predicted with respective first confidence scores to catalyze the type of reaction for analoging of the target natural product, by the first predictive machine learning model;

d) removing from the pool of candidate sequences, any sequence that is predicted to perform a different function by a second predictive machine learning model with a second confidence score if the ratio of the first confidence score to the second confidence score falls beyond a preselected threshold, thereby producing a filtered pool of candidate sequences;

e) manufacturing one or more microbial cells to each express a sequence from the filtered pool of candidate sequences from step (d), f) culturing the manufactured host cells of step (e), and lysing the cultured cells, thereby creating an analoging enzyme panel library;

g) incubating individual enzymes from the analoging enzyme panel library with the target natural product, or a precursor to the target natural product, thereby producing reaction mixtures;

h) analyzing at least one of the reaction mixtures of step (g), for the presence of the target natural product and/or analogs of said target natural product; and i) selecting an enzyme from the analoging enzyme panel, wherein the selected enzyme produces a desired analog of the target natural product, as determined by the analysis of step (h), thereby analoging the target natural product.

72.1 A method for biosynthetic analoging of a target natural product, said method comprising the steps of:

a) accessing a training data set comprising a genetic sequence input variable and a phenotypic performance output variable;

i) wherein the genetic sequence input variable comprises one or more amino acid sequences of enzymes that are known or predicted to catalyze a type of reaction for analoging of the target natural product, and ii) wherein the phenotypic performance output variable comprises one or more phenotypic performance features that are associated with the one or more amino acid sequences;

b) developing a first predictive machine learning model that is populated with the training data set;

c) applying, using a computer processor, the first predictive machine learning model to a sequence library (e.g., a metagenomic library) containing amino acid sequences from one or more organisms to identify a pool of candidate sequences within the metagenomic library, wherein said candidate sequences are predicted with respective first confidence scores to catalyze the type of reaction for analoging of the target natural product, by the first predictive machine learning model, thereby generating a pool of candidate sequences;

d) manufacturing one or more microbial cells to each express a sequence from the pool of candidate sequences from step (c), e) culturing the manufactured host cells of step (d), and lysing the cultured cells, thereby creating an analoging enzyme panel library;

f) incubating individual enzymes from the analoging enzyme panel library with the target natural product, or a precursor to the target natural product, thereby producing reaction mixtures;

g) analyzing at least one of the reaction mixtures of step (f), for the presence of the target natural product and/or analogs of said target natural product; and h) selecting an enzyme from the analoging enzyme panel, wherein the selected enzyme produces a desired analog of the target natural product, as determined by the analysis of step (g), thereby analoging the target natural product.

73. A method for biosynthetic analoging of a target natural product, said method comprising the steps of:

a) accessing a training data set comprising a genetic sequence input variable and a phenotypic performance output variable;

i) wherein the genetic sequence input variable comprises one or more amino acid sequences of enzymes that are known or predicted to catalyze a type of reaction for analoging of the target natural product, and ii) wherein the phenotypic performance output variable comprises one or more phenotypic performance features that are associated with the one or more amino acid sequences;

b) developing a first predictive machine learning model that is populated with the training data set;

c) applying, using a computer processor, the first predictive machine learning model to a sequence library (e.g., a metagenomic library) containing amino acid sequences from one or more organisms to identify a pool of candidate sequences within the metagenomic library, wherein said candidate sequences are predicted with respective first confidence scores to catalyze the type of reaction for analoging of the target natural product, by the first predictive machine learning model;

d) removing from the pool of candidate sequences, any sequence that is predicted to perform a different function by a second predictive machine learning model with a second confidence score if the ratio of the first confidence score to the second confidence score falls beyond a preselected threshold, thereby producing a filtered pool of candidate sequences;

e) perturbing the genome of one or more microbial cells of a base microbial strain to each express a sequence from the filtered pool of candidate sequences from step (d), wherein the base microbial strain is capable of synthesizing the target natural product, thereby creating an analoging enzyme panel library of microbial strains;

f) culturing individual microbial strains from the analoging enzyme panel library of microbial strains;

g) analyzing spent media from the cultures of step (f), for the presence of the target natural product and/or analogs of said target natural product; and h) selecting a microbial strain from the analoging enzyme panel of microbial strains, wherein the selected microbial strain produces a desired analog of the target natural product, as determined by the analysis of step (g), thereby analoging the target natural product.

73.1 A method for biosynthetic analoging of a target natural product, said method comprising the steps of:

a) accessing a training data set comprising a genetic sequence input variable and a phenotypic performance output variable;

i) wherein the genetic sequence input variable comprises one or more amino acid sequences of enzymes that are known or predicted to catalyze a type of reaction for analoging of the target natural product, and ii) wherein the phenotypic performance output variable comprises one or more phenotypic performance features that are associated with the one or more amino acid sequences;

b) developing a first predictive machine learning model that is populated with the training data set;

c) applying, using a computer processor, the first predictive machine learning model to a sequence library (e.g., a metagenomic library) containing amino acid sequences from one or more organisms to identify a pool of candidate sequences within the metagenomic library, wherein said candidate sequences are predicted with respective first confidence scores to catalyze the type of reaction for analoging of the target natural product, by the first predictive machine learning model, thereby producing a pool of candidate sequences;

d) perturbing the genome of one or more microbial cells of a base microbial strain to each express a sequence from the pool of candidate sequences from step (c), wherein the base microbial strain is capable of synthesizing the target natural product, thereby creating an analoging enzyme panel library of microbial strains;

e) culturing individual microbial strains from the analoging enzyme panel library of microbial strains;

f) analyzing spent media from the cultures of step (e), for the presence of the target natural product and/or analogs of said target natural product; and g) selecting a microbial strain from the analoging enzyme panel of microbial strains, wherein the selected microbial strain produces a desired analog of the target natural product, as determined by the analysis of step (f), thereby analoging the target natural product.

73.2. A method for identifying enzymes capable of analoging natural products, said method comprising the steps of:

a) accessing a training data set comprising a genetic sequence input variable and a phenotypic performance output variable;

i) wherein the genetic sequence input variable comprises one or more amino acid sequences of enzymes that are known or predicted to catalyze a type of reaction for analoging of the target natural product, and ii) wherein the phenotypic performance output variable comprises one or more phenotypic performance features that are associated with the one or more amino acid sequences;

b) developing a first predictive machine learning model that is populated with the training data set;

c) applying, using a computer processor, the first predictive machine learning model to a sequence library (e.g., a metagenomic library) containing amino acid sequences from one or more organisms to identify a pool of candidate sequences within the metagenomic library, wherein said candidate sequences are predicted with respective first confidence scores to catalyze the type of reaction for analoging of the target natural product, by the first predictive machine learning model, thereby producing a pool of candidate sequences predicted to be capable of analoging natural products.

73.3 The method of any one of embodiments 72-73.2, comprising the step of identifying all sequences within the sequence library that are computationally predicted to contain multi-gene clusters, and removing sequences from the pool of candidate sequences of step (c) that are not located within a predicted multi-gene cluster.

73.4 The method of embodiment 73.2 or 73.3, comprising the step of:

d) manufacturing one or more microbial cells to each express a sequence from the pool of candidate sequences.

73.5 The method of embodiment 73.4, comprising the step of e) culturing the manufactured host cells of step (d), and lysing the cultured cells, thereby creating an analoging enzyme panel library.

73.6 The method of embodiment 73.5, comprising the step of f) incubating individual enzymes from the analoging enzyme panel library with the target natural product, or a precursor to the target natural product, thereby producing reaction mixtures.

73.7 The method of embodiment 73.6, comprising the step of g) analyzing at least one of the reaction mixtures of step (0, for the presence of the target natural product and/or analogs of said target natural product.

73.8 The method of embodiment 73.7, comprising the step of h) selecting an enzyme from the analoging enzyme panel, wherein the selected enzyme produces a desired analog of the target natural product, as determined by the analysis of step (g).

74. The method of any one of embodiments 72 and 73.8, further comprising adding to the training data set of step (a):

i) at least one of the sequence(s) that was expressed in the microbial cells of step (e); and ii) the phenotypic performance measurement(s) corresponding to the at least one sequence of (i), as measured in step (h), thereby creating an updated training data set.

75. The method of any one of embodiments 72.1-73, further comprising adding to the training data set of step (a):

i) at least one of the sequence(s) that was expressed in the analoging enzyme panel library of microbial strains of step (cl/e), and ii) the phenotypic performance measurement(s) corresponding to the at least one sequence of (i), as measured in step (g), thereby creating an updated training data set.

75.1 The method of embodiment 73.1, further comprising adding to the training data set of step (a):

i) at least one of the sequence(s) that was expressed in the analoging enzyme panel library of microbial strains of step (d), and ii) the phenotypic performance measurement(s) corresponding to the at least one sequence of (i), as measured in step (f), thereby creating an updated training data set.

76. The method of any one of embodiment 74-75.1, wherein the phenotypic performance measurement indicates the amount of the analog of the target natural product that was present.

77. The method of any one of embodiment 74-75.1, wherein the penultimate step is repeating all previous steps at least once with the updated training data set.

78. The method of any one of embodiments 72-77, wherein the training data set comprises amino acid sequences of proteins that have either been:

i) empirically shown to catalyze the type of reaction for analoging of the target natural product; or ii) predicted with a high degree of confidence through other mechanisms to catalyze the type of reaction for analoging of the target natural product.

78.1 The method of any one of embodiments 72-78, wherein the predictive machine learning model is a Hidden Markov Model (HMM).

79. A method for producing an analog of a target natural product, said method comprising the steps of:

a) providing a first multi-gene cluster known to produce the target natural product;

b) developing a predictive model based on said first multi-gene cluster;

c) querying, in silico, a digital metagenomics library for new multi-gene clusters, wherein said new multi-gene clusters are predicted, by the predictive model, to produce the target natural product or a variant of the target natural product, thereby producing a pool of candidate multi-gene clusters;

d) identifying, in silico with an annotation engine, individual genes encoding biosynthetic enzymes within one or more of the new multi-gene clusters of the pool of candidate multi-gene clusters of step (c), thereby producing an analoging enzyme panel library comprising biosynthetic genes from the new multi-gene clusters;

e) perturbing the genome of a base microbial host cell to express a gene from the analoging enzyme panel library, wherein the base microbial host cell comprises the first multi-gene cluster;

f) culturing at least one of the microbial host cells manufactured in step (e);

g) analyzing spent media from the cultures of step (0, for the target natural product and/or analogs of said target natural product; and h) selecting a microbial host cell from the microbial host cells cultured in step (0, wherein the selected microbial host cell produces an analog of the target natural product as determined by the analysis of step (g), thereby producing an analog of the target natural product.

80. A method for producing an analog of a target natural product, said method comprising the steps of:

a) providing a first multi-gene cluster known to produce the target natural product;

b) developing a predictive model based on said first multi-gene cluster;

c) querying, in silico, a digital metagenomics library for new multi-gene clusters, wherein said new multi-gene clusters are predicted, by the predictive model, to produce the target natural product or a variant of the target natural product, thereby producing a pool of candidate multi-gene clusters;

d) manufacturing one or more microbial host cells to each express at least one multi-gene cluster from the pool of candidate multi-gene clusters;

e) culturing at least one of the microbial host cells manufactured in step (d);

f) analyzing spent media from the cultures of step (e), for the target natural product and/or analogs of said target natural product; and g) selecting a microbial host cell from the microbial host cells cultured in step (e), wherein the selected microbial host cell produces an analog of the target natural product as determined by the analysis of step (f), thereby producing an analog of the target natural product.

81. The method of embodiment 80, further comprising the steps of:

h) perturbing the genome of a base microbial host cell to express a gene from the candidate multi-gene cluster comprised within the selected microbial host cell of step (g), wherein the base microbial host cell comprises the first multi-gene cluster, thereby producing a modified base host cell.

82. The method of embodiment 81, wherein step (h) comprises replacing an original gene from the first multi-gene cluster with a corresponding gene from the candidate multi-gene cluster.

83. The method of embodiment 81, wherein step (h) comprises knocking out an original gene from the first multi-gene cluster.

84. A method for producing an analog of a target natural product, said method comprising the steps of:

a) providing a base microbial host cell comprising a multi-gene cluster known to produce the target natural product;

b) perturbing the genome of the base microbial host cell to mutate or knock out the expression of one or more genes within the multi-gene cluster, thereby creating a library of mutated microbial host cells;

c) culturing a microbial host cell from the library of mutated microbial host cells;

d) analyzing spent media from the cultures of step (c), for the presence of the target natural product and/or analogs of said target natural product, and e) selecting a microbial host cell from the microbial host cells cultured in step (c), wherein the selected microbial host cell produces an analog of the target natural product as determined by the analysis of step (d), thereby producing an analog of the target natural product.

84.1 A method for producing an analog of a target natural product, said method comprising the steps of:

a) providing a plurality of multi-gene clusters known or predicted to produce the target natural product or related natural products;

b) identifying, in silico with an annotation engine, individual genes encoding biosynthetic enzymes within the plurality of multi-gene clusters of step (a), thereby producing an analoging enzyme panel library comprising biosynthetic genes from the plurality of multi-gene clusters;

c) perturbing the genome of a base microbial host cell to express a gene from the analoging enzyme panel library, wherein the base microbial host cell comprises a first multi-gene cluster capable of producing the target natural product, thereby manufacturing a microbial cell;

d) culturing at least one of the microbial host cells manufactured in step (c);

e) analyzing spent media or lysate from the cultures of step (d), for the target natural product and/or analogs of said target natural product; and f) selecting a microbial host cell from the microbial host cells cultured in step (d), wherein the selected microbial host cell produces an analog of the target natural product as determined by the analysis of step (e), thereby producing an analog of the target natural product.

84.2 The methods of any one of embodiments 62-84.1, wherein the digital metagenomics library was produced according to the methods of any one of embodiments 32-61.

85. An in silico method for identifying a candidate multi-gene cluster (MGC) that does not encode for a known resistance gene, said method comprising the steps of:

a) providing the sequence of a known or predicted MGC;

b) computationally predicting natural product multi-gene cluster feature sets within a long-assembly digital metagenomic library and supplying the output of said prediction as a plurality of signal-associated multi-gene cluster digital feature sets;

c) selecting a candidate MGC from amongst the plurality of signal-associated multi-gene cluster digital feature sets of step (b), said candidate MGC comprising at least one similarity factor selected from the group consisting of:

i) sequence homology of 1, 2, 3, 4, 5, 6, 7, or 8 biosynthetic enzymes within the known or predicted MGC and the candidate MGC;

ii) same number of each type of biosynthetic module(s) within the known or predicted MGC and the candidate MGC; and iii) similarity of the predicted chemical structures of natural products produced by the known/predicted MGC and the candidate MGC;

thereby identifying the candidate MGC that does not encode for a known resistance gene.

86. The method of embodiment 85, wherein the known or predicted MGC comprises a putative resistance gene.

87. The method of any one of embodiments 85-86, wherein the similarity factor of step (c)(i) comprises sequence homology of at least 10%, 20%, 30%, 40%, 50%, 60%, 70%, 80%, 90%, or 100% of the biosynthetic enzymes in the candidate MGC with at least one of the biosynthetic enzymes of known or predicted MGC.

88. The method of any one of embodiments 85-87, wherein homology of the biosynthetic enzyme is determined via sequence identity.

89. The method of embodiment 88, wherein a biosynthetic enzyme in the candidate MGC is a homolog if it exhibits at least 80%, 81%, 82%, 83%, 84%, 85%, 86%, 87%, 88%, 89%, 90%, 91%, 92%, 93%, 94%, 95%, 96%, 97%, 98%, or 99% sequence identity with a biosynthetic enzyme within the known or predicted MGC.

90. The method of any one of embodiments 85-87, wherein homology of the biosynthetic enzymes is determined via an HMM tool.

91. The method of embodiment 90, wherein a biosynthetic enzyme in the candidate MGC is a homolog if the ratio of its candidate bitscore to best match bitscore is greater than 0.6, 0.7, 0.8, or 0.9.

92. The method of any one of embodiments 85-91, wherein the biosynthetic enzyme(s) are core biosynthetic enzymes.

93. The method of any one of embodiments 85-92, wherein similarity of the predicted chemical structures in the candidate MGC and the known or predicted MGC is determined by the Tanimoto coefficient.

94. The method of embodiment 93, wherein a predicted chemical structure of a candidate MGC is similar to the known or predicted chemical structure of a known or predicted MGC, if they exhibits a Tanimoto coefficient of at least 0.7, 0.8, 0.9, or 0.95.

95. The method of any one of embodiments 85-94, wherein the putative resistance gene is located within the predicted MGC, and is not involved in the synthesis of the natural product.

96. The method according to any one of embodiments 85-95, wherein the long-assembly digital metagenomics library comprises an N50 length of at least about 10 kb, 15 kb, 20 kb, 25 kb, 30 kb, 35 kb, or 40 kb.

97. The method according to any one of embodiments 85-96, wherein the digital metagenomics library is at least about 50 Mb, 75 Mb, 100 Mb, 200 Mb, 300 Mb, 400 Mb, 500 Mb, 600 Mb, 700 Mb, 800 Mb, 900 Mb, 1000 Mb, 1100 Mb, 1200 Mb, 1300 Mb, or 1400 Mb in size.

98. The method according to any one of embodiments 85-95, wherein the multi-gene cluster feature set digital metagenomics library comprises an N50 length of at least about 10 kb, 15 kb, or 20 kb and the digital metagenomics library is at least about 500 MB in size.

99. The method according to any one of embodiments 85-95, wherein the multi-gene cluster feature set digital metagenomics library comprises: sequenced and digitally assembled contig sequences having an N50 length of at least about 10 kb, 15 kb, or 20 kb and the digital metagenomics library is at least about 1 TB in size.

100. The method according to any one of embodiments 85-95, wherein the multi-gene cluster feature set digital metagenomics library comprises: sequenced and digitally assembled sequences having an N50 length of at least about 10 kb, 15 kb, or 20 kb and the digital metagenomics library is about 500 MB to about 1 TB in size.

101. The method according to any one of embodiments 85-95, wherein the multi-gene cluster feature set digital metagenomics library comprises: sequenced and digitally assembled contig sequences having an N50 length of at least about 10 kb 15 kb, or 20 kb, wherein a majority of the assembled sequence in the library is from uncultured microorganisms.

102. The method according to any one of embodiments 85-95, wherein the multi-gene cluster feature set digital metagenomics library comprises: sequenced and digitally assembled contig sequences having an N50 length of at least about 10 kb, 15 kb, or 20 kb, wherein substantially all of the sequence in the library is from uncultured microorganisms.

103. The method according to any one of embodiments 85-95, wherein the multi-gene cluster feature set digital metagenomics library comprises: sequenced and digitally assembled contig sequences having an N50 length of at least about 10 kb, 15 kb, or 20 kb, wherein a majority of the sequence in the library is from uncultured microorganisms, physical copies of said digitally assembled contig sequences being arrayed into a corresponding physical cosmid, fosmid, BAC, YAC, or a combination thereof, library.

104. The method according to any one of embodiments 85-95, wherein the multi-gene cluster feature set digital metagenomics library comprises: sequenced and digitally assembled contig sequences having an N50 length of at least about 10 kb, 15 kb, or 20 kb, wherein a majority of the sequence in the library is from uncultured microorganisms, at least some of which are derived from a soil sample, physical copies of said digitally assembled contig sequences being arrayed into a corresponding physical cosmid library.

105. The method of any one of embodiments embodiment 85-104, comprising the step of:

d) manufacturing a host cell, wherein the manufactured host cell comprises the candidate MGC(s) identified in step (c), or a refactored version thereof.

106. The method of embodiment 105, comprising the step of:

e) culturing the manufactured host cells of step (d).

107. The method of embodiment 106, comprising the step of:

f) analyzing lysates and/or spent cultures from the culture of step (e) for the presence of a natural product, wherein said natural product is not present in cultures of control host cells lacking the candidate MGC sequence present in the manufactured host cell.

108. An in silico method for identifying a candidate multi-gene cluster (MGC), said method comprising the steps of:

a) identifying the core biosynthetic enzymes of a known or predicted MGC;

b) querying a long-assembly digital metagenomics library for homologs of each of the core biosynthetic enzymes identified in (a), wherein said digital metagenomics library comprises digitally assembled contigs; and c) identifying a new MGC based on the presence of homologs of the core biosynthetic enzymes within single contig of the digital metagenomics library.

109. The method of embodiment 108, wherein an enzyme encoded in the digital metagenomics library is considered a homolog if it exhibits a sequence homology of at least 10%, 20%, 30%, 40%, 50%, 60%, 70%, 80%, 90%, or 100% with at least one of the core biosynthetic enzyme of the known or predicted MGC.

109.1 The method of any one of embodiments 108-109, wherein homology of the core biosynthetic enzyme is determined via sequence identity.

109.2 The method of embodiment 109.1, wherein a gene in the new MGC is a homolog if it exhibits at least 80%, 81%, 82%, 83%, 84%, 85%, 86%, 87%, 88%, 89%, 90%, 91%, 92%, 93%, 94%, 95%, 96%, 97%, 98%, or 99% sequence identity with a biosynthetic enzyme within the known or predicted MGC.

110. The method of embodiment 108, wherein homology of the biosynthetic enzyme is determined via an HMM tool.

111. The method of embodiment 110, wherein an enzyme in the digital metagenomics library is a homolog if the ratio of its core biosynthetic bitscore to best match bitscore is greater than 0.6, 0.7, 0.8, or 0.9.

112. The method according to any one of embodiments 108-111 wherein the long-assembly digital metagenomics library comprises an N50 length of at least about 10 kb, 15 kb, 20 kb, 25 kb, 30 kb, 35 kb, or 40 kb.

112.1 The method according to any one of embodiments 108-112, wherein the digital metagenomics library is at least about 50 Mb, 75 Mb, 100 Mb, 200 Mb, 300 Mb, 400 Mb, 500 Mb, 600 Mb, 700 Mb, 800 Mb, 900 Mb, 1000 Mb, 1100 Mb, 1200 Mb, 1300 Mb, or 1400 Mb in size.

113. The method according to any one of embodiments 108-111, wherein the multi-gene cluster feature set digital metagenomics library comprises an N50 length of at least about 10 kb, 15 kb, or 20 kb and the digital metagenomics library is at least about 500 MB in size.

114. The method according to any one of embodiments 108-111, wherein the multi-gene cluster feature set digital metagenomics library comprises: sequenced and digitally assembled contig sequences having an N50 length of at least about 10 kb, 15 kb, or 20 kb and the digital metagenomics library is at least about 1 TB in size.

115. The method according to any one of embodiments 108-111, wherein the multi-gene cluster feature set digital metagenomics library comprises: sequenced and digitally assembled sequences having an N50 length of at least about 10 kb, 15 kb, or 20 kb and the digital metagenomics library is about 500 MB to about 1 TB in size.

116. The method according to any one of embodiments 108-111, wherein the multi-gene cluster feature set digital metagenomics library comprises: sequenced and digitally assembled contig sequences having an N50 length of at least about 10 kb 15 kb, or 20 kb, wherein a majority of the assembled sequence in the library is from uncultured microorganisms.

117. The method according to any one of embodiments 108-111, wherein the multi-gene cluster feature set digital metagenomics library comprises: sequenced and digitally assembled contig sequences having an N50 length of at least about 10 kb, 15 kb, or 20 kb, wherein substantially all of the sequence in the library is from uncultured microorganisms.

118. The method according to any one of embodiments 108-111, wherein the multi-gene cluster feature set digital metagenomics library comprises: sequenced and digitally assembled contig sequences having an N50 length of at least about 10 kb, 15 kb, or 20 kb, wherein a majority of the sequence in the library is from uncultured microorganisms, physical copies of said digitally assembled contig sequences being arrayed into a corresponding physical cosmid, fosmid, BAC, YAC, or a combination thereof, library.

119. The method according to any one of embodiments 108-111, wherein the multi-gene cluster feature set digital metagenomics library comprises: sequenced and digitally assembled contig sequences having an N50 length of at least about 10 kb, 15 kb, or 20 kb, wherein a majority of the sequence in the library is from uncultured microorganisms, at least some of which are derived from a soil sample, physical copies of said digitally assembled contig sequences being arrayed into a corresponding physical cosmid library.

120. The method of any one of embodiments embodiment 108-119, comprising the step of:
  d) manufacturing one or more host cell(s), wherein each manufactured host cell comprises the new MGC identified in step (c).

121. The method of embodiment 120, comprising the step of:
  e) culturing the manufactured host cells of step (d).

122. The method of embodiment 121, comprising the step of:
  f) analyzing lysates and/or spent cultures from the culture of step (e) for the presence of a natural product, wherein said natural product is not present in cultures of control host cells lacking the new MGC sequence present in the manufactured host cell.

123. The methods of any one of embodiments 85-122, wherein the digital metagenomics library was produced according to the methods of any one of embodiments 32-61.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world.

The invention claimed is:

1. A method for searching digital metagenomics library and identifying a natural product of interest, comprising:
  a) querying a digital metagenomics library for a signal indicative of a natural product multi-gene cluster feature set; said querying comprising utilizing a predictive model to search the digital metagenomics library for a homolog of a gene of interest,
  b) supplying the output of said query as a plurality of signal-associated multi-gene cluster digital feature sets;
  c) determining and assigning biologic relevancy to the signal-associated multi-gene cluster digital feature sets, by:
    determining a computationally predicted biosynthetic functionality of a plurality of genes from the signal-associated multi-gene cluster digital feature set and digitally assembling a computationally determined natural product multi-gene cluster (MGC) feature set comprising one or more biosynthetic operon(s); and
    determining a computationally predicted biological resistance gene functionality of at least one gene from a signal-associated multi-gene cluster digital feature set to thereby identify a computationally determined biological resistance gene;
  d) identifying an MGC encoding for the natural product of interest based upon a computationally determined biological resistance gene being located within a threshold parameter of a computationally determined natural product multi-gene cluster feature set comprising one or more biosynthetic operon(s);

e) manufacturing a host cell, wherein the host cell comprises the MGC encoding for the natural product of interest identified in step (d), or a refactored version thereof;

f) culturing the manufactured host cell of step (e); and g) analyzing the culture of step (f) for the presence of a natural product, wherein said natural product is not present in a culture of a control host cell lacking the MGC sequence present in the manufactured host cell;

wherein the predictive model is a HMM and wherein the homolog exhibits a bitscore greater than 50 on the HMM.

2. The method according to claim 1, wherein the digital metagenomics library is a long-assembly digital metagenomics library comprising an N50 length of at least about 15 kb.

3. The method according to claim 1, wherein the digital metagenomics library is at least about 500 Mb in size.

4. The method according to claim 1, wherein the digital metagenomics library comprises an N50 length of at least about 15 kb, and is at least about 500 MB in size.

5. The method according to claim 1, wherein a majority of the digital metagenomics library's assembled sequence is from uncultured microorganisms.

6. The method according to claim 1, wherein substantially all of the digital metagenomics library's assembled sequence is from uncultured microorganisms.

7. The method according to claim 1, wherein the multi-gene cluster feature set digital metagenomics library comprises: sequenced and digitally assembled contig sequences having an N50 length of at least about 15 kb, and wherein physical copies of said digitally assembled contig sequences are arrayed in a corresponding physical cosmid, fosmid, BAC, YAC, or a combination thereof, library.

8. The method according to claim 1, wherein the gene of interest is a known resistance gene or variant or homolog thereof.

9. The method according to claim 1, wherein digitally assembling the computationally determined natural product multi-gene cluster feature set comprising one or more biosynthetic operon(s) in step c) is performed with a genetic algorithm.

10. The method according to claim 9, wherein the genetic algorithm is selected from the group consisting of: BAGEL, ClustScan, NP.searcher, SMURF, antiSMASH, ClusterFinder, PRISM, EvoMining, RODEO, and ARTS.

11. An in silico method for searching a multi-gene cluster feature set digital metagenomics library and identifying a natural product of interest, comprising:

a) identifying, within a digital metagenomics library, sequences that are computationally predicted to contain multi-gene clusters (MGCs), comprising one or more biosynthetic operons;

b) utilizing a predictive model to search the digital metagenomics library for a homolog of a gene of interest, thereby computationally determining a biological resistance gene; and c) identifying an MGC encoding for the natural product of interest based upon a computationally determined biological resistance gene being located within a threshold parameter of a computationally predicted multi-gene cluster comprising a one or more biosynthetic operons;

wherein the predictive model is a HMM and wherein the homolog exhibits a bitscore greater than 50 on the HMM model.

12. The method according to claim 11, wherein the gene of interest is a known resistance gene or variant or homolog thereof.

13. The method according to claim 11, wherein the digital metagenomics library comprises an N50 length of at least about 15 kb, and is at least about 500 MB in size.

14. The method according to claim 11, comprising the step of:

d) manufacturing a host cell, wherein the host cell comprises the MGC encoding for the natural product of interest identified in step (c), or a refactored version thereof.

15. An in silico method for searching a multi-gene cluster feature set digital metagenomics library and identifying a natural product of interest, comprising:

a) utilizing a predictive model to search the digital metagenomics library for a homolog of a gene of interest, thereby computationally determining a biological resistance gene;

b) identifying, within the digital metagenomics library, sequences that are computationally predicted to contain multi-gene clusters (MGCs), comprising one or more biosynthetic operons; and c) identifying an MGC encoding for the natural product of interest based upon a computationally determined biological resistance gene being located within a threshold parameter of a computationally predicted multi-gene cluster comprising a one or more biosynthetic operons;

wherein the predictive model is a HMM and wherein the homolog exhibits a bitscore greater than 50 on the HMM model.

16. The method according to claim 15, wherein the gene of interest is a known resistance gene or variant or homolog thereof.

17. The method according to claim 15, wherein the digital metagenomics library comprises an N50 length of at least about 15 kb, and is at least about 500 MB in size.

18. A method for searching a digital metagenomics library and identifying a natural product of interest, comprising:

a) querying a digital metagenomics library for a signal indicative of a natural product multi-gene cluster feature set; wherein said querying step comprises identifying sequences that are computationally predicted to contain multi-gene clusters comprising one or more biosynthetic operons;

b) supplying the output of said query as a plurality of signal-associated multi-gene cluster digital feature sets;

c) determining and assigning biologic relevancy to the signal-associated multi-gene cluster digital feature sets, by:

utilizing a predictive model to search the signal-associated multi-gene cluster digital feature sets for a homolog of a gene of interest, thereby identifying a computationally determined biological resistance gene;

d) identifying a multi-gene duster (MGC) encoding for the natural product of interest based upon a computationally determined biological resistance gene being located within a threshold parameter of a computationally predicted multi-gene cluster comprising one or more biosynthetic operons;

e) manufacturing a host cell, wherein the host cell comprises the MGC encoding for the natural product of interest identified in step (d), or a refactored version thereof;
f) culturing the manufactured host cell of step (e); and
g) analyzing the culture of step (f) for the presence of a natural product, wherein said natural product is not present in a culture of a control host cell lacking the MGC sequence present in the manufactured host cell; wherein the predictive model is a HMM and wherein the homolog exhibits a bitscore greater than 50 on the HMM model.

19. The method according to claim 18, wherein identifying sequences that are computationally predicted to contain multi-gene clusters is performed with antibiotics and secondary metabolite analysis shell (Anti SMASH) algorithm and pipeline or DeepBGC algorithm and pipeline.

20. The method according to claim 18, wherein the digital metagenomics library is a long-assembly digital metagenomics library comprising an N50 length of at least about 15 kb.

21. The method according to claim 18, wherein the digital metagenomics library is at least about 500 Mb in size.

22. The method according to claim 18, wherein the digital metagenomics library comprises an N50 length of at least about 15 kb, and is at least about 500 MB in size.

23. The method according to claim 18, wherein a majority of the digital metagenomics library's assembled sequence is from uncultured microorganisms.

24. The method according to claim 18, wherein substantially all of the digital metagenomics library's assembled sequence is from uncultured microorganisms.

25. The method according to claim 18, wherein the multi-gene cluster feature set digital metagenomics library comprises: sequenced and digitally assembled contig sequences having an N50 length of at least about 15 kb, and wherein physical copies of said digitally assembled contig sequences are arrayed in a corresponding physical cosmid, fosmid, BAC, YAC, or a combination thereof, library.

* * * * *